US010081665B2

(12) United States Patent
Mahr et al.

(10) Patent No.: US 10,081,665 B2
(45) Date of Patent: Sep. 25, 2018

(54) PEPTIDES AND COMBINATION OF PEPTIDES FOR USE IN IMMUNOTHERAPY AGAINST VARIOUS TUMORS

(71) Applicant: immatics biotechnologies GmbH, Tuebingen (DE)

(72) Inventors: Andrea Mahr, Tuebingen (DE); Toni Weinschenk, Aichwald (DE); Oliver Schoor, Tuebingen (DE); Jens Fritsche, Dusslingen (DE); Harpreet Singh, Munich (DE); Lea Stevermann, Tuebingen (DE)

(73) Assignee: immatics biotechnologies GmbH, Tübingen (DE)

( * ) Notice: Subject to any disclaimer, the term of this patent is extended or adjusted under 35 U.S.C. 154(b) by 0 days.

(21) Appl. No.: 15/082,999

(22) Filed: Mar. 28, 2016

(65) Prior Publication Data

US 2016/0279217 A1    Sep. 29, 2016

Related U.S. Application Data

(60) Provisional application No. 62/139,189, filed on Mar. 27, 2015.

(51) Int. Cl.
| | | |
|---|---|---|
| *A61K 38/00* | (2006.01) | |
| *C07K 14/74* | (2006.01) | |
| *G01N 33/569* | (2006.01) | |
| *A61K 39/00* | (2006.01) | |
| *C07K 16/28* | (2006.01) | |
| *A61K 45/06* | (2006.01) | |
| *C07K 14/725* | (2006.01) | |
| *C12Q 1/6886* | (2018.01) | |
| *C07K 14/47* | (2006.01) | |
| *C07K 16/30* | (2006.01) | |
| *A61K 38/08* | (2006.01) | |
| *C07K 7/02* | (2006.01) | |
| *C07K 7/06* | (2006.01) | |
| *G01N 33/566* | (2006.01) | |
| *C07K 16/18* | (2006.01) | |
| *C12N 5/0783* | (2010.01) | |
| *C12N 9/64* | (2006.01) | |

(Continued)

(52) U.S. Cl.
CPC ........ *C07K 14/70539* (2013.01); *A61K 38/06* (2013.01); *A61K 38/08* (2013.01); *A61K 38/1774* (2013.01); *A61K 39/0005* (2013.01); *A61K 39/0011* (2013.01); *A61K 45/06* (2013.01); *C07K 7/02* (2013.01); *C07K 7/06* (2013.01); *C07K 14/001* (2013.01); *C07K 14/47* (2013.01); *C07K 14/4702* (2013.01); *C07K 14/4748* (2013.01); *C07K 14/7051* (2013.01); *C07K 16/18* (2013.01); *C07K 16/2833* (2013.01); *C07K 16/30* (2013.01); *C12N 5/0636* (2013.01); *C12N 5/0638* (2013.01); *C12N 9/6491* (2013.01); *C12Q 1/6886* (2013.01); *G01N 33/505* (2013.01); *G01N 33/5088* (2013.01); *G01N 33/566* (2013.01); *G01N 33/56972* (2013.01); *G01N 33/56977* (2013.01); *A61K 2039/5158* (2013.01); *A61K 2039/54* (2013.01); *A61K 2039/57* (2013.01); *A61K 2039/572* (2013.01); *A61K 2039/585* (2013.01); *C07K 2317/24* (2013.01); *C07K 2317/31* (2013.01); *C07K 2317/34* (2013.01); *C07K 2319/00* (2013.01); *C07K 2319/40* (2013.01); *C12N 2501/998* (2013.01); *C12N 2502/11* (2013.01); *C12Q 2600/106* (2013.01); *C12Q 2600/158* (2013.01); *C12Y 304/24* (2013.01); *G01N 2333/47* (2013.01); *G01N 2333/7051* (2013.01); *G01N 2333/70503* (2013.01); *G01N 2333/70539* (2013.01); *G01N 2500/10* (2013.01)

(58) Field of Classification Search
None
See application file for complete search history.

(56) References Cited

U.S. PATENT DOCUMENTS

| | | |
|---|---|---|
| 4,772,557 A | 9/1988 | Eisen et al. |
| 6,255,055 B1 | 7/2001 | Ross |

(Continued)

FOREIGN PATENT DOCUMENTS

| | | |
|---|---|---|
| EP | 1347046 A1 | 9/2003 |
| WO | 2001057275 A2 | 8/2001 |

(Continued)

OTHER PUBLICATIONS

Guo, et al., Nature. Nov. 26, 1992; 360:364-366 (see p. 366, col. 1, lines 1-10).

(Continued)

*Primary Examiner* — Sheela J. Huff
(74) *Attorney, Agent, or Firm* — McBee Moore Woodward & Vanik IP, LLC; Susan McBee

(57) ABSTRACT

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

9 Claims, 65 Drawing Sheets
Specification includes a Sequence Listing.

(51) Int. Cl.
*C07K 14/00* (2006.01)
*A61K 38/17* (2006.01)
*G01N 33/50* (2006.01)
*A61K 38/06* (2006.01)

(56) References Cited

U.S. PATENT DOCUMENTS

| | | |
|---|---|---|
| 6,794,151 B2 | 9/2004 | Ross |
| 6,869,951 B1 | 3/2005 | Stallings et al. |
| 6,934,639 B1 | 8/2005 | Chen et al. |
| 7,094,890 B1 | 8/2006 | Crowl et al. |
| 7,258,860 B2 | 8/2007 | Wang et al. |
| 7,259,253 B2 | 8/2007 | Einat et al. |
| 7,311,914 B2 | 12/2007 | Zhang et al. |
| 7,335,504 B2 | 2/2008 | Haupts et al. |
| 7,368,548 B2 | 5/2008 | Dahary et al. |
| 7,494,775 B2 | 2/2009 | Veiby |
| 7,569,662 B2 | 8/2009 | Pollock et al. |
| 7,579,160 B2 | 8/2009 | Bangur et al. |
| 7,585,506 B2 | 9/2009 | Wang et al. |
| 7,667,001 B1 | 2/2010 | Pollock et al. |
| 7,705,120 B2 | 4/2010 | Lillie et al. |
| 7,749,505 B2 | 7/2010 | Wang et al. |
| 7,807,392 B1 | 10/2010 | Domon et al. |
| 7,919,467 B2 | 4/2011 | Ramakrishna et al. |
| 8,323,657 B2 | 12/2012 | Nishimura |
| 8,323,906 B2 | 12/2012 | Veiby et al. |
| 8,586,006 B2 | 11/2013 | Hood et al. |
| 8,603,752 B2 | 12/2013 | Hood et al. |
| 2003/0108890 A1 | 6/2003 | Baranova et al. |
| 2003/0170630 A1 | 9/2003 | Alsobrook et al. |
| 2005/0037445 A1 | 2/2005 | Poulsen et al. |
| 2005/0053918 A1 | 3/2005 | Barnea et al. |
| 2005/0175581 A1 | 8/2005 | Haupts et al. |
| 2007/0292415 A1 | 12/2007 | Dillon et al. |
| 2009/0098533 A1 | 4/2009 | Munnes et al. |
| 2011/0189694 A1 | 8/2011 | Woloszczuk et al. |
| 2011/0229451 A2 | 9/2011 | Bookbinder et al. |
| 2011/0318380 A1 | 12/2011 | Brix et al. |
| 2012/0129843 A1 | 5/2012 | Zhang et al. |
| 2012/0302569 A1 | 11/2012 | Jackson et al. |
| 2013/0011496 A1 | 1/2013 | Cebon et al. |
| 2013/0203096 A1 | 8/2013 | Kearney et al. |
| 2013/0225443 A1 | 8/2013 | Osafune et al. |
| 2013/0303826 A1 | 11/2013 | Jurisica et al. |
| 2014/0271609 A1 | 9/2014 | Keller et al. |
| 2015/0064801 A1 | 3/2015 | Futami |

FOREIGN PATENT DOCUMENTS

| | | |
|---|---|---|
| WO | 2002034945 A2 | 5/2002 |
| WO | 2002068649 A2 | 9/2002 |
| WO | 2002094981 A2 | 11/2002 |
| WO | 2003018746 A2 | 3/2003 |
| WO | 03063689 A2 | 8/2003 |
| WO | 2004076613 A2 | 9/2004 |
| WO | 2005051990 A2 | 6/2005 |
| WO | 2005072053 A2 | 8/2005 |
| WO | 2006037993 A2 | 4/2006 |
| WO | 2006067198 A2 | 6/2006 |
| WO | 2008016356 A2 | 2/2008 |
| WO | 2008021290 A2 | 2/2008 |
| WO | 2010102262 A1 | 9/2010 |
| WO | 2011059836 A2 | 5/2011 |
| WO | 2012162468 A1 | 11/2012 |
| WO | 2013126726 A1 | 8/2013 |
| WO | 2013151668 A2 | 10/2013 |
| WO | 2013166051 A1 | 11/2013 |
| WO | 2013178635 A1 | 12/2013 |

OTHER PUBLICATIONS

Shastri, et al. J. Immunol. 1995; 155:4339-4346.
Englehard (Curr Opin Immunol. Feb. 1994;6(1):13-23.
Rammensee, et al. (Immunogenetics. 1995; 41:178-228).
Berge et al., "Pharmaceutical Salts", J. Pharm. Sci. (1977) 66(1):1-19.
Yoshii et al. (Cancer Sci. 2009, 100(5): 821-827).
Yu et al. (FASEB J., 2007, 21:851-854, abstract).
Healthline, 2015.
Ezzell (J. NIH Res. 1995, 7:46).
Spitler (Cancer Biotherapy 1995, 10:1-3).
Boon (Adv. Can. Res. 1992, 58:177-210).
Michael A. Rieger, Dissertation, "CYP4Z1 und CYP4Z2P: Identifizierung neuer Mitglieder der humanen Cytochrom P450 Familie mit praferentieller Expression in Brustdrusengewebe und Mammakarzimom" ("CYP4Z1 and CYP4Z2P: Identification of new members of the human cytochrome P450 family with preferential expression in mammary gland tissue and breast carcinoma"), Germany, Jun. 30, 2004.
Reay et al. (J. Immunol., 152: 3946-3957, 1994).
Krieger et al. (J. Immonl. 146: 2331-2340, 1991).
Khan, et al., "The Structure and Stability of an HLA-A *0201/Octameric Tax Peptide Complex with an Empty Conserved Peptide-N-Terminal Binding Site," J. Immunology (2000) 6398-6405.
Lax, Rodney, "The Future of Peptide Development in the Pharmaceutical Industry," PharManufacturing the International Peptide Review 10-15.
Uhlig, et al., "The emergence of peptides in the pharmaceutical business: From exploration to exploitation," EuPA Open Proteomics (2014) vol. 4: 58-69.
Guo, et al., "Comparison of the P2 specificity pocket in three human histocompatibility antigens: HLA-A*6801, HLA-A*0201, and HLA-B*2705," Proc. Natl. Acad. Sci. USA (1993) Vik, 90: 8053-8057.
Hillig, et al., "High-resolution Structure of HLA-A*0201 in Complex with a Tumour-specific Antigenic Peptide Encoded by the MAGE-A4 Gene," J. Mol. Biol. (2001) vol. 310: 1167-1176.
Martinez-Hackert, et al., "Structural Basis for Degenerate Recognition of Natural HIV Peptide Variants by Cytotoxic Lymphocytes," J. Biol. Chem. (2006) vol. 281, No. 29: 20205-20212.
Reiser, et al., "Analysis of Relationships between Peptide/MHC Structural Features and Naive T Cell Frequency in Humans," J. Immunology (2014) vol. 193: 5816-5826.
Wucherpfennig, Kai W., "The First Structures of T Cell Receptors Bound to Peptide-MCH," J. Immunology (2010) vol. 185: 6391-6393.

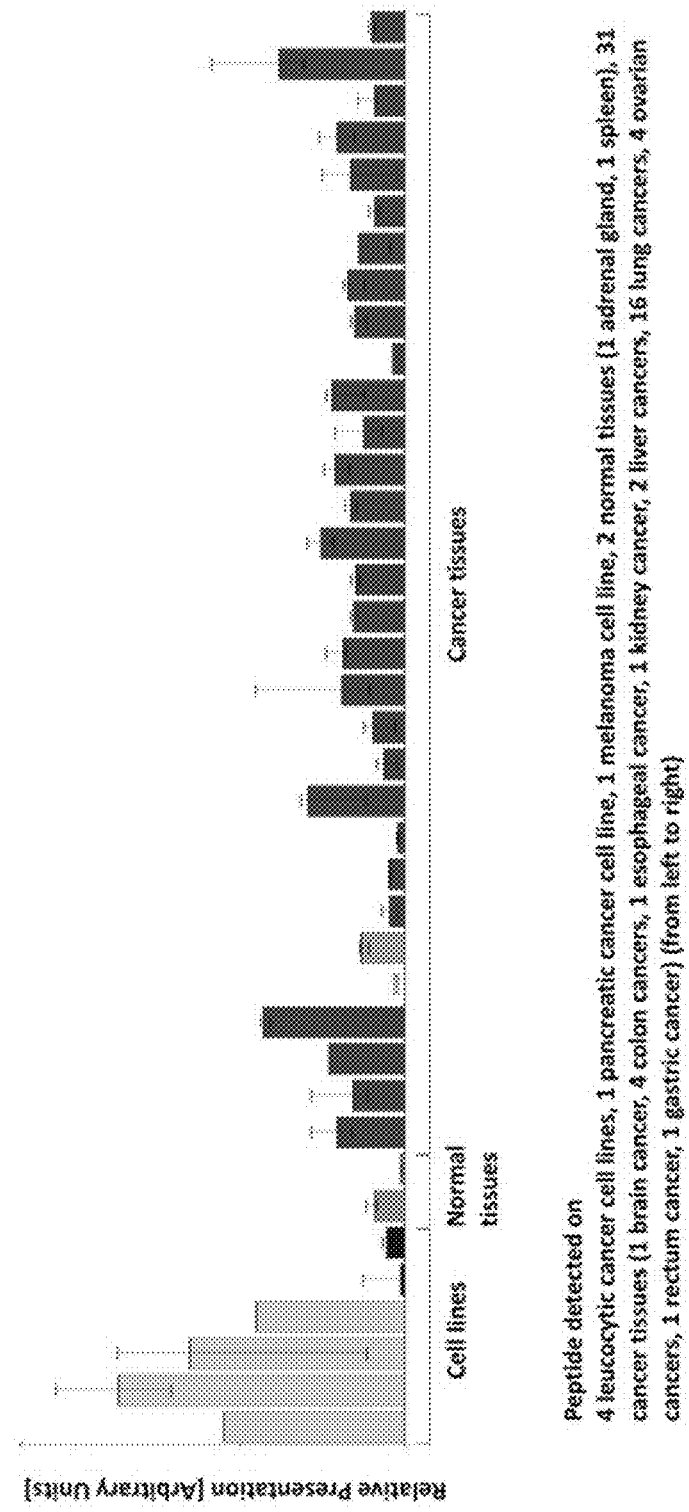

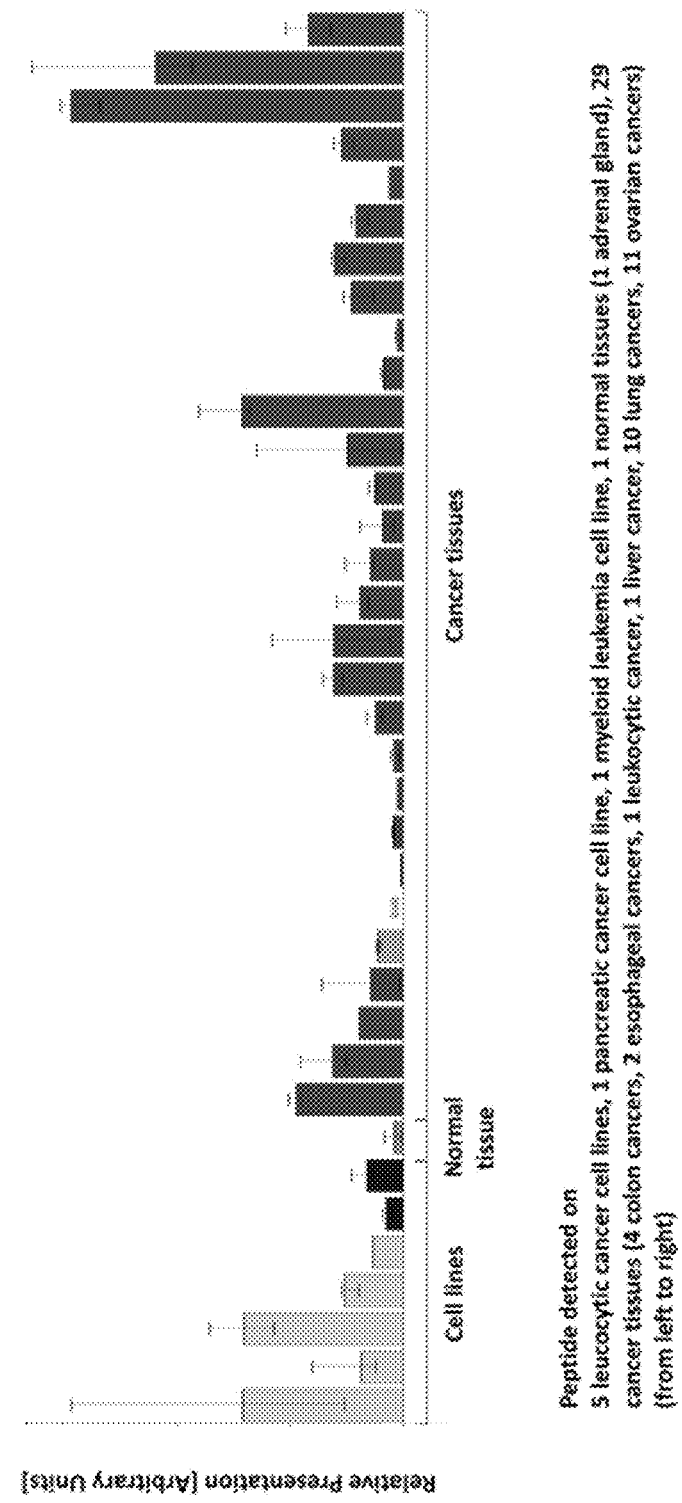
Figure 1B - Peptide: QLIEKNWLL (A*02:01)

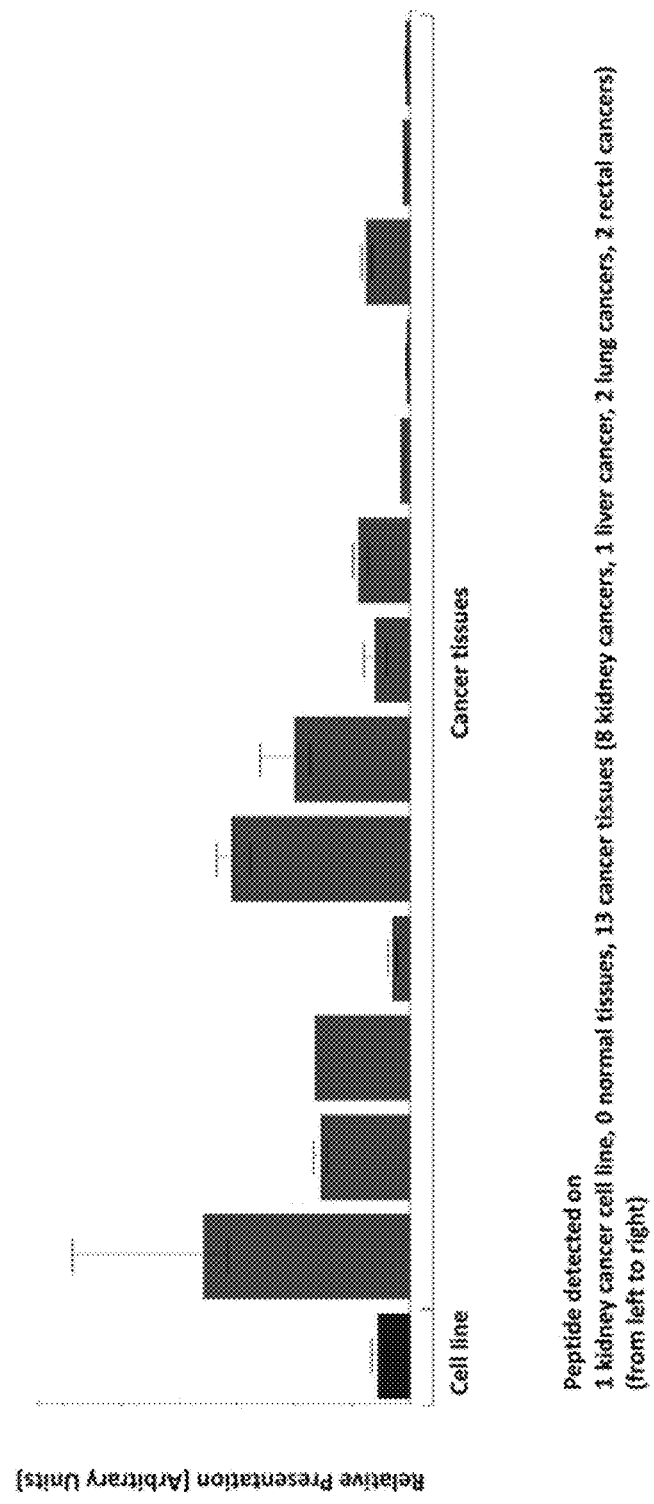

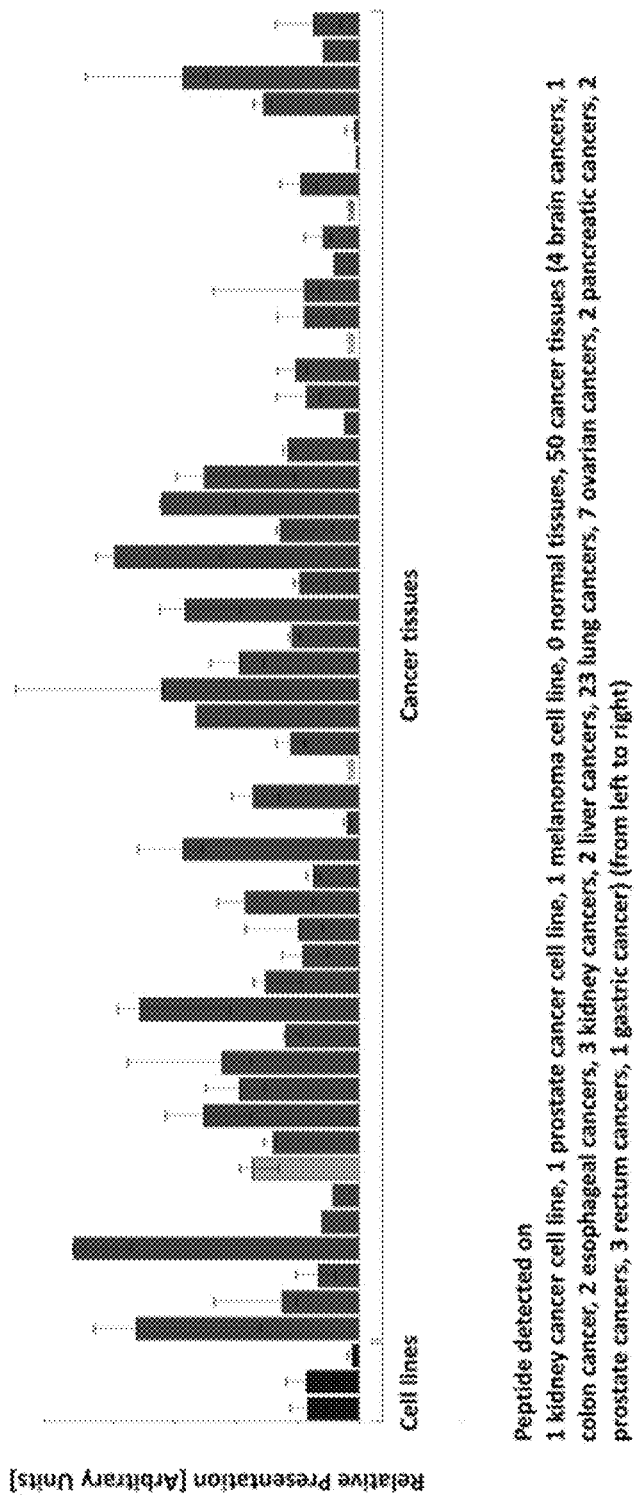

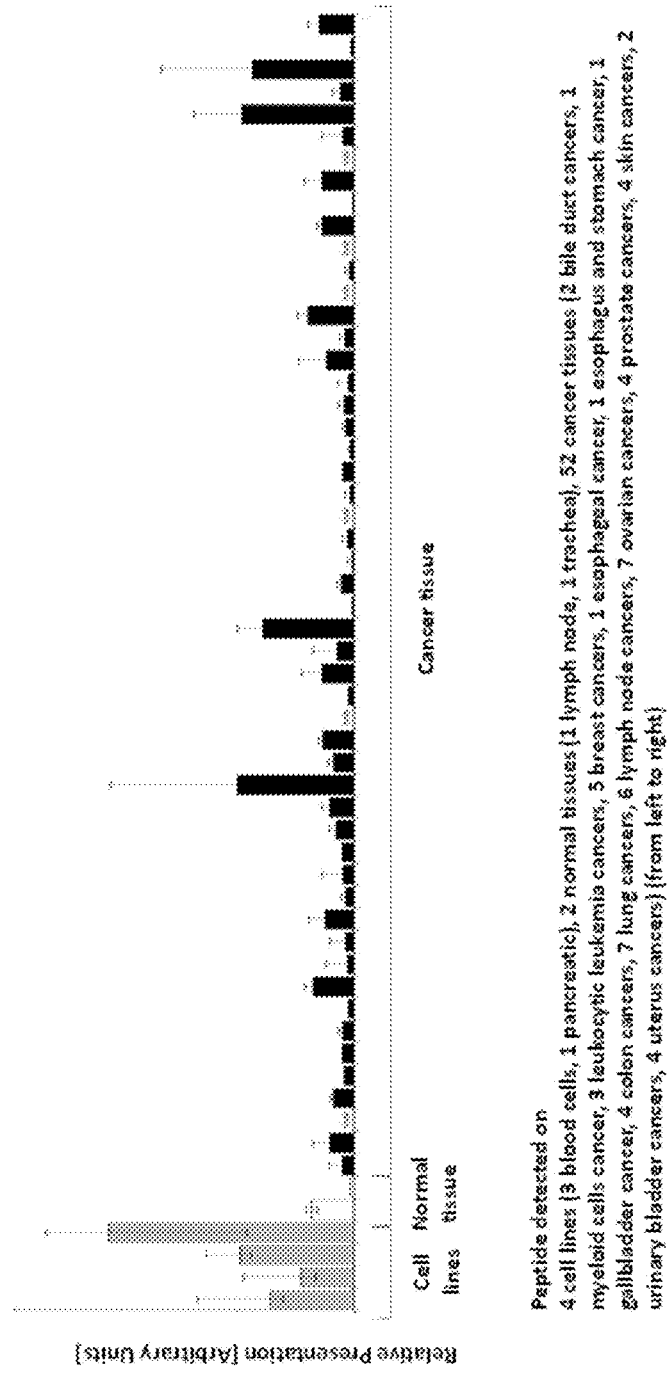

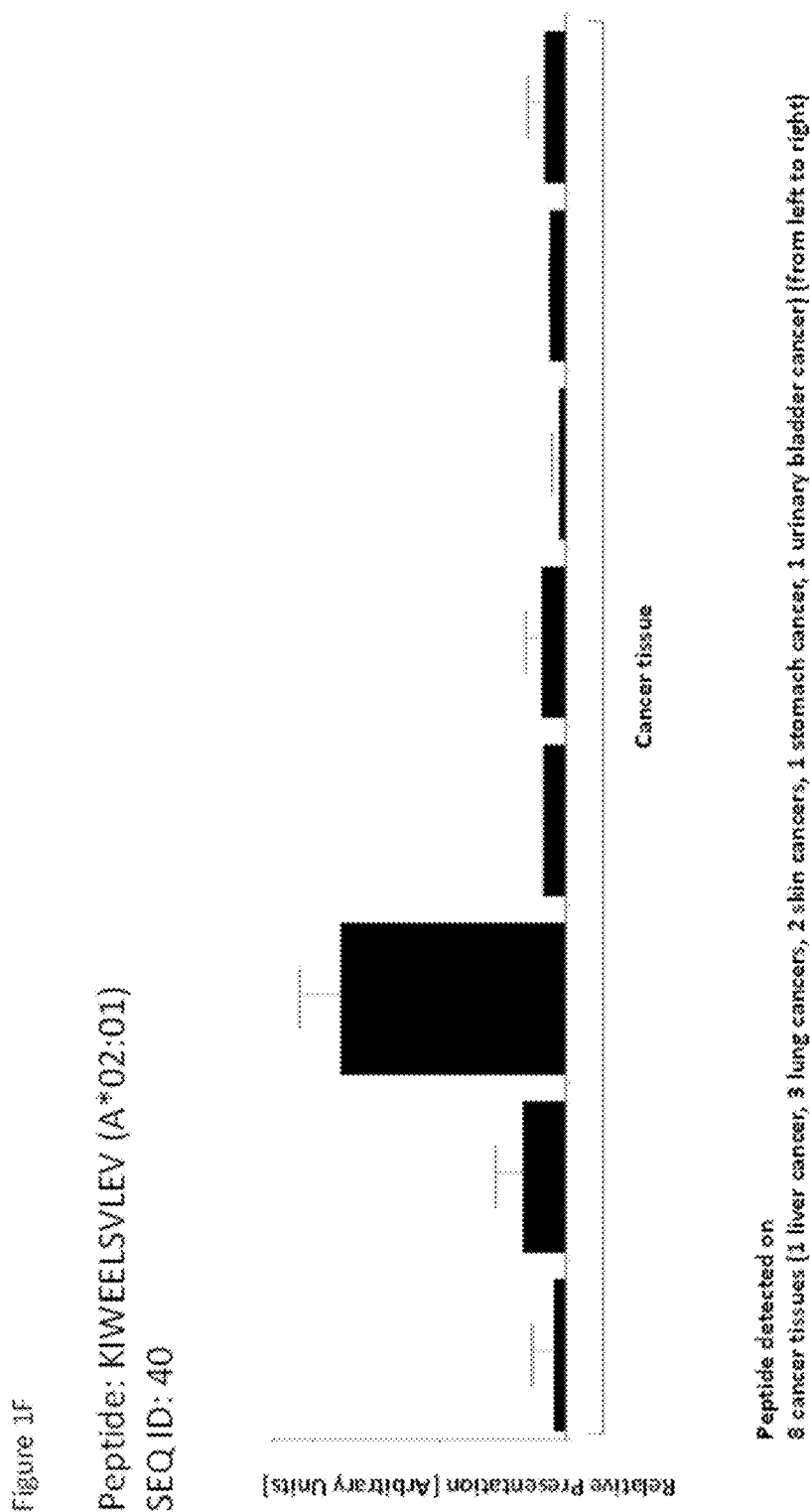

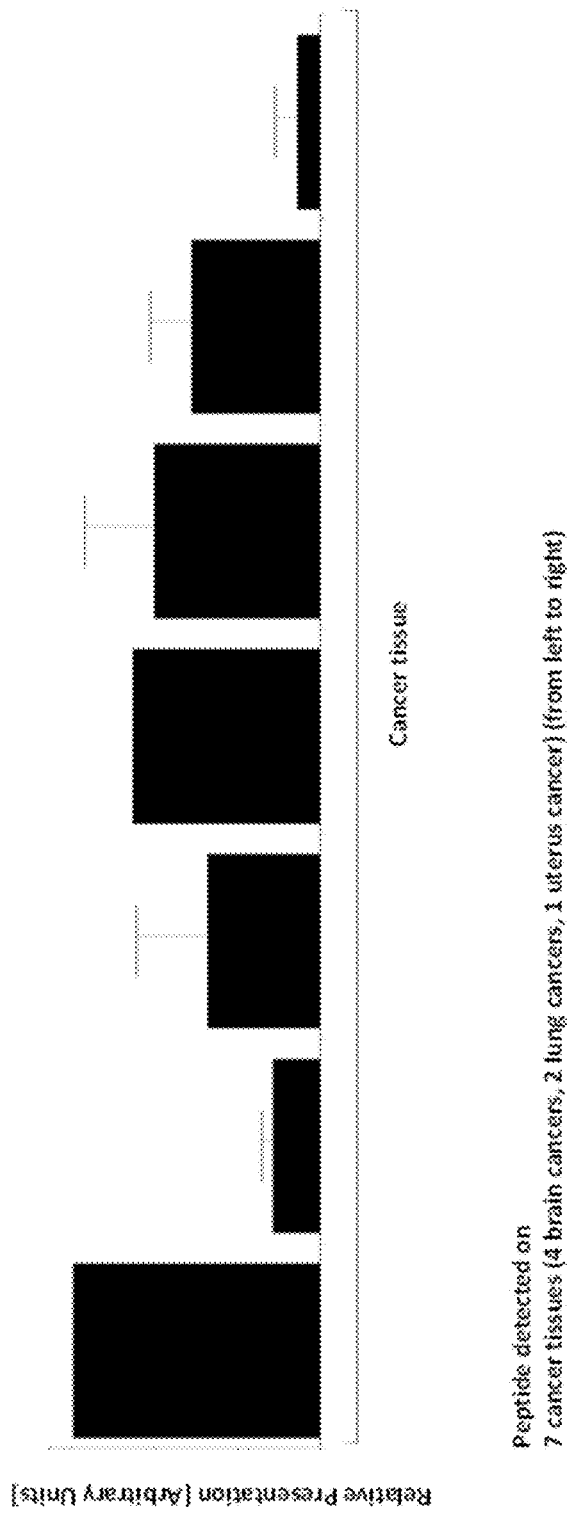

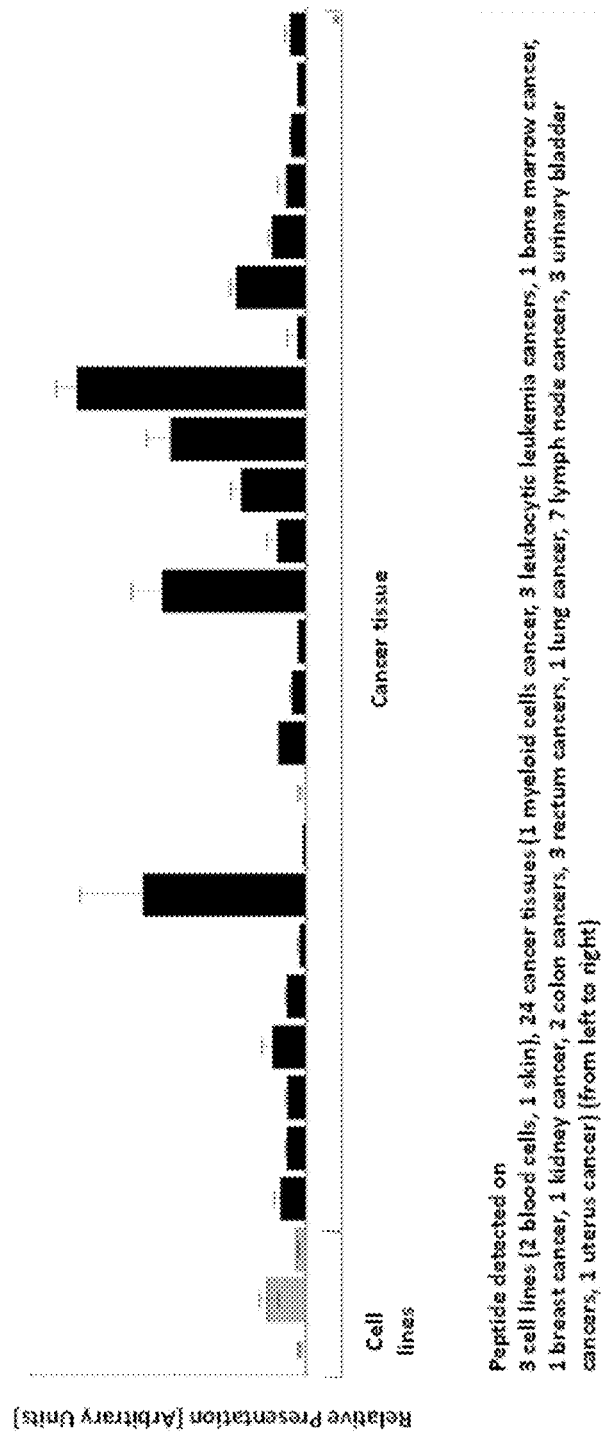

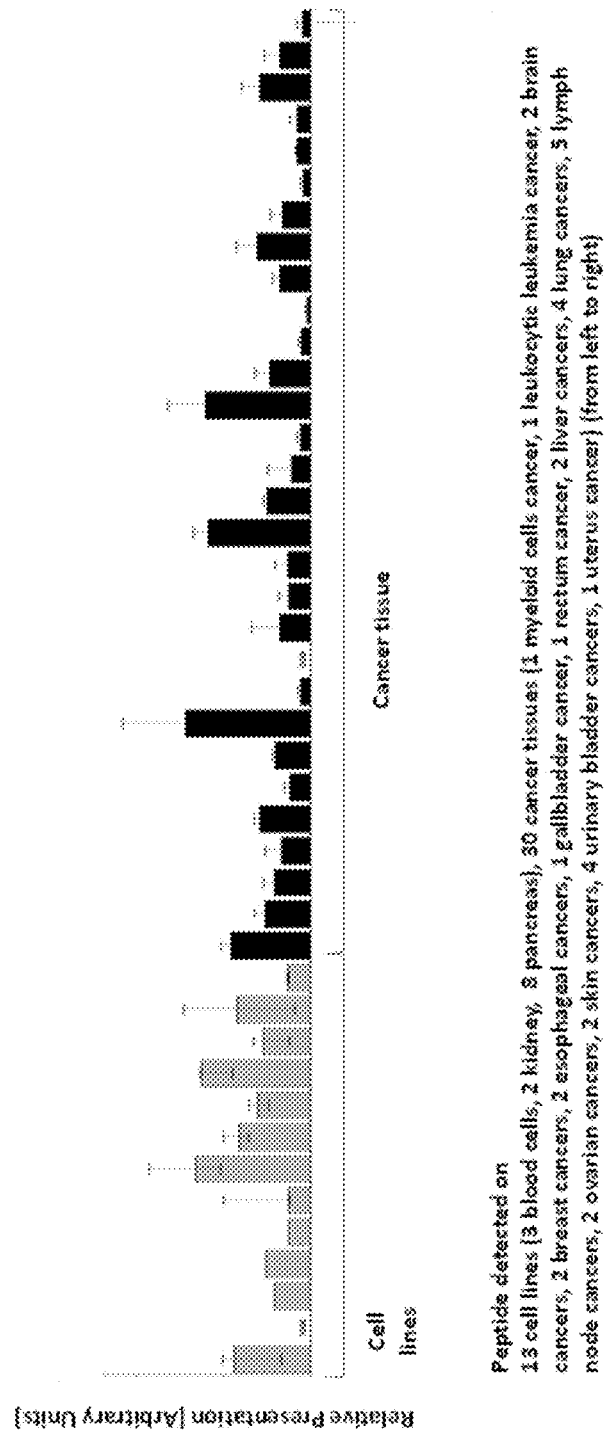

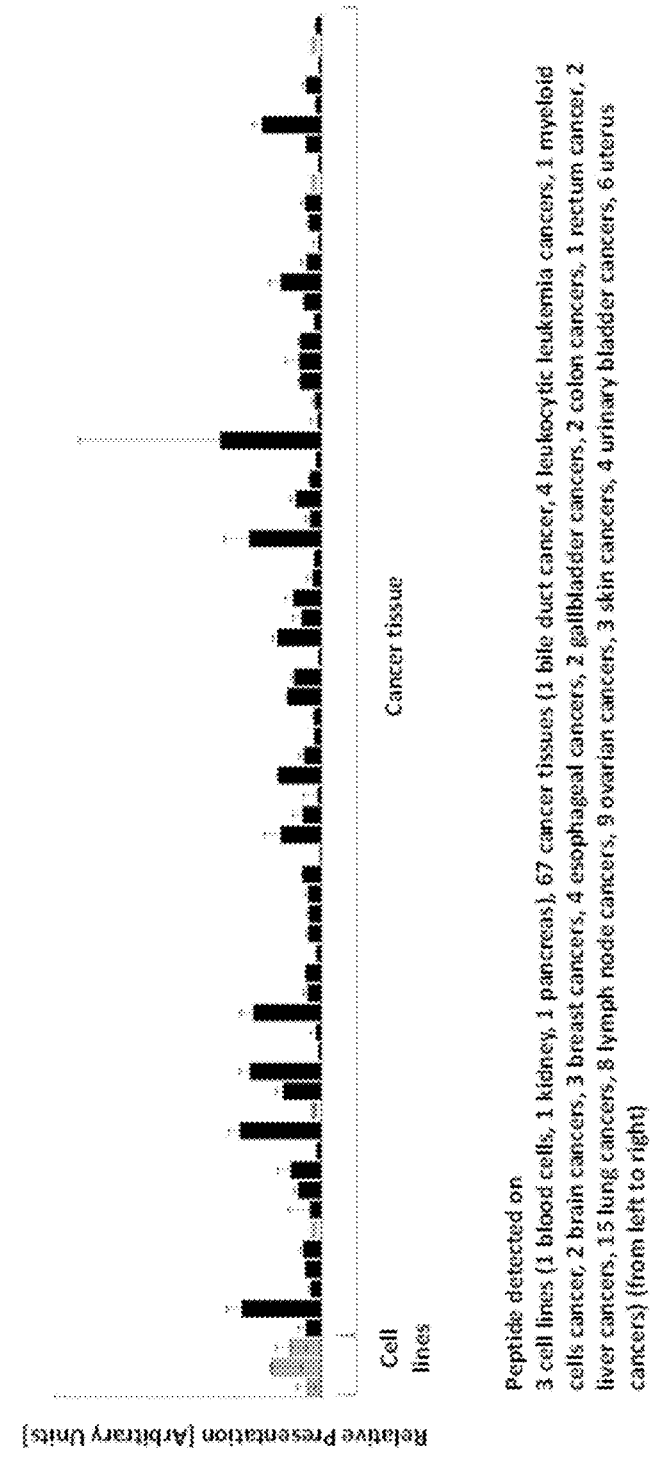

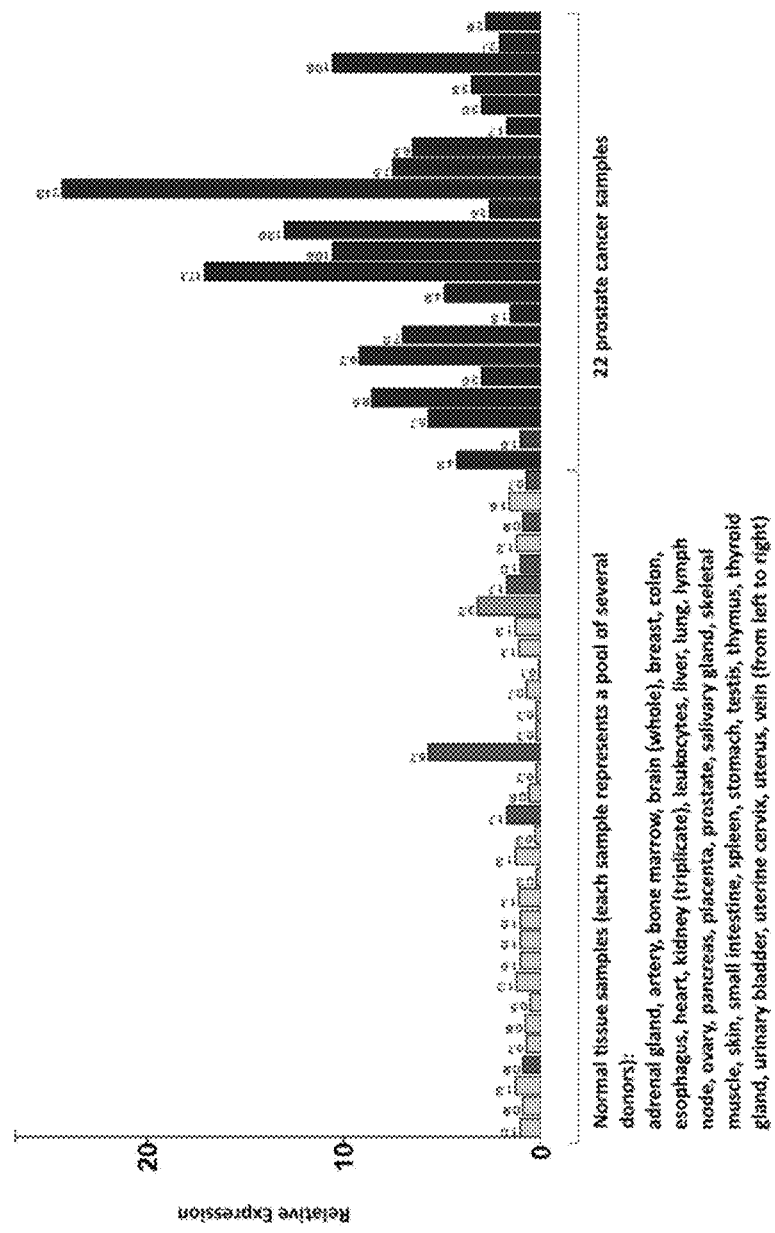
Figure 2A Gene: PRIM2

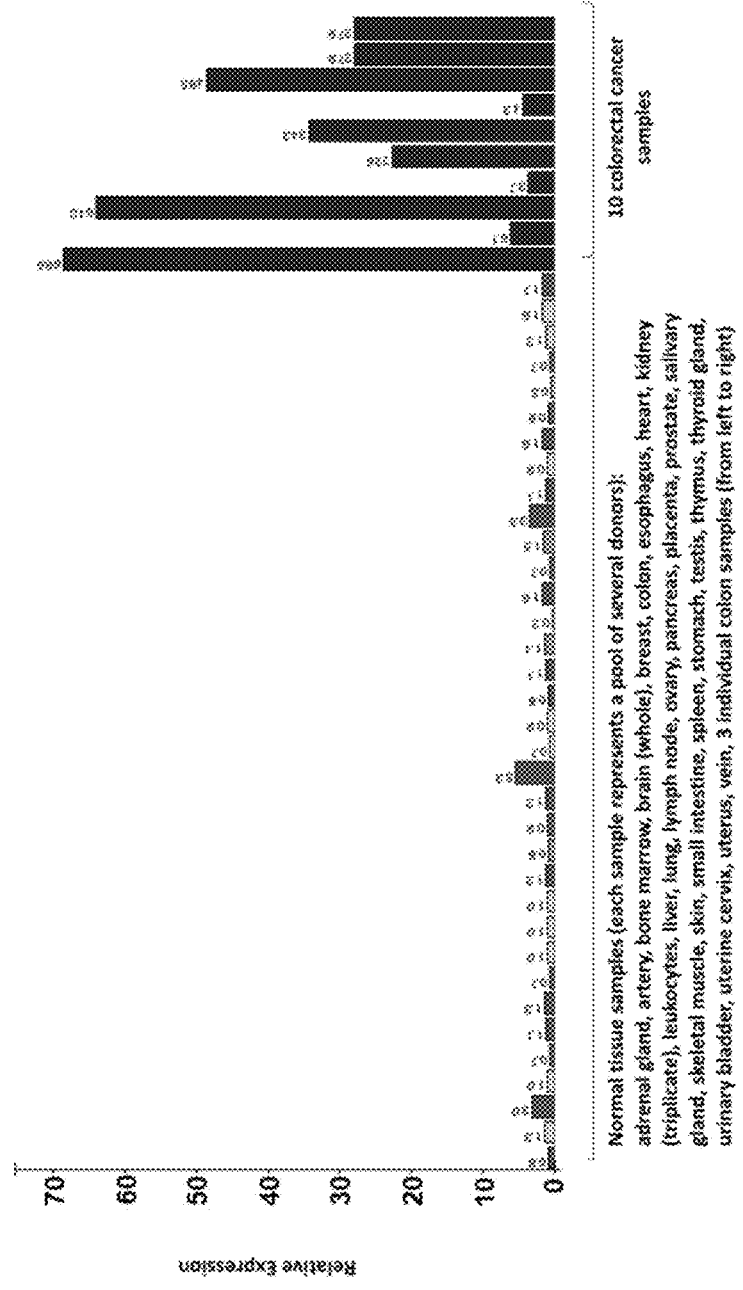
Figure 2B Gene: CHEK1

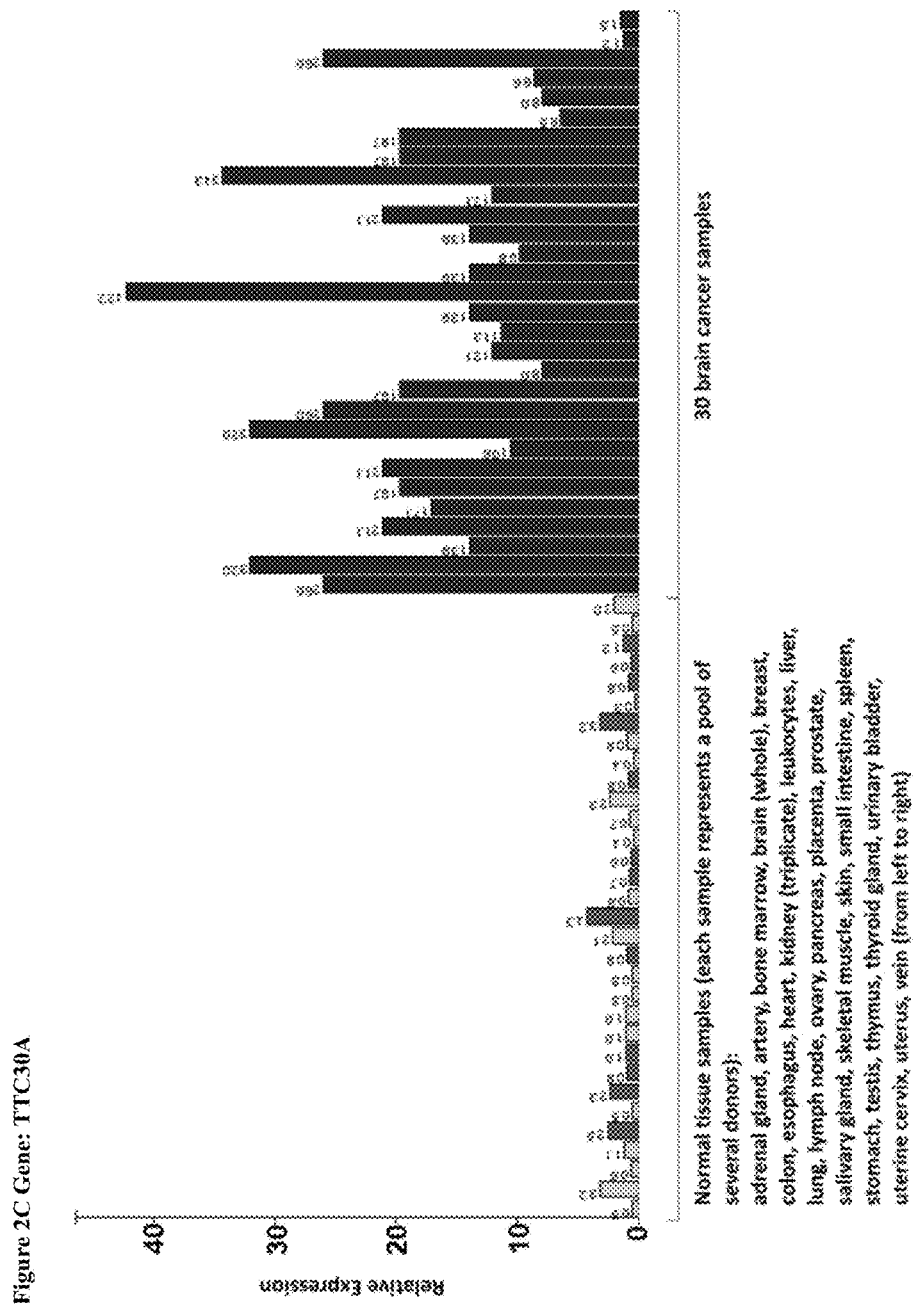

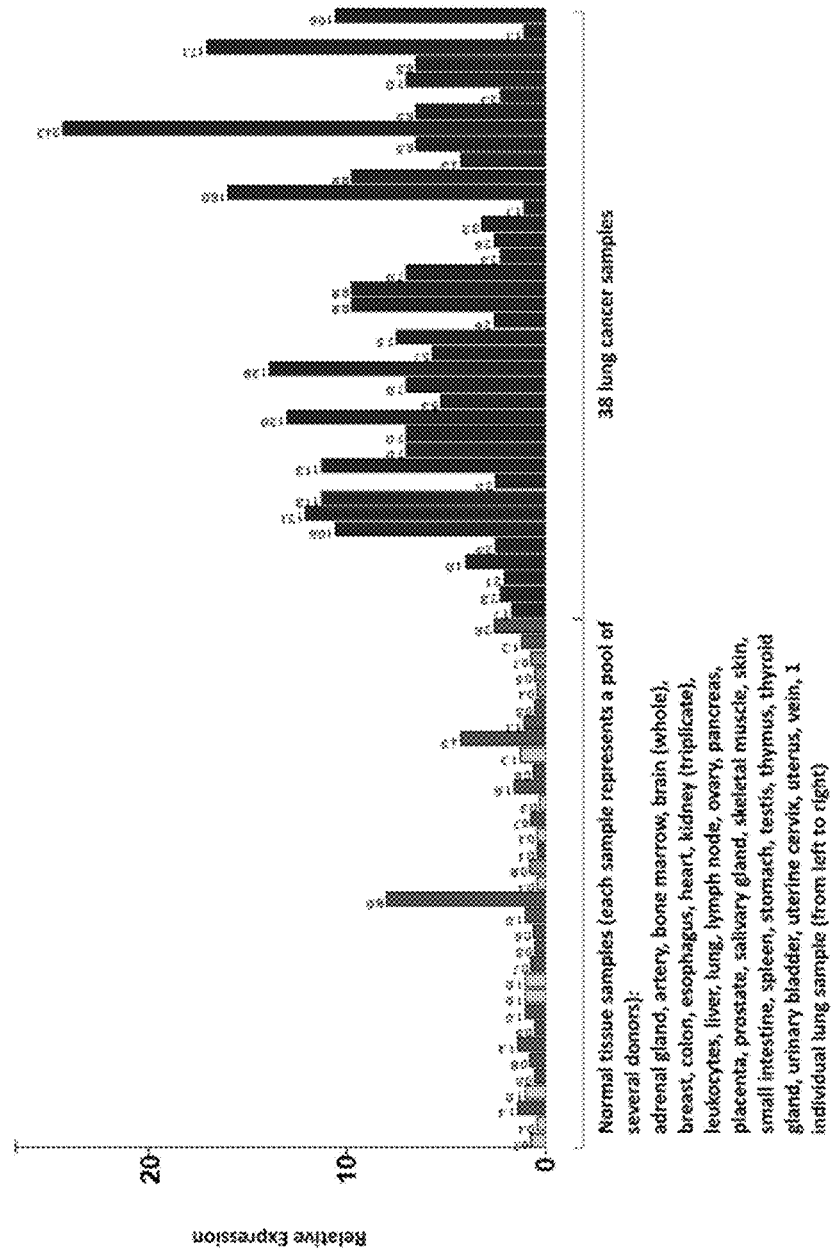

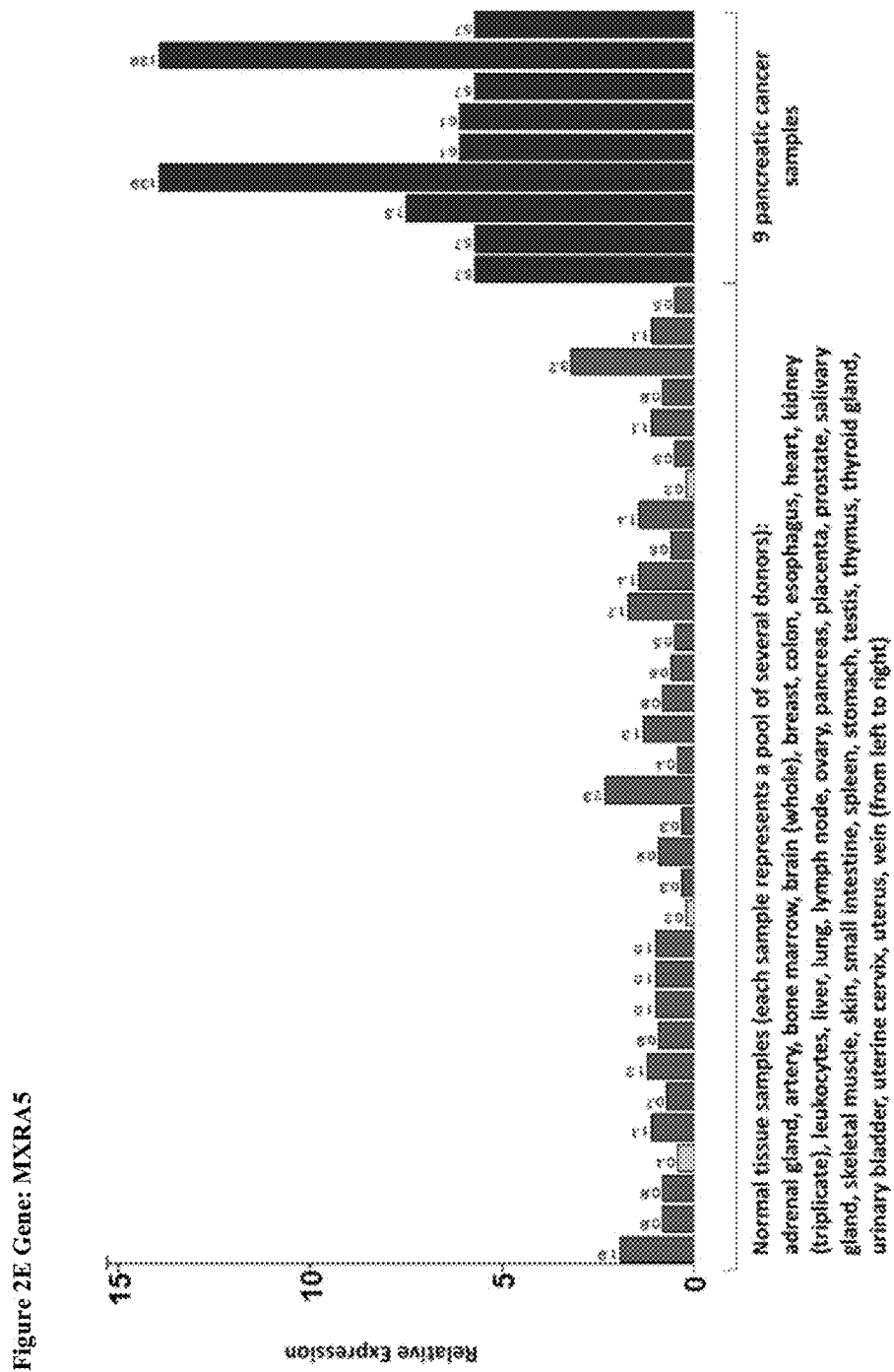
Figure 2E Gene: MXRA5

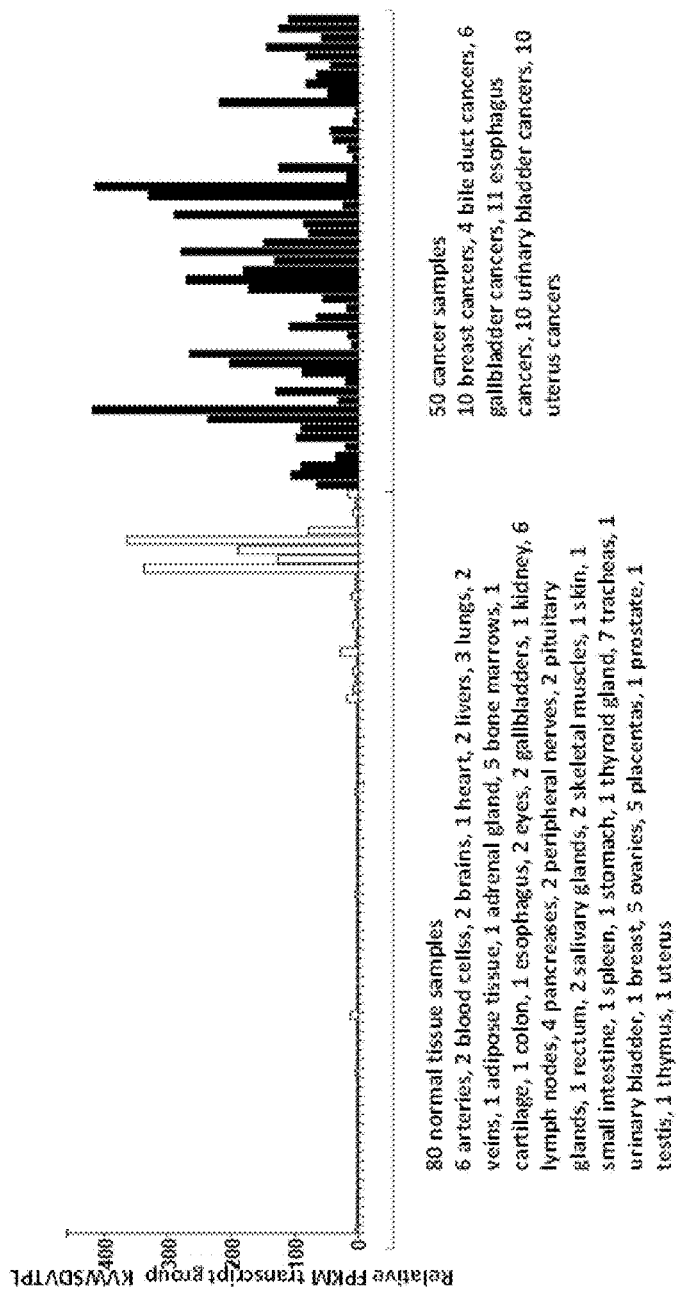

Gene: HORMAD1
Peptide: VIFEGEPMYL
SEQ ID: 168

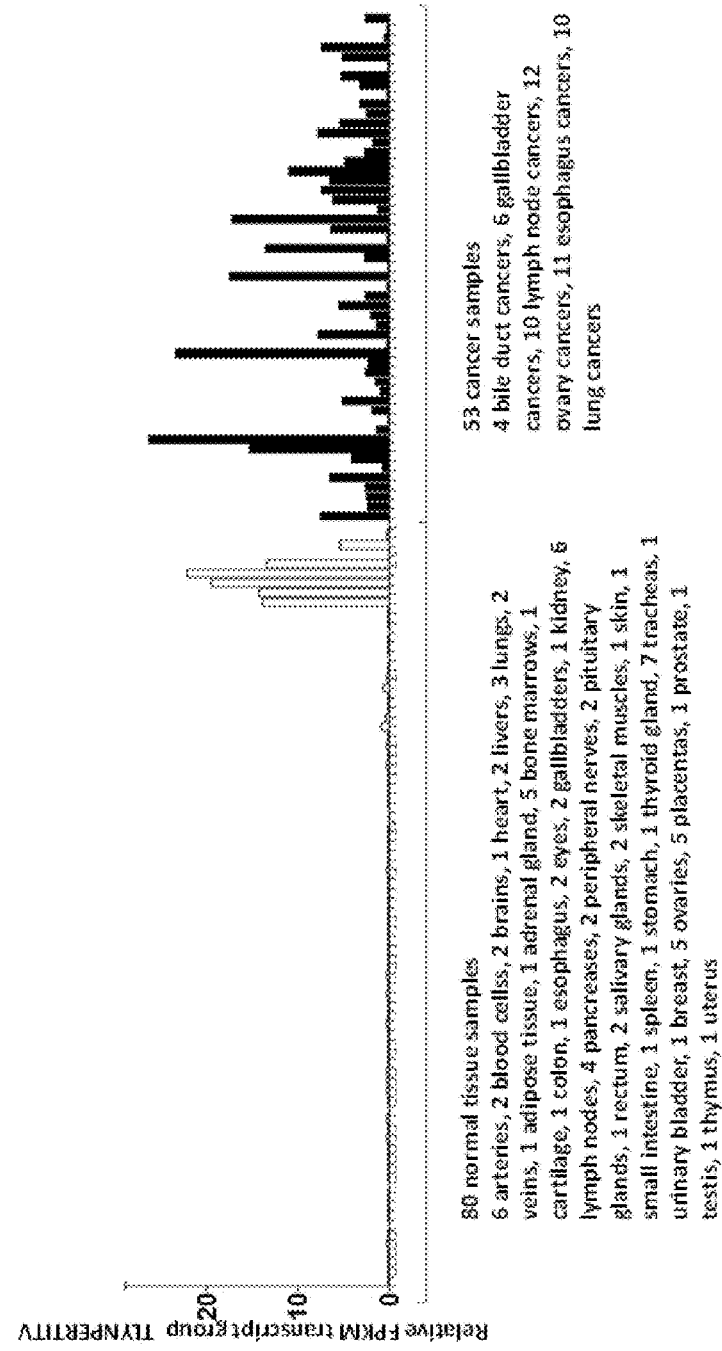

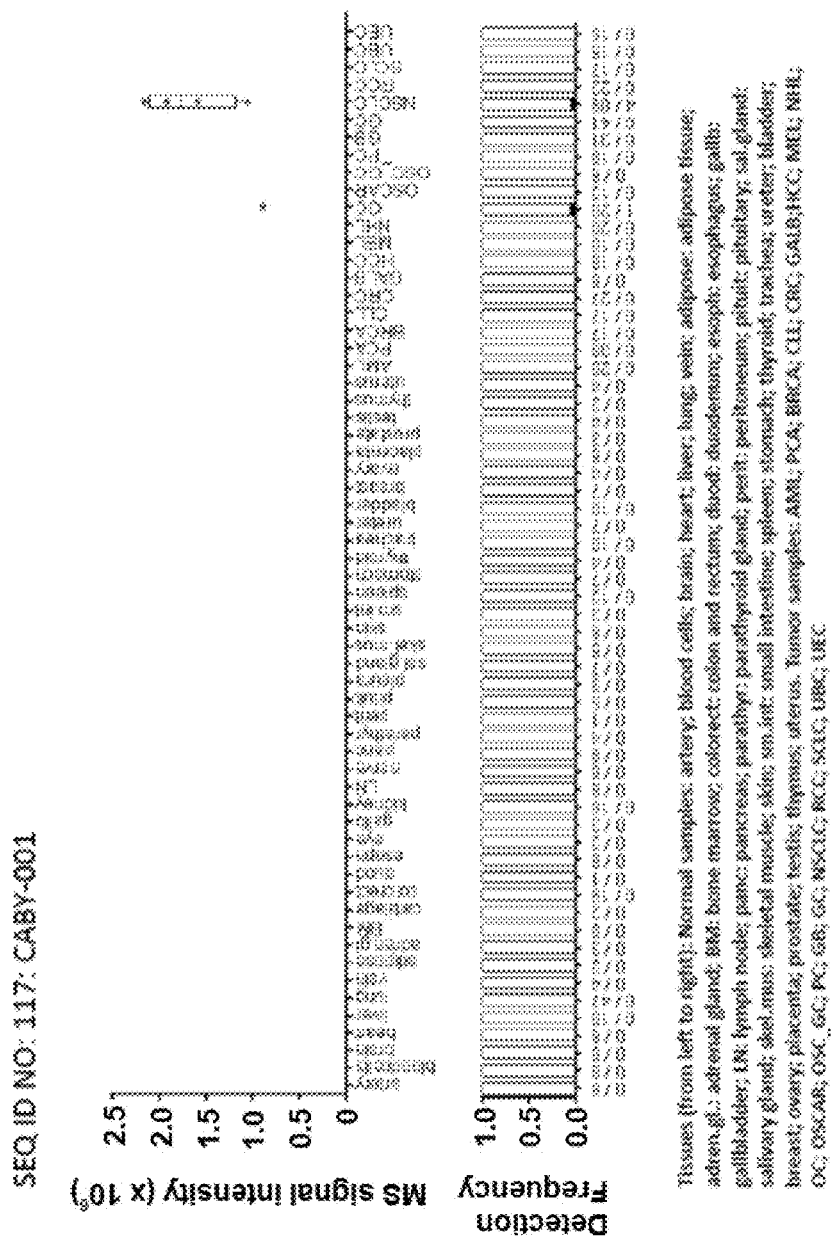

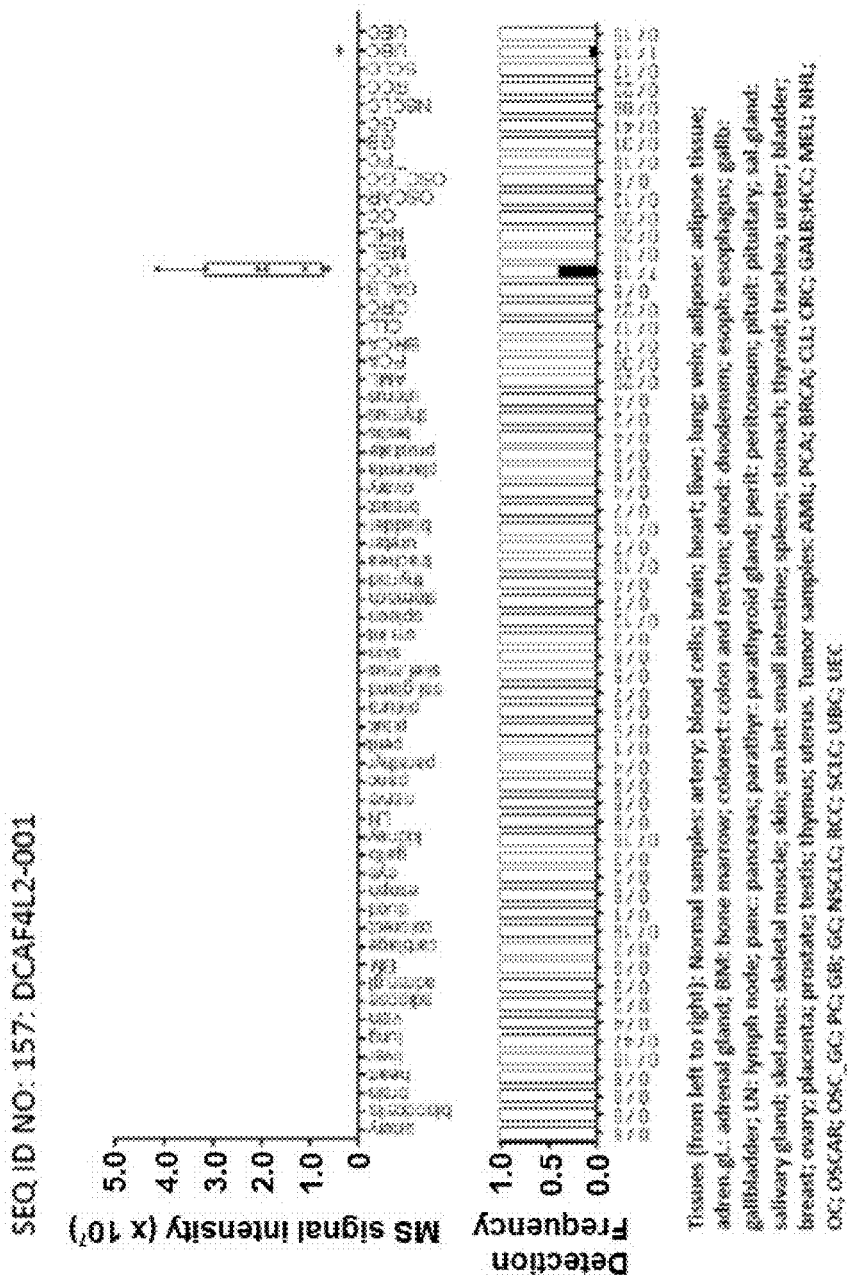

SEQ ID NO: 11: HAVCR1-001

Figure 5B

SEQ ID NO: 14: MMP1-003

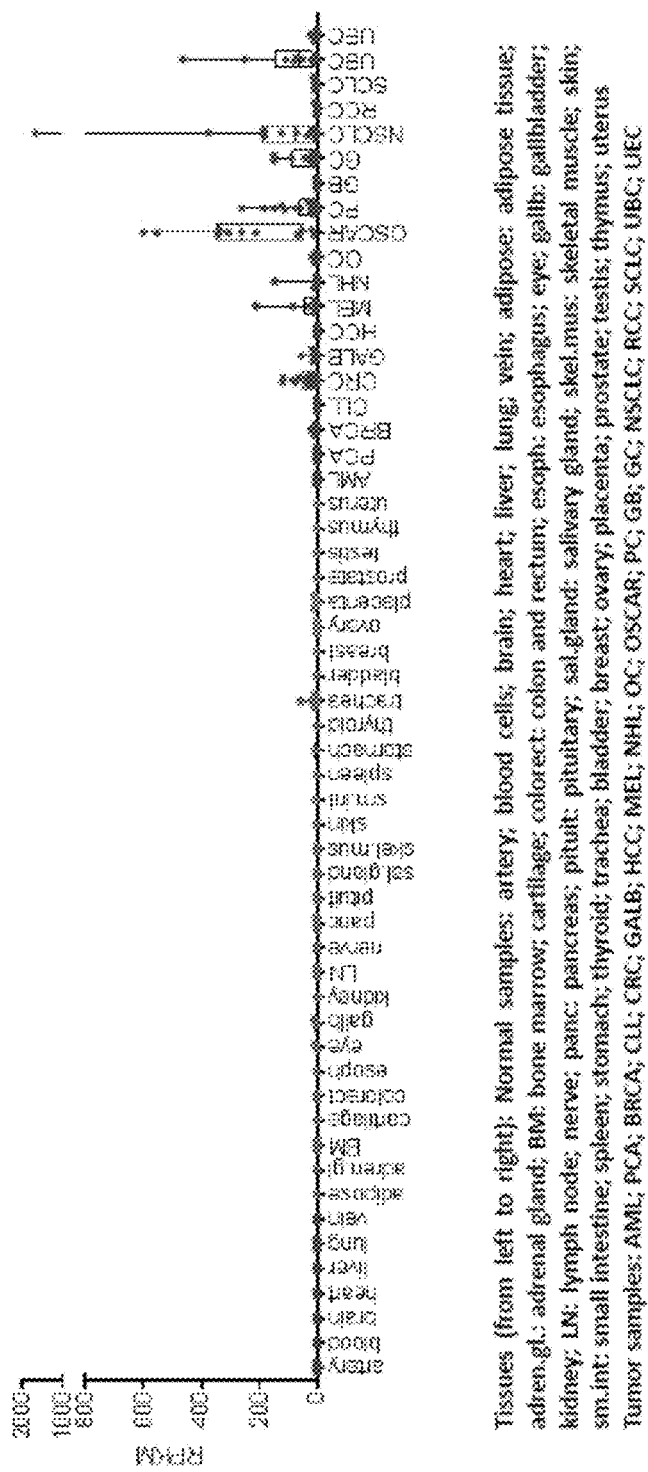

Tissues (from left to right): Normal samples: artery; blood cells; brain; heart; liver; lung; vein; adipose: adipose tissue; adren.gl.: adrenal gland; BM: bone marrow; cartilage; colorect: colon and rectum; esoph: esophagus; eye; gallb: gallbladder; kidney; LN: lymph node; nerve; panc: pancreas; pituit: pituitary; sal.gland: salivary gland; skel.mus.: skeletal muscle; skin; sm.int: small intestine; spleen; stomach; thyroid; trachea; bladder; breast; ovary; placenta; prostate; testis; thymus; uterus
Tumor samples: AML; PCA; BRCA; CLL; CRC; GALB; HCC; MEL; NHL; OC; OSCAR; PC; GB; GC; NSCLC; RCC; SCLC; UBC; UEC Figure 5C
SEQ ID NO: 21: COL6A3-015

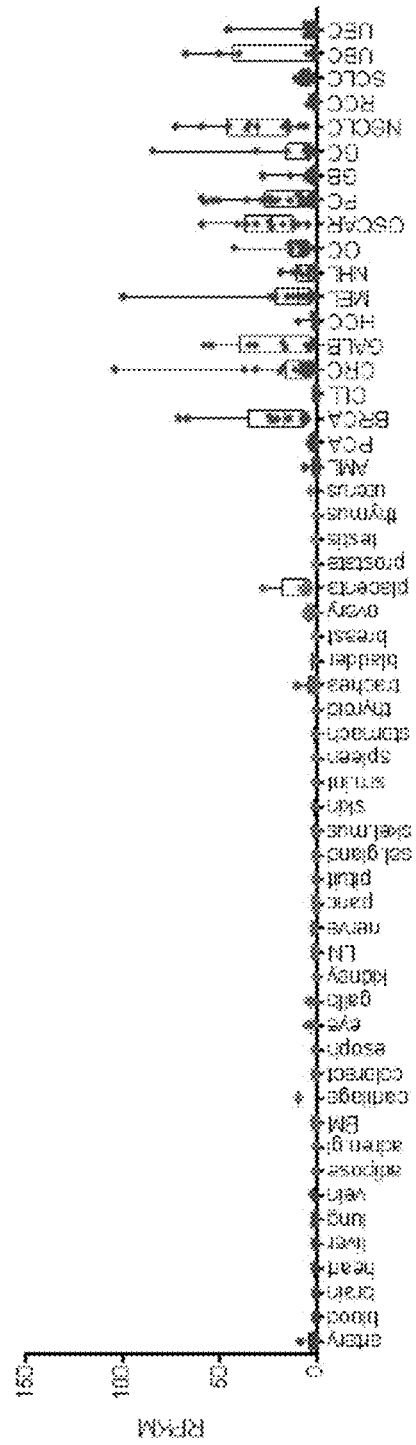

Tissues (from left to right): Normal samples: artery; blood cells; brain; heart; liver; lung; vein; adipose tissue; adren.gl.: adrenal gland; BM: bone marrow; cartilage; colorect: colon and rectum; esoph: esophagus; eye; galb: gallbladder; kidney; LN: lymph node; nerve; panc: pancreas; pituit: pituitary; sal.gland: salivary gland; skel.mus.: skeletal muscle; skin; sm.int: small intestine; spleen; stomach; thyroid; trachea; bladder; breast; ovary; placenta; prostate; testis; thymus; uterus
Tumor samples: AML; PCA; BRCA; CLL; CRC; GALB; HCC; MEL; NHL; OC; OSCAR; PC; GB; GC; NSCLC; RCC; SCLC; UBC; UEC

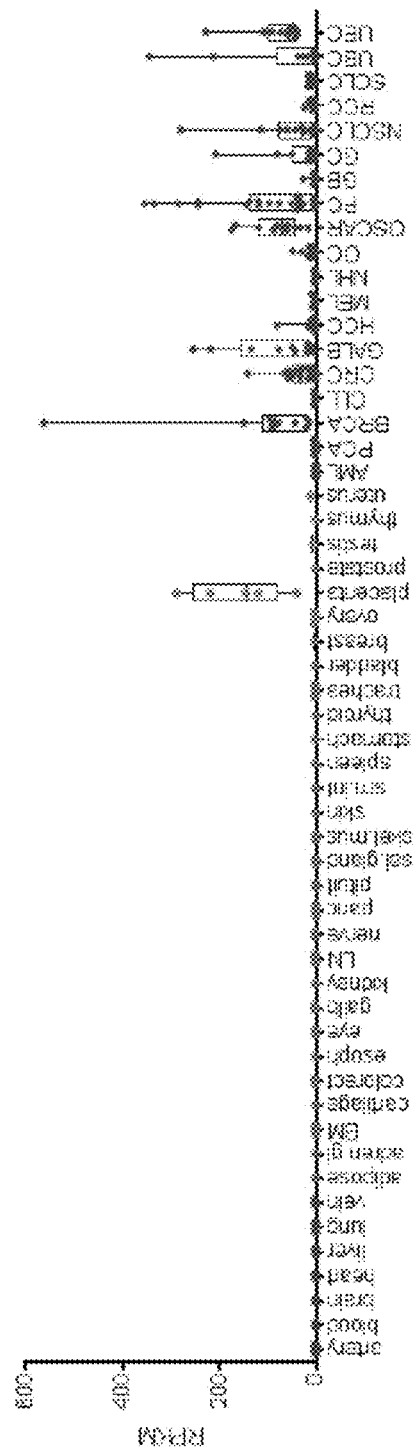

Figure 5D
SEQ ID NO: 24; MMP-002

Tissues (from left to right): Normal samples: artery; blood cells; brain; heart; liver; lung; vein; adipose: adipose tissue; adren.gl: adrenal gland; BM: bone marrow; cartilage; colorect: colon and rectum; esoph: esophagus; eye; galb: gallbladder; kidney; LN: lymph node; nerve; panc: pancreas; pituit: pituitary; sal.gland: salivary gland; skel.mus: skeletal muscle; skin; sm.int: small intestine; spleen; stomach; thyroid; trachea; bladder; breast; ovary; placenta; prostate; testis; thymus; uterus
Tumor samples: AML; PCA; BRCA; CLL; CRC; GALB; HCC; MEL; NHL; OC; OSCAR; PC; GB; GC; NSCLC; RCC; SCLC; UBC; UEC

Figure 5E

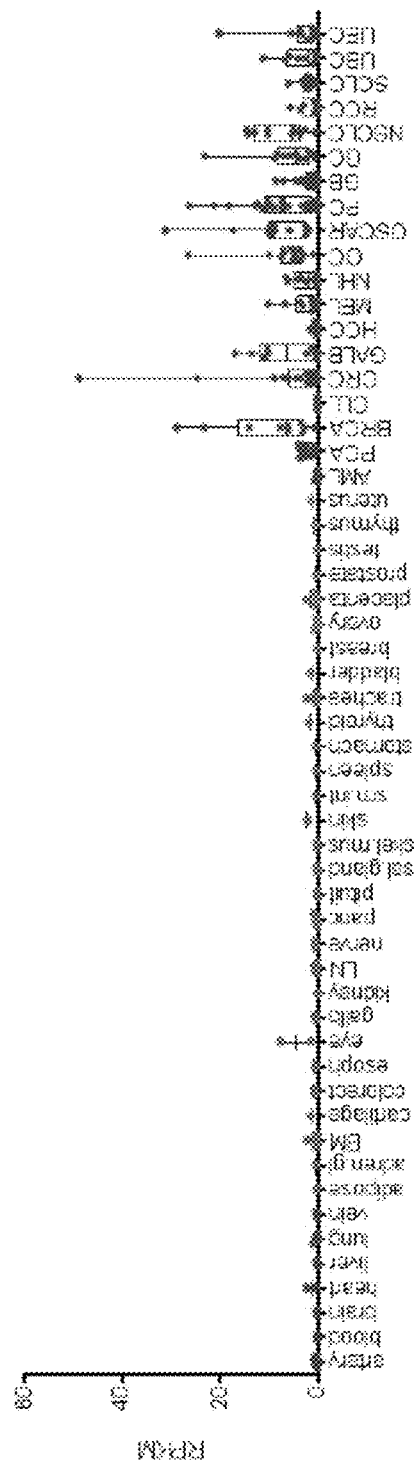

SEQ ID NO: 25: MXRA5-003

Tissues (from left to right):Normal samples: artery; blood cells; brain; heart; liver; lung; vein; adipose; adipose tissue; adren.gl.: adrenal gland; BM: bone marrow; cartilage; coloret: colon and rectum; esoph: esophagus; eye; galb: gallbladder; kidney; LN: lymph node; nerve; panc: pancreas; pituit: pituitary; sal.gland: salivary gland; skel.musc: skeletal muscle; skin; sm.int: small intestine; spleen; stomach; thyroid; trachea; bladder; breast; ovary; placenta; prostate; testis; thymus; uterus
Tumor samples: AML; PCA; BRCA; CLL; CRC; GAIB: HCC; MEL; NHL; OC; OSCAR; PC; GB; GC; NSCLC; RCC; SCLC; UBC; UEC Figure 5F
SEQ ID NO: 40: MAGEA3-003

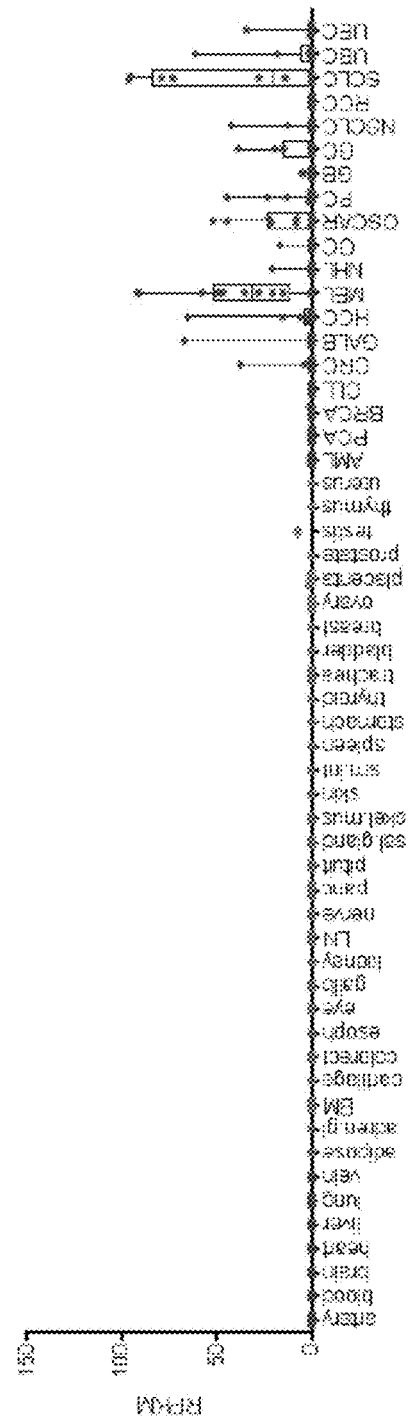

Tissues (from left to right):Normal samples: artery; blood cells; brain; heart; liver; lung; vein; adipose; adipose tissue; adren.gl.: adrenal gland; BM: bone marrow; cartilage; colorect: colon and rectum; esoph: esophagus; eye; galbr: gallbladder; kidney; LN: lymph node; nerve; panc: pancreas; pituit: pituitary; sal.gland: salivary gland; skel.mus.: skeletal muscle; skin; sm.int: small intestine; spleen; stomach; thyroid; trachea; bladder; breast; ovary; placenta; prostate; testis; thymus; uterus
Tumor samples: AML; PCA; BRCA; CLL; CRC; GALB; HCC; MEL; NHL; OC; OSCAR; PC; GB; GC; NSCLC; RCC; SCLC; UBC; UEC

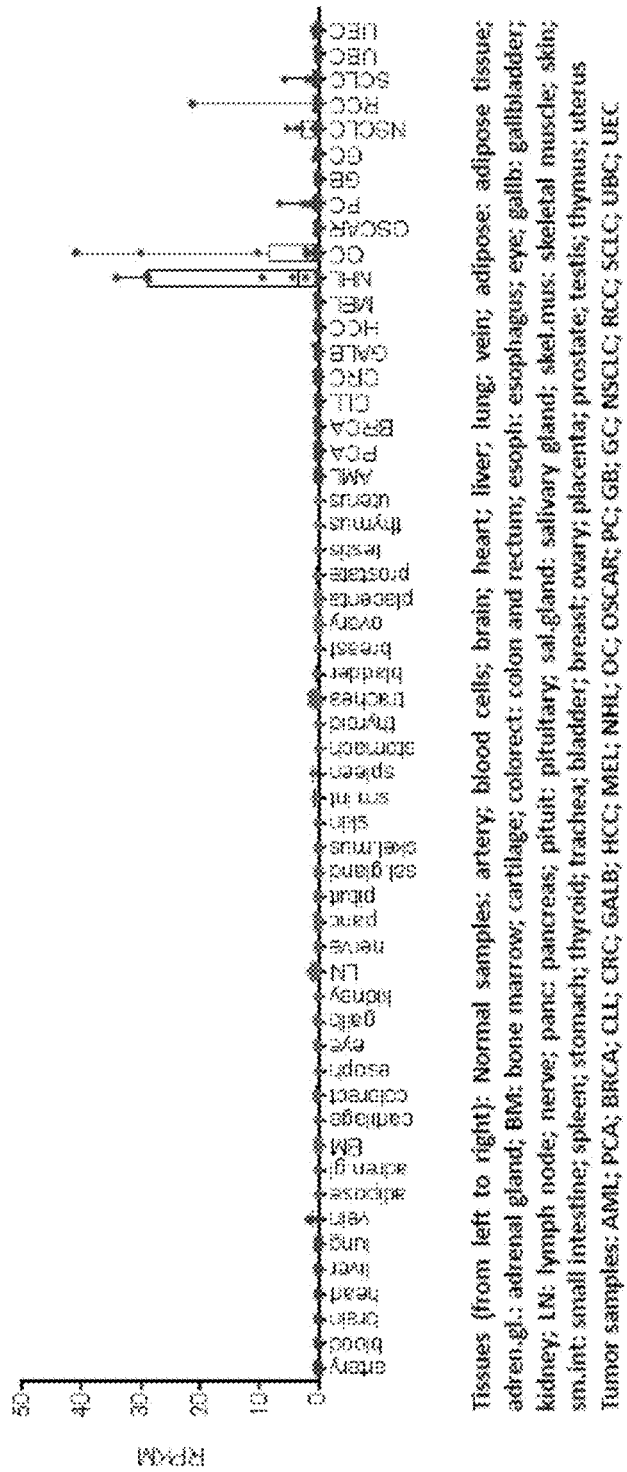

Figure 5H
SEQ ID NO: 89: HTR3A-001

Tissues (from left to right): Normal samples: artery; blood; blood cells; brain; heart; liver; lung; vein; adipose; adipose tissue; adren.gl.: adrenal gland; BM: bone marrow; cartilage; colorect: colon and rectum; esoph: esophagus; eye; gallb: gallbladder; kidney; LN: lymph node; nerve; panc: pancreas; pituit: pituitary; sal.gland: salivary gland; skel.mus: skeletal muscle; skin; sm.int: small intestine; spleen; stomach; thyroid; trachea; bladder; breast; ovary; placenta; prostate; testis; thymus; uterus. Tumor samples: AML; PCA; BRCA; CLL; CRC; GALB; HCC; MEL; NHL; OC; OSCAR; PC; GB; GC; NSCLC; RCC; SCLC; UBC; UEC

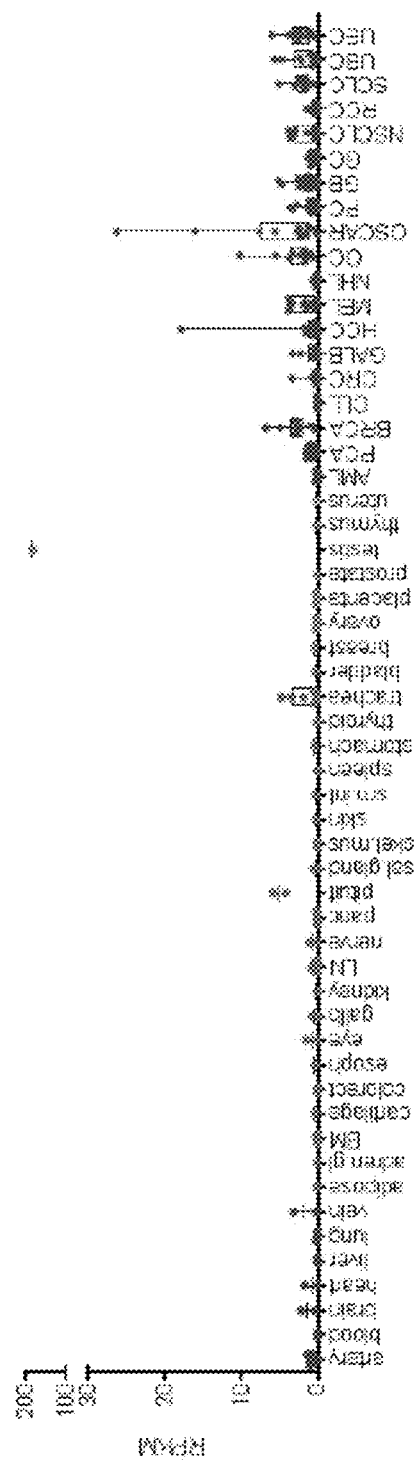

Figure 5I
SEQ ID NO: 117: CABY-001

Tissues (from left to right): Normal samples: artery; blood cells; brain; heart; liver; lung; vein; adipose; adipose tissue; adren.gl.: adrenal gland; BM: bone marrow; cartilage; colorect: colon and rectum; esoph: esophagus; eye; galb: gallbladder; kidney; LN: lymph node; nerve; panc: pancreas; pituit: pituitary; sal.gland: salivary gland; skel.mus: skeletal muscle; skin; sm.int: small intestine; spleen; stomach; thyroid; trachea; bladder; breast; ovary; placenta; prostate; testis; thymus; uterus
Tumor samples: AML; PCA; BRCA; CLL; CRC; GALB; HCC; MEL; NHL; OC; OSCAR; PC; GB; GC; NSCLC; RCC; SCLC; UBC; UEC

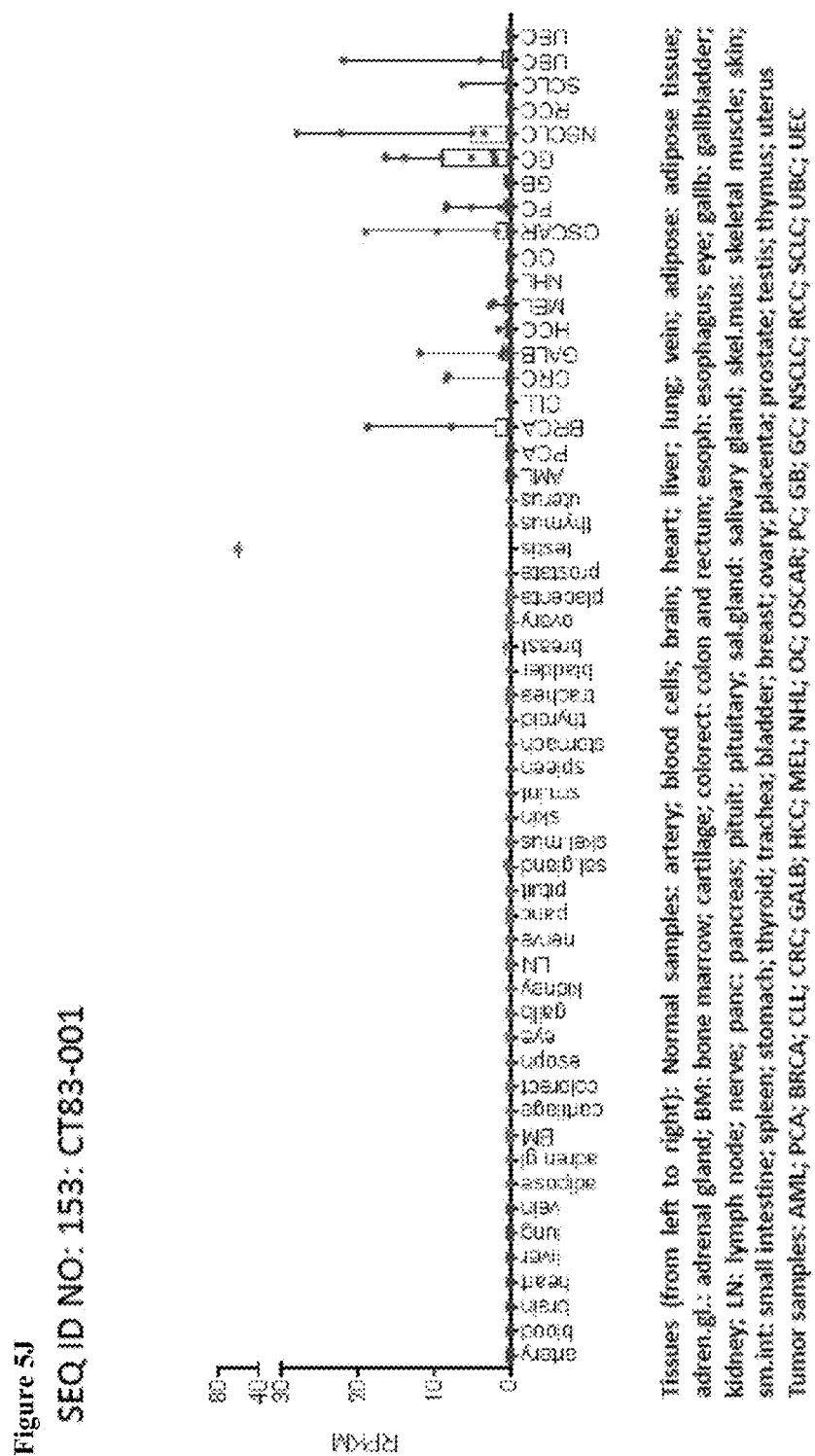

Figure 5J
SEQ ID NO: 153: CT83-001

Tissues (from left to right): Normal samples: artery; blood cells; brain; heart; liver; lung; vein; adipose; adipose tissue; adren.gl.: adrenal gland; BM: bone marrow; cartilage; colorect: colon and rectum; esoph: esophagus; eye; gallb: gallbladder; kidney; LN: lymph node; nerve; panc: pancreas; pituit: pituitary; sal.gland: salivary gland; skel.mus.: skeletal muscle; skin; sm.int: small intestine; spleen; stomach; thyroid; trachea; bladder; breast; ovary; placenta; prostate; testis; thymus; uterus. Tumor samples: AML; PCA; BRCA; CLL; CRC; GALB; HCC; MEL; NHL; OC; OSCAR; PC; GB; GC; NSCLC; RCC; SCLC; UBC; UEC

SEQ ID NO: 155: CYP4Z-001

SEQ ID NO: 157: DCAF4L2-001

Figure 5M
SEQ ID NO: 168: HORMAD1-001

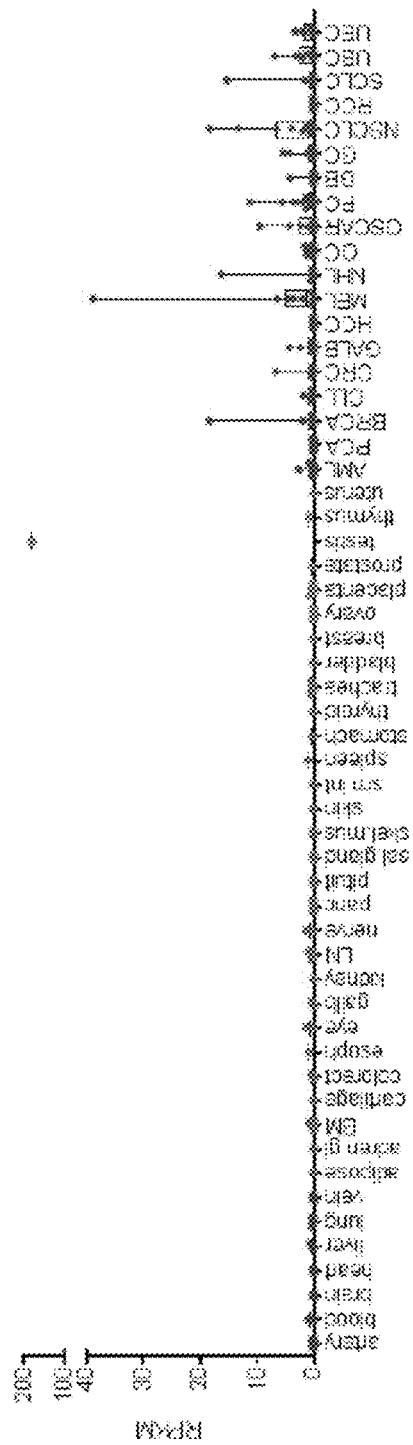

Tissues (from left to right): Normal samples: artery; blood cells; brain; heart; liver; lung; vein; adipose; adipose tissue; adren.gl.: adrenal gland; BM: bone marrow; cartilage; colorect: colon and rectum; esoph: esophagus; eye; gallb: gallbladder; kidney; LN: lymph node; nerve; panc: pancreas; pituit: pituitary; sal.gland: salivary gland; skel.mus: skeletal muscle; skin; sm.int: small intestine; spleen; stomach; thyroid; trachea; bladder; breast; ovary; placenta; prostate; testis; thymus; uterus
Tumor samples: AML; PCA; BRCA; CLL; CRC; GALB; HCC; MEL; NHL; OC; OSCAR; PC; GB; GC; NSCLC; RCC; SCLC; UBC; UEC Figure 5N
SEQ ID NO: 233: ZFP42-001

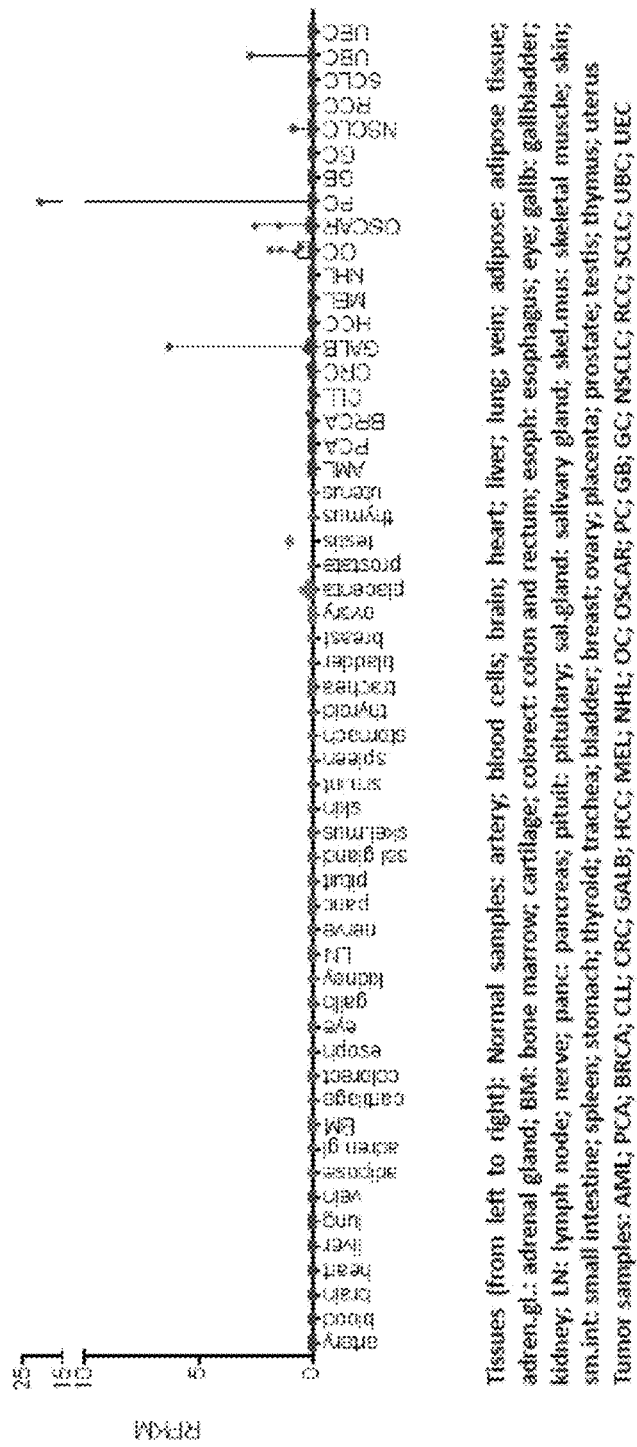

Tissues (from left to right): Normal samples: artery; blood cells; brain; heart; liver; lung; vein; adipose: adipose tissue; adren.gl.: adrenal gland; BM: bone marrow; cartilage; colorect: colon and rectum; esoph: esophagus; eye; galb: gallbladder; kidney; LN: lymph node; nerve; panc: pancreas; pituit: pituitary; sal.gland: salivary gland; skel.mus: skeletal muscle; skin; sm.int: small intestine; spleen; stomach; thyroid; trachea; bladder; breast; ovary; placenta; prostate; testis; thymus; uterus
Tumor samples: AML; PCA; BRCA; CLL; CRC; GALB; HCC; MEL; NHL; OC; OSCAR; PC; GB; GC; NSCLC; RCC; SCLC; UBC; UEC Figure 50
SEQ ID NO: 245: MAGEA4-003

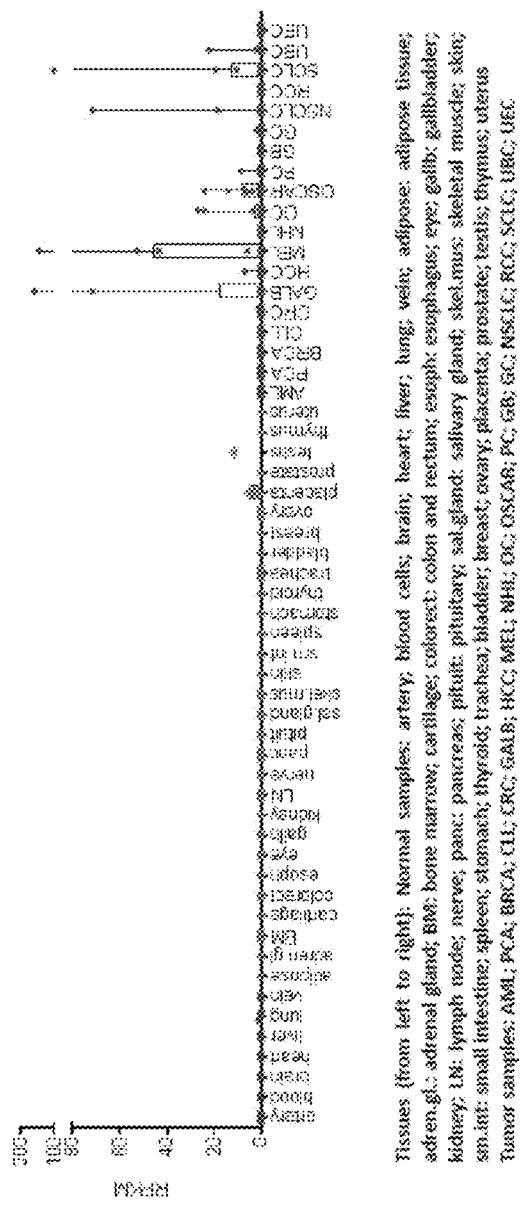

Tissues (from left to right): Normal samples: artery; blood cells; brain; heart; liver; lung; vein; adipose: adipose tissue; adren.gl.: adrenal gland; BM: bone marrow; cartilage; colorect: colon and rectum; esoph: esophagus; eye; galb: gallbladder; kidney; LN: lymph node; nerve; panc: pancreas; pituit: pituitary; sal.gland: salivary gland; skel.mus: skeletal muscle; skin; sm.int: small intestine; spleen; stomach; thyroid; trachea; bladder; breast; ovary; placenta; prostate; testis; thymus; uterus Tumor samples: AML; PCA; BRCA; CLL; CRC; GALB; HCC; MEL; NHL; OC; OSCAR; PC; GB; GC; NSCLC; RCC; SCLC; UBC; UEC Figure 5P
SEQ ID NO: 253: RAD54B-002

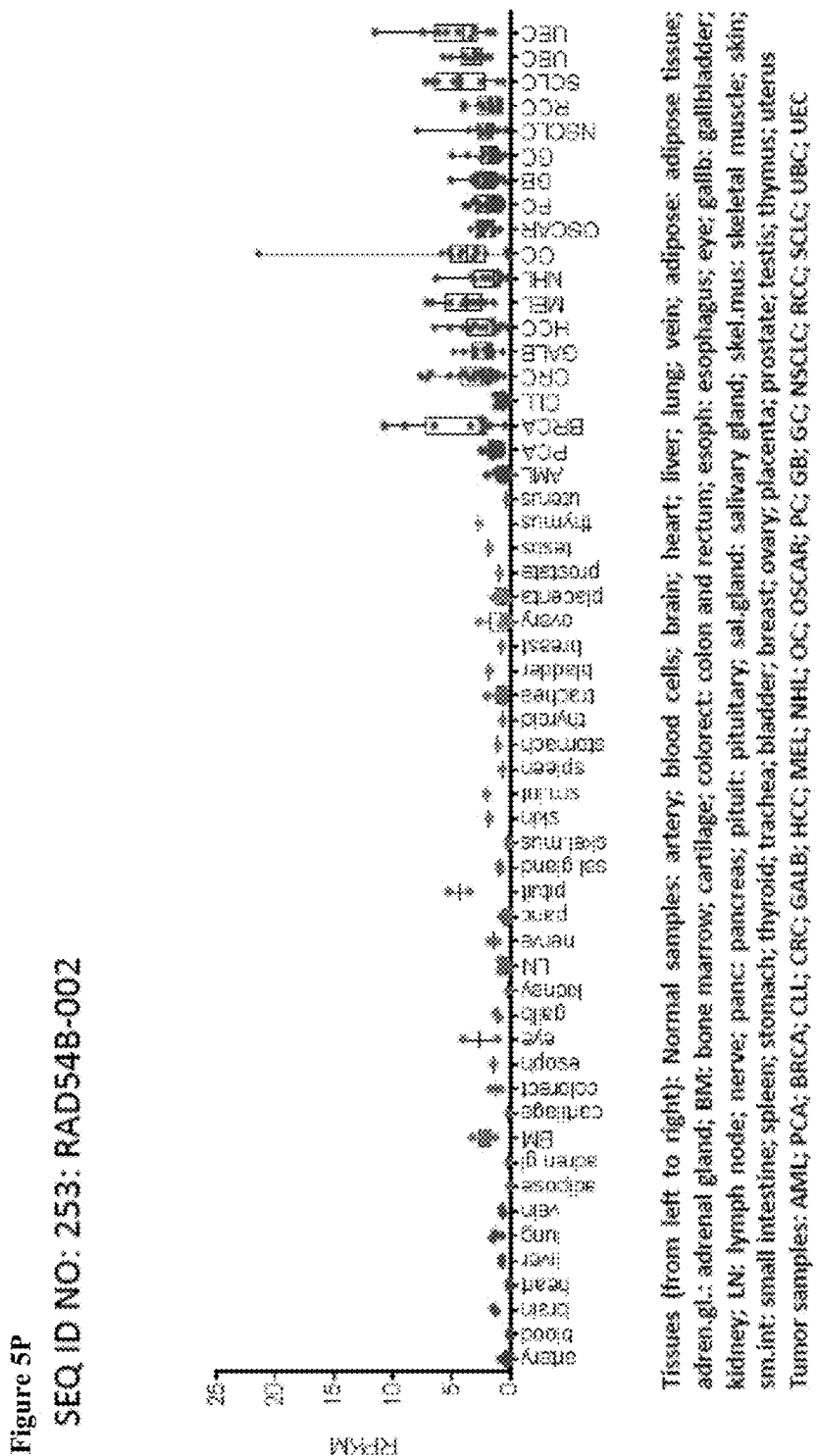

Tissues (from left to right): Normal samples: artery; blood cells; brain; heart; liver; lung; vein; adipose: adipose tissue; adren.gl.: adrenal gland; BM: bone marrow; cartilage; colorect: colon and rectum; esoph: esophagus; eye: gallb: gallbladder; kidney; LN: lymph node; nerve; panc: pancreas; pituit: pituitary; sal.gland: salivary gland; skel.mus: skeletal muscle; skin; sm.int: small intestine; spleen; stomach; thyroid; trachea; bladder; breast; ovary; placenta; prostate; testis; thymus; uterus Tumor samples: AML; PCA; BRCA; CLL; CRC; GALB; HCC; MEL; NHL; OC; OSCAR; PC; GB; GC; NSCLC; RCC; SCLC; UBC; UEC Figure 5Q
SEQ ID NO: 264: ESR1-001

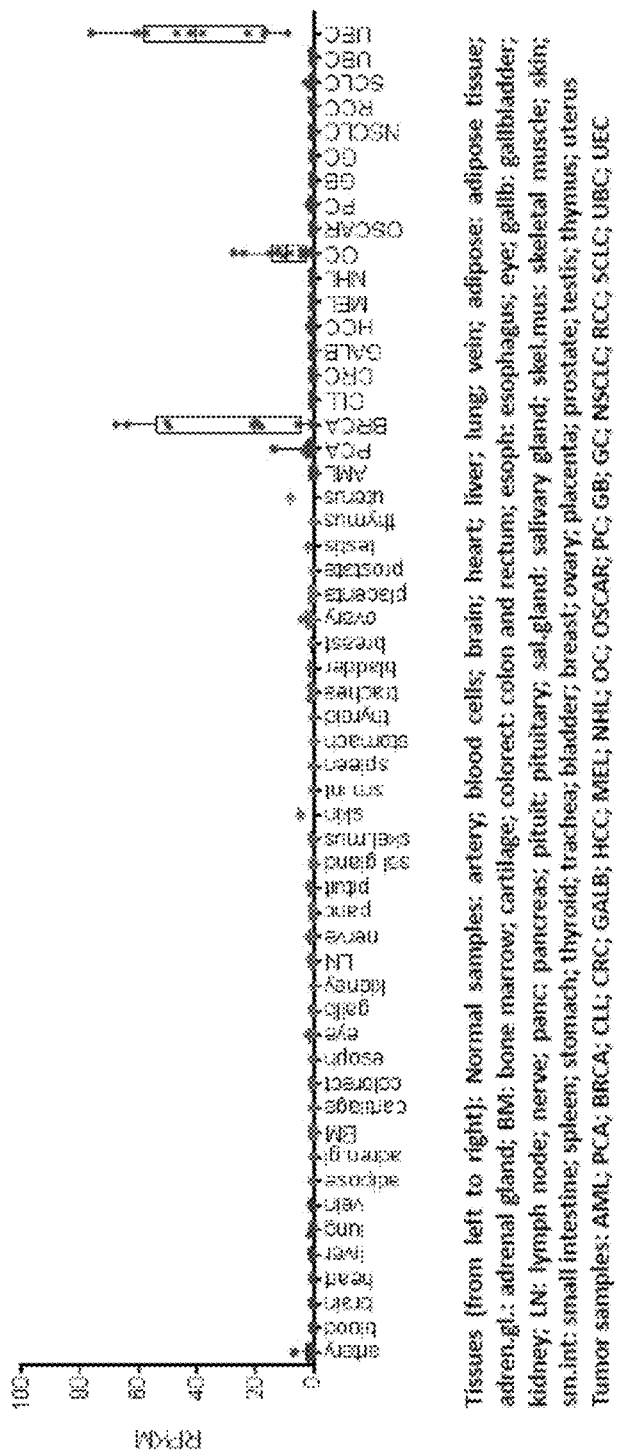

Tissues (from left to right): Normal samples: artery; blood cells; brain; heart; liver; lung; vein; adipose: adipose tissue; adren.gl.: adrenal gland; BM: bone marrow; cartilage; colorect: colon and rectum; esoph: esophagus; eye; galb: gallbladder; kidney; LN: lymph node; nerve; panc: pancreas; pituit: pituitary; sal.gland: salivary gland; skel.mus: skeletal muscle; skin; sm.int: small intestine; spleen; stomach; thyroid; trachea; bladder; breast; ovary; placenta; prostate; testis; thymus; uterus
Tumor samples: AML; PCA; BRCA; CLL; CRC; GALB; HCC; MEL; NHL; OC; OSCAR; PC; GB; GC; NSCLC; RCC; SCLC; UBC; UEC

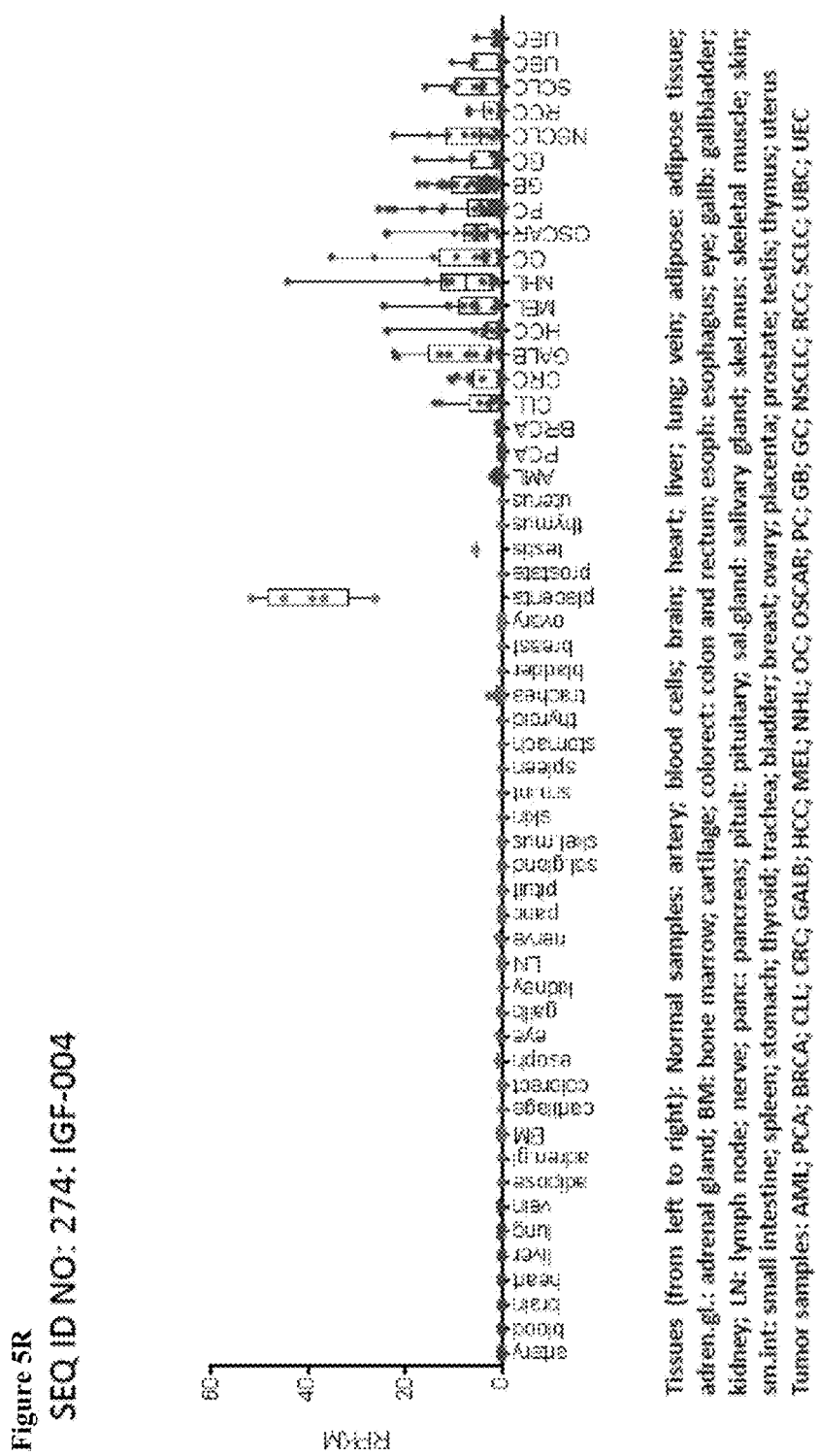

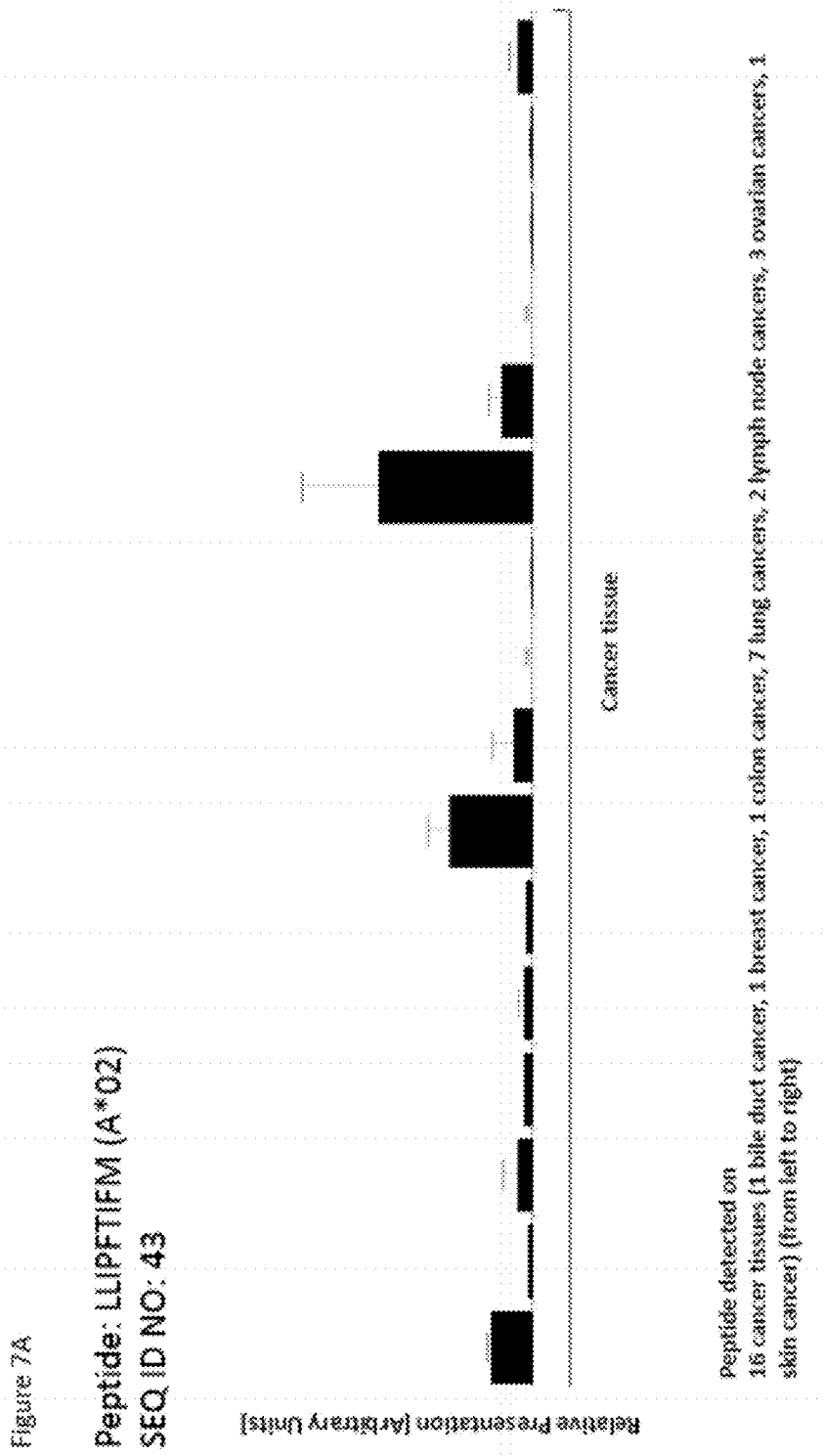

Peptide: ILVTSIFFL (A*02)
SEQ ID NO: 152

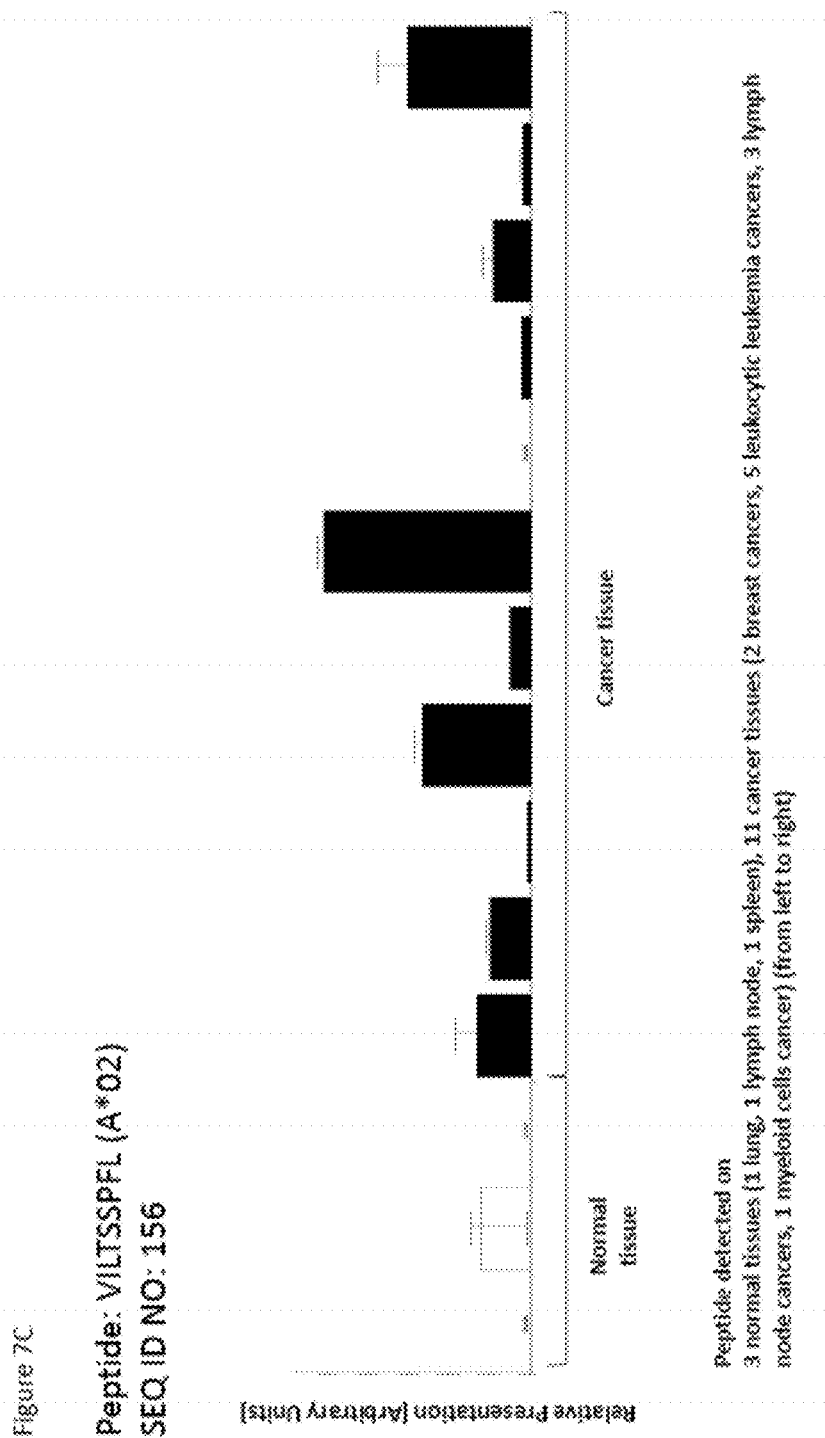

SEQUENCE LISTING

```
<160> NUMBER OF SEQ ID NOS: 290

<210> SEQ ID NO 1
<211> LENGTH: 9
<212> TYPE: PRT
<213> ORGANISM: Homo sapiens

<400> SEQUENCE: 1

Lys Leu Gln Glu Lys Ile Gln Glu Leu
1               5

<210> SEQ ID NO 2
<211> LENGTH: 10
<212> TYPE: PRT
<213> ORGANISM: Homo sapiens

<400> SEQUENCE: 2

Ser Val Leu Glu Lys Glu Ile Tyr Ser Ile
1               5                   10

<210> SEQ ID NO 3
<211> LENGTH: 11
<212> TYPE: PRT
<213> ORGANISM: Homo sapiens

<400> SEQUENCE: 3

Arg Val Ile Asp Asp Ser Leu Val Val Gly Val
1               5                   10

<210> SEQ ID NO 4
<211> LENGTH: 9
<212> TYPE: PRT
<213> ORGANISM: Homo sapiens
```

```
<400> SEQUENCE: 4

Val Leu Phe Gly Glu Leu Pro Ala Leu
1               5

<210> SEQ ID NO 5
<211> LENGTH: 9
<212> TYPE: PRT
<213> ORGANISM: Homo sapiens

<400> SEQUENCE: 5

Gly Leu Val Asp Ile Met Val His Leu
1               5

<210> SEQ ID NO 6
<211> LENGTH: 9
<212> TYPE: PRT
<213> ORGANISM: Homo sapiens

<400> SEQUENCE: 6

Phe Leu Asn Ala Ile Glu Thr Ala Leu
1               5

<210> SEQ ID NO 7
<211> LENGTH: 9
<212> TYPE: PRT
<213> ORGANISM: Homo sapiens

<400> SEQUENCE: 7

Ala Leu Leu Gln Ala Leu Met Glu Leu
1               5

<210> SEQ ID NO 8
<211> LENGTH: 9
<212> TYPE: PRT
<213> ORGANISM: Homo sapiens

<400> SEQUENCE: 8

Ala Leu Ser Ser Ser Gln Ala Glu Val
1               5

<210> SEQ ID NO 9
<211> LENGTH: 11
<212> TYPE: PRT
<213> ORGANISM: Homo sapiens

<400> SEQUENCE: 9

Ser Leu Ile Thr Gly Gln Asp Leu Leu Ser Val
1               5                   10

<210> SEQ ID NO 10
<211> LENGTH: 9
<212> TYPE: PRT
<213> ORGANISM: Homo sapiens

<400> SEQUENCE: 10

Gln Leu Ile Glu Lys Asn Trp Leu Leu
1               5

<210> SEQ ID NO 11
<211> LENGTH: 9
<212> TYPE: PRT
<213> ORGANISM: Homo sapiens

<400> SEQUENCE: 11
```

```
Leu Leu Asp Pro Lys Thr Ile Phe Leu
1               5
```

<210> SEQ ID NO 12
<211> LENGTH: 10
<212> TYPE: PRT
<213> ORGANISM: Homo sapiens

<400> SEQUENCE: 12

```
Arg Leu Leu Asp Pro Lys Thr Ile Phe Leu
1               5                   10
```

<210> SEQ ID NO 13
<211> LENGTH: 9
<212> TYPE: PRT
<213> ORGANISM: Homo sapiens

<400> SEQUENCE: 13

```
Arg Leu His Asp Glu Asn Ile Leu Leu
1               5
```

<210> SEQ ID NO 14
<211> LENGTH: 9
<212> TYPE: PRT
<213> ORGANISM: Homo sapiens

<400> SEQUENCE: 14

```
Tyr Thr Phe Ser Gly Asp Val Gln Leu
1               5
```

<210> SEQ ID NO 15
<211> LENGTH: 9
<212> TYPE: PRT
<213> ORGANISM: Homo sapiens

<400> SEQUENCE: 15

```
Gly Leu Pro Ser Ala Thr Thr Thr Val
1               5
```

<210> SEQ ID NO 16
<211> LENGTH: 9
<212> TYPE: PRT
<213> ORGANISM: Homo sapiens

<400> SEQUENCE: 16

```
Ser Leu Ala Asp Leu Ser Leu Leu Leu
1               5
```

<210> SEQ ID NO 17
<211> LENGTH: 11
<212> TYPE: PRT
<213> ORGANISM: Homo sapiens

<400> SEQUENCE: 17

```
Gly Leu Leu Pro Ser Ala Glu Ser Ile Lys Leu
1               5                   10
```

<210> SEQ ID NO 18
<211> LENGTH: 9
<212> TYPE: PRT
<213> ORGANISM: Homo sapiens

<400> SEQUENCE: 18

```
Lys Thr Ala Ser Ile Asn Gln Asn Val
1               5
```

<210> SEQ ID NO 19
<211> LENGTH: 10
<212> TYPE: PRT
<213> ORGANISM: Homo sapiens

<400> SEQUENCE: 19

Lys Val Phe Glu Leu Asp Leu Val Thr Leu
1               5                   10

<210> SEQ ID NO 20
<211> LENGTH: 10
<212> TYPE: PRT
<213> ORGANISM: Homo sapiens

<400> SEQUENCE: 20

Ala Leu Val Glu Lys Gly Glu Phe Ala Leu
1               5                   10

<210> SEQ ID NO 21
<211> LENGTH: 9
<212> TYPE: PRT
<213> ORGANISM: Homo sapiens

<400> SEQUENCE: 21

Tyr Leu Met Asp Asp Phe Ser Ser Leu
1               5

<210> SEQ ID NO 22
<211> LENGTH: 9
<212> TYPE: PRT
<213> ORGANISM: Homo sapiens

<400> SEQUENCE: 22

Leu Met Tyr Pro Tyr Ile Tyr His Val
1               5

<210> SEQ ID NO 23
<211> LENGTH: 9
<212> TYPE: PRT
<213> ORGANISM: Homo sapiens

<400> SEQUENCE: 23

Ala Leu Leu Ser Pro Leu Ser Leu Ala
1               5

<210> SEQ ID NO 24
<211> LENGTH: 9
<212> TYPE: PRT
<213> ORGANISM: Homo sapiens

<400> SEQUENCE: 24

Lys Val Trp Ser Asp Val Thr Pro Leu
1               5

<210> SEQ ID NO 25
<211> LENGTH: 11
<212> TYPE: PRT
<213> ORGANISM: Homo sapiens

<400> SEQUENCE: 25

Leu Leu Trp Gly His Pro Arg Val Ala Leu Ala
1               5                   10

```
<210> SEQ ID NO 26
<211> LENGTH: 9
<212> TYPE: PRT
<213> ORGANISM: Homo sapiens

<400> SEQUENCE: 26

Val Leu Asp Gly Lys Val Ala Val Val
1               5

<210> SEQ ID NO 27
<211> LENGTH: 9
<212> TYPE: PRT
<213> ORGANISM: Homo sapiens

<400> SEQUENCE: 27

Gly Leu Leu Gly Lys Val Thr Ser Val
1               5

<210> SEQ ID NO 28
<211> LENGTH: 11
<212> TYPE: PRT
<213> ORGANISM: Homo sapiens

<400> SEQUENCE: 28

Ile Lys Val Thr Asp Pro Gln Leu Leu Glu Leu
1               5                   10

<210> SEQ ID NO 29
<211> LENGTH: 9
<212> TYPE: PRT
<213> ORGANISM: Homo sapiens

<400> SEQUENCE: 29

Lys Met Ile Ser Ala Ile Pro Thr Leu
1               5

<210> SEQ ID NO 30
<211> LENGTH: 9
<212> TYPE: PRT
<213> ORGANISM: Homo sapiens

<400> SEQUENCE: 30

Ile Ile Thr Glu Val Ile Thr Arg Leu
1               5

<210> SEQ ID NO 31
<211> LENGTH: 11
<212> TYPE: PRT
<213> ORGANISM: Homo sapiens

<400> SEQUENCE: 31

Gly Leu Leu Glu Thr Thr Gly Leu Leu Ala Thr
1               5                   10

<210> SEQ ID NO 32
<211> LENGTH: 9
<212> TYPE: PRT
<213> ORGANISM: Homo sapiens

<400> SEQUENCE: 32

Val Val Met Val Leu Val Leu Met Leu
1               5

<210> SEQ ID NO 33
<211> LENGTH: 9
```

```
<212> TYPE: PRT
<213> ORGANISM: Homo sapiens

<400> SEQUENCE: 33

Thr Leu Asp Arg Asn Ser Leu Tyr Val
1               5

<210> SEQ ID NO 34
<211> LENGTH: 9
<212> TYPE: PRT
<213> ORGANISM: Homo sapiens

<400> SEQUENCE: 34

Thr Leu Asn Thr Leu Asp Ile Asn Leu
1               5

<210> SEQ ID NO 35
<211> LENGTH: 9
<212> TYPE: PRT
<213> ORGANISM: Homo sapiens

<400> SEQUENCE: 35

Val Ile Ile Lys Gly Leu Glu Glu Ile
1               5

<210> SEQ ID NO 36
<211> LENGTH: 9
<212> TYPE: PRT
<213> ORGANISM: Homo sapiens

<400> SEQUENCE: 36

Thr Val Leu Gln Glu Leu Ile Asn Val
1               5

<210> SEQ ID NO 37
<211> LENGTH: 9
<212> TYPE: PRT
<213> ORGANISM: Homo sapiens

<400> SEQUENCE: 37

Gln Ile Val Glu Leu Ile Glu Lys Ile
1               5

<210> SEQ ID NO 38
<211> LENGTH: 9
<212> TYPE: PRT
<213> ORGANISM: Homo sapiens

<400> SEQUENCE: 38

Val Leu Gln Gln Glu Ser Asn Phe Leu
1               5

<210> SEQ ID NO 39
<211> LENGTH: 9
<212> TYPE: PRT
<213> ORGANISM: Homo sapiens

<400> SEQUENCE: 39

Tyr Leu Glu Asp Gly Phe Ala Tyr Val
1               5

<210> SEQ ID NO 40
<211> LENGTH: 11
<212> TYPE: PRT
<213> ORGANISM: Homo sapiens
```

```
<400> SEQUENCE: 40

Lys Ile Trp Glu Glu Leu Ser Val Leu Glu Val
1               5                   10

<210> SEQ ID NO 41
<211> LENGTH: 9
<212> TYPE: PRT
<213> ORGANISM: Homo sapiens

<400> SEQUENCE: 41

Ile Val Thr Glu Ile Ile Ser Glu Ile
1               5

<210> SEQ ID NO 42
<211> LENGTH: 9
<212> TYPE: PRT
<213> ORGANISM: Homo sapiens

<400> SEQUENCE: 42

Lys Gln Met Ser Ile Ser Thr Gly Leu
1               5

<210> SEQ ID NO 43
<211> LENGTH: 9
<212> TYPE: PRT
<213> ORGANISM: Homo sapiens

<400> SEQUENCE: 43

Leu Leu Ile Pro Phe Thr Ile Phe Met
1               5

<210> SEQ ID NO 44
<211> LENGTH: 9
<212> TYPE: PRT
<213> ORGANISM: Homo sapiens

<400> SEQUENCE: 44

Ala Val Phe Asn Leu Val His Val Val
1               5

<210> SEQ ID NO 45
<211> LENGTH: 9
<212> TYPE: PRT
<213> ORGANISM: Homo sapiens

<400> SEQUENCE: 45

Phe Leu Pro Val Ser Val Val Tyr Val
1               5

<210> SEQ ID NO 46
<211> LENGTH: 10
<212> TYPE: PRT
<213> ORGANISM: Homo sapiens

<400> SEQUENCE: 46

Ile Ser Leu Asp Glu Val Ala Val Ser Leu
1               5                   10

<210> SEQ ID NO 47
<211> LENGTH: 9
<212> TYPE: PRT
<213> ORGANISM: Homo sapiens

<400> SEQUENCE: 47
```

```
Gly Leu Asn Gly Phe Asn Val Leu Leu
1               5
```

<210> SEQ ID NO 48
<211> LENGTH: 10
<212> TYPE: PRT
<213> ORGANISM: Homo sapiens

<400> SEQUENCE: 48

```
Lys Ile Ser Asp Phe Gly Leu Ala Thr Val
1               5                   10
```

<210> SEQ ID NO 49
<211> LENGTH: 11
<212> TYPE: PRT
<213> ORGANISM: Homo sapiens

<400> SEQUENCE: 49

```
Lys Leu Ile Gly Asn Ile His Gly Asn Glu Val
1               5                   10
```

<210> SEQ ID NO 50
<211> LENGTH: 9
<212> TYPE: PRT
<213> ORGANISM: Homo sapiens

<400> SEQUENCE: 50

```
Ile Leu Leu Ser Val Leu His Gln Leu
1               5
```

<210> SEQ ID NO 51
<211> LENGTH: 9
<212> TYPE: PRT
<213> ORGANISM: Homo sapiens

<400> SEQUENCE: 51

```
Leu Asp Ser Glu Ala Leu Leu Thr Leu
1               5
```

<210> SEQ ID NO 52
<211> LENGTH: 9
<212> TYPE: PRT
<213> ORGANISM: Homo sapiens

<400> SEQUENCE: 52

```
Thr Ile Gly Ile Pro Phe Pro Asn Val
1               5
```

<210> SEQ ID NO 53
<211> LENGTH: 9
<212> TYPE: PRT
<213> ORGANISM: Homo sapiens

<400> SEQUENCE: 53

```
Ala Gln His Leu Ser Thr Leu Leu Leu
1               5
```

<210> SEQ ID NO 54
<211> LENGTH: 9
<212> TYPE: PRT
<213> ORGANISM: Homo sapiens

<400> SEQUENCE: 54

```
Tyr Leu Val Pro Gly Leu Val Ala Ala
```

```
<210> SEQ ID NO 55
<211> LENGTH: 9
<212> TYPE: PRT
<213> ORGANISM: Homo sapiens

<400> SEQUENCE: 55

His Leu Phe Asp Lys Ile Ile Lys Ile
1               5

<210> SEQ ID NO 56
<211> LENGTH: 13
<212> TYPE: PRT
<213> ORGANISM: Homo sapiens

<400> SEQUENCE: 56

Val Leu Gln Glu Asn Ser Ser Asp Tyr Gln Ser Asn Leu
1               5                   10

<210> SEQ ID NO 57
<211> LENGTH: 10
<212> TYPE: PRT
<213> ORGANISM: Homo sapiens

<400> SEQUENCE: 57

Thr Leu Tyr Pro Gly Arg Phe Asp Tyr Val
1               5                   10

<210> SEQ ID NO 58
<211> LENGTH: 11
<212> TYPE: PRT
<213> ORGANISM: Homo sapiens

<400> SEQUENCE: 58

His Leu Leu Gly Glu Gly Ala Phe Ala Gln Val
1               5                   10

<210> SEQ ID NO 59
<211> LENGTH: 11
<212> TYPE: PRT
<213> ORGANISM: Homo sapiens

<400> SEQUENCE: 59

Ala Leu Ala Asp Gly Ile Lys Ser Phe Leu Leu
1               5                   10

<210> SEQ ID NO 60
<211> LENGTH: 10
<212> TYPE: PRT
<213> ORGANISM: Homo sapiens

<400> SEQUENCE: 60

Tyr Leu Phe Ser Gln Gly Leu Gln Gly Leu
1               5                   10

<210> SEQ ID NO 61
<211> LENGTH: 9
<212> TYPE: PRT
<213> ORGANISM: Homo sapiens

<400> SEQUENCE: 61

Ala Leu Tyr Pro Lys Glu Ile Thr Leu
1               5
```

```
<210> SEQ ID NO 62
<211> LENGTH: 9
<212> TYPE: PRT
<213> ORGANISM: Homo sapiens

<400> SEQUENCE: 62

Ser Leu Val Glu Asn Ile His Val Leu
1               5

<210> SEQ ID NO 63
<211> LENGTH: 9
<212> TYPE: PRT
<213> ORGANISM: Homo sapiens

<400> SEQUENCE: 63

Lys Leu Leu Pro Met Val Ile Gln Leu
1               5

<210> SEQ ID NO 64
<211> LENGTH: 10
<212> TYPE: PRT
<213> ORGANISM: Homo sapiens

<400> SEQUENCE: 64

Ser Leu Tyr Ala Gly Ser Asn Asn Gln Val
1               5                   10

<210> SEQ ID NO 65
<211> LENGTH: 9
<212> TYPE: PRT
<213> ORGANISM: Homo sapiens

<400> SEQUENCE: 65

Ser Leu Ser Glu Lys Ser Pro Glu Val
1               5

<210> SEQ ID NO 66
<211> LENGTH: 10
<212> TYPE: PRT
<213> ORGANISM: Homo sapiens

<400> SEQUENCE: 66

Ala Met Phe Pro Asp Thr Ile Pro Arg Val
1               5                   10

<210> SEQ ID NO 67
<211> LENGTH: 9
<212> TYPE: PRT
<213> ORGANISM: Homo sapiens

<400> SEQUENCE: 67

Phe Leu Ile Glu Asn Leu Leu Ala Ala
1               5

<210> SEQ ID NO 68
<211> LENGTH: 9
<212> TYPE: PRT
<213> ORGANISM: Homo sapiens

<400> SEQUENCE: 68

Gln Leu Met Asn Leu Ile Arg Ser Val
1               5

<210> SEQ ID NO 69
```

```
<211> LENGTH: 10
<212> TYPE: PRT
<213> ORGANISM: Homo sapiens

<400> SEQUENCE: 69

Leu Lys Val Leu Lys Ala Asp Val Val Leu
1               5                   10

<210> SEQ ID NO 70
<211> LENGTH: 9
<212> TYPE: PRT
<213> ORGANISM: Homo sapiens

<400> SEQUENCE: 70

Gly Leu Thr Glu Lys Thr Val Leu Val
1               5

<210> SEQ ID NO 71
<211> LENGTH: 9
<212> TYPE: PRT
<213> ORGANISM: Homo sapiens

<400> SEQUENCE: 71

His Met Ser Gly Lys Leu Thr Asn Val
1               5

<210> SEQ ID NO 72
<211> LENGTH: 9
<212> TYPE: PRT
<213> ORGANISM: Homo sapiens

<400> SEQUENCE: 72

Val Leu Ser Thr Arg Val Thr Asn Val
1               5

<210> SEQ ID NO 73
<211> LENGTH: 8
<212> TYPE: PRT
<213> ORGANISM: Homo sapiens

<400> SEQUENCE: 73

Ser Val Pro Lys Thr Leu Gly Val
1               5

<210> SEQ ID NO 74
<211> LENGTH: 9
<212> TYPE: PRT
<213> ORGANISM: Homo sapiens

<400> SEQUENCE: 74

Gly Leu Ala Phe Leu Pro Ala Ser Val
1               5

<210> SEQ ID NO 75
<211> LENGTH: 9
<212> TYPE: PRT
<213> ORGANISM: Homo sapiens

<400> SEQUENCE: 75

Ala Leu Leu Asp Gly Ala Leu Gln Leu
1               5

<210> SEQ ID NO 76
<211> LENGTH: 9
<212> TYPE: PRT
```

-continued

<213> ORGANISM: Homo sapiens

<400> SEQUENCE: 76

Phe Thr Ala Glu Phe Leu Glu Lys Val
1               5

<210> SEQ ID NO 77
<211> LENGTH: 9
<212> TYPE: PRT
<213> ORGANISM: Homo sapiens

<400> SEQUENCE: 77

Ala Leu Tyr Gly Asn Val Gln Gln Val
1               5

<210> SEQ ID NO 78
<211> LENGTH: 9
<212> TYPE: PRT
<213> ORGANISM: Homo sapiens

<400> SEQUENCE: 78

Leu Phe Gln Ser Arg Ile Ala Gly Val
1               5

<210> SEQ ID NO 79
<211> LENGTH: 10
<212> TYPE: PRT
<213> ORGANISM: Homo sapiens

<400> SEQUENCE: 79

Thr Val Leu Glu Glu Ile Gly Asn Arg Val
1               5                   10

<210> SEQ ID NO 80
<211> LENGTH: 9
<212> TYPE: PRT
<213> ORGANISM: Homo sapiens

<400> SEQUENCE: 80

Val Leu Thr Gly Gln Val His Glu Leu
1               5

<210> SEQ ID NO 81
<211> LENGTH: 9
<212> TYPE: PRT
<213> ORGANISM: Homo sapiens

<400> SEQUENCE: 81

Ile Leu Ala Glu Glu Pro Ile Tyr Ile
1               5

<210> SEQ ID NO 82
<211> LENGTH: 11
<212> TYPE: PRT
<213> ORGANISM: Homo sapiens

<400> SEQUENCE: 82

Ile Leu Ala Glu Glu Pro Ile Tyr Ile Arg Val
1               5                   10

<210> SEQ ID NO 83
<211> LENGTH: 9
<212> TYPE: PRT
<213> ORGANISM: Homo sapiens

```
<400> SEQUENCE: 83

Gly Leu Leu Glu Asn Ser Pro His Leu
1               5

<210> SEQ ID NO 84
<211> LENGTH: 9
<212> TYPE: PRT
<213> ORGANISM: Homo sapiens

<400> SEQUENCE: 84

Phe Leu Leu Glu Arg Glu Gln Leu Leu
1               5

<210> SEQ ID NO 85
<211> LENGTH: 10
<212> TYPE: PRT
<213> ORGANISM: Homo sapiens

<400> SEQUENCE: 85

Lys Leu Leu Asp Lys Pro Glu Gln Phe Leu
1               5                   10

<210> SEQ ID NO 86
<211> LENGTH: 9
<212> TYPE: PRT
<213> ORGANISM: Homo sapiens

<400> SEQUENCE: 86

Ser Leu Phe Ser Asn Ile Glu Ser Val
1               5

<210> SEQ ID NO 87
<211> LENGTH: 9
<212> TYPE: PRT
<213> ORGANISM: Homo sapiens

<400> SEQUENCE: 87

Lys Leu Leu Ser Leu Leu Glu Glu Ala
1               5

<210> SEQ ID NO 88
<211> LENGTH: 10
<212> TYPE: PRT
<213> ORGANISM: Homo sapiens

<400> SEQUENCE: 88

Leu Leu Leu Pro Leu Glu Leu Ser Leu Ala
1               5                   10

<210> SEQ ID NO 89
<211> LENGTH: 9
<212> TYPE: PRT
<213> ORGANISM: Homo sapiens

<400> SEQUENCE: 89

Ser Leu Ala Glu Thr Ile Phe Ile Val
1               5

<210> SEQ ID NO 90
<211> LENGTH: 11
<212> TYPE: PRT
<213> ORGANISM: Homo sapiens

<400> SEQUENCE: 90
```

```
Ala Ile Leu Asn Val Asp Glu Lys Asn Gln Val
1               5                   10
```

<210> SEQ ID NO 91
<211> LENGTH: 9
<212> TYPE: PRT
<213> ORGANISM: Homo sapiens

<400> SEQUENCE: 91

```
Leu Leu Pro Ser Ile Phe Leu Met Val
1               5
```

<210> SEQ ID NO 92
<211> LENGTH: 9
<212> TYPE: PRT
<213> ORGANISM: Homo sapiens

<400> SEQUENCE: 92

```
Arg Leu Phe Glu Glu Val Leu Gly Val
1               5
```

<210> SEQ ID NO 93
<211> LENGTH: 9
<212> TYPE: PRT
<213> ORGANISM: Homo sapiens

<400> SEQUENCE: 93

```
Arg Leu Tyr Gly Tyr Phe His Asp Ala
1               5
```

<210> SEQ ID NO 94
<211> LENGTH: 9
<212> TYPE: PRT
<213> ORGANISM: Homo sapiens

<400> SEQUENCE: 94

```
Tyr Leu Asp Glu Val Ala Phe Met Leu
1               5
```

<210> SEQ ID NO 95
<211> LENGTH: 11
<212> TYPE: PRT
<213> ORGANISM: Homo sapiens

<400> SEQUENCE: 95

```
Lys Leu Ile Asp Glu Asp Glu Pro Leu Phe Leu
1               5                   10
```

<210> SEQ ID NO 96
<211> LENGTH: 9
<212> TYPE: PRT
<213> ORGANISM: Homo sapiens

<400> SEQUENCE: 96

```
Ala Leu Asp Thr Thr Arg His Glu Leu
1               5
```

<210> SEQ ID NO 97
<211> LENGTH: 9
<212> TYPE: PRT
<213> ORGANISM: Homo sapiens

<400> SEQUENCE: 97

```
Lys Leu Phe Glu Lys Ser Thr Gly Leu
1               5
```

```
<210> SEQ ID NO 98
<211> LENGTH: 9
<212> TYPE: PRT
<213> ORGANISM: Homo sapiens

<400> SEQUENCE: 98

Phe Val Gln Glu Lys Ile Pro Glu Leu
1               5

<210> SEQ ID NO 99
<211> LENGTH: 10
<212> TYPE: PRT
<213> ORGANISM: Homo sapiens

<400> SEQUENCE: 99

Thr Leu Phe Gly Ile Gln Leu Thr Glu Ala
1               5                   10

<210> SEQ ID NO 100
<211> LENGTH: 9
<212> TYPE: PRT
<213> ORGANISM: Homo sapiens

<400> SEQUENCE: 100

Ala Leu Gln Ser Phe Glu Phe Arg Val
1               5

<210> SEQ ID NO 101
<211> LENGTH: 11
<212> TYPE: PRT
<213> ORGANISM: Homo sapiens

<400> SEQUENCE: 101

Ser Leu Leu Glu Val Asn Glu Ala Ser Ser Val
1               5                   10

<210> SEQ ID NO 102
<211> LENGTH: 10
<212> TYPE: PRT
<213> ORGANISM: Homo sapiens

<400> SEQUENCE: 102

Gly Leu Tyr Pro Val Thr Leu Val Gly Val
1               5                   10

<210> SEQ ID NO 103
<211> LENGTH: 9
<212> TYPE: PRT
<213> ORGANISM: Homo sapiens

<400> SEQUENCE: 103

Tyr Leu Ala Asp Thr Val Gln Lys Leu
1               5

<210> SEQ ID NO 104
<211> LENGTH: 12
<212> TYPE: PRT
<213> ORGANISM: Homo sapiens

<400> SEQUENCE: 104

Asp Leu Pro Thr Gln Glu Pro Ala Leu Gly Thr Thr
1               5                   10
```

```
<210> SEQ ID NO 105
<211> LENGTH: 9
<212> TYPE: PRT
<213> ORGANISM: Homo sapiens

<400> SEQUENCE: 105

Ala Met Leu Ala Ser Gln Thr Glu Ala
1               5

<210> SEQ ID NO 106
<211> LENGTH: 10
<212> TYPE: PRT
<213> ORGANISM: Homo sapiens

<400> SEQUENCE: 106

Val Leu Leu Gly Ser Val Val Ile Phe Ala
1               5                   10

<210> SEQ ID NO 107
<211> LENGTH: 11
<212> TYPE: PRT
<213> ORGANISM: Homo sapiens

<400> SEQUENCE: 107

Arg Val Leu Pro Gly Gln Ala Val Thr Gly Val
1               5                   10

<210> SEQ ID NO 108
<211> LENGTH: 11
<212> TYPE: PRT
<213> ORGANISM: Homo sapiens

<400> SEQUENCE: 108

Phe Ile Ala Asn Leu Pro Pro Glu Leu Lys Ala
1               5                   10

<210> SEQ ID NO 109
<211> LENGTH: 9
<212> TYPE: PRT
<213> ORGANISM: Homo sapiens

<400> SEQUENCE: 109

Ile Leu Gly Ser Phe Glu Leu Gln Leu
1               5

<210> SEQ ID NO 110
<211> LENGTH: 9
<212> TYPE: PRT
<213> ORGANISM: Homo sapiens

<400> SEQUENCE: 110

Gln Ile Gln Gly Gln Val Ser Glu Val
1               5

<210> SEQ ID NO 111
<211> LENGTH: 10
<212> TYPE: PRT
<213> ORGANISM: Homo sapiens

<400> SEQUENCE: 111

Ala Gln Leu Glu Gly Lys Leu Val Ser Ile
1               5                   10

<210> SEQ ID NO 112
<211> LENGTH: 9
```

```
<212> TYPE: PRT
<213> ORGANISM: Homo sapiens

<400> SEQUENCE: 112

Ile Leu Ala Gln Asp Val Ala Gln Leu
1               5

<210> SEQ ID NO 113
<211> LENGTH: 9
<212> TYPE: PRT
<213> ORGANISM: Homo sapiens

<400> SEQUENCE: 113

Phe Leu Phe Leu Lys Glu Val Lys Val
1               5

<210> SEQ ID NO 114
<211> LENGTH: 10
<212> TYPE: PRT
<213> ORGANISM: Homo sapiens

<400> SEQUENCE: 114

Leu Leu Phe Pro Ser Asp Val Gln Thr Leu
1               5                   10

<210> SEQ ID NO 115
<211> LENGTH: 9
<212> TYPE: PRT
<213> ORGANISM: Homo sapiens

<400> SEQUENCE: 115

Ile Leu His Gly Glu Val Asn Lys Val
1               5

<210> SEQ ID NO 116
<211> LENGTH: 9
<212> TYPE: PRT
<213> ORGANISM: Homo sapiens

<400> SEQUENCE: 116

Ala Leu Leu Ser Ser Val Ala Glu Ala
1               5

<210> SEQ ID NO 117
<211> LENGTH: 9
<212> TYPE: PRT
<213> ORGANISM: Homo sapiens

<400> SEQUENCE: 117

Thr Leu Leu Glu Gly Ile Ser Arg Ala
1               5

<210> SEQ ID NO 118
<211> LENGTH: 10
<212> TYPE: PRT
<213> ORGANISM: Homo sapiens

<400> SEQUENCE: 118

Ile Ala Tyr Asn Pro Asn Gly Asn Ala Leu
1               5                   10

<210> SEQ ID NO 119
<211> LENGTH: 9
<212> TYPE: PRT
<213> ORGANISM: Homo sapiens
```

<400> SEQUENCE: 119

Ser Leu Ile Glu Glu Ser Glu Glu Leu
1               5

<210> SEQ ID NO 120
<211> LENGTH: 11
<212> TYPE: PRT
<213> ORGANISM: Homo sapiens

<400> SEQUENCE: 120

Leu Gln Leu Ser Pro Leu Lys Gly Leu Ser Leu
1               5                   10

<210> SEQ ID NO 121
<211> LENGTH: 9
<212> TYPE: PRT
<213> ORGANISM: Homo sapiens

<400> SEQUENCE: 121

Ala Leu Tyr Val Gln Ala Pro Thr Val
1               5

<210> SEQ ID NO 122
<211> LENGTH: 9
<212> TYPE: PRT
<213> ORGANISM: Homo sapiens

<400> SEQUENCE: 122

Ser Ile Ile Asp Thr Glu Leu Lys Val
1               5

<210> SEQ ID NO 123
<211> LENGTH: 11
<212> TYPE: PRT
<213> ORGANISM: Homo sapiens

<400> SEQUENCE: 123

Gln Thr Ala Pro Glu Glu Ala Phe Ile Lys Leu
1               5                   10

<210> SEQ ID NO 124
<211> LENGTH: 9
<212> TYPE: PRT
<213> ORGANISM: Homo sapiens

<400> SEQUENCE: 124

Ala Leu Leu Leu Arg Leu Phe Thr Ile
1               5

<210> SEQ ID NO 125
<211> LENGTH: 9
<212> TYPE: PRT
<213> ORGANISM: Homo sapiens

<400> SEQUENCE: 125

Ala Ala Leu Glu Val Leu Ala Glu Val
1               5

<210> SEQ ID NO 126
<211> LENGTH: 9
<212> TYPE: PRT
<213> ORGANISM: Homo sapiens

<400> SEQUENCE: 126

```
Gln Leu Arg Glu Ala Phe Glu Gln Leu
1               5

<210> SEQ ID NO 127
<211> LENGTH: 11
<212> TYPE: PRT
<213> ORGANISM: Homo sapiens

<400> SEQUENCE: 127

Ile Met Lys Ala Thr Gly Leu Gly Ile Gln Leu
1               5                   10

<210> SEQ ID NO 128
<211> LENGTH: 9
<212> TYPE: PRT
<213> ORGANISM: Homo sapiens

<400> SEQUENCE: 128

Ser Ile Leu Thr Asn Ile Ser Glu Val
1               5

<210> SEQ ID NO 129
<211> LENGTH: 9
<212> TYPE: PRT
<213> ORGANISM: Homo sapiens

<400> SEQUENCE: 129

Lys Met Ala Ser Lys Val Thr Gln Val
1               5

<210> SEQ ID NO 130
<211> LENGTH: 9
<212> TYPE: PRT
<213> ORGANISM: Homo sapiens

<400> SEQUENCE: 130

Gln Leu Tyr Gly Ser Ala Ile Thr Leu
1               5

<210> SEQ ID NO 131
<211> LENGTH: 9
<212> TYPE: PRT
<213> ORGANISM: Homo sapiens

<400> SEQUENCE: 131

Ser Leu Tyr Pro His Phe Thr Leu Leu
1               5

<210> SEQ ID NO 132
<211> LENGTH: 9
<212> TYPE: PRT
<213> ORGANISM: Homo sapiens

<400> SEQUENCE: 132

Ala Leu Leu Asn Asn Val Ile Glu Val
1               5

<210> SEQ ID NO 133
<211> LENGTH: 9
<212> TYPE: PRT
<213> ORGANISM: Homo sapiens

<400> SEQUENCE: 133

Phe Leu Asp Gly Arg Pro Leu Thr Leu
```

-continued

```
<210> SEQ ID NO 134
<211> LENGTH: 9
<212> TYPE: PRT
<213> ORGANISM: Homo sapiens

<400> SEQUENCE: 134

Ser Leu Tyr Lys Ser Phe Leu Gln Leu
1               5

<210> SEQ ID NO 135
<211> LENGTH: 9
<212> TYPE: PRT
<213> ORGANISM: Homo sapiens

<400> SEQUENCE: 135

His Leu Asp Thr Val Lys Ile Glu Val
1               5

<210> SEQ ID NO 136
<211> LENGTH: 9
<212> TYPE: PRT
<213> ORGANISM: Homo sapiens

<400> SEQUENCE: 136

Leu Leu Trp Asp Ala Pro Ala Lys Cys
1               5

<210> SEQ ID NO 137
<211> LENGTH: 10
<212> TYPE: PRT
<213> ORGANISM: Homo sapiens

<400> SEQUENCE: 137

Lys Leu Ile Tyr Lys Asp Leu Val Ser Val
1               5                   10

<210> SEQ ID NO 138
<211> LENGTH: 9
<212> TYPE: PRT
<213> ORGANISM: Homo sapiens

<400> SEQUENCE: 138

Gly Ile Ile Asn Lys Leu Val Thr Val
1               5

<210> SEQ ID NO 139
<211> LENGTH: 9
<212> TYPE: PRT
<213> ORGANISM: Homo sapiens

<400> SEQUENCE: 139

Ile Ile Leu Glu Asn Ile Gln Ser Leu
1               5

<210> SEQ ID NO 140
<211> LENGTH: 9
<212> TYPE: PRT
<213> ORGANISM: Homo sapiens

<400> SEQUENCE: 140

Phe Leu Asp Ser Gln Ile Thr Thr Val
1               5
```

```
<210> SEQ ID NO 141
<211> LENGTH: 9
<212> TYPE: PRT
<213> ORGANISM: Homo sapiens

<400> SEQUENCE: 141

Asn Ile Asp Ile Asn Asn Asn Glu Leu
1               5

<210> SEQ ID NO 142
<211> LENGTH: 9
<212> TYPE: PRT
<213> ORGANISM: Homo sapiens

<400> SEQUENCE: 142

Leu Leu Asp Ala Ala His Ala Ser Ile
1               5

<210> SEQ ID NO 143
<211> LENGTH: 9
<212> TYPE: PRT
<213> ORGANISM: Homo sapiens

<400> SEQUENCE: 143

Met Leu Trp Glu Ser Ile Met Arg Val
1               5

<210> SEQ ID NO 144
<211> LENGTH: 9
<212> TYPE: PRT
<213> ORGANISM: Homo sapiens

<400> SEQUENCE: 144

Phe Leu Ile Ser Gln Thr Pro Leu Leu
1               5

<210> SEQ ID NO 145
<211> LENGTH: 9
<212> TYPE: PRT
<213> ORGANISM: Homo sapiens

<400> SEQUENCE: 145

Ala Leu Glu Glu Lys Leu Glu Asn Val
1               5

<210> SEQ ID NO 146
<211> LENGTH: 9
<212> TYPE: PRT
<213> ORGANISM: Homo sapiens

<400> SEQUENCE: 146

Val Val Ala Ala His Leu Ala Gly Ala
1               5

<210> SEQ ID NO 147
<211> LENGTH: 9
<212> TYPE: PRT
<213> ORGANISM: Homo sapiens

<400> SEQUENCE: 147

Gly Leu Leu Ser Ala Leu Glu Asn Val
1               5

<210> SEQ ID NO 148
```

```
<211> LENGTH: 9
<212> TYPE: PRT
<213> ORGANISM: Homo sapiens

<400> SEQUENCE: 148

Tyr Leu Ile Leu Ser Ser His Gln Leu
1               5

<210> SEQ ID NO 149
<211> LENGTH: 10
<212> TYPE: PRT
<213> ORGANISM: Homo sapiens

<400> SEQUENCE: 149

Asn Met Ala Asp Gly Gln Leu His Gln Val
1               5                   10

<210> SEQ ID NO 150
<211> LENGTH: 9
<212> TYPE: PRT
<213> ORGANISM: Homo sapiens

<400> SEQUENCE: 150

Val Leu Leu Asp Met Val His Ser Leu
1               5

<210> SEQ ID NO 151
<211> LENGTH: 9
<212> TYPE: PRT
<213> ORGANISM: Homo sapiens

<400> SEQUENCE: 151

Asp Ile Ser Lys Arg Ile Gln Ser Leu
1               5

<210> SEQ ID NO 152
<211> LENGTH: 9
<212> TYPE: PRT
<213> ORGANISM: Homo sapiens

<400> SEQUENCE: 152

Ile Leu Val Thr Ser Ile Phe Phe Leu
1               5

<210> SEQ ID NO 153
<211> LENGTH: 9
<212> TYPE: PRT
<213> ORGANISM: Homo sapiens

<400> SEQUENCE: 153

Lys Leu Val Glu Leu Glu His Thr Leu
1               5

<210> SEQ ID NO 154
<211> LENGTH: 9
<212> TYPE: PRT
<213> ORGANISM: Homo sapiens

<400> SEQUENCE: 154

Ala Ile Ile Lys Glu Ile Gln Thr Val
1               5

<210> SEQ ID NO 155
<211> LENGTH: 9
<212> TYPE: PRT
```

```
<213> ORGANISM: Homo sapiens

<400> SEQUENCE: 155

Thr Leu Asp Ser Tyr Leu Lys Ala Val
1               5

<210> SEQ ID NO 156
<211> LENGTH: 9
<212> TYPE: PRT
<213> ORGANISM: Homo sapiens

<400> SEQUENCE: 156

Val Ile Leu Thr Ser Ser Pro Phe Leu
1               5

<210> SEQ ID NO 157
<211> LENGTH: 9
<212> TYPE: PRT
<213> ORGANISM: Homo sapiens

<400> SEQUENCE: 157

Ile Leu Gln Asp Gly Gln Phe Leu Val
1               5

<210> SEQ ID NO 158
<211> LENGTH: 9
<212> TYPE: PRT
<213> ORGANISM: Homo sapiens

<400> SEQUENCE: 158

Tyr Leu Asp Pro Leu Trp His Gln Leu
1               5

<210> SEQ ID NO 159
<211> LENGTH: 9
<212> TYPE: PRT
<213> ORGANISM: Homo sapiens

<400> SEQUENCE: 159

Gln Leu Gly Pro Val Pro Val Thr Ile
1               5

<210> SEQ ID NO 160
<211> LENGTH: 9
<212> TYPE: PRT
<213> ORGANISM: Homo sapiens

<400> SEQUENCE: 160

Thr Leu Gln Glu Trp Leu Thr Glu Val
1               5

<210> SEQ ID NO 161
<211> LENGTH: 9
<212> TYPE: PRT
<213> ORGANISM: Homo sapiens

<400> SEQUENCE: 161

Asn Leu Leu Asp Glu Asn Val Cys Leu
1               5

<210> SEQ ID NO 162
<211> LENGTH: 10
<212> TYPE: PRT
<213> ORGANISM: Homo sapiens
```

<400> SEQUENCE: 162

Gly Leu Leu Gly Asn Leu Leu Thr Ser Leu
1               5                   10

<210> SEQ ID NO 163
<211> LENGTH: 9
<212> TYPE: PRT
<213> ORGANISM: Homo sapiens

<400> SEQUENCE: 163

Gly Leu Glu Glu Arg Leu Tyr Thr Ala
1               5

<210> SEQ ID NO 164
<211> LENGTH: 9
<212> TYPE: PRT
<213> ORGANISM: Homo sapiens

<400> SEQUENCE: 164

Met Leu Ile Ile Arg Val Pro Ser Val
1               5

<210> SEQ ID NO 165
<211> LENGTH: 9
<212> TYPE: PRT
<213> ORGANISM: Homo sapiens

<400> SEQUENCE: 165

Ser Leu Leu Asp Tyr Glu Val Ser Ile
1               5

<210> SEQ ID NO 166
<211> LENGTH: 9
<212> TYPE: PRT
<213> ORGANISM: Homo sapiens

<400> SEQUENCE: 166

Leu Leu Gly Asp Ser Ser Phe Phe Leu
1               5

<210> SEQ ID NO 167
<211> LENGTH: 11
<212> TYPE: PRT
<213> ORGANISM: Homo sapiens

<400> SEQUENCE: 167

Leu Val Val Asp Glu Gly Ser Leu Val Ser Val
1               5                   10

<210> SEQ ID NO 168
<211> LENGTH: 10
<212> TYPE: PRT
<213> ORGANISM: Homo sapiens

<400> SEQUENCE: 168

Val Ile Phe Glu Gly Glu Pro Met Tyr Leu
1               5                   10

<210> SEQ ID NO 169
<211> LENGTH: 9
<212> TYPE: PRT
<213> ORGANISM: Homo sapiens

<400> SEQUENCE: 169

Ala Leu Ala Asp Leu Ser Val Ala Val
1               5

<210> SEQ ID NO 170
<211> LENGTH: 9
<212> TYPE: PRT
<213> ORGANISM: Homo sapiens

<400> SEQUENCE: 170

Phe Ile Ala Ala Val Val Glu Lys Val
1               5

<210> SEQ ID NO 171
<211> LENGTH: 9
<212> TYPE: PRT
<213> ORGANISM: Homo sapiens

<400> SEQUENCE: 171

Leu Leu Leu Leu Asp Val Pro Thr Ala
1               5

<210> SEQ ID NO 172
<211> LENGTH: 12
<212> TYPE: PRT
<213> ORGANISM: Homo sapiens

<400> SEQUENCE: 172

Ser Leu Tyr Leu Gln Met Asn Ser Leu Arg Thr Glu
1               5                   10

<210> SEQ ID NO 173
<211> LENGTH: 9
<212> TYPE: PRT
<213> ORGANISM: Homo sapiens

<400> SEQUENCE: 173

Arg Leu Ile Asp Ile Tyr Lys Asn Val
1               5

<210> SEQ ID NO 174
<211> LENGTH: 10
<212> TYPE: PRT
<213> ORGANISM: Homo sapiens

<400> SEQUENCE: 174

Ala Leu Tyr Ser Gly Asp Leu His Ala Ala
1               5                   10

<210> SEQ ID NO 175
<211> LENGTH: 9
<212> TYPE: PRT
<213> ORGANISM: Homo sapiens

<400> SEQUENCE: 175

Ser Leu Leu Asp Leu Val Gln Ser Leu
1               5

<210> SEQ ID NO 176
<211> LENGTH: 9
<212> TYPE: PRT
<213> ORGANISM: Homo sapiens

<400> SEQUENCE: 176

Val Gln Ser Gly Leu Arg Ile Leu Leu
1               5

<210> SEQ ID NO 177
<211> LENGTH: 9
<212> TYPE: PRT
<213> ORGANISM: Homo sapiens

<400> SEQUENCE: 177

Ala Leu Ile Asn Val Leu Asn Ala Leu
1               5

<210> SEQ ID NO 178
<211> LENGTH: 9
<212> TYPE: PRT
<213> ORGANISM: Homo sapiens

<400> SEQUENCE: 178

Ser Leu Val Ser Trp Gln Leu Leu Leu
1               5

<210> SEQ ID NO 179
<211> LENGTH: 9
<212> TYPE: PRT
<213> ORGANISM: Homo sapiens

<400> SEQUENCE: 179

Thr Leu Gly Glu Ile Ile Lys Gly Val
1               5

<210> SEQ ID NO 180
<211> LENGTH: 9
<212> TYPE: PRT
<213> ORGANISM: Homo sapiens

<400> SEQUENCE: 180

Arg Leu Tyr Glu Glu Glu Ile Arg Ile
1               5

<210> SEQ ID NO 181
<211> LENGTH: 9
<212> TYPE: PRT
<213> ORGANISM: Homo sapiens

<400> SEQUENCE: 181

Leu Leu Trp Ala Pro Thr Ala Gln Ala
1               5

<210> SEQ ID NO 182
<211> LENGTH: 10
<212> TYPE: PRT
<213> ORGANISM: Homo sapiens

<400> SEQUENCE: 182

Gly Leu Gln Asp Gly Phe Gln Ile Thr Val
1               5                   10

<210> SEQ ID NO 183
<211> LENGTH: 9
<212> TYPE: PRT
<213> ORGANISM: Homo sapiens

<400> SEQUENCE: 183

Ala Leu Ser Tyr Ile Leu Pro Tyr Leu
1               5

```
<210> SEQ ID NO 184
<211> LENGTH: 9
<212> TYPE: PRT
<213> ORGANISM: Homo sapiens

<400> SEQUENCE: 184

Ala Leu Asp Ser Thr Ile Ala His Leu
1               5

<210> SEQ ID NO 185
<211> LENGTH: 10
<212> TYPE: PRT
<213> ORGANISM: Homo sapiens

<400> SEQUENCE: 185

Thr Leu Tyr Gln Gly Leu Pro Ala Glu Val
1               5                   10

<210> SEQ ID NO 186
<211> LENGTH: 9
<212> TYPE: PRT
<213> ORGANISM: Homo sapiens

<400> SEQUENCE: 186

Ser Leu Leu Ser Leu Glu Ser Arg Leu
1               5

<210> SEQ ID NO 187
<211> LENGTH: 9
<212> TYPE: PRT
<213> ORGANISM: Homo sapiens

<400> SEQUENCE: 187

Ser Ile Leu Lys Glu Asp Pro Phe Leu
1               5

<210> SEQ ID NO 188
<211> LENGTH: 9
<212> TYPE: PRT
<213> ORGANISM: Homo sapiens

<400> SEQUENCE: 188

Val Leu Gly Glu Glu Gln Glu Gly Val
1               5

<210> SEQ ID NO 189
<211> LENGTH: 9
<212> TYPE: PRT
<213> ORGANISM: Homo sapiens

<400> SEQUENCE: 189

Met Ala Val Ser Asp Leu Leu Ile Leu
1               5

<210> SEQ ID NO 190
<211> LENGTH: 9
<212> TYPE: PRT
<213> ORGANISM: Homo sapiens

<400> SEQUENCE: 190

Ser Leu Ser Thr Glu Leu Phe Lys Val
1               5

<210> SEQ ID NO 191
<211> LENGTH: 9
```

<212> TYPE: PRT
<213> ORGANISM: Homo sapiens

<400> SEQUENCE: 191

Ala Ala Ile Glu Ile Phe Glu Lys Val
1               5

<210> SEQ ID NO 192
<211> LENGTH: 11
<212> TYPE: PRT
<213> ORGANISM: Homo sapiens

<400> SEQUENCE: 192

Thr Leu Leu Pro Ser Ser Gly Leu Val Thr Leu
1               5                   10

<210> SEQ ID NO 193
<211> LENGTH: 9
<212> TYPE: PRT
<213> ORGANISM: Homo sapiens

<400> SEQUENCE: 193

Ala Leu Phe His Met Asn Ile Leu Leu
1               5

<210> SEQ ID NO 194
<211> LENGTH: 9
<212> TYPE: PRT
<213> ORGANISM: Homo sapiens

<400> SEQUENCE: 194

Lys Leu Leu Glu Glu Val Gln Leu Leu
1               5

<210> SEQ ID NO 195
<211> LENGTH: 9
<212> TYPE: PRT
<213> ORGANISM: Homo sapiens

<400> SEQUENCE: 195

Val Ile Ile Gln Asn Leu Pro Ala Leu
1               5

<210> SEQ ID NO 196
<211> LENGTH: 9
<212> TYPE: PRT
<213> ORGANISM: Homo sapiens

<400> SEQUENCE: 196

Thr Leu His Gln Trp Ile Tyr Tyr Leu
1               5

<210> SEQ ID NO 197
<211> LENGTH: 10
<212> TYPE: PRT
<213> ORGANISM: Homo sapiens

<400> SEQUENCE: 197

Leu Gly Gly Pro Thr Ser Leu Leu His Val
1               5                   10

<210> SEQ ID NO 198
<211> LENGTH: 9
<212> TYPE: PRT
<213> ORGANISM: Homo sapiens

```
<400> SEQUENCE: 198

Ile Leu Thr Asn Lys Val Val Ser Val
1               5

<210> SEQ ID NO 199
<211> LENGTH: 9
<212> TYPE: PRT
<213> ORGANISM: Homo sapiens

<400> SEQUENCE: 199

Ser Val Ala Asp Leu Ala His Val Leu
1               5

<210> SEQ ID NO 200
<211> LENGTH: 10
<212> TYPE: PRT
<213> ORGANISM: Homo sapiens

<400> SEQUENCE: 200

Ile Met Pro Thr Phe Asp Leu Thr Lys Val
1               5                   10

<210> SEQ ID NO 201
<211> LENGTH: 9
<212> TYPE: PRT
<213> ORGANISM: Homo sapiens

<400> SEQUENCE: 201

Leu Leu Phe Ser Leu Leu Cys Glu Ala
1               5

<210> SEQ ID NO 202
<211> LENGTH: 9
<212> TYPE: PRT
<213> ORGANISM: Homo sapiens

<400> SEQUENCE: 202

Ala Leu Ala Lys Asp Glu Leu Ser Leu
1               5

<210> SEQ ID NO 203
<211> LENGTH: 9
<212> TYPE: PRT
<213> ORGANISM: Homo sapiens

<400> SEQUENCE: 203

Phe Leu Phe Val Asp Pro Glu Leu Val
1               5

<210> SEQ ID NO 204
<211> LENGTH: 11
<212> TYPE: PRT
<213> ORGANISM: Homo sapiens

<400> SEQUENCE: 204

Ser Glu Trp Gly Ser Pro His Ala Ala Val Pro
1               5                   10

<210> SEQ ID NO 205
<211> LENGTH: 9
<212> TYPE: PRT
<213> ORGANISM: Homo sapiens

<400> SEQUENCE: 205
```

Leu Ala Phe Gly Tyr Asp Asp Glu Leu
1               5

<210> SEQ ID NO 206
<211> LENGTH: 9
<212> TYPE: PRT
<213> ORGANISM: Homo sapiens

<400> SEQUENCE: 206

Gly Leu Asp Ala Phe Arg Ile Phe Leu
1               5

<210> SEQ ID NO 207
<211> LENGTH: 9
<212> TYPE: PRT
<213> ORGANISM: Homo sapiens

<400> SEQUENCE: 207

Lys Leu Phe Glu Thr Val Glu Glu Leu
1               5

<210> SEQ ID NO 208
<211> LENGTH: 9
<212> TYPE: PRT
<213> ORGANISM: Homo sapiens

<400> SEQUENCE: 208

His Leu Asn Asn Asp Arg Asn Pro Leu
1               5

<210> SEQ ID NO 209
<211> LENGTH: 10
<212> TYPE: PRT
<213> ORGANISM: Homo sapiens

<400> SEQUENCE: 209

Val Leu Gln Thr Glu Glu Leu Val Ala Asn
1               5                   10

<210> SEQ ID NO 210
<211> LENGTH: 9
<212> TYPE: PRT
<213> ORGANISM: Homo sapiens

<400> SEQUENCE: 210

Gly Leu Ala Gly Asp Asn Ile Tyr Leu
1               5

<210> SEQ ID NO 211
<211> LENGTH: 9
<212> TYPE: PRT
<213> ORGANISM: Homo sapiens

<400> SEQUENCE: 211

Leu Leu Thr Thr Val Leu Ile Asn Ala
1               5

<210> SEQ ID NO 212
<211> LENGTH: 9
<212> TYPE: PRT
<213> ORGANISM: Homo sapiens

<400> SEQUENCE: 212

Met Thr Leu Ser Glu Ile His Ala Val

```
<210> SEQ ID NO 213
<211> LENGTH: 10
<212> TYPE: PRT
<213> ORGANISM: Homo sapiens

<400> SEQUENCE: 213

Ile Leu Ala Val Asp Gly Val Leu Ser Val
1               5                   10

<210> SEQ ID NO 214
<211> LENGTH: 9
<212> TYPE: PRT
<213> ORGANISM: Homo sapiens

<400> SEQUENCE: 214

Ala Leu Phe Glu Thr Leu Ile Gln Leu
1               5

<210> SEQ ID NO 215
<211> LENGTH: 9
<212> TYPE: PRT
<213> ORGANISM: Homo sapiens

<400> SEQUENCE: 215

Gln Ile Ala Asp Ile Val Thr Ser Val
1               5

<210> SEQ ID NO 216
<211> LENGTH: 9
<212> TYPE: PRT
<213> ORGANISM: Homo sapiens

<400> SEQUENCE: 216

Ala Leu Ser Thr Val Thr Pro Arg Ile
1               5

<210> SEQ ID NO 217
<211> LENGTH: 9
<212> TYPE: PRT
<213> ORGANISM: Homo sapiens

<400> SEQUENCE: 217

Leu Leu Trp Pro Ser Ser Val Pro Ala
1               5

<210> SEQ ID NO 218
<211> LENGTH: 9
<212> TYPE: PRT
<213> ORGANISM: Homo sapiens

<400> SEQUENCE: 218

Ser Leu Thr Gly Ala Asn Ile Thr Val
1               5

<210> SEQ ID NO 219
<211> LENGTH: 9
<212> TYPE: PRT
<213> ORGANISM: Homo sapiens

<400> SEQUENCE: 219

Gly Val Val Pro Thr Ile Gln Lys Val
1               5
```

```
<210> SEQ ID NO 220
<211> LENGTH: 9
<212> TYPE: PRT
<213> ORGANISM: Homo sapiens

<400> SEQUENCE: 220

Ala Leu Ser Glu Leu Glu Arg Val Leu
1               5

<210> SEQ ID NO 221
<211> LENGTH: 9
<212> TYPE: PRT
<213> ORGANISM: Homo sapiens

<400> SEQUENCE: 221

Ile Met Leu Asn Ser Val Glu Glu Ile
1               5

<210> SEQ ID NO 222
<211> LENGTH: 9
<212> TYPE: PRT
<213> ORGANISM: Homo sapiens

<400> SEQUENCE: 222

Leu Leu Thr Gly Val Phe Ala Gln Leu
1               5

<210> SEQ ID NO 223
<211> LENGTH: 9
<212> TYPE: PRT
<213> ORGANISM: Homo sapiens

<400> SEQUENCE: 223

Ala Leu His Pro Val Gln Phe Tyr Leu
1               5

<210> SEQ ID NO 224
<211> LENGTH: 13
<212> TYPE: PRT
<213> ORGANISM: Homo sapiens

<400> SEQUENCE: 224

Leu Leu Phe Asp Trp Ser Gly Thr Gly Arg Ala Asp Ala
1               5                   10

<210> SEQ ID NO 225
<211> LENGTH: 10
<212> TYPE: PRT
<213> ORGANISM: Homo sapiens

<400> SEQUENCE: 225

Phe Leu Pro Gln Pro Val Pro Leu Ser Val
1               5                   10

<210> SEQ ID NO 226
<211> LENGTH: 9
<212> TYPE: PRT
<213> ORGANISM: Homo sapiens

<400> SEQUENCE: 226

Ser Leu Ala Gly Asn Leu Gln Glu Leu
1               5

<210> SEQ ID NO 227
```

-continued

```
<211> LENGTH: 9
<212> TYPE: PRT
<213> ORGANISM: Homo sapiens

<400> SEQUENCE: 227

Ser Glu Met Glu Glu Leu Pro Ser Val
1               5

<210> SEQ ID NO 228
<211> LENGTH: 12
<212> TYPE: PRT
<213> ORGANISM: Homo sapiens

<400> SEQUENCE: 228

Ser Leu Leu Glu Leu Asp Gly Ile Asn Leu Arg Leu
1               5                   10

<210> SEQ ID NO 229
<211> LENGTH: 9
<212> TYPE: PRT
<213> ORGANISM: Homo sapiens

<400> SEQUENCE: 229

Tyr Leu Tyr Glu Leu Glu His Ala Leu
1               5

<210> SEQ ID NO 230
<211> LENGTH: 9
<212> TYPE: PRT
<213> ORGANISM: Homo sapiens

<400> SEQUENCE: 230

Lys Leu Leu Asn Met Ile Phe Ser Ile
1               5

<210> SEQ ID NO 231
<211> LENGTH: 9
<212> TYPE: PRT
<213> ORGANISM: Homo sapiens

<400> SEQUENCE: 231

Leu Leu Asp Asp Ile Phe Ile Arg Leu
1               5

<210> SEQ ID NO 232
<211> LENGTH: 9
<212> TYPE: PRT
<213> ORGANISM: Homo sapiens

<400> SEQUENCE: 232

Leu Val Val Gly Gly Ile Ala Thr Val
1               5

<210> SEQ ID NO 233
<211> LENGTH: 9
<212> TYPE: PRT
<213> ORGANISM: Homo sapiens

<400> SEQUENCE: 233

Ser Leu Phe Glu Ser Leu Glu Tyr Leu
1               5

<210> SEQ ID NO 234
<211> LENGTH: 10
<212> TYPE: PRT
```

<213> ORGANISM: Homo sapiens

<400> SEQUENCE: 234

Val Leu Leu Asn Glu Ile Leu Glu Gln Val
1               5                   10

<210> SEQ ID NO 235
<211> LENGTH: 9
<212> TYPE: PRT
<213> ORGANISM: Homo sapiens

<400> SEQUENCE: 235

Ser Leu Leu Asn Gln Pro Lys Ala Val
1               5

<210> SEQ ID NO 236
<211> LENGTH: 9
<212> TYPE: PRT
<213> ORGANISM: Homo sapiens

<400> SEQUENCE: 236

Lys Met Ser Glu Leu Gln Thr Tyr Val
1               5

<210> SEQ ID NO 237
<211> LENGTH: 11
<212> TYPE: PRT
<213> ORGANISM: Homo sapiens

<400> SEQUENCE: 237

Ala Leu Leu Glu Gln Thr Gly Asp Met Ser Leu
1               5                   10

<210> SEQ ID NO 238
<211> LENGTH: 9
<212> TYPE: PRT
<213> ORGANISM: Homo sapiens

<400> SEQUENCE: 238

His Leu Gln Glu Lys Leu Gln Ser Leu
1               5

<210> SEQ ID NO 239
<211> LENGTH: 11
<212> TYPE: PRT
<213> ORGANISM: Homo sapiens

<400> SEQUENCE: 239

Val Ile Ile Lys Gly Leu Glu Glu Ile Thr Val
1               5                   10

<210> SEQ ID NO 240
<211> LENGTH: 9
<212> TYPE: PRT
<213> ORGANISM: Homo sapiens

<400> SEQUENCE: 240

Ser Val Gln Glu Asn Ile Gln Gln Lys
1               5

<210> SEQ ID NO 241
<211> LENGTH: 9
<212> TYPE: PRT
<213> ORGANISM: Homo sapiens -continued

```
<400> SEQUENCE: 241

Lys Gln Phe Glu Gly Thr Val Glu Ile
1               5

<210> SEQ ID NO 242
<211> LENGTH: 9
<212> TYPE: PRT
<213> ORGANISM: Homo sapiens

<400> SEQUENCE: 242

Lys Leu Gln Glu Glu Ile Pro Val Leu
1               5

<210> SEQ ID NO 243
<211> LENGTH: 9
<212> TYPE: PRT
<213> ORGANISM: Homo sapiens

<400> SEQUENCE: 243

Gly Leu Ala Glu Phe Gln Glu Asn Val
1               5

<210> SEQ ID NO 244
<211> LENGTH: 9
<212> TYPE: PRT
<213> ORGANISM: Homo sapiens

<400> SEQUENCE: 244

Asn Val Ala Glu Ile Val Ile His Ile
1               5

<210> SEQ ID NO 245
<211> LENGTH: 9
<212> TYPE: PRT
<213> ORGANISM: Homo sapiens

<400> SEQUENCE: 245

Ala Leu Leu Glu Glu Glu Glu Gly Val
1               5

<210> SEQ ID NO 246
<211> LENGTH: 9
<212> TYPE: PRT
<213> ORGANISM: Homo sapiens

<400> SEQUENCE: 246

Ala Leu Ala Gly Ile Val Thr Asn Val
1               5

<210> SEQ ID NO 247
<211> LENGTH: 12
<212> TYPE: PRT
<213> ORGANISM: Homo sapiens

<400> SEQUENCE: 247

Asn Leu Leu Ile Asp Asp Lys Gly Thr Ile Lys Leu
1               5                   10

<210> SEQ ID NO 248
<211> LENGTH: 10
<212> TYPE: PRT
<213> ORGANISM: Homo sapiens

<400> SEQUENCE: 248
```

Val Leu Met Gln Asp Ser Arg Leu Tyr Leu
1               5                   10

<210> SEQ ID NO 249
<211> LENGTH: 9
<212> TYPE: PRT
<213> ORGANISM: Homo sapiens

<400> SEQUENCE: 249

Tyr Leu Tyr Gln Ile Leu Gln Gly Ile
1               5

<210> SEQ ID NO 250
<211> LENGTH: 9
<212> TYPE: PRT
<213> ORGANISM: Homo sapiens

<400> SEQUENCE: 250

Leu Met Gln Asp Ser Arg Leu Tyr Leu
1               5

<210> SEQ ID NO 251
<211> LENGTH: 9
<212> TYPE: PRT
<213> ORGANISM: Homo sapiens

<400> SEQUENCE: 251

Leu Leu Trp Gly Asn Leu Pro Glu Ile
1               5

<210> SEQ ID NO 252
<211> LENGTH: 9
<212> TYPE: PRT
<213> ORGANISM: Homo sapiens

<400> SEQUENCE: 252

Ser Leu Met Glu Lys Asn Gln Ser Leu
1               5

<210> SEQ ID NO 253
<211> LENGTH: 9
<212> TYPE: PRT
<213> ORGANISM: Homo sapiens

<400> SEQUENCE: 253

Lys Leu Leu Ala Val Ile His Glu Leu
1               5

<210> SEQ ID NO 254
<211> LENGTH: 10
<212> TYPE: PRT
<213> ORGANISM: Homo sapiens

<400> SEQUENCE: 254

Ala Leu Gly Asp Lys Phe Leu Leu Arg Val
1               5                   10

<210> SEQ ID NO 255
<211> LENGTH: 11
<212> TYPE: PRT
<213> ORGANISM: Homo sapiens

<400> SEQUENCE: 255

Phe Leu Met Lys Asn Ser Asp Leu Tyr Gly Ala
1               5                   10

```
<210> SEQ ID NO 256
<211> LENGTH: 9
<212> TYPE: PRT
<213> ORGANISM: Homo sapiens

<400> SEQUENCE: 256

Phe Leu Asn Asp Ile Phe Glu Arg Ile
1               5

<210> SEQ ID NO 257
<211> LENGTH: 10
<212> TYPE: PRT
<213> ORGANISM: Homo sapiens

<400> SEQUENCE: 257

Lys Leu Ile Asp His Gln Gly Leu Tyr Leu
1               5                   10

<210> SEQ ID NO 258
<211> LENGTH: 9
<212> TYPE: PRT
<213> ORGANISM: Homo sapiens

<400> SEQUENCE: 258

Gln Leu Val Gln Arg Val Ala Ser Val
1               5

<210> SEQ ID NO 259
<211> LENGTH: 12
<212> TYPE: PRT
<213> ORGANISM: Homo sapiens

<400> SEQUENCE: 259

Gly Pro Gly Ile Phe Pro Pro Pro Pro Gln Pro
1               5                   10

<210> SEQ ID NO 260
<211> LENGTH: 9
<212> TYPE: PRT
<213> ORGANISM: Homo sapiens

<400> SEQUENCE: 260

Ala Leu Asn Glu Ser Leu Val Glu Cys
1               5

<210> SEQ ID NO 261
<211> LENGTH: 9
<212> TYPE: PRT
<213> ORGANISM: Homo sapiens

<400> SEQUENCE: 261

Gly Leu Ala Ala Leu Ala Val His Leu
1               5

<210> SEQ ID NO 262
<211> LENGTH: 9
<212> TYPE: PRT
<213> ORGANISM: Homo sapiens

<400> SEQUENCE: 262

Leu Leu Leu Glu Ala Val Trp His Leu
1               5
```

<210> SEQ ID NO 263
<211> LENGTH: 9
<212> TYPE: PRT
<213> ORGANISM: Homo sapiens

<400> SEQUENCE: 263

Ser Ile Ile Glu Tyr Leu Pro Thr Leu
1               5

<210> SEQ ID NO 264
<211> LENGTH: 9
<212> TYPE: PRT
<213> ORGANISM: Homo sapiens

<400> SEQUENCE: 264

Thr Leu His Asp Gln Val His Leu Leu
1               5

<210> SEQ ID NO 265
<211> LENGTH: 11
<212> TYPE: PRT
<213> ORGANISM: Homo sapiens

<400> SEQUENCE: 265

Phe Leu Leu Asp Lys Pro Gln Asp Leu Ser Ile
1               5                   10

<210> SEQ ID NO 266
<211> LENGTH: 9
<212> TYPE: PRT
<213> ORGANISM: Homo sapiens

<400> SEQUENCE: 266

Phe Leu Leu Asp Lys Pro Gln Asp Leu
1               5

<210> SEQ ID NO 267
<211> LENGTH: 10
<212> TYPE: PRT
<213> ORGANISM: Homo sapiens

<400> SEQUENCE: 267

Tyr Leu Leu Asp Met Pro Leu Trp Tyr Leu
1               5                   10

<210> SEQ ID NO 268
<211> LENGTH: 9
<212> TYPE: PRT
<213> ORGANISM: Homo sapiens

<400> SEQUENCE: 268

Ser Leu Asp Lys Asp Ile Val Ala Leu
1               5

<210> SEQ ID NO 269
<211> LENGTH: 9
<212> TYPE: PRT
<213> ORGANISM: Homo sapiens

<400> SEQUENCE: 269

Gly Leu Leu Asp Cys Pro Ile Phe Leu
1               5

<210> SEQ ID NO 270
<211> LENGTH: 9

```
<212> TYPE: PRT
<213> ORGANISM: Homo sapiens

<400> SEQUENCE: 270

Thr Leu Leu Thr Phe Phe His Glu Leu
1               5

<210> SEQ ID NO 271
<211> LENGTH: 9
<212> TYPE: PRT
<213> ORGANISM: Homo sapiens

<400> SEQUENCE: 271

Val Leu Ile Glu Tyr Asn Phe Ser Ile
1               5

<210> SEQ ID NO 272
<211> LENGTH: 10
<212> TYPE: PRT
<213> ORGANISM: Homo sapiens

<400> SEQUENCE: 272

Phe Val Met Glu Gly Glu Pro Pro Lys Leu
1               5                   10

<210> SEQ ID NO 273
<211> LENGTH: 9
<212> TYPE: PRT
<213> ORGANISM: Homo sapiens

<400> SEQUENCE: 273

Ser Leu Asn Lys Gln Ile Glu Thr Val
1               5

<210> SEQ ID NO 274
<211> LENGTH: 11
<212> TYPE: PRT
<213> ORGANISM: Homo sapiens

<400> SEQUENCE: 274

Thr Leu Tyr Asn Pro Glu Arg Thr Ile Thr Val
1               5                   10

<210> SEQ ID NO 275
<211> LENGTH: 9
<212> TYPE: PRT
<213> ORGANISM: Homo sapiens

<400> SEQUENCE: 275

Ala Val Pro Pro Pro Pro Ser Ser Val
1               5

<210> SEQ ID NO 276
<211> LENGTH: 9
<212> TYPE: PRT
<213> ORGANISM: Homo sapiens

<400> SEQUENCE: 276

Arg Met Pro Thr Val Leu Gln Cys Val
1               5

<210> SEQ ID NO 277
<211> LENGTH: 9
<212> TYPE: PRT
<213> ORGANISM: Homo sapiens
```

<400> SEQUENCE: 277

Lys Leu Gln Glu Glu Leu Asn Lys Val
1               5

<210> SEQ ID NO 278
<211> LENGTH: 9
<212> TYPE: PRT
<213> ORGANISM: Homo sapiens

<400> SEQUENCE: 278

Val Leu Glu Asp Lys Val Leu Ser Val
1               5

<210> SEQ ID NO 279
<211> LENGTH: 11
<212> TYPE: PRT
<213> ORGANISM: Homo sapiens

<400> SEQUENCE: 279

Val Leu Met Asp Glu Gly Ala Val Leu Thr Leu
1               5                   10

<210> SEQ ID NO 280
<211> LENGTH: 9
<212> TYPE: PRT
<213> ORGANISM: Homo sapiens

<400> SEQUENCE: 280

His Leu Trp Gly His Ala Leu Phe Leu
1               5

<210> SEQ ID NO 281
<211> LENGTH: 12
<212> TYPE: PRT
<213> ORGANISM: Homo sapiens

<400> SEQUENCE: 281

Leu Leu Leu Glu Ser Asp Pro Lys Val Tyr Ser Leu
1               5                   10

<210> SEQ ID NO 282
<211> LENGTH: 9
<212> TYPE: PRT
<213> ORGANISM: Homo sapiens

<400> SEQUENCE: 282

Ser Leu Tyr Ala Leu His Val Lys Ala
1               5

<210> SEQ ID NO 283
<211> LENGTH: 9
<212> TYPE: PRT
<213> ORGANISM: Homo sapiens

<400> SEQUENCE: 283

Ala Leu Ser Glu Leu Leu Gln Gln Val
1               5

<210> SEQ ID NO 284
<211> LENGTH: 11
<212> TYPE: PRT
<213> ORGANISM: Homo sapiens

<400> SEQUENCE: 284

```
Lys Leu Met Asp Pro Gly Ser Leu Pro Pro Leu
1               5                   10

<210> SEQ ID NO 285
<211> LENGTH: 9
<212> TYPE: PRT
<213> ORGANISM: Homo sapiens

<400> SEQUENCE: 285

Met Leu Leu Asp Thr Val Gln Lys Val
1               5

<210> SEQ ID NO 286
<211> LENGTH: 9
<212> TYPE: PRT
<213> ORGANISM: Homo sapiens

<400> SEQUENCE: 286

Phe Leu Thr Glu Met Val His Phe Ile
1               5

<210> SEQ ID NO 287
<211> LENGTH: 9
<212> TYPE: PRT
<213> ORGANISM: Homo sapiens

<400> SEQUENCE: 287

Lys Ile Gln Glu Ile Leu Thr Gln Val
1               5

<210> SEQ ID NO 288
<211> LENGTH: 9
<212> TYPE: PRT
<213> ORGANISM: Homo sapiens

<400> SEQUENCE: 288

Ser Leu Tyr Lys Gly Leu Leu Ser Val
1               5

<210> SEQ ID NO 289
<211> LENGTH: 10
<212> TYPE: PRT
<213> ORGANISM: Homo sapiens

<400> SEQUENCE: 289

Glu Leu Ala Gly Ile Gly Ile Leu Thr Val
1               5                   10

<210> SEQ ID NO 290
<211> LENGTH: 9
<212> TYPE: PRT
<213> ORGANISM: Homo sapiens

<400> SEQUENCE: 290

Tyr Leu Leu Pro Ala Ile Val His Ile
1               5
```

PEPTIDES AND COMBINATION OF PEPTIDES FOR USE IN IMMUNOTHERAPY AGAINST VARIOUS TUMORS

CROSS REFERENCE TO RELATED APPLICATIONS

This application claims the benefit of U.S. Provisional Application Ser. No. 62/139,189, filed Mar. 27, 2015, and Great Britain Application No. 1505305.1, filed Mar. 27, 2015, the content of each these applications is herein incorporated by reference in their entirety.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "2912919-042011_SEQ_LIST.txt," created on Mar. 28, 2016, and 44,970 bytes in size) is submitted concurrently with the instant application, and the entire contents of the Sequence Listing are incorporated herein by reference.

FIELD

The present invention relates to peptides, proteins, nucleic acids and cells for use in immunotherapeutic methods. In particular, the present invention relates to the immunotherapy of cancer. The present invention furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T cells ex vivo and transfer into patients. Peptides bound to molecules of the major histocompatibility complex (MHC), or peptides as such, can also be targets of antibodies, soluble T-cell receptors, and other binding molecules.

The present invention relates to several novel peptide sequences and their variants derived from HLA class I molecules of human tumor cells that can be used in vaccine compositions for eliciting anti-tumor immune responses, or as targets for the development of pharmaceutically/immunologically active compounds and cells.

BACKGROUND OF THE INVENTION

According to the World Health Organization (WHO), cancer ranged among the four major non-communicable deadly diseases worldwide in 2012. For the same year, colorectal cancer, breast cancer and respiratory tract cancers were listed within the top 10 causes of death in high income countries.

Epidemiology

In 2012, 14.1 million new cancer cases, 32.6 million patients suffering from cancer (within 5 years of diagnosis) and 8.2 million cancer deaths were estimated worldwide (Ferlay et al., 2013; Bray et al., 2013).

Within the groups of brain cancer, leukemia and lung cancer the current invention specifically focuses on glioblastoma (GB), chronic lymphocytic leukemia (CLL) and acute myeloid leukemia (AML), non-small cell and small cell lung cancer (NSCLC and SCLC), respectively.

GB is the most common central nervous system malignancy with an age-adjusted incidence rate of 3.19 per 100,000 inhabitants within the United States. GB has a very poor prognosis with a 1-year survival rate of 35% and a 5-year survival rate lower than 5%. Male gender, older age and ethnicity appear to be risk factors for GB (Thakkar et al., 2014).

CLL is the most common leukemia in the Western world where it comprises about one third of all leukemias. Incidence rates are similar in the US and Europe, and estimated new cases are about 16,000 per year. CLL is more common in Caucasians than in Africans, rarer in Hispanics and Native Americans and seldom in Asians. In people of Asian origin, CLL incidence rates are 3 fold lower than in Caucasians (Gunawardana et al., 2008). The five-year overall survival for patients with CLL is about 79%.

Lung cancer is the most common type of cancer worldwide and the leading cause of death from cancer in many countries. Lung cancer is subdivided into small cell lung cancer and non-small cell lung cancer. NSCLC includes the histological types adenocarcinoma, squamous cell carcinoma and large cell carcinoma and accounts for 85% of all lung cancers in the United States. The incidence of NSCLC is closely correlated with smoking prevalence, including current and former smokers and the five year survival rate was reported to be 15% (World Cancer Report, 2014; Molina et al., 2008).

Therapy

Breast Cancer

The standard treatment for breast cancer patients depends on different parameters: tumor stage, hormone receptor status and HER2 expression pattern. The standard of care includes complete surgical resection of the tumor followed by radiation therapy. Chemotherapy with mainly anthracyclines and taxanes may be started prior to or after resection. Patients with HER2-positive tumors receive the anti-HER2 antibody trastuzumab in addition to the chemotherapeutics (S3-Leitlinie Mammakarzinom, 2012). Breast cancer is an immunogenic cancer entity and different types of infiltrating immune cells in primary tumors exhibit distinct prognostic and predictive significance. A large number of early phase immunotherapy trials have been conducted in breast cancer patients. Clinical data on the effects of immune checkpoint modulation with ipilimumab and other T cell-activating antibodies in breast cancer patients are emerging (Emens, 2012).

Chronic Lymphocytic Leukemia

While CLL is not curable at present, many patients show only slow progression of the disease or worsening of symptoms. For patients with symptomatic or rapidly progressing disease, several treatment options are available. These include chemotherapy, targeted therapy, immune-based therapies like monoclonal antibodies, chimeric antigen-receptors (CARs) and active immunotherapy, and stem cell transplants.

Several completed and ongoing trials are based on engineered autologous chimeric antigen receptor (CAR)-modified T cells with CD19 specificity (Maus et al., 2014). So far, only the minority of patients showed detectable or persistent CARs. One partial response (PR) and two complete responses (CR) have been detected in the CAR T-cell trials by Porter et al. and Kalos et al. (Kalos et al., 2011; Porter et al., 2011).

Active immunotherapy includes the following strategies: gene therapy, whole modified tumor cell vaccines, DC-based vaccines and tumor associated antigen (TAA)-derived peptide vaccines.

Several TAAs are over-expressed in CLL and are suitable for vaccinations. These include fibromodulin (Mayr et al., 2005), RHAMM/CD168 (Giannopoulos et al., 2006), MDM2 (Mayr et al., 2006), hTERT (Counter et al., 1995), the oncofetal antigen-immature laminin receptor protein (OFAiLRP) (Siegel et al., 2003), adipophilin (Schmidt et al., 2004), survivin (Granziero et al., 2001), KW1 to KW14 (Krackhardt et al., 2002) and the tumor-derived IgVHCDR3 region (Harig et al., 2001; Carballido et al., 2012). A phase I clinical trial was conducted using the RHAMM-derived R3 peptide as a vaccine. 5 of 6 patients had detectable R3-specific CD8+ T-cell responses (Giannopoulos et al., 2010).

Colorectal Cancer

Depending on the colorectal cancer (CRC) stage, different standard therapies are available for colon and rectal cancer. Standard procedures include surgery, radiation therapy, chemotherapy and targeted therapy for CRC (Berman et al., 2015a; Berman et al., 2015b).

Latest clinical trials analyze active immunotherapy as a treatment option against CRC. Those strategies include the vaccination with peptides from tumor-associated antigens (TAAs), whole tumor cells, dendritic cell (DC) vaccines and viral vectors (Koido et al., 2013).

Peptide vaccines have so far been directed against carcinoembryonic antigen (CEA), mucin 1, EGFR, squamous cell carcinoma antigen recognized by T cells 3 (SART3), beta-human chorionic gonadotropin (beta-hCG), Wilms' Tumor antigen 1 (WT1), Survivin-2B, MAGE3, p53, ring finger protein 43 and translocase of the outer mitochondrial membrane 34 (TOMM34), or mutated KRAS. In several phase I and II clinical trials patients showed antigen-specific CTL responses or antibody production. In contrast to immunological responses, many patients did not benefit from peptide vaccines on the clinical level (Koido et al., 2013; Miyagi et al., 2001; Moulton et al., 2002; Okuno et al., 2011).

Dendritic cell vaccines comprise DCs pulsed with either TAA-derived peptides, tumor cell lysates, apoptotic tumor cells, or tumor RNA or DC-tumor cell fusion products. While many patients in phase I/II trials showed specific immunological responses, only the minority had a clinical benefit (Koido et al., 2013).

Esophageal Cancer

The primary treatment strategy for esophageal cancer depends on tumor stage and location, histological type and the medical condition of the patient. Chemotherapeutic regimens include oxaliplatin plus fluorouracil, carboplatin plus paclitaxel, cisplatin plus fluorouracil, FOLFOX and cisplatin plus irinotecan. Patients with HER2-positive tumors should be treated according to the guidelines for gastric cancer, as randomized data for targeted therapies in esophageal cancer are very limited (Stahl et al., 2013).

Data on immunotherapeutic approaches in esophageal cancer are scarce, as only a very limited number of early phase clinical trials have been performed. A vaccine consisting of three peptides derived from three different cancer-testis antigens (TTK protein kinase, lymphocyte antigen 6 complex locus K and insulin-like growth factor (IGF)-II mRNA binding protein 3) was administered to patients with advanced esophageal cancer in a phase I trial with moderate results. Intra-tumoral injection of activated T cells after in vitro challenge with autologous malignant cells elicited complete or partial tumor responses in four of eleven patients in a phase I/II study (Toomey et al., 2013).

Gastric Cancer

Gastric cancer (GC) begins in the cells lining the mucosal layer and spreads through the outer layers as it grows. Four types of standard treatment are used. Treatment for gastric cancer may involve endoscopic or surgical resection, chemotherapy, radiation therapy or chemoradiation (Leitlinie Magenkarzinom, 2012).

The efficacy of current therapeutic regimens for advanced GC is poor, resulting in low 5-year survival rates. Immunotherapy might be an alternative approach to ameliorate the survival of GC patients. Adoptive transfer of tumor-associated lymphocytes and cytokine induced killer cells, peptide-based vaccines targeting HER2/neu, MAGE-3 or vascular endothelial growth factor receptor 1 and 2 and dendritic cell-based vaccines targeting HER2/neu showed promising results in clinical GC trials. Immune checkpoint inhibition and engineered T cells might represent additional therapeutic options, which is currently evaluated in pre-clinical and clinical studies (Matsueda and Graham, 2014).

Glioblastoma

The therapeutic options for glioblastoma (WHO grade IV) are very limited. Different immunotherapeutic approaches are investigated for the treatment of GB, including immune-checkpoint inhibition, vaccination and adoptive transfer of engineered T cells.

Different vaccination strategies for GB patients are currently investigated, including peptide-based vaccines, heat-shock protein vaccines, autologous tumor cell vaccines, dendritic cell-based vaccines and viral protein-based vaccines. In these approaches peptides derived from GB-associated proteins like epidermal growth factor receptor variant III (EGFRvIII) or heat shock proteins or dendritic cells pulsed with autologous tumor cell lysate or cytomegalovirus components are applied to induce an anti-tumor immune response in GB patients. Several of these studies reveal good safety and tolerability profiles as well as promising efficacy data.

Adoptive transfer of genetically modified T cells is an additional immunotherapeutic approach for the treatment of GB. Different clinical trials currently evaluate the safety and efficacy of chimeric antigen receptor bearing T cells directed against HER2, IL-13 receptor alpha 2 and EGFRvIII (Ampie et al., 2015).

Liver Cancer

Disease management depends on the tumor stage at the time of diagnosis and the overall condition of the liver. Chemotherapy against HCC includes combinations of doxorubicin, 5-fluorouracil and cisplatin for systemic therapy and doxorubicin, floxuridine and mitomycin C for hepatic artery infusions. However, most HCC show a high resistance to chemotherapeutics (Enguita-German and Fortes, 2014).

Therapeutic options in advanced non-resectable HCC are limited to Sorafenib, a multi-tyrosine kinase inhibitor (Chang et al., 2007; Wilhelm et al., 2004). Sorafenib is the only systemic drug confirmed to increase survival by about 3 months and currently represents the only experimental treatment option for such patients (Chapiro et al., 2014; Llovet et al., 2008).

Lately, a limited number of immunotherapy trials for HCC have been conducted. Cytokines have been used to activate subsets of immune cells and/or increase the tumor immunogenicity (Reinisch et al., 2002; Sangro et al., 2004). Other trials have focused on the infusion of Tumor-infiltrating lymphocytes or activated peripheral blood lymphocytes (Shi et al., 2004; Takayama et al., 1991; Takayama et al., 2000).

So far, a small number of therapeutic vaccination trials have been executed. Butterfield et al. conducted two trials using peptides derived from alpha-fetoprotein (AFP) as a vaccine or DCs loaded with AFP peptides ex vivo (Butterfield et al., 2003; Butterfield et al., 2006). In two different studies, autologous dendritic cells (DCs) were pulsed ex vivo with autologous tumor lysate (Lee et al., 2005) or lysate of the hepatoblastoma cell line HepG2 (Palmer et al., 2009). So far, vaccination trials have only shown limited improvements in clinical outcomes.

Melanoma

The standard therapy in melanoma is complete surgical resection with surrounding healthy tissue Therapeutic options include monochemotherapy, polychemotherapy and targeted therapies with specific inhibitors (S3-Leitlinie Melanom, 2013).

Several different vaccination approaches have already been evaluated in patients with advanced melanoma. So far, phase Ill trials revealed rather disappointing results and vaccination strategies clearly need to be improved. Therefore, new clinical trials, like the OncoVEX GM-CSF trial or the DERMA trial, aim at improving clinical efficacy without reducing tolerability.

Adoptive T cell transfer shows great promise for the treatment of advanced stage melanoma. In vitro expanded autologous tumor infiltrating lymphocytes as well as T cells harboring a high affinity T cell receptor for the cancer-testis antigen NY-ESO-1 had significant beneficial and low toxic effects upon transfer into melanoma patients. Unfortunately, T cells with high affinity T cell receptors for the melanocyte specific antigens MART1 and gp100 and the cancer-testis antigen MAGEA3 induced considerable toxic effects in clinical trials. Thus, adoptive T cell transfer has high therapeutic potential, but safety and tolerability of these treatments needs to be further increased (Phan and Rosenberg, 2013; Hinrichs and Restifo, 2013).

Non-Small Cell Lung Cancer

Treatment options are determined by the type (small cell or non-small cell) and stage of cancer and include surgery, radiation therapy, chemotherapy, and targeted biological therapies such as bevacizumab, erlotinib and gefitinib (S3-Leitlinie Lungenkarzinom, 2011).

To expand the therapeutic options for NSCLC, different immunotherapeutic approaches have been studied or are still under investigation. While vaccination with L-BLP25 or MAGEA3 failed to demonstrate a vaccine-mediated survival advantage in NSCLC patients, an allogeneic cell line-derived vaccine showed promising results in clinical studies. Additionally, further vaccination trials targeting gangliosides, the epidermal growth factor receptor and several other antigens are currently ongoing. An alternative strategy to enhance the patient's anti-tumor T cell response consists of blocking inhibitory T cell receptors or their ligands with specific antibodies. The therapeutic potential of several of these antibodies, including ipilimumab, nivolumab, pembrolizumab, MPDL3280A and MEDI-4736, in NSCLC is currently evaluated in clinical trials (Reinmuth et al., 2015).

Ovarian Cancer

Surgical resection is the primary therapy in early as well as advanced stage ovarian carcinoma (S3-Leitlinie maligne Ovarialtumore, 2013).

Immunotherapy appears to be a promising strategy to ameliorate the treatment of ovarian cancer patients, as the presence of pro-inflammatory tumor infiltrating lymphocytes, especially CD8-positive T cells, correlates with good prognosis and T cells specific for tumor-associated antigens can be isolated from cancer tissue.

Therefore, a lot of scientific effort is put into the investigation of different immunotherapies in ovarian cancer. A considerable number of pre-clinical and clinical studies has already been performed and further studies are currently ongoing. Clinical data are available for cytokine therapy, vaccination, monoclonal antibody treatment, adoptive cell transfer and immunomodulation.

Phase I and II vaccination studies, using single or multiple peptides, derived from several tumor-associated proteins (Her2/neu, NY-ESO-1, p53, Wilms tumor-1) or whole tumor antigens, derived from autologous tumor cells revealed good safety and tolerability profiles, but only low to moderate clinical effects.

Adoptive transfer of immune cells achieved heterogeneous results in clinical trials. Adoptive transfer of autologous, in vitro expanded tumor infiltrating T cells was shown to be a promising approach in a pilot trial. In contrast, transfer of T cells harboring a chimeric antigen receptor specific for folate receptor alpha did not induce a significant clinical response in a phase I trial. Dendritic cells pulsed with tumor cell lysate or tumor-associated proteins in vitro were shown to enhance the anti-tumor T cell response upon transfer, but the extent of T cell activation did not correlate with clinical effects. Transfer of natural killer cells caused significant toxicities in a phase II study.

Intrinsic anti-tumor immunity as well as immunotherapy are hampered by an immunosuppressive tumor microenvironment. To overcome this obstacle immunomodulatory drugs, like cyclophosphamide, anti-CD25 antibodies and pegylated liposomal doxorubicin are tested in combination with immunotherapy. Most reliable data are currently available for ipilimumab, an anti-CTLA4 antibody, which enhances T cell activity. Ipilimumab was shown to exert significant anti-tumor effects in ovarian cancer patients (Mantia-Smaldone et al., 2012).

Pancreatic Cancer

Therapeutic options for pancreatic cancer patients are very limited. One major problem for effective treatment is the typically advanced tumor stage at diagnosis.

Vaccination strategies are investigated as further innovative and promising alternative for the treatment of pancreatic cancer. Peptide-based vaccines targeting KRAS mutations, reactive telomerase, gastrin, survivin, CEA and MUC1 have already been evaluated in clinical trials, partially with promising results. Furthermore, clinical trials for dendritic cell-based vaccines, allogeneic GM-CSF-secreting vaccines and algenpantucel-L in pancreatic cancer patients also revealed beneficial effects of immunotherapy. Additional clinical trials further investigating the efficiency of different vaccination protocols are currently ongoing (Salman et al., 2013).

Prostate Cancer

The therapeutic strategy for prostate cancer mainly depends on the cancer stage. For locally restricted non-metastasizing prostate cancer, treatment options include active surveillance (wait and watch), complete surgical resection of the prostate and local high dose radiation therapy with or without brachytherapy (S3-Leitlinie Prostatakarzinom, 2014).

The dendritic cell-based vaccine sipuleucel-T was the first anti-cancer vaccine to be approved by the FDA. Due to its positive effect on survival in patients with CRPC, much effort is put into the development of further immunotherapies. Regarding vaccination strategies, the peptide vaccine prostate-specific antigen (PSA)-TRICOM, the personalized peptide vaccine PPV, the DNA vaccine pTVG-HP and the whole cell vaccine expressing GM-CSF GVAX showed promising results in different clinical trials. Furthermore, dendritic cell-based vaccines other than sipuleucel-T, namely BPX-101 and DCVAC/Pa were shown to elicited clinical responses in prostate cancer patients. Immune checkpoint inhibitors like ipilimumab and nivolumab are currently evaluated in clinical studies as monotherapy as well as in combination with other treatments, including androgen deprivation therapy, local radiation therapy, PSA-TRICOM and GVAX. The immunomodulatory substance tasquinimod, which significantly slowed progression and increased progression free survival in a phase II trial, is currently further investigated in a phase III trial. Lenalidomide, another immunomodulator, induced promising effects in early phase clinical studies, but failed to improve survival in a phase III trial. Despite these disappointing results further lenalidomide trials are ongoing (Quinn et al., 2015).

Renal Cell Carcinoma

Initial treatment is most commonly either partial or complete removal of the affected kidney(s) and remains the mainstay of curative treatment (Rini et al., 2008). For first-line treatment of patients with poor prognostic score a guidance elaborated by several cancer organizations and societies recommend the receptor tyrosine kinase inhibitors (TKIs) sunitinib and pazopanib, the monoclonal antibody bevacizumab combined with interferon-α (IFN-α) and the mTOR inhibitor temsirolimus. Based on guidelines elaborated by the US NCCN as well as the European EAU and ESMO, the TKIs sorafenib, pazopanib or recently axitinib are recommended as second-line therapy in RCC patients who have failed prior therapy with cytokines (IFN-α, IL-2). The NCCN guidelines advise also sunitinib in this setting (high-level evidence according to NCCN Category I).

The known immunogenity of RCC has represented the basis supporting the use of immunotherapy and cancer vaccines in advanced RCC. The interesting correlation between lymphocytes PD-1 expression and RCC advanced stage, grade and prognosis, as well as the selective PD-L1 expression by RCC tumor cells and its potential association with worse clinical outcomes, have led to the development of new anti PD-1/PD-L1 agents, alone or in combination with anti-angiogenic drugs or other immunotherapeutic approaches, for the treatment of RCC (Massari et al., 2015). In advanced RCC, a phase III cancer vaccine trial called TRIST study evaluates whether TroVax (a vaccine using a tumor-associated antigen, 5T4, with a pox virus vector), added to first-line standard of care therapy, prolongs survival of patients with locally advanced or mRCC. Median survival had not been reached in either group with 399 patients (54%) remaining on study however analysis of the data confirms prior clinical results, demonstrating that TroVax is both immunologically active and that there is a correlation between the strength of the 5T4-specific antibody response and improved survival. Further there are several studies searching for peptide vaccines using epitopes being overexpressed in RCC.

Various approaches of tumor vaccines have been under investigation. Studies using whole-tumor approaches, including tumor cell lysates, fusions of dendritic cells with tumor cells, or whole-tumor RNA were done in RCC patients, and remissions of tumor lesions were reported in some of these trials (Avigan et al., 2004; Holtl et al., 2002; Marten et al., 2002; Su et al., 2003; Wittig et al., 2001).

Small Cell Lung Cancer

The treatment and prognosis of SCLC depend strongly on the diagnosed cancer stage. The staging of SCLC based on clinical results is more common than the pathologic staging. The clinical staging uses the results of the physical examination, various imaging tests and biopsies. The standard chemo treatment of SCLC uses the combination of either etoposide or irinotecan with either cisplatin or carboplatin (American Cancer Society, 2015; S3-Leitlinie Lungenkarzinom, 2011).

The immune therapy presents an excessively investigated field of cancer therapy. Various approaches are studded in the treatment of SCLC. One of the approaches targets the blocking of CTLA-4, a natural human immune suppressor. The inhibition of CTLA-4 intends to boost the immune system to combat the cancer. Recently, the development of promising immune check point inhibitors for treatment of SCLC has been started. Another approach is based on anti-cancer vaccines which is currently available for treatment of SCLC in clinical studies (American Cancer Society, 2015; National Cancer Institute, 2015).

Acute Myeloid Leukemia

AML treatment is divided into two phases: induction therapy and post-remission/"consolidation therapy". Induction therapy is administered to induce remission and consists of combinational chemotherapy. Consolidation therapy consists of additional chemotherapy or hematopoietic cell transplantation (HCT) (Showel and Levis, 2014).

Clinical trials are recommended for patients who belong to the prognostic groups unfavorable and intermediate-2. Treatment options include hypomethylating agents (HMAs) as Azacitidine or decitabine, CPX-351, which is a liposomal formulation of daunorubicin and cytarabine in a 1:5 "optimal" molar ratio, and volasertib, which is an inhibitor of polo kinases. Volasertib is given in combination with LDAC (low-dose cytarabine). Several different FLT3 inhibitors can be administered in case of FLT3 mutations. These include sorafenib, which is given in combination with 3+7, quizartinib, a more selective inhibitor of FLT3 ITD that also inhibits CKIT, crenolanib, and midostaurin, an unselective FLT3 ITD inhibitor. Another treatment option is targeting CD33 with antibody-drug conjugates (anti-CD33+calechiamicin, SGN-CD33a, anti-CD33+actinium-225), bispecific antibodies (recognition of CD33+CD3 (AMG 330) or CD33+CD16) and chimeric antigen receptors (CARs) (Estey, 2014).

Non-Hodgkin Lymphoma

NHL has over 60 subtypes. The three most common subtypes are diffuse large B-cell lymphoma (DLBCL, the most common subtype), follicular lymphoma (FL, the second most common subtype) and small lymphocytic lymphoma/chronic lymphocytic lymphoma (SLL/CLL, the third most common subtype). DLBCL, FL and SLL/CLL account for about 85% of NHL (Li et al., 2015). Treatment of NHL depends on the histologic type and stage (National Cancer Institute, 2015).

Spontaneous tumor regression can be observed in lymphoma patients. Therefore, active immunotherapy is a therapy option (Palomba, 2012).

An important vaccination option includes Id vaccines. B lymphocytes express surface immunoglobulins with a specific amino acid sequence in the variable regions of their heavy and light chains, unique to each cell clone (=idiotype, Id). The idiotype functions as a tumor associated antigen.

Active immunization includes the injection of recombinant protein (Id) conjugated to an adjuvant (KLH), given together with GM-CSF as an immune adjuvant. Tumor-specific Id is produced by hybridoma cultures or using recombinant DNA technology (plasmids) by bacterial, insect or mammalian cell culture.

Uterine Cancer

More than 80% of endometrial cancers occur as endometrioid adenocarcinomas (type I), a form that is associated with estrogen exposure and that is well to moderately differentiated. Treatment of endometrial carcinomas and cervical cancers is stage-dependent (World Cancer Report, 2014).

There are also some immunotherapeutic approaches that are currently being tested. In a Phase I/II Clinical Trial patients suffering from uterine cancer were vaccinated with autologous dendritic cells (DCs) electroporated with Wilms' tumor gene 1 (WT1) mRNA.

Besides one case of local allergic reaction to the adjuvant, no adverse side effects were observed and 3 out of 6 patients showed an immunological response (Coosemans et al., 2013).

Gallbladder Adenocarcinoma and Cholangiocarcinoma

Cholangiocarcinoma (CCC) is difficult to treat and is usually lethal. The only curative treatment option is complete resection (RO). The efficacy of biological therapies in biliary tract cancers has been mixed. Drugs targeting blood vessel growth such as sorafenib, bevacizumab, pazopanib and regorafenib are now studied for the treatment of CCC. Additionally, drugs that target EGFR such as cetuximab and panitumumab are used in clinical studies in combination with chemotherapy (American Cancer Society, 2015). For most drugs tested so far disease control and overall survival were not improved significantly but there are further clinical trials ongoing.

Gallbladder cancer (GBC) is the most common and aggressive malignancy of the biliary tract worldwide. Due to the rarity of carcinomas of the biliary tract in general there are only a few GBC or CCC specific studies, while most of them include all biliary tract cancers. This is the reason why treatment did not improve during the last decades and RO resection still is the only curative treatment option.

Urinary Bladder Cancer

The standard treatment for bladder cancer includes surgery, radiation therapy, chemotherapy and immunotherapy (National Cancer Institute, 2015).

An effective immunotherapeutic approach is established in the treatment of aggressive non-muscle invasive bladder cancer (NMIBC). Thereby, a weakened form of the bacterium *Mycobacterium bovis* (*bacillus* Calmette-Guérin=BCG) is applied as an intravesical solution. The major effect of BCG treatment is a significant long-term (up to 10 years) protection from cancer recurrence and reduced progression rate. In principle, the treatment with BCG induces a local inflammatory response which stimulates the cellular immune response. The immune response to BCG is based on the following key steps: infection of urothelial and bladder cancer cells by BCG, followed by increased expression of antigen-presenting molecules, induction of immune response mediated via cytokine release, induction of anti-tumor activity via involvement of various immune cells (thereunder cytotoxic T lymphocytes, neutrophils, natural killer cells, and macrophages) (Fuge et al., 2015; Gandhi et al., 2013).

Considering the severe side-effects and expense associated with treating cancer, there is a need to identify factors that can be used in the treatment of cancer in general and hepatocellular carcinoma (HCC), colorectal carcinoma (CRC), glioblastoma (GB), gastric cancer (GC), esophageal cancer, non-small cell lung cancer (NSCLC), pancreatic cancer (PC), renal cell carcinoma (RCC), benign prostate hyperplasia (BPH), prostate cancer (PCA), ovarian cancer (OC), melanoma, breast cancer, chronic lymphocytic leukemia (CLL), Merkel cell carcinoma (MCC), small cell lung cancer (SCLC), Non-Hodgkin lymphoma (NHL), acute myeloid leukemia (AML), gallbladder cancer and cholangiocarcinoma (GBC, CCC), urinary bladder cancer (UBC), uterine cancer (UEC), in particular. There is also a need to identify factors representing biomarkers for cancer in general and the above-mentioned cancer types in particular, leading to better diagnosis of cancer, assessment of prognosis, and prediction of treatment success.

Immunotherapy of cancer represents an option of specific targeting of cancer cells while minimizing side effects. Cancer immunotherapy makes use of the existence of tumor associated antigens. The current classification of tumor associated antigens (TAAs) comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members and NY-ESO-1.

b) Differentiation antigens: These TAAs are shared between tumors and the normal tissue from which the tumor arose. Most of the known differentiation antigens are found in melanomas and normal melanocytes. Many of these melanocyte lineage-related proteins are involved in biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, survivin, telomerase, or WT1.

d) Tumor-specific antigens: These unique TAAs arise from mutations of normal genes (such as β-catenin, CDK4, etc.). Some of these molecular changes are associated with neoplastic transformation and/or progression. Tumor-specific antigens are generally able to induce strong immune responses without bearing the risk for autoimmune reactions against normal tissues. On the other hand, these TAAs are in most cases only relevant to the exact tumor on which they were identified and are usually not shared between many individual tumors. Tumor-specificity (or -association) of a peptide may also arise if the peptide originates from a tumor-(-associated) exon in case of proteins with tumor-specific (-associated) isoforms.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

T-cell based immunotherapy targets peptide epitopes derived from tumor-associated or tumor-specific proteins, which are presented by molecules of the major histocompatibility complex (MHC). The antigens that are recognized by the tumor specific T lymphocytes, that is, the epitopes thereof, can be molecules derived from all protein classes, such as enzymes, receptors, transcription factors, etc. which are expressed and, as compared to unaltered cells of the same origin, usually up-regulated in cells of the respective tumor.

There are two classes of MHC-molecules, MHC class I and MHC class II. MHC class I molecules are composed of an alpha heavy chain and beta-2-microglobulin, MHC class II molecules of an alpha and a beta chain. Their three-dimensional conformation results in a binding groove, which is used for non-covalent interaction with peptides.

MHC class I molecules can be found on most nucleated cells. They present peptides that result from proteolytic cleavage of predominantly endogenous proteins, defective ribosomal products (DRIPs) and larger peptides. However, peptides derived from endosomal compartments or exogenous sources are also frequently found on MHC class I molecules. This non-classical way of class I presentation is referred to as cross-presentation in literature (Brossart and Bevan, 1997; Rock et al., 1990). MHC class II molecules can be found predominantly on professional antigen presenting cells (APCs), and primarily present peptides of exogenous or transmembrane proteins that are taken up by APCs e.g. during endocytosis, and are subsequently processed.

Complexes of peptide and MHC class I are recognized by CD8-positive T cells bearing the appropriate T-cell receptor (TCR), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic et al., 2003). At the tumor site, T helper cells, support a cytotoxic T cell-(CTL-) friendly cytokine milieu (Mortara et al., 2006) and attract effector cells, e.g. CTLs, natural killer (NK) cells, macrophages, and granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have been found to express MHC class II molecules (Dengjel et al., 2006).

Elongated peptides of the invention can act as MHC class II active epitopes.

T-helper cells, activated by MHC class II epitopes, play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

It was shown in mammalian animal models, e.g., mice, that even in the absence of CD8-positive T lymphocytes, CD4-positive T cells are sufficient for inhibiting manifestation of tumors via inhibition of angiogenesis by secretion of interferon-gamma (IFNγ) (Beatty and Paterson, 2001; Mumberg et al., 1999). There is evidence for CD4 T cells as direct anti-tumor effectors (Braumuller et al., 2013; Tran et al., 2014).

Since the constitutive expression of HLA class II molecules is usually limited to immune cells, the possibility of isolating class II peptides directly from primary tumors was previously not considered possible. However, Dengjel et al. were successful in identifying a number of MHC Class II epitopes directly from tumors (WO 2007/028574, EP 1 760 088 B1).

Since both types of response, CD8 and CD4 dependent, contribute jointly and synergistically to the anti-tumor effect, the identification and characterization of tumor-associated antigens recognized by either CD8+ T cells (ligand: MHC class I molecule+peptide epitope) or by CD4-positive T-helper cells (ligand: MHC class II molecule+peptide epitope) is important in the development of tumor vaccines.

For an MHC class I peptide to trigger (elicit) a cellular immune response, it also must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules expressed by tumor cells, they subsequently also have to be recognized by T cells bearing specific T cell receptors (TCR).

For proteins to be recognized by T-lymphocytes as tumor-specific or -associated antigens, and to be used in a therapy, particular prerequisites must be fulfilled. The antigen should be expressed mainly by tumor cells and not, or in comparably small amounts, by normal healthy tissues. In a preferred embodiment, the peptide should be over-presented by tumor cells as compared to normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to their function, e.g. in cell cycle control or suppression of apoptosis. Additionally, downstream targets of the proteins directly causative for a transformation may be up-regulated and thus may be indirectly tumor-associated. Such indirect tumor-associated antigens may also be targets of a vaccination approach (Singh-Jasuja et al., 2004). It is essential that epitopes are present in the amino acid sequence of the antigen, in order to ensure that such a peptide ("immunogenic peptide"), being derived from a tumor associated antigen, leads to an in vitro or in vivo T-cell-response.

Basically, any peptide able to bind an MHC molecule may function as a T-cell epitope. A prerequisite for the induction of an in vitro or in vivo T-cell-response is the presence of a T cell having a corresponding TCR and the absence of immunological tolerance for this particular epitope.

Therefore, TAAs are a starting point for the development of a T cell based therapy including but not limited to tumor vaccines. The methods for identifying and characterizing the TAAs are usually based on the use of T-cells that can be isolated from patients or healthy subjects, or they are based on the generation of differential transcription profiles or differential peptide expression patterns between tumors and normal tissues. However, the identification of genes overexpressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and the immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of targeting peptide-MHC by specific TCRs (e.g. soluble TCRs) and antibodies or other binding molecules (scaffolds) according to the invention, the immunogenicity of the underlying peptides is secondary. In these cases, the presentation is the determining factor.

SUMMARY OF THE INVENTION

In a first aspect of the present invention, the present invention relates to a peptide comprising an amino acid sequence selected from the group consisting of SEQ ID NO: 1 to SEQ ID NO: 288 or a variant sequence thereof which is at least 77%, preferably at least 88%, homologous (preferably at least 77% or at least 88% identical) to SEQ ID NO: 1 to SEQ ID NO: 288, wherein said variant binds to MHC and/or induces T cells cross-reacting with said peptide, or a pharmaceutical acceptable salt thereof, wherein said peptide is not the underlying full-length polypeptide.

While the most important criterion for a peptide to function as cancer therapy target is its over-presentation on primary tumor tissues as compared to normal tissues, also the RNA expression profile of the corresponding gene can help to select appropriate peptides. Particularly, some peptides are hard to detect by mass spectrometry, either due to their chemical properties or to their low copy numbers on cells, and a screening approach focusing on detection of peptide presentation may fail to identify these targets. However, these targets may be detected by an alternative approach starting with analysis of gene expression in normal tissues and secondarily assessing peptide presentation and gene expression in tumors. This approach was realized in this invention using mRNA data from a publicly available database (Lonsdale, 2013) in combination with further gene expression data (including tumor samples), as well as peptide presentation data. If the mRNA of a gene is nearly absent in normal tissues, especially in vital organ systems, targeting the corresponding peptides by even very potent strategies (such as bispecific affinity-optimized antibodies or T-cell receptors), is more likely to be safe. Such peptides, even if identified on only a small percentage of tumor tissues, represent interesting targets. Routine mass spectrometry analysis is not sensitive enough to assess target coverage on the peptide level. Rather, tumor mRNA expression can be used to assess coverage. For detection of the peptide itself, a targeted mass spectrometry approach with higher sensitivity than in the routine screening may be necessary and may lead to a better estimation of coverage on the level of peptide presentation.

The present invention further relates to a peptide of the present invention comprising a sequence that is selected from the group consisting of SEQ ID NO: 1 to SEQ ID NO: 288 or a variant thereof, which is at least 77%, preferably at least 88%, homologous (preferably at least 77% or at least 88% identical) to SEQ ID NO: 1 to SEQ ID NO: 288, wherein said peptide or variant thereof has an overall length of between 8 and 100, preferably between 8 and 30, and most preferred of between 8 and 14 amino acids.

The following tables show the peptides according to the present invention, their respective SEQ ID NOs, and the prospective source (underlying) genes for these peptides. All peptides in Table 1 and Table 2 bind to HLA-A*02. The peptides in Table 2 have been disclosed before in large listings as results of high-throughput screenings with high error rates or calculated using algorithms, but have not been associated with cancer at all before.

TABLE 1

Peptides according to the present invention

| SEQ ID No. | Sequence | Gene ID(s) | Official Gene Symbol(s) |
|---|---|---|---|
| 1 | KLQEKIQEL | 1062 | CENPE |
| 2 | SVLEKEIYSI | 127602 | DNAH14 |
| 3 | RVIDDSLVVGV | 2187 | FANCB |
| 4 | VLFGELPAL | 8701 | DNAH11 |
| 5 | GLVDIMVHL | 8701 | DNAH11 |
| 6 | FLNAIETAL | 8701 | DNAH11 |
| 7 | ALLQALMEL | 51236, 728071 | FAM203A, FAM203B |
| 8 | ALSSSQAEV | 3833 | KIFC1 |
| 9 | SLITGQDLLSV | 51804 | SIX4 |
| 10 | QLIEKNWLL | 56992 | KIF15 |

TABLE 1-continued

Peptides according to the present invention

| SEQ ID No. | Sequence | Gene ID(s) | Official Gene Symbol(s) |
|---|---|---|---|
| 11 | LLDPKTIFL | 26762 | HAVCR1 |
| 12 | RLLDPKTIFL | 26762 | HAVCR1 |
| 13 | RLHDENILL | 23322 | RPGRIP1L |
| 14 | YTFSGDVQL | 4312 | MMP1 |
| 15 | GLPSATTTV | 94025 | MUC16 |
| 16 | SLADLSLLL | 134391 | GPR151 |
| 17 | GLLPSAESIKL | 132989 | C4orf36 |
| 18 | KTASINQNV | 81930 | KIF18A |
| 19 | KVFELDLVTL | 1063 | CENPF |
| 20 | ALVEKGEFAL | 1063 | CENPF |
| 21 | YLMDDFSSL | 1293 | COL6A3 |
| 22 | LMYPYIYHV | 54954 | FAM120C |
| 23 | ALLSPLSLA | 4017, 9583 | LOXL2, ENTPD4 |
| 24 | KVWSDVTPL | 4320, 4322 | MMP11, MMP13 |
| 25 | LLWGHPRVALA | 25878 | MXRA5 |
| 26 | VLDGKVAVV | 6660 | SOX5 |
| 27 | GLLGKVTSV | 51297 | BPIFA1 |
| 28 | IKVTDPQLLEL | 51297 | BPIFA1 |
| 29 | KMISAIPTL | 94025 | MUC16 |
| 30 | IITEVITRL | 94025 | MUC16 |
| 31 | GLLETTGLLAT | 94025 | MUC16 |
| 32 | VVMVLVLML | 94025 | MUC16 |
| 33 | TLDRNSLYV | 94025 | MUC16 |
| 34 | TLNTLDINL | 94025 | MUC16 |
| 35 | VIIKGLEEI | 3832 | KIF11 |
| 36 | TVLQELINV | 3832 | KIF11 |
| 37 | QIVELIEKI | 3832 | KIF11 |
| 38 | VLQQESNFL | 63967 | CLSPN |
| 39 | YLEDGFAYV | 5558 | PRIM2 |
| 40 | KIWEELSVLEV | 4102, 4105 | MAGEA3, MAGEA6 |
| 41 | IVTEIISEI | 64151 | NCAPG |
| 42 | KQMSISTGL | 64151 | NCAPG |
| 43 | LLIPFTIFM | 1237 | CCR8 |
| 44 | AVFNLVHVV | 56923 | NMUR2 |
| 45 | FLPVSVVYV | 56923 | NMUR2 |
| 46 | ISLDEVAVSL | 144455 | E2F7 |
| 47 | GLNGFNVLL | 144455 | E2F7 |

TABLE 1-continued

Peptides according to the present invention

| SEQ ID No. | Sequence | Gene ID(s) | Official Gene Symbol(s) |
|---|---|---|---|
| 48 | KISDFGLATV | 1111 | CHEK1 |
| 49 | KLIGNIHGNEV | 8532 | CPZ |
| 50 | ILLSVLHQL | 8532 | CPZ |
| 51 | LDSEALLTL | 84467 | FBN3 |
| 52 | TIGIPFPNV | 83990 | BRIP1 |
| 53 | AQHLSTLLL | 1469 | CST1 |
| 54 | YLVPGLVAA | 64180 | DPEP3 |
| 55 | HLFDKIIKI | 654463 | FER1L6 |
| 56 | VLQENSSDYQSNL | 3188 | HNRNPH2 |
| 57 | TLYPGRFDYV | 338322 | NLRP10 |
| 58 | HLLGEGAFAQV | 699 | BUB1 |
| 59 | ALADGIKSFLL | 5296 | PIK3R2 |
| 60 | YLFSQGLQGL | 2491 | CENPI |
| 61 | ALYPKEITL | 203102 | ADAM32 |
| 62 | SLVENIHVL | 675 | BRCA2 |
| 63 | KLLPMVIQL | 246 | ALOX15 |
| 64 | SLYAGSNNQV | 246 | ALOX15 |
| 65 | SLSEKSPEV | 158511, 728461 | CSAG1, CSAG2 |
| 66 | AMFPDTIPRV | 285220 | EPHA6 |
| 67 | FLIENLLAA | 3166 | HMX1 |
| 68 | QLMNLIRSV | 51124 | IER3IP1 |
| 69 | LKVLKADVVL | 259307 | IL4I1 |
| 70 | GLTEKTVLV | 24137, 285643 | KIF4A, KIF4B |
| 71 | HMSGKLTNV | 55771 | PRR11 |
| 72 | VLSTRVTNV | 55771 | PRR11 |
| 73 | SVPKTLGV | 11280 | SCN11A |
| 74 | GLAFLPASV | 6570 | SLC18A1 |
| 75 | ALLDGALQL | 6570 | SLC18A1 |
| 76 | FTAEFLEKV | 79801 | SHCBP1 |
| 77 | ALYGNVQQV | 91646 | TDRD12 |
| 78 | LFQSRIAGV | 7579 | ZSCAN20 |
| 79 | TVLEEIGNRV | 9133 | CCNB2 |
| 80 | VLTGQVHEL | 10715 | CERS1 |
| 81 | ILAEEPIYI | 55655 | NLRP2 |
| 82 | ILAEEPIYIRV | 55655 | NLRP2 |
| 83 | GLLENSPHL | 25788 | RAD54B |
| 84 | FLLEREQLL | 165055 | CCDC138 |
| 85 | KLLDKPEQFL | 342184 | FMN1 |

TABLE 1-continued

Peptides according to the present invention

| SEQ ID No. | Sequence | Gene ID(s) | Official Gene Symbol(s) |
|---|---|---|---|
| 86 | SLFSNIESV | 54848 | ARHGEF38 |
| 87 | KLLSLLEEA | 54848 | ARHGEF38 |
| 88 | LLLPLELSLA | 374946 | DRAXIN |
| 89 | SLAETIFIV | 3359 | HTR3A |
| 90 | AILNVDEKNQV | 3359 | HTR3A |
| 91 | LLPSIFLMV | 3359 | HTR3A |
| 92 | RLFEEVLGV | 9816 | URB2 |
| 93 | RLYGYFHDA | 6790 | AURKA |
| 94 | YLDEVAFML | 1238 | CCBP2 |
| 95 | KLIDEDEPLFL | 1767 | DNAH5 |
| 96 | ALDTTRHEL | 93323 | HAUS8 |
| 97 | KLFEKSTGL | 23421 | ITGB3BP |
| 98 | FVQEKIPEL | 84944 | MAEL |
| 99 | TLFGIQLTEA | 84944 | MAEL |
| 100 | ALQSFEFRV | 56130 | PCDHB6 |
| 101 | SLLEVNEASSV | 149628 | PYHIN1 |
| 102 | GLYPVTLVGV | 83696 | TRAPPC9 |
| 103 | YLADTVQKL | 100526761, 54937 | CCDC169-SOHLH2, SOHLH2 |
| 104 | DLPTQEPALGTT | 354 | KLK3 |
| 105 | AMLASQTEA | 4295 | MLN |
| 106 | VLLGSVVIFA | 4477 | MSMB |
| 107 | RVLPGQAVTGV | 55247 | NEIL3 |
| 108 | FIANLPPELKA | 6013 | RLN1 |
| 109 | ILGSFELQL | 7047 | TGM4 |
| 110 | QIQGQVSEV | 7047 | TGM4 |
| 111 | AQLEGKLVSI | 3161 | HMMR |
| 112 | ILAQDVAQL | 24137 | KIF4A |
| 113 | FLFLKEVKV | 54596 | L1TD1 |
| 114 | LLFPSDVQTL | 23397 | NCAPH |
| 115 | ILHGEVNKV | 54830 | NUP62CL |
| 116 | ALLSSVAEA | 9048 | ARTN |
| 117 | TLLEGISRA | 26256 | CABYR |
| 118 | IAYNPNGNAL | 3824 | KLRD1 |
| 119 | SLIEESEEL | 284217 | LAMA1 |
| 120 | LQLJPLKGLSL | 6241 | RRM2 |
| 121 | ALYVQAPTV | 9319 | TRIP13 |
| 122 | SIIDTELKV | 9319 | TRIP13 |

TABLE 1-continued

Peptides according to the present invention

| SEQ ID No. | Sequence | Gene ID(s) | Official Gene Symbol(s) |
|---|---|---|---|
| 123 | QTAPEEAFIKL | 150737, 92104 | TTC30B, TTC30A |
| 124 | ALLLRLFTI | 11169 | WDHD1 |
| 125 | AALEVLAEV | 11130 | ZWINT |
| 126 | QLREAFEQL | 11130 | ZWINT |
| 127 | IMKATGLGIQL | 154664 | ABCA13 |
| 128 | SILTNISEV | 24 | ABCA4 |
| 129 | KMASKVTQV | 132612 | ADAD1 |
| 130 | QLYGSAITL | 158067 | AK8 |
| 131 | SLYPHFTLL | 440138 | ALG11 |
| 132 | ALLNNVIEV | 57101 | ANO2 |
| 133 | FLDGRPLTL | 83734 | ATG10 |
| 134 | SLYKSFLQL | 527 | ATP6V0C |
| 135 | HLDTVKIEV | 135152 | B3GAT2 |
| 136 | LLWDAPAKC | 192134 | B3GNT6 |
| 137 | KLIYKDLVSV | 85016 | C11orf70 |
| 138 | GIINKLVTV | 440087 | C12orf69 |
| 139 | IILENIQSL | 55732 | C1orf112 |
| 140 | FLDSQITTV | 255119 | C4orf22 |
| 141 | NIDINNNEL | 57082 | CASC5 |
| 142 | LLDAAHASI | 284992 | CCDC150 |
| 143 | MLWESIMRV | 166979 | CDC20B |
| 144 | FLISQTPLL | 60437 | CDH26 |
| 145 | ALEEKLENV | 79172 | CENPO |
| 146 | VVAAHLAGA | 148113 | CILP2 |
| 147 | GLLSALENV | 1269 | CNR2 |
| 148 | YLILSSHQL | 1269 | CNR2 |
| 149 | NMADGQLHQV | 728577, 79937 | CNTNAP3B, CNTNAP3 |
| 150 | VLLDMVHSL | 100507170, 255313, 653282, 728036, 728042, 728049, 728062, 728072, 728075, 728082, 728090, 728096 | CT47A12, CT47A11, CT47A7, CT47A10, CT47A9, CT47A8, CT47A6, CT47A5, CT47A4, CT47A3, CT47A2, CT47A1 |
| 151 | DISKRIQSL | 100128553, 220429, 341689, 4253, 64693 | CTAGE4, CTAGE10P, CTAGE16P, CTAGE5, CTAGE1 |
| 152 | ILVTSIFFL | 643 | CXCR5 |
| 153 | KLVELEHTL | 203413 | CXorf61 |
| 154 | AIIKEIQTV | 1588 | CYP19A1 |
| 155 | TLDSYLKAV | 163720, 199974 | CYP4Z2P, CYP4Z1 |

TABLE 1-continued

Peptides according to the present invention

| SEQ ID No. | Sequence | Gene ID(s) | Official Gene Symbol(s) |
|---|---|---|---|
| 156 | VILTSSPFL | 10800 | CYSLTR1 |
| 157 | ILQDGQFLV | 138009 | DCAF4L2 |
| 158 | YLDPLWHQL | 2072 | ERCC4 |
| 159 | QLGPVPVTI | 285966 | FAM115C |
| 160 | TLQEWLTEV | 167555 | FAM151B |
| 161 | NLLDENVCL | 26290 | GALNT8 |
| 162 | GLLGNLLTSL | 51608 | GET4 |
| 163 | GLEERLYTA | 29933 | GPR132 |
| 164 | MLIIRVPSV | 80000 | GREB1L |
| 165 | SLLDYEVSI | 116444 | GRIN3B |
| 166 | LLGDSSFFL | 283254 | HARBI1 |
| 167 | LVVDEGSLVSV | 92797 | HELB |
| 168 | VIFEGEPMYL | 84072 | HORMAD1 |
| 169 | ALADLSVAV | 3363 | HTR7 |
| 170 | FIAAVVEKV | 203100 | HTRA4 |
| 171 | LLLLDVPTA | 10437 | IFI30 |
| 172 | SLYLQMNSLRTE | 28426 | IGHV3-43 |
| 173 | RLIDIYKNV | 338567 | KCNK18 |
| 174 | ALYSGDLHAA | 157855 | KCNU1 |
| 175 | SLLDLVQSL | 57536 | KIAA1328 |
| 176 | VQSGLRILL | 57650 | KIAA1524 |
| 177 | ALINVLNAL | 146909 | KIF18B |
| 178 | SLVSWQLLL | 3814 | KISS1 |
| 179 | TLGEIIKGV | 402569 | KPNA7 |
| 180 | RLYEEEIRI | 3887, 3889 | KRT81, KRT83 |
| 181 | LLWAPTAQA | 389812 | LCN15 |
| 182 | GLQDGFQITV | 284194, 654346 | LGALS9B, LGALS9C |
| 183 | ALSYILPYL | 147172 | LRRC37BP1 |
| 184 | ALDSTIAHL | 149499 | LRRC71 |
| 185 | TLYQGLPAEV | 80131 | LRRC8E |
| 186 | SLLSLESRL | 57408 | LRTM1 |
| 187 | SILKEDPFL | 346389 | MACC1 |
| 188 | VLGEEQEGV | 4108, 728269 | MAGEA9, MAGEA9B |
| 189 | MAVSDLLIL | 2862 | MLNR |
| 190 | SLSTELFKV | 4622, 4626 | MYH4, MYH8 |
| 191 | AAIEIFEKV | 55728 | N4BP2 |
| 192 | TLLPSSGLVTL | 344148 | NCKAP5 |
| 193 | ALFHMNILL | 126206 | NLRP5 |

TABLE 1-continued

Peptides according to the present invention

| SEQ ID No. | Sequence | Gene ID(s) | Official Gene Symbol(s) |
|---|---|---|---|
| 194 | KLLEEVQLL | 126206 | NLRP5 |
| 195 | VIIQNLPAL | 387129 | NPSR1 |
| 196 | TLHQWIYYL | 120406 | NXPE2 |
| 197 | LGGPTSLLHV | 390038 | OR51D1 |
| 198 | ILTNKVVSV | 119678 | OR52E2 |
| 199 | SVADLAHVL | 27334 | P2RY10 |
| 200 | IMPTFDLTKV | 203569, 389860 | PAGE2, PAGE2B |
| 201 | LLFSLLCEA | 51050 | PI15 |
| 202 | ALAKDELSL | 120379 | PIH1D2 |
| 203 | FLFVDPELV | 146850 | PIK3R6 |
| 204 | SEWGSPHAAVP | 5539 | PPY |
| 205 | LAFGYDDEL | 391004, 654348 | PRAMEF17, PRAMEF16 |
| 206 | GLDAFRIFL | 431704 | RGS21 |
| 207 | KLFETVEEL | 6121 | RPE65 |
| 208 | HLNNDRNPL | 6406 | SEMG1 |
| 209 | VLQTEELVAN | 6406 | SEMG1 |
| 210 | GLAGDNIYL | 6582 | SLC22A2 |
| 211 | LLTTVLINA | 6582 | SLC22A2 |
| 212 | MTLSEIHAV | 9153 | SLC28A2 |
| 213 | ILAVDGVLSV | 169026 | SLC30A8 |
| 214 | ALFETLIQL | 139420 | SMEK3P |
| 215 | QIADIVTSV | 139420 | SMEK3P |
| 216 | ALSTVTPRI | 166378 | SPATA5 |
| 217 | LLWPSSVPA | 246777, 79400 | SPESP1, NOX5 |
| 218 | SLTGANITV | 83932 | SPRTN |
| 219 | GVVPTIQKV | 64220 | STRA6 |
| 220 | ALSELERVL | 51298 | THEG |
| 221 | IMLNSVEEI | 387357 | THEMIS |
| 222 | LLTGVFAQL | 388564 | TMEM238 |
| 223 | ALHPVQFYL | 93587 | TRMT10A |
| 224 | LLFDWSGTGRADA | 79465 | ULBP3 |
| 225 | FLPQPVPLSV | 57695 | USP37 |
| 226 | SLAGNLQEL | 11023 | VAX1 |
| 227 | SEMEELPSV | 26609, 425054, 51481 | VCX, VCX3B, VCX3A |
| 228 | SLLELDGINLRL | 221806 | VWDE |
| 229 | YLYELEHAL | 80217 | WDR96 |
| 230 | KLLNMIFSI | 2829 | XCR1 |

TABLE 1-continued

Peptides according to the present invention

| SEQ ID No. | Sequence | Gene ID(s) | Official Gene Symbol(s) |
|---|---|---|---|
| 231 | LLDDIFIRL | 143570 | XRRA1 |
| 232 | LVVGGIATV | 84614 | ZBTB37 |
| 233 | SLFESLEYL | 132625 | ZFP42 |

TABLE 2

Additional peptides according to the present invention

| SEQ ID No. | Sequence | Gene ID(s) | Official Gene Symbol(s) |
|---|---|---|---|
| 234 | VLLNEILEQV | 64151 | NCAPG |
| 235 | SLLNQPKAV | 63967 | CLSPN |
| 236 | KMSELQTYV | 1063 | CENPF |
| 237 | ALLEQTGDMSL | 1063 | CENPF |
| 238 | HLQEKLQSL | 1063 | CENPF |
| 239 | VIIKGLEEITV | 3832 | KIF11 |
| 240 | SVQENIQQK | 3832 | KIF11 |
| 241 | KQFEGTVEI | 675 | BRCA2 |
| 242 | KLQEEIPVL | 1062 | CENPE |
| 243 | GLAEFQENV | 57405 | SPC25 |
| 244 | NVAEIVIHI | 83540 | NUF2 |
| 245 | ALLEEEEGV | 4103 | MAGEA4 |
| 246 | ALAGIVTNV | 11077 | HSF2BP |
| 247 | NLLIDDKGTIKL | 983 | CDK1 |
| 248 | VLMQDSRLYL | 983 | CDK1 |
| 249 | YLYQILQGI | 983 | CDK1 |
| 250 | LMQDSRLYL | 983 | CDK1 |
| 251 | LLWGNLPEI | 653820, 729533 | FAM72B, FAM72A |
| 252 | SLMEKNQSL | 24137, 285643 | KIF4A, KIF4B |
| 253 | KLLAVIHEL | 25788 | RAD54B |
| 254 | ALGDKFLLRV | 4608 | MYBPH |
| 255 | FLMKNSDLYGA | 79801 | SHCBP1 |
| 256 | FLNDIFERI | 337873, 337874 | HIST2H2BC, HIST2H2BD |
| 257 | KLIDHQGLYL | 7579 | ZSCAN20 |
| 258 | QLVQRVASV | 5683 | PSMA2 |
| 259 | GPGIFPPPPQP | 10879 | SMR3B |
| 260 | ALNESLVEC | 55165 | CEP55 |
| 261 | GLAALAVHL | 2175 | FANCA |
| 262 | LLLEAVWHL | 2175 | FANCA |
| 263 | SIIEYLPTL | 79915 | ATAD5 |
| 264 | TLHDQVHLL | 2099 | ESR1 |
| 265 | FLLDKPQDLSI | 346389 | MACC1 |
| 266 | FLLDKPQDL | 346389 | MACC1 |
| 267 | YLLDMPLWYL | 7153 | TOP2A |
| 268 | SLDKDIVAL | 7153 | TOP2A |
| 269 | GLLDCPIFL | 2177 | FANCD2 |
| 270 | TLLTFFHEL | 55215 | FANCI |
| 271 | VLIEYNFSI | 55215 | FANCI |
| 272 | FVMEGEPPKL | 348654 | GEN1 |
| 273 | SLNKQIETV | 57650 | KIAA1524 |
| 274 | TLYNPERTITV | 10642, 10643 | IGF2BP1, IGF2BP3 |
| 275 | AVPPPPSSV | 10642 | IGF2BP1 |
| 276 | RMPTVLQCV | 9622 | KLK4 |
| 277 | KLQEELNKV | 3161 | HMMR |
| 278 | VLEDKVLSV | 128239 | IQGAP3 |
| 279 | VLMDEGAVLTL | 54596 | L1TD1 |
| 280 | HLWGHALFL | 89866 | SEC16B |
| 281 | LLLESDPKVYSL | 6491 | STIL |
| 282 | SLYALHVKA | 79001 | VKORC1 |
| 283 | ALSELLQQV | 9816 | URB2 |
| 284 | KLMDPGSLPPL | 2118 | ETV4 |
| 285 | MLLDTVQKV | 54892 | NCAPG2 |
| 286 | FLTEMVHFI | 93517 | SDR42E1 |
| 287 | KIQEILTQV | 10643 | IGF2BP3 |
| 288 | SLYKGLLSV | 25788 | RAD54B |

J = Phosphoserine

Particularly preferred are the peptides—alone or in combination—according to the present invention selected from the group consisting of SEQ ID NO: 1 to SEQ ID NO: 288. More preferred are the peptides—alone or in combination—selected from the group consisting of SEQ ID NO: 1 to SEQ ID NO: 126 (see Table 1), and their uses in the immunotherapy of hepatocellular carcinoma (HCC), colorectal carcinoma (CRC), glioblastoma (GB), gastric cancer (GC), esophageal cancer, non-small cell lung cancer (NSCLC), pancreatic cancer (PC), renal cell carcinoma (RCC), benign prostate hyperplasia (BPH), prostate cancer (PCA), ovarian cancer (OC), melanoma, breast cancer, chronic lymphocytic leukemia (CLL), Merkel cell carcinoma (MCC), small cell lung cancer (SCLC), Non-Hodgkin lymphoma (NHL), acute myeloid leukemia (AML), gallbladder cancer and cholangiocarcinoma (GBC, CCC), urinary bladder cancer (UBC), uterine cancer (UEC).

Most preferred are the peptides—alone or in combination—selected from the group consisting of SEQ ID NO: 274, 14, 21, 23, 25, 157, 168, 11, 253, 85, 89, 40, 264, 155, 233, and 245 (see Tables 1, 2, and 10), and their uses in the immunotherapy of HCC, CRC, GB, GC, esophageal cancer, NSCLC, PC, RCC, BPH/PCA, OC, MCC, melanoma, breast cancer, SCLC, NHL, AML, GBC, CCC, UBC, UEC, and CLL.

The present invention furthermore relates to peptides according to the present invention that have the ability to bind to a molecule of the human major histocompatibility complex (MHC) class-I or—in an elongated form, such as a length-variant—MHC class-II.

The present invention further relates to the peptides according to the present invention wherein said peptides (each) consist or consist essentially of an amino acid sequence according to SEQ ID NO: 1 to SEQ ID NO: 288.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention. The present invention further relates to the nucleic acid according to the present invention that is DNA, cDNA, PNA, RNA or combinations thereof.

The present invention further relates to an expression vector capable of expressing and/or expressing a nucleic acid according to the present invention.

The present invention further relates to a peptide according to the present invention, a nucleic acid according to the present invention or an expression vector according to the present invention for use in the treatment of diseases and in medicine, in particular in the treatment of cancer.

The present invention further relates to antibodies that are specific against the peptides according to the present invention or complexes of said peptides according to the present invention with MHC, and methods of making these.

The present invention further relates to T-cell receptors (TCRs), in particular soluble TCR (sTCRs) and cloned TCRs engineered into autologous or allogeneic T cells, and methods of making these, as well as NK cells or other cells bearing said TCR or cross-reacting with said TCRs.

The antibodies and TCRs are additional embodiments of the immunotherapeutic use of the peptides according to the invention at hand.

The present invention further relates to a host cell comprising a nucleic acid according to the present invention or an expression vector as described before. The present invention further relates to the host cell according to the present invention that is an antigen presenting cell, and preferably is a dendritic cell.

The present invention further relates to a method for producing a peptide according to the present invention, said method comprising culturing the host cell according to the present invention, and isolating the peptide from said host cell or its culture medium.

The present invention further relates to said method according to the present invention, wherein the antigen is loaded onto class I or II MHC molecules expressed on the surface of a suitable antigen-presenting cell or artificial antigen-presenting cell by contacting a sufficient amount of the antigen with an antigen-presenting cell.

The present invention further relates to the method according to the present invention, wherein the antigen-presenting cell comprises an expression vector capable of expressing or expressing said peptide containing SEQ ID No. 1 to SEQ ID No.: 288, preferably containing SEQ ID No. 1 to SEQ ID No.: 126, or a variant amino acid sequence.

The present invention further relates to activated T cells, produced by the method according to the present invention, wherein said T cell selectively recognizes a cell which expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as produced according to the present invention.

The present invention further relates to the use of any peptide as described, the nucleic acid according to the present invention, the expression vector according to the present invention, the cell according to the present invention, the activated T lymphocyte, the T cell receptor or the antibody or other peptide- and/or peptide-MHC-binding molecules according to the present invention as a medicament or in the manufacture of a medicament. Preferably, said medicament is active against cancer.

Preferably, said medicament is suitable and used for a cellular therapy, a vaccine or a protein based on a soluble TCR or antibody.

The present invention further relates to a use according to the present invention, wherein said cancer cells are HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL cells.

The present invention further relates to biomarkers based on the peptides according to the present invention, herein called "targets" that can be used in the diagnosis of cancer, preferably HCC, CRC, GB, GC, esophageal cancer, NSCLC, PC, RCC, BPH/PCA, OC, MCC, melanoma, breast cancer, SCLC, NHL, AML, GBC, CCC, UBC, UEC, and CLL. The marker can be either over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC.

Optionally the antibody carries a further effector function such as an immune stimulating domain or toxin.

The present invention also relates to the use of these novel targets in the context of cancer treatment.

CABYR encodes a protein which localizes to the principal piece of the sperm flagellum in association with the fibrous sheath and exhibits calcium-binding when phosphorylated during the process of capacitation (RefSeq, 2002). Knock-down of the CABYR isoforms CABYR-a and CABYR-b in the non-small cell lung cancer cell lines NCI-H460 and A549 was shown to result in inhibition of proliferation and attenuation of constitutively active Akt phosphorylation (Qian et al., 2014). Silencing of CABYR expression was shown to impact down-stream components of the Akt pathways such as phospho-GSK-3beta and the p53 and p27 proteins (Qian et al., 2014). Furthermore, CABYR knock-down was shown to significantly increase chemosensitivity in response to chemotherapeutic drugs and drug-induced apoptosis, both in vitro and in vivo, and may thus be a novel method to improve the apoptotic response and chemosensitivity in lung cancer (Qian et al., 2014). CABYR was described as an initially testis-specific protein which was subsequently shown to be present in brain tumors, pancreas cancer and lung cancer (Hsu et al., 2005; Luo et al., 2007; Li et al., 2012). CABYR was shown to be up-regulated in hepatocellular carcinoma and may play an oncogenic role in hepatocarcinogenesis as well as its progression (Li et al., 2012).

COL6A3 encodes collagen, type VI, alpha 3, one of the three alpha chains of type VI collagen, a beaded filament collagen found in most connective tissues, and important in organizing matrix components (RefSeq, 2002). COL6A3 encodes the alpha-3 chain of type VI collagen, a beaded filament collagen found in most connective tissues, playing an important role in the organization of matrix components (RefSeq, 2002). COL6A3 is alternatively spliced in colon, bladder and prostate cancer. The long isoform of COL6A3 is expressed almost exclusively in cancer samples and could potentially serve as a new cancer marker (Thorsen et al., 2008). COL6A3 is highly expressed in pancreatic ductal adenocarcinoma tissue and undergoes tumor-specific alternative splicing (Kang et al., 2014). COL6A3 has been demonstrated to correlate with high-grade ovarian cancer and contributes to cisplatin resistance. COL6A3 was observed to be frequently over-expressed in gastric cancer tissues (Xie et al., 2014). COL6A3 mutation(s) significantly predicted a better overall survival in patients with colorectal carcinoma independent of tumor differentiation and TNM staging (Yu et al., 2015). COL6A3 expression was reported to be increased in pancreatic cancer, colon cancer, gastric cancer, mucoepidermoid carcinomas and ovarian cancer. Cancer associated transcript variants including exons 3, 4 and 6 were detected in colon cancer, bladder cancer, prostate cancer and pancreatic cancer (Arafat et al., 2011; Smith et al., 2009; Yang et al., 2007; Xie et al., 2014; Leivo et al., 2005; Sherman-Baust et al., 2003; Gardina et al., 2006; Thorsen et al., 2008). In ovarian cancer COL6A3 levels correlated with higher tumor grade and in pancreatic cancer COL6A3 was shown to represent a suitable diagnostic serum biomarker (Sherman-Baust et al., 2003; Kang et al., 2014).

CXorf61, also known as CT83, encodes the cancer/testis antigen 83 and is located on chromosome Xq23 (RefSeq, 2002). Expression of CXorf61 has been described in different cancer types, including breast cancer and lung cancer (Yao et al., 2014; Hanagiri et al., 2013; Baba et al., 2013). CXorf61 was shown to be an immunogenic cancer-testis antigen in lung cancer. Therefore, it might represent a promising candidate for anti-cancer immunotherapy (Fukuyama et al., 2006).

CYP4Z1 encodes a member of the cytochrome P450 superfamily of enzymes. The cytochrome P450 proteins are monooxygenases which catalyze many reactions involved in drug metabolism and synthesis of cholesterol, steroids and other lipids (RefSeq, 2002). CYP4Z1 over-expression in breast cancer is associated with high tumor grade and poor prognosis. Functionally, CYP4Z1 promotes tumor angiogenesis and growth in breast cancer partly via PI3/Akt and ERK1/2 signaling (Yu et al., 2012; Murray et al., 2010). Additionally, CYP4Z1 was described to play a role in non-small-cell lung cancer progression (Bankovic et al., 2010). In prostate cancer and ovarian cancer, CYP4Z1 has been identified as independent predictive marker (Tradonsky et al., 2012; Downie et al., 2005). CYP4Z2P is a pseudogene located on chromosome 1p33 (RefSeq, 2002).

DCAF4L2 encodes the DDB1 and CUL4 associated factor 4-like 2. The specific function of this protein remains to be elucidated; nevertheless the DCAF4L2 gene was shown to be associated with optic disc morphology and cleft lip development (Springelkamp et al., 2015; Beaty et al., 2013).

ESR1 encodes an estrogen receptor, a ligand-activated transcription factor important for hormone binding, DNA binding and activation of transcription, that is essential for sexual development and reproductive function (RefSeq, 2002). Mutations and single nucleotide polymorphisms of ESR1 are associated with risk for different cancer types including liver, prostate, gallbladder and breast cancer. The up-regulation of ESR1 expression is connected with cell proliferation and tumor growth but the overall survival of patients with ESR1 positive tumors is better due to the successfully therapy with selective estrogen receptor modulators (Sun et al., 2015; Hayashi et al., 2003; Bogush et al., 2009; Miyoshi et al., 2010; Xu et al., 2011; Yakimchuk et al., 2013; Fuqua et al., 2014). ESR1 signaling interferes with different pathways responsible for cell transformation, growth and survival like the EGFR/IGFR, PI3K/Akt/mTOR, p53, HER2, NFkappaB and TGF-beta pathways (Frasor et al., 2015; Band and Laiho, 2011; Berger et al., 2013; Skandalis et al., 2014; Mehta and Tripathy, 2014; Ciruelos Gil, 2014).

FMN1 encodes formin1 a protein that has a role in the formation of adherent junctions and the polymerization of linear actin cables (RefSeq, 2002). A single nucleotide polymorphism in FMN1 is associated with an increased risk of prostate cancer (Lisitskaia et al., 2010).

HAVCR1, also known as hepatitis A virus cellular receptor 1 or KIM-1, encodes a membrane receptor protein for both human hepatitis A virus and TIMD4 and may be involved in the moderation of asthma and allergic diseases (RefSeq, 2002). HAVCR1 was described as a novel biomarker candidate associated with ovarian clear cell carcinoma and renal cell carcinoma (Bonventre, 2014; Kobayashi et al., 2015). HAVCR1 was shown to activate the IL-6/STAT-3/HIF-1A axis in clear cell renal cell carcinoma-derived cell lines and determines tumor progression and patient outcome (Cuadros et al., 2014). Constitutive expression of HAVCR1 in the kidney was described as a potential susceptibility trait for clear cell renal cell carcinoma development (Cuadros et al., 2013). Furthermore, enhanced HAVCR1 ecto-domain shedding was shown to promote an invasive phenotype in vitro and more aggressive tumors in vivo (Cuadros et al., 2013). HAVCR1 was described as being up-regulated in renal cell and ovarian clear cell carcinomas and colorectal cancer (Wang et al., 2013b).

HAVCR1 up-regulation was described as a potential diagnostic biomarker for colorectal cancer and a prognostic marker for a longer disease-free interval after surgery, which may also be involved in the metastatic cascade in colorectal cancer (Wang et al., 2013b). HAVCR1 was shown to be associated with T cell large granular lymphocyte leukemia (Wlodarski et al., 2008).

HORMAD1 (also called CT46) encodes a NORMA domain-containing protein that may play a role in meiosis. NORMA domains are involved in chromatin binding and cell cycle regulation (RefSeq, 2002). HORMAD1 is a cancer/testis antigen over-expressed in different cancer types including breast, gastric and ovarian cancer and thereby a potential biomarker and immunotherapeutic target (Yao et al., 2014; Shahzad et al., 2013; Chen et al., 2005; Aung et al., 2006; Adelaide et al., 2007). HORMAD1 down-regulation leads to reduction of invasion, migration and tumor weight and decreased VEGF protein levels (Shahzad et al., 2013).

HSF2BP encodes the HSF2 binding protein which associates with HSF2 and may be involved in modulating HSF2 activation (RefSeq, 2002).

HSF4 encodes heat-shock transcription factor 4, which activates heat-shock response genes under conditions of heat or other stresses (RefSeq, 2002). HSF4 was shown to be down-regulated in glioblastoma (Mustafa et al., 2010).

HTR3A encodes a 5-hydroxytryptamine (serotonin) receptor belonging to the ligand-gated ion channel receptor superfamily that causes fast, depolarizing responses in neurons after activation (RefSeq, 2002). HTR3A (also called 5-HT3) is de-regulated in several cancer types for example a down-regulation in mantle cell lymphomas, a differential expression in diverse B cell tumors and a decreased expression in breast cancer cell lines (Pai et al., 2009; Rinaldi et al., 2010; Ek et al., 2002).

IGF2BP1, also known as CRD-BP, encodes a member of the insulin-like growth factor 2 mRNA-binding protein family which functions by binding to the mRNAs of certain genes and regulating their translation (RefSeq, 2002). Two members of the IGF2 mRNA binding protein family, including IGF2BP1 were described as bona fide oncofetal proteins which are de novo synthesized in various human cancers and which may be powerful post-transcriptional oncogenes enhancing tumor growth, drug-resistance and metastasis (Lederer et al., 2014). Expression of IGF2BP1 was reported to correlate with an overall poor prognosis and metastasis in various human cancers (Lederer et al., 2014). Thus, IGF2BP1 was suggested to be a powerful biomarker and candidate target for cancer therapy (Lederer et al., 2014). IGF2BP family members were described to be highly associated with cancer metastasis and expression of oncogenic factors such as KRAS, MYC and MDR1 (Bell et al., 2013). IGF2BP1 was shown to interact with C-MYC and was found to be expressed in the vast majority of colon and breast tumors and sarcomas as well as in benign tumors such as breast fibroadenomas and meningiomas (Ioannidis et al., 2003). IGF2BP1 was shown to be up-regulated in hepatocellular carcinoma and basal cell carcinoma (Noubissi et al., 2014; Zhang et al., 2015a). Up-regulation of IGF2BP1 and other genes was shown to be significantly associated with poor post-surgery prognosis in hepatocellular carcinoma (Zhang et al., 2015a). IGF2BP1 was shown to be a target of the tumor suppressor miR-9 and miR-372 in hepatocellular carcinoma and in renal cell carcinoma, respectively (Huang et al., 2015; Zhang et al., 2015a). Loss of stromal IGF2BP1 was shown to promote a tumorigenic microenvironment in the colon, indicating that IGF2BP1 plays a tumor-suppressive role in colon stromal cells (Hamilton et al., 2015). IGF2BP1 was shown to be associated with stage 4 tumors, decreased patient survival and MYCN gene amplification in neuroblastoma and may therefore be a potential oncogene and an independent negative prognostic factor in neuroblastoma (Bell et al., 2015). IGF2BP1 was described as a direct target of WNT/11-catenin signaling which regulates GLI1 expression and activities in the development of basal cell carcinoma (Noubissi et al., 2014).

IGF2BP3 encodes insulin-like growth factor II mRNA binding protein 3, an oncofetal protein, which represses translation of insulin-like growth factor II (RefSeq, 2002). Several studies have shown that IGF2BP3 acts in various important aspects of cell function, such as cell polarization, migration, morphology, metabolism, proliferation and differentiation. In vitro studies have shown that IGF2BP3 promotes tumor cell proliferation, adhesion, and invasion. Furthermore, IGF2BP3 has been shown to be associated with aggressive and advanced cancers (Bell et al., 2013; Gong et al., 2014). IGF2BP3 over-expression has been described in numerous tumor types and correlated with poor prognosis, advanced tumor stage and metastasis, as for example in neuroblastoma, colorectal carcinoma, intrahepatic cholangiocarcinoma, hepatocellular carcinoma, prostate cancer, and renal cell carcinoma (Bell et al., 2013; Findeis-Hosey and Xu, 2012; Hu et al., 2014; Szarvas et al., 2014; Jeng et al., 2009; Chen et al., 2011; Chen et al., 2013; Hoffmann et al., 2008; Lin et al., 2013; Yuan et al., 2009).

MAGEA3 encodes melanoma-associated antigen family member A3. MAGEA3 is widely known as cancer-testis antigen (RefSeq, 2002; Pineda et al., 2015; De et al., 1994). MAGEA3 has been known long time for being used in therapeutic vaccination trials of metastatic melanoma cancer. The currently performed percutaneous peptide immunization with MAGEA3 and 4 other antigens of patients with advanced malignant melanoma was shown to contribute significantly to longer overall survival by complete responders compared to incomplete responders (Coulie et al., 2002; Fujiyama et al., 2014). In NSCLC, MAGEA3 was shown to be frequently expressed. The expression of MAGEA3 correlated with higher number of tumor necrosis in NSCLC tissue samples and was shown to inhibit the proliferation and invasion and promote the apoptosis in lung cancer cell line. By the patients with adenocarcinomas, the expression of MAGEA3 was associated with better survival. The whole cell anti MAGEA3 vaccine is currently under the investigation in the promising phase III clinical trial for treatment of NSCLC (Perez et al., 2011; Reck, 2012; Hall et al., 2013; Grah et al., 2014; Liu et al., 2015). MAGEA3 together with 4 other genes was shown to be frequently expressed in HCC. The expression of those genes was correlated with the number of circulating tumor cells, high tumor grade and advanced stage in HCC patients. The frequency of liver metastasis was shown to be significantly higher in cases with tumor samples that expressed MAGE3 than in those that did not express this gene (Bahnassy et al., 2014; Hasegawa et al., 1998). Cancer stem cell-like side populations isolated from a bladder cancer cell line as well as from lung, colon, or breast cancer cell lines showed expression of MAGEA3 among other cancer-testis antigens. In general, cancer stem cells are known for being resistant to current cancer therapy and cause post-therapeutic cancer recurrence and progression. Thus, MAGEA3 may serve as a novel target for immunotherapeutic treatment in particular of bladder cancer (Yamada et al., 2013; Yin et al., 2014). In head and neck squamous cell carcinoma, the expression of MAGEA3 was shown to be associated with better disease-free survival (Zamuner et al., 2015). Furthermore, MAGEA3 can be used as a prognostic marker for ovarian cancer (Szajnik et al., 2013).

MAGEA4, also known as MAGE4, encodes a member of the MAGEA gene family and is located on chromosome Xq28 (RefSeq, 2002). MAGEA4 was described as a cancer testis antigen which was found to be expressed in a small fraction of classic seminomas but not in non-seminomatous testicular germ cell tumors, in breast carcinoma, Epstein-Barr Virus-negative cases of Hodgkin's lymphoma, esophageal carcinoma, lung carcinoma, bladder carcinoma, head and neck carcinoma, and colorectal cancer, oral squamous cell carcinoma, and hepatocellular carcinoma (Ries et al., 2005; Bode et al., 2014; Li et al., 2005; Ottaviani et al., 2006; Hennard et al., 2006; Chen et al., 2003). MAGEA4 was shown to be frequently expressed in primary mucosal melanomas of the head and neck and thus may be a potential target for cancer testis antigen-based immunotherapy (Prasad et al., 2004). MAGEA4 was shown to be preferentially expressed in cancer stem-like cells derived from LHK2 lung adenocarcinoma cells, SW480 colon adenocarcinoma cells and MCF7 breast adenocarcinoma cells (Yamada et al., 2013). Over-expression of MAGEA4 in spontaneously transformed normal oral keratinocytes was shown to promote growth by preventing cell cycle arrest and by inhibiting apoptosis mediated by the p53 transcriptional targets BAX and CDKN1A (Bhan et al., 2012). MAGEA4 was shown to be more frequently expressed in hepatitis C virus-infected patients with cirrhosis and late-stage hepatocellular carcinoma compared to patients with early stage hepatocellular carcinoma, thus making the detection of MAGEA4 transcripts potentially helpful to predict prognosis (Hussein et al., 2012). MAGEA4 was shown to be one of several cancer/testis antigens that are expressed in lung cancer and which may function as potential candidates in lung cancer patients for polyvalent immunotherapy (Kim et al., 2012). MAGEA4 was described as being up-regulated in esophageal carcinoma and hepatocellular carcinoma (Zhao et al., 2002; Wu et al., 2011). A MAGEA4-derived native peptide analogue called p286-1Y2L9L was described as a novel candidate epitope suitable to develop peptide vaccines against esophageal cancer (Wu et al., 2011). Several members of the MAGE gene family, including MAGEA4, were shown to be frequently mutated in melanoma (Caballero et al., 2010).

MAGEA6 encodes melanoma-associated antigen family member A6. MAGEA3 is widely known as cancer-testis antigen (RefSeq, 2002; Pineda et al., 2015; De et al., 1994). MAGEA6 was shown to be frequently expressed in melanoma, advanced myeloma, pediatric rhabdomyosarcoma, sarcoma, lung, bladder, prostate, breast, and colorectal cancers, head and neck squamous cell, esophageal squamous cell, and oral squamous cell carcinomas (Ries et al., 2005; Hasegawa et al., 1998; Gibbs et al., 2000; Dalerba et al., 2001; Otte et al., 2001; van der Bruggen et al., 2002; Lin et al., 2004; Tanaka et al., 1997). MAGEA6 expression has been associated with shorter progression-free survival in multiple myeloma patients. In contrast in head and neck squamous cell carcinoma, the expression of MAGEA6 was shown to be associated with better disease-free survival (van et al., 2011; Zamuner et al., 2015). MAGEA6 was among a set of genes overexpressed in a paclitaxel-resistant ovarian cancer cell line. Moreover, transfection of MAGEA6 also conferred increased drug resistance to paclitaxel-sensitive cells (Duan et al., 2003). MAGEA6 can be used as a prognostic marker for ovarian cancer (Szajnik et al., 2013). Cancer stem cell-like side populations isolated from lung, colon, or breast cancer cell lines showed expression of MAGEA6 among other cancer-testis antigens (Yamada et al., 2013).

MAGEA9, also known as MAGE9 or MAGE-A9, encodes a member of the MAGEA gene family and is located on chromosome Xq28 (RefSeq, 2002). High expression of MAGEA9 in tumor and stromal cells of non-small cell lung cancer was shown to be correlated with poor survival (Zhang et al., 2015b). MAGEA9 expression was described as an independent prognostic factor for the five-year overall survival rate in non-small cell lung cancer (Zhang et al., 2015b). MAGEA9 presence in newly diagnosed cases of multiple myeloma was shown to be associated with shorter overall survival (van et al., 2011). MAGEA9 was described as a renal cell carcinoma antigen whose application in dendritic cell vaccination in BALB/c mice was shown to result in rejection of low-dose RENCA-MAGEA9 renal cell carcinoma grafts (Herbert et al., 2010). MAGEA9 peptide-specific cytotoxic T-lymphocyte lines were shown to display high cytotoxic activity against peptide-loaded T2 cells and naturally MAGEA9 expressing renal cell carcinoma cell lines, which makes MAGEA9 a potential suitable target for immunotherapy of renal cell carcinoma (Oehlrich et al., 2005). MAGEA9 was shown to be one of the most commonly expressed cancer testis antigens in uterine cancers (Risinger et al., 2007). MAGEA9 was described as a MAGE family member, which is expressed in testicular cancer (Zhan et al., 2015). High MAGEA9 expression was shown to be associated with venous invasion and lymph node metastasis in colorectal cancer (Zhan et al., 2015). MAGEA9 expression was shown to be associated with a lower survival rate in colorectal cancer and high MAGEA9 expression was described as a poor prognostic factor in colorectal cancer patients (Zhan et al., 2015). Thus, MAGEA9 is expected to become a new target for colorectal cancer treatment (Zhan et al., 2015). MAGEA9 over-expression was shown to be predictive of poor prognosis in epithelial ovarian cancer, invasive ductal breast cancer, laryngeal squamous cell carcinoma and hepatocellular carcinoma (Gu et al., 2014; Han et al., 2014; Xu et al., 2014; Xu et al., 2015). MAGEA9 was shown to be up-regulated in laryngeal squamous cell carcinoma, invasive ductal breast cancer, epithelial ovarian cancer, colorectal cancer and hepatocellular carcinoma (Gu et al., 2014; Han et al., 2014; Xu et al., 2014; Xu et al., 2015; Zhan et al., 2015).

MAGEA9B encodes a duplication of the MAGEA9 protein on the X chromosome (RefSeq, 2002). MAGEA9B expression in tumor stage 1b non-small cell lung cancer is correlated with patient survival (Urgard et al., 2011).

MMP1 encodes a member of the peptidase M10 family of matrix metalloproteinases (MMPs). Proteins in this family are involved in the breakdown of extracellular matrix in normal physiological processes, such as embryonic development, reproduction, and tissue remodeling, as well as in disease processes, such as arthritis and metastasis (RefSeq, 2002). Many authors have demonstrated a positive correlation between the pattern of MMP expression and the tumor invasive and metastatic potential including: rectal and gastric cancer, lung carcinoma, breast, ovarian, prostate, thyroid cancer and brain tumors (Velinov et al., 2010). MMP1 was identified as a biomarker with tumor stage-dependent expression in laryngeal squamous cell carcinoma (Hui et al., 2015). Breast cancer patients with circulating tumor cells with epithelial-mesenchymal transition (CTC_EMT) in peripheral blood had significantly increased expression of MMP1 in tumor cells ($p=0.02$) and tumor associated stroma ($p=0.05$) than those of patients without CTC_EMT (Cierna et al., 2014). In a mouse model MMP1 expression and secretion was blocked by a specific anti-FGFR3 monoclonal antibody which substantially blocked tumor progression (Du et al., 2014).

Proteins of the matrix metalloproteinase (MMP) family are involved in the breakdown of extracellular matrix in normal physiological processes, such as embryonic development, reproduction, and tissue remodeling, as well as in disease processes, such as arthritis and metastasis. However, the enzyme encoded by this gene is activated intracellularly by furin within the constitutive secretory pathway. Also in contrast to other MMP's, this enzyme cleaves alpha 1-proteinase inhibitor but weakly degrades structural proteins of the extracellular matrix (RefSeq, 2002). MMP-11, also named stromelysin-3, is a member of the stromelysin subgroup belonging to MMPs superfamily, which has been detected in cancer cells, stromal cells and adjacent microenvironment. Differently, MMP-11 exerts a dual effect on tumors. On the one hand MMP-11 promotes cancer development by inhibiting apoptosis as well as enhancing migration and invasion of cancer cells; on the other hand MMP-11 plays a negative role against cancer development via suppressing metastasis in animal models. Overexpression of MMP-11 was discovered in sera of cancer patients compared with normal control group as well as in multiple tumor tissue specimens, such as gastric cancer, breast cancer, and pancreatic cancer (Zhang et al., 2016). MMP-11 was demonstrated to be over-expressed at mRNA level and protein level in CRC tissue than paired normal mucosa. Further MMP-11 expression was correlated with CRC lymph node metastasis; distant metastasis and TNM stage (Tian et al., 2015). MMP-11 overexpression is associated with aggressive tumor phenotype and unfavorable clinical outcome in upper urinary tract urothelial carcinomas (UTUC) and urinary bladder urothelial carcinomas (UBUC), suggesting it may serve as a novel prognostic and therapeutic target (Li et al., 2016).

MXRA5 encodes one of the matrix-remodeling associated proteins, which contains 7 leucine-rich repeats and 12 immunoglobulin-like C2-type domains related to perlecan (RefSeq, 2002). A Chinese study identified MXRA5 as the second most frequently mutated gene in non-small cell lung cancer (Xiong et al., 2012). In colon cancer, MXRA5 was shown to be over-expressed and might serve as a biomarker for early diagnosis and omental metastasis (Zou et al., 2002; Wang et al., 2013a).

RAD54 encodes a protein belonging to the DEAD-like helicase superfamily. It shares similarity with *Saccharomyces cerevisiae* RAD54 and RDH54, both of which are involved in homologous recombination and repair of DNA. This protein binds to double-stranded DNA, and displays ATPase activity in the presence of DNA. This gene is highly expressed in testis and spleen, which suggests active roles in meiotic and mitotic recombination (RefSeq, 2002). Homozygous mutations of RAD54B were observed in primary lymphoma and colon cancer (Hiramoto et al., 1999). RAD54B counteracts genome-destabilizing effects of direct binding of RAD51 to dsDNA in human tumor cells (Mason et al., 2015).

ZFP42 (also called REX1) encodes a zinc finger protein used as stem cell marker and essential for pluripotency and re-programming (Son et al., 2013; Mongan et al., 2006). The expression of ZFP42 is down-regulated in prostate cancer cells and renal cell carcinoma, but in contrast up-regulated in squamous cell carcinoma (Raman et al., 2006; Lee et al., 2010; Reinisch et al., 2011). ZFP42 inhibits the JAK/STAT signaling pathway via the regulation of SOCS3 expression, which modulates cell differentiation (Xu et al., 2008).

Stimulation of an immune response is dependent upon the presence of antigens recognized as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

The term "T-cell response" means the specific proliferation and activation of effector functions induced by a peptide in vitro or in vivo. For MHC class I restricted cytotoxic T cells, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, or 13 amino acids or longer, and in case of MHC class II peptides (elongated variants of the peptides of the invention) they can be as long as 14, 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present invention differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 1

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24:02 | Japan | 59% |
| A*24 | Malaysia | 58% |
| A*24:02 | Philippines | 54% |
| A*24 | India | 47% |
| A*24 | South Korea | 40% |
| A*24 | Sri Lanka | 37% |
| A*24 | China | 32% |
| A*24:02 | India | 29% |
| A*24 | Australia West | 22% |
| A*24 | USA | 22% |
| A*24 | Russia Samara | 20% |

TABLE 1-continued

Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F = 1 - (1 - Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

| Allele | Population | Calculated phenotype from allele frequency |
|---|---|---|
| A*24 | South America | 20% |
| A*24 | Europe | 18% |

The peptides of the invention, preferably when included into a vaccine of the invention as described herein bind to A*02. A vaccine may also include pan-binding MHC class II peptides. Therefore, the vaccine of the invention can be used to treat cancer in patients that are A*02 positive, whereas no selection for MHC class II allotypes is necessary due to the pan-binding nature of these peptides.

If A*02 peptides of the invention are combined with peptides binding to another allele, for example A*24, a higher percentage of any patient population can be treated compared with addressing either MHC class I allele alone. While in most populations less than 50% of patients could be addressed by either allele alone, a vaccine comprising HLA-A*24 and HLA-A*02 epitopes can treat at least 60% of patients in any relevant population. Specifically, the following percentages of patients will be positive for at least one of these alleles in various regions: USA 61%, Western Europe 62%, China 75%, South Korea 77%, Japan 86%.

In a preferred embodiment, the term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

$$\text{percent identity} = 100[1-(C/R)]$$

wherein C is the number of differences between the Reference Sequence and the Compared Sequence over the length of alignment between the Reference Sequence and the Compared Sequence, wherein
(i) each base or amino acid in the Reference Sequence that does not have a corresponding aligned base or amino acid in the Compared Sequence and
(ii) each gap in the Reference Sequence and
(iii) each aligned base or amino acid in the Reference Sequence that is different from an aligned base or amino acid in the Compared Sequence, constitutes a difference and
(iv) the alignment has to start at position 1 of the aligned sequences;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

As mentioned above, the present invention thus provides a peptide comprising a sequence that is selected from the group of consisting of SEQ ID NO: 1 to SEQ ID NO: 288 or a variant thereof which is 88% homologous to SEQ ID NO: 1 to SEQ ID NO: 288, or a variant thereof that will induce T cells cross-reacting with said peptide. The peptides of the invention have the ability to bind to a molecule of the human major histocompatibility complex (MHC) class-I or elongated versions of said peptides to class II.

In the present invention, the term "homologous" refers to the degree of identity (see percent identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 288. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T cells.

These T cells can subsequently cross-react with cells and kill cells that express a polypeptide that contains the natural amino acid sequence of the cognate peptide as defined in the aspects of the invention. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO 288, by maintaining the known anchor residues, and would be able to determine whether such variants maintain the ability to bind MHC class I or II molecules. The variants of the present invention retain the ability to bind to the TCR of activated T cells, which can subsequently cross-react with and kill cells that express a polypeptide containing the natural amino acid sequence of the cognate peptide as defined in the aspects of the invention.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, non-standard amino acids (i.e., other than the common naturally occurring proteinogenic amino acids) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than four positions within the peptide would be simultaneously substituted.

A peptide consisting essentially of the amino acid sequence as indicated herein can have one or two non-anchor amino acids (see below regarding the anchor motif) exchanged without that the ability to bind to a molecule of the human major histocompatibility complex (MHC) class-I or —II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or —II is substantially changed, or is negatively affected, when compared to the non-modified peptide.

The amino acid residues that do not substantially contribute to interactions with the T-cell receptor can be modified by replacement with other amino acids whose incorporation do not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 2

Variants and motif of the peptides according to SEQ ID NO.: 4, 13, and 15

| | Position | | | | | | | | |
|---|---|---|---|---|---|---|---|---|---|
| | 1 | 2 | 3 | 4 | 5 | 6 | 7 | 8 | 9 |
| SEQ ID NO. 4 Variants | V | L | F | G | E | L | P | A | L |
| | | | | | | | | | V |
| | | | | | | | | | I |
| | | | | | | | | | A |
| | | M | | | | | | | V |
| | | M | | | | | | | I |
| | | M | | | | | | | |
| | | M | | | | | | | A |
| | | A | | | | | | | V |
| | | A | | | | | | | I |
| | | A | | | | | | | |
| | | A | | | | | | | A |
| | | V | | | | | | | V |
| | | V | | | | | | | I |
| | | V | | | | | | | |
| | | V | | | | | | | A |
| | | T | | | | | | | V |
| | | T | | | | | | | I |
| | | T | | | | | | | |
| | | T | | | | | | | A |
| | | Q | | | | | | | V |
| | | Q | | | | | | | I |
| | | Q | | | | | | | |
| | | Q | | | | | | | A |
| SEQ ID NO. 15 Variants | G | L | P | S | A | T | T | T | V |
| | | I | | | | | | | L |
| | | I | | | | | | | I |
| | | I | | | | | | | |
| | | I | | | | | | | A |
| | | M | | | | | | | L |
| | | M | | | | | | | I |
| | | M | | | | | | | |
| | | M | | | | | | | A |
| | | A | | | | | | | L |
| | | A | | | | | | | I |
| | | A | | | | | | | |
| | | A | | | | | | | A |
| | | V | | | | | | | L |
| | | V | | | | | | | I |
| | | V | | | | | | | |
| | | V | | | | | | | A |
| | | T | | | | | | | L |
| | | T | | | | | | | I |
| | | T | | | | | | | |
| | | T | | | | | | | A |
| | | Q | | | | | | | L |
| | | Q | | | | | | | I |
| | | Q | | | | | | | |
| | | Q | | | | | | | A |

TABLE 2-continued

Variants and motif of the peptides according to SEQ ID NO.: 4, 13, and 15

| | Position | | | | | | | | |
|---|---|---|---|---|---|---|---|---|---|
| | 1 | 2 | 3 | 4 | 5 | 6 | 7 | 8 | 9 |
| SEQ ID NO. 13 | R | L | H | D | E | N | I | L | L |
| Variants | | | | | | | | | V |
| | | | | | | | | | I |
| | | | | | | | | | A |
| | | M | | | | | | | V |
| | | M | | | | | | | I |
| | | M | | | | | | | |
| | | M | | | | | | | A |
| | | A | | | | | | | V |
| | | A | | | | | | | I |
| | | A | | | | | | | |
| | | A | | | | | | | A |
| | | V | | | | | | | V |
| | | V | | | | | | | I |
| | | V | | | | | | | |
| | | V | | | | | | | A |
| | | T | | | | | | | V |
| | | T | | | | | | | I |
| | | T | | | | | | | |
| | | T | | | | | | | A |
| | | Q | | | | | | | V |
| | | Q | | | | | | | I |
| | | Q | | | | | | | |
| | | Q | | | | | | | A |

Longer (elongated) peptides may also be suitable. It is possible that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

The peptides of the invention can be elongated by up to four amino acids, that is 1, 2, 3 or 4 amino acids can be added to either end in any combination between 4:0 and 0:4. Combinations of the elongations according to the invention can be found in Table 3.

TABLE 3

Combinations of the elongations of peptides of the invention

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present invention may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. This may lead to MHC class II binding peptides. Binding to MHC class II can be tested by methods known in the art.

Accordingly, the present invention provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the elongated class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I or II. Binding of a peptide or a variant to a MHC complex may be tested by methods known in the art.

Preferably, when the T cells specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 µM, and most preferably no more than about 10 pM. It is also preferred that the substituted peptide be recognized by T cells from more than one individual, at least two, and more preferably three individuals.

In a particularly preferred embodiment of the invention the peptide consists or consists essentially of an amino acid sequence according to SEQ ID NO: 1 to SEQ ID NO: 288.

"Consisting essentially of" shall mean that a peptide according to the present invention, in addition to the sequence according to any of SEQ ID NO: 1 to SEQ ID NO 288 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is part of a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells as described herein.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) (Meziere et al., 1997), incorporated herein by reference. This approach involves making pseudopeptides containing changes involving the backbone, and not the orientation of side chains. Meziere et al. (Meziere et al., 1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —$CH_2$—NH, —$CH_2$S—, —$CH_2CH_2$—, —CH=CH—, —$COCH_2$—, —CH(OH)$CH_2$—, and —$CH_2$SO—. U.S. Pat. No. 4,897,445 provides a method for the solid phase synthesis of non-peptide bonds (—$CH_2$—NH) in polypeptide chains which involves polypeptides synthesized by standard procedures and the non-peptide bond synthesized by reacting an amino aldehyde and an amino acid in the presence of $NaCNBH_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2004 (Lundblad, 2004), which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as SIGMA-ALDRICH provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly (ethylene)glycol and the major site of modification in the glycosylation of proteins. Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from e.g. Calbiochem-Novabiochem (Nottingham, UK).

Purification may be performed by any one, or a combination of, techniques such as re-crystal I ization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

For the identification of peptides of the present invention, the database of publicly available RNA expression data (Lonsdale, 2013) from about 3000 normal tissue samples was screened for genes with near-absent expression in vital organ systems, and low expression in other important organ systems. In a second step, cancer-associated peptides derived from the protein products of these genes were identified by mass spectrometry using the XPRESIDENT™ platform as described herein.

In detail, to select genes of interest using RNASeq data from said database, vital organ systems were considered to be: brain, heart, blood vessel, lung, and liver. The median of reads per kilobase per million reads (RPKM) for vital organs was required to be less than 2, and the 75% percentile was required to be less than 5 RPKM for selection of the gene. If the organ systems were covered by more than one sample class, e.g. different brain regions that had been analyzed separately, the maximal median and maximal 75% percentile over the multiple sample classes was used for the calculation. Other important organ systems were considered to be: skin, nerve, pituitary, colon, kidney, adipose tissue, adrenal gland, urinary bladder, whole blood, esophagus, muscle, pancreas, salivary gland, small intestine, stomach, breast, spleen, thyroid gland. The maximal median RPKM for these organs was required to be less than 10 for selection of the gene. Other organs were considered as non-vital and thus no cut-off value for gene expression was applied. These organs were cervix uteri and uterus, fallopian tube, vagina, prostate, testis, and ovary. Using this screen, around 14,000 candidate genes were selected. Next, presentation profiles of peptides derived from the corresponding proteins were analyzed. Peptides were considered interesting if they were presented on less than five normal samples in a set of more than 170 normal (i.e. non-cancerous) samples analyzed, and if the highest normal tissue presentation was less than 30% of the median tumor signal (over all tumor samples).

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (Pinheiro et al., 2015) adjusting for multiple testing by False Discovery Rate (Benjamini and Hochberg, 1995).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural TUMAPs recorded from primary tumor samples with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue.

Sample numbers were (altogether/QC-pass samples): for PC N=39 (36), for RCC N=22 (18), for CRC N=31 (28), for esophageal carcinoma N=14 (11), for BPH and prostate cancer N=53 (43), for HCC N=15 (15), for NSCLC N=96 (87), for GC N=35 (33), for GB N=38 (27), for breast cancer N=2 (2), for melanoma N=5 (2), for ovarian cancer N=21 (20), for CLL N=5 (4), for SCLC N=18 (17), NHL N=18 (18), AML N=23 (18), GBC, CCC N=18 (17), for UBC N=17 (15), for UEC N=19 (16). Samples have passed QC if 5 mass spectrometry replicates are acquired or the sample is consumed completely, and peptides used to calculate the normalization factor (i.e. occurring in technical replicates of the same sample with less than 50% variance, and occurring at least in 2 independent samples) are at least 30% of all peptides measured in the sample. Samples that were subtyped resulting in a rare subtype (such as A*02:05, A*02:06) were excluded for selection of the peptides of this invention.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from primary HCC, CRC, GB, GC, esophageal cancer, NSCLC, PC, RCC, BPH/PCA, OC, MCC, melanoma, breast cancer, SCLC, NHL, AML, GBC, CCC, UBC, UEC, and CLL samples were purified and HLA-associated peptides were isolated and analyzed by LC-MS (see examples). All TUMAPs contained in the present application were identified with this approach on HCC, CRC, GB, GC, esophageal cancer, NSCLC, PC, RCC, BPH/PCA, OC, MCC, melanoma, breast cancer, SCLC, NHL, AML, GBC, CCC, UBC, UEC, and/or CLL samples, confirming their presentation on these tumor types.

TUMAPs identified on multiple tumor and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

Furthermore, the discovery pipeline XPRESIDENT® v2.x allows the direct absolute quantitation of MHC-, preferably HLA-restricted, peptide levels on cancer or other infected tissues. Briefly, the total cell count was calculated from the total DNA content of the analyzed tissue sample. The total peptide amount for a TUMAP in a tissue sample was measured by nanoLC-MS/MS as the ratio of the natural TUMAP and a known amount of an isotope-labelled version of the TUMAP, the so-called internal standard. The efficiency of TUMAP isolation was determined by spiking peptide:MHC complexes of all selected TUMAPs into the tissue lysate at the earliest possible point of the TUMAP isolation procedure and their detection by nanoLC-MS/MS following completion of the peptide isolation procedure. The total cell count and the amount of total peptide were calculated from triplicate measurements per tissue sample. The peptide-specific isolation efficiencies were calculated as an average from 10 spike experiments each measured as a triplicate (see Example 6 and Table 11).

This combined analysis of RNA expression and mass spectrometry data resulted in the 288 peptides of the present invention. In many cases the peptide was identified only on a low number of tumors. However, due to the limited sensitivity of routine mass spectrometry analysis, RNA data provide a much better basis for coverage estimation (see Example 2).

The present invention provides peptides that are useful in treating cancers/tumors, preferably HCC, CRC, GB, GC, esophageal cancer, NSCLC, PC, RCC, BPH/PCA, OC, MCC, melanoma, breast cancer, SCLC, NHL, AML, GBC, CCC, UBC, UEC, and CLL that over- or exclusively present the peptides of the invention. These peptides were shown by mass spectrometry to be naturally presented by HLA molecules on primary human HCC, CRC, GB, GC, esophageal cancer, NSCLC, RCC, BPH/PCA, OC, MCC, melanoma, breast cancer, SCLC, NHL, AML, GBC, CCC, UBC, UEC, CLL samples, and/or on PC samples.

Many of the source gene/proteins (also designated "full-length proteins" or "underlying proteins") from which the peptides are derived were shown to be highly over-expressed in cancer compared with normal tissues—"normal tissues" in relation to this invention shall mean either healthy tissues of the tumor-corresponding type (liver, colon/rectum, brain, stomach, esophagus, lung, pancreas, kidney, prostate, ovary, skin, breast and leukocytes) or other normal tissue cells, demonstrating a high degree of tumor association of the source genes (see Example 2). Moreover, the peptides themselves are strongly over-presented on tumor tissue—"tumor tissue" in relation to this invention shall mean a sample from a patient suffering from HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL, but not on normal tissues (see Example 1).

HLA-bound peptides can be recognized by the immune system, specifically T lymphocytes. T cells can destroy the cells presenting the recognized HLA/peptide complex, e.g. HCC, CRC, GB, GC, esophageal cancer, NSCLC, RCC, BPH/PCA, OC, MCC, melanoma, breast cancer, PC, SCLC, NHL, AML, GBC, CCC, UBC, UEC, or CLL cells presenting the derived peptides.

The peptides of the present invention have been shown to be capable of stimulating T cell responses and/or are over-presented and thus can be used for the production of antibodies and/or TCRs, such as soluble TCRs, according to the present invention (see Example 3, Example 4). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The present description further relates to T-cell receptors (TCRs) comprising an alpha chain and a beta chain ("alpha/beta TCRs"). Also provided are peptides capable of binding to TCRs and antibodies when presented by an MHC molecule. The present description also relates to nucleic acids, vectors and host cells for expressing TCRs and peptides of the present description; and methods of using the same.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule. The term also includes so-called gamma/delta TCRs.

In one embodiment the description provides a method of producing a TCR as described herein, the method comprising culturing a host cell capable of expressing the TCR under conditions suitable to promote expression of the TCR.

The description in another aspect relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

TCRs of the present description preferably bind to a peptide-HLA molecule complex with a binding affinity (KD) of about 100 µM or less, about 50 µM or less, about 25 µM or less, or about 10 µM or less. More preferred are high affinity TCRs having binding affinities of about 1 µM or less, about 100 nM or less, about 50 nM or less, about 25 nM or less. Non-limiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity (KD) for a peptide-HLA molecule complex of 100 µM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta hetero-dimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, an peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens. It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance, meaning that only T-cells with low-affinity TCRs for self-antigens remain. Therefore, affinity of TCRs or variants of the present description to the peptides according to the invention can be enhanced by methods well known in the art.

The present description further relates to a method of identifying and isolating a TCR according to the present description, said method comprising incubating PBMCs from HLA-A*02-negative healthy donors with A2/peptide monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with peptide of interest, incubating PBMCs obtained from the transgenic mice with tetramer-phycoerythrin (PE), and isolating the high avidity T-cells by fluorescence activated cell sorting (FACS)-Calibur analysis.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter, elongation factor (EF)-1a and the spleen focus-forming virus (SFFV) promoter. In a preferred embodiment, the promoter is heterologous to the nucleic acid being expressed.

In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bi-cistronic constructs in a single vector, which has been shown to be capable of over-coming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced. (Schmitt et al. 2009).

Nucleic acids encoding TCRs of the present description may be codon optimized to increase expression from a host cell. Redundancy in the genetic code allows some amino acids to be encoded by more than one codon, but certain codons are less "op-timal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion). (Schmitt et al. 2009).

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A "pharmaceutical composition" is a composition suitable for administration to a human being in a medical setting. Preferably, a pharmaceutical composition is sterile and produced according to GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

Preferably, the medicament of the present invention is an immunotherapeutics such as a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and (Longenecker et al., 1993)). The peptide may also be tagged, may be a fusion protein, or may be a hybrid molecule. The peptides whose sequence is given in the present invention are expected to stimulate CD4 or CD8 T cells. However, stimulation of CD8 T cells is more efficient in the presence of help provided by CD4 T-helper cells. Thus, for MHC Class I epitopes that stimulate CD8 T cells the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 288, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al. (Cohen et al., 1972) and (Green and Sambrook, 2012). Transformation of yeast cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CD8-positive T cells and helper-T (TH) cells to an antigen, and would thus be considered useful in the medicament of the present invention. Suitable adjuvants include, but are not limited to, 1018 ISS, aluminum salts, AMPLIVAX®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMA-TRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, nonnucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are anti-CD40, imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod and resiquimod. In a preferred embodiment of the pharmaceutical composition according to the invention, the adjuvant is cyclophosphamide, imiquimod or resiquimod. Even more preferred adjuvants are Montanide IMS 1312, Montanide ISA 206, Montanide ISA 50V, Montanide ISA-51, poly-ICLC (Hiltonol®) and anti-CD40 mAB, or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253.

It is important to realize that the immune response triggered by the vaccine according to the invention attacks the cancer in different cell-stages and different stages of development. Furthermore different cancer associated signaling pathways are attacked. This is an advantage over vaccines that address only one or few targets, which may cause the tumor to easily adapt to the attack (tumor escape). Furthermore, not all individual tumors express the same pattern of antigens. Therefore, a combination of several tumor-associated peptides ensures that every single tumor bears at least some of the targets. The composition is designed in such a way that each tumor is expected to express several of the antigens and cover several independent pathways necessary for tumor growth and maintenance. Thus, the vaccine can easily be used "off-the-shelf" for a larger patient population. This means that a pre-selection of patients to be treated with the vaccine can be restricted to HLA typing, does not require any additional biomarker assessments for antigen expression, but it is still ensured that several targets are simultaneously attacked by the induced immune response, which is important for efficacy (Banchereau et al., 2001; Walter et al., 2012).

As used herein, the term "scaffold" refers to a molecule that specifically binds to an (e.g. antigenic) determinant. In one embodiment, a scaffold is able to direct the entity to which it is attached (e.g. a (second) antigen binding moiety) to a target site, for example to a specific type of tumor cell or tumor stroma bearing the antigenic determinant (e.g. the complex of a peptide with MHC, according to the application at hand). In another embodiment a scaffold is able to activate signaling through its target antigen, for example a T cell receptor complex antigen. Scaffolds include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T cells. To assess whether a molecule is a scaffold binding to a target, binding assays can be performed.

"Specific" binding means that the scaffold binds the peptide-MHC-complex of interest better than other naturally occurring peptide-MHC-complexes, to an extent that a scaffold armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e. not derived from the human HLA-peptidome. Tests to assess target cell killing are well known in the art. They should be performed using target cells (primary cells or cell lines) with unaltered peptide-MHC presentation, or cells loaded with peptides such that naturally occurring peptide-MHC levels are reached.

Each scaffold can comprise a labelling which provides that the bound scaffold can be detected by determining the presence or absence of a signal provided by the label. For example, the scaffold can be labelled with a fluorescent dye or any other applicable cellular marker molecule. Such marker molecules are well known in the art. For example a fluorescence-labelling, for example provided by a fluorescence dye, can provide a visualization of the bound aptamer by fluorescence or laser scanning microscopy or flow cytometry.

Each scaffold can be conjugated with a second active molecule such as for example IL-21, anti-CD3, and anti-CD28.

For further information on polypeptide scaffolds see for example the background section of WO 2014/071978A1 and the references cited therein.

The present invention further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. Further, it could be shown that some of the aptamers are taken up by tumor cells and thus can function as molecular vehicles for the targeted delivery of anti-cancer agents such as siRNA into tumor cells.

Aptamers can be selected against complex targets such as cells and tissues and complexes of the peptides comprising, preferably consisting of, a sequence according to any of SEQ ID NO 1 to SEQ ID NO 288, according to the invention at hand with the MHC molecule, using the cell-SELEX (Systematic Evolution of Ligands by Exponential enrichment) technique.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Respective methods for producing such antibodies and single chain class I major histocompatibility complexes, as well as other tools for the production of these antibodies are disclosed in WO 03/068201, WO 2004/084798, WO 01/72768, WO 03/070752, and in publications (Cohen et al., 2003a; Cohen et al., 2003b; Denkberg et al., 2003), which for the purposes of the present invention are all explicitly incorporated by reference in their entireties.

Preferably, the antibody is binding with a binding affinity of below 20 nanomolar, preferably of below 10 nanomolar, to the complex, which is also regarded as "specific" in the context of the present invention.

The present invention relates to a peptide comprising a sequence that is selected from the group consisting of SEQ ID NO: 1 to SEQ ID NO: 288, or a variant thereof which is at least 88% homologous (preferably identical) to SEQ ID NO: 1 to SEQ ID NO: 288 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 288 or a variant thereof which is at least 88% homologous (preferably identical) to SEQ ID NO: 1 to SEQ ID NO: 288, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 288.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the complete (full) human protein.

The present invention further relates to the nucleic acid according to the invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine, in particular in the treatment of HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL.

The present invention further relates to a host cell comprising a nucleic acid according to the invention or an expression vector according to the invention.

The present invention further relates to the host cell according to the present invention that is an antigen presenting cell, and preferably a dendritic cell.

The present invention further relates to a method of producing a peptide according to the present invention, said method comprising culturing the host cell according to the present invention, and isolating the peptide from said host cell or its culture medium.

The present invention further relates to the method according to the present invention, wherein the antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 288 or said variant amino acid sequence.

The present invention further relates to activated T cells, produced by the method according to the present invention, wherein said T cells selectively recognizes a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of T cells as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament. The present invention further relates to a use according to the present invention, wherein the medicament is active against cancer.

The present invention further relates to a use according to the invention, wherein the medicament is a vaccine. The present invention further relates to a use according to the invention, wherein the medicament is active against cancer.

The present invention further relates to a use according to the invention, wherein said cancer cells are HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL cells.

The present invention further relates to particular marker proteins and biomarkers based on the peptides according to the present invention, herein called "targets" that can be used in the diagnosis and/or prognosis of HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL. The present invention also relates to the use of these novel targets for cancer treatment.

The term "antibody" or "antibodies" is used herein in a broad sense and includes both polyclonal and monoclonal antibodies. In addition to intact or "full" immunoglobulin molecules, also included in the term "antibodies" are fragments (e.g. CDRs, Fv, Fab and Fc fragments) or polymers of those immunoglobulin molecules and humanized versions of immunoglobulin molecules, as long as they exhibit any of the desired properties (e.g., specific binding of a HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL marker (poly)peptide, delivery of a toxin to a HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL cell expressing a cancer marker gene at an increased level, and/or inhibiting the activity of a HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL marker polypeptide) according to the invention.

Whenever possible, the antibodies of the invention may be purchased from commercial sources. The antibodies of the invention may also be generated using well-known methods. The skilled artisan will understand that either full length HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 288 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Greenfield, 2014 (Greenfield, 2014)). For example, the antibodies may be tested in ELISA assays or, Western blots, immunohistochemical staining of formalin-fixed cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody, preferably for treating HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL, the efficacy of the therapeutic antibody can be assessed in various ways well known to the skilled practitioner. For instance, the size, number, and/or distribution of cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of cancer.

It is a further aspect of the invention to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), and domains recruiting effector cells such as an anti-CD3 domain, etc., in order to execute particular functions on target cells. Moreover, it could be expressed in T cells used for adoptive transfer. Further information can be found in WO 2004/033685A1 and WO 2004/074322A1. A combination of sTCRs is described in WO 2012/056407A1. Further methods for the production are disclosed in WO 2013/057586A1.

In addition, the peptides and/or the TCRs or antibodies or other binding molecules of the present invention can be used to verify a pathologist's diagnosis of a cancer based on a biopsied sample.

The antibodies or TCRs may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than $1\times10$ μM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and *Drosophila* cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Ljunggren et al. (Ljunggren and Karre, 1985).

Preferably, before transfection the host cell expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive T cells.

If an antigen-presenting cell is transfected to express such an epitope, preferably the cell comprises an expression vector capable of expressing a peptide containing SEQ ID NO: 1 to SEQ ID NO: 288, or a variant amino acid sequence thereof.

A number of other methods may be used for generating T cells in vitro. For example, autologous tumor-infiltrating lymphocytes can be used in the generation of CTL. Plebanski et al. (Plebanski et al., 1995) made use of autologous peripheral blood lymphocytes (PLBs) in the preparation of T cells. Furthermore, the production of autologous T cells by pulsing dendritic cells with peptide or polypeptide, or via infection with recombinant virus is possible. Also, B cells can be used in the production of autologous T cells. In addition, macrophages pulsed with peptide or polypeptide, or infected with recombinant virus, may be used in the preparation of autologous T cells. S. Walter et al. (Walter et al., 2003) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively eliciting high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e.g. cytokines, like interleukin-12.

Allogeneic cells may also be used in the preparation of T cells and a method is described in detail in WO 97/26328, incorporated herein by reference. For example, in addition to *Drosophila* cells and T2 cells, other cells may be used to present antigens such as CHO cells, baculovirus-infected insect cells, bacteria, yeast, and vaccinia-infected target cells. In addition plant viruses may be used (see, for example, Porta et al. (Porta et al., 1994) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO 288.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattioni et al. and Morgan et al. (Gattinoni et al., 2006; Morgan et al., 2006).

Another aspect of the present invention includes the use of the peptides complexed with MHC to generate a T-cell receptor whose nucleic acid is cloned and is introduced into a host cell, preferably a T cell. This engineered T cell can then be transferred to a patient for therapy of cancer.

Any molecule of the invention, i.e. the peptide, nucleic acid, antibody, expression vector, cell, activated T cell, T-cell receptor or the nucleic acid encoding it, is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

The present invention further provides a medicament that is useful in treating cancer, in particular HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL and other malignancies.

The present invention is further directed at a kit comprising:

(a) a container containing a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthalmic, subcutaneous, intradermal, intramuscular, intravenous or transdermal. Preferably, the administration is s.c., and most preferably i.d. administration may be by infusion pump.

Since the peptides of the invention were isolated from HCC, CRC, GB, GC, esophageal cancer, NSCLC, PC, RCC, BPH/PCA, OC, MCC, melanoma, breast cancer, SCLC, NHL, AML, GBC, CCC, UBC, UEC, and CLL, the medicament of the invention is preferably used to treat HCC, CRC, GB, GC, esophageal cancer, NSCLC, PC, RCC, BPH/PCA, OC, MCC, melanoma, breast cancer, SCLC, NHL, AML, GBC, CCC, UBC, UEC, and CLL.

The present invention further relates to a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. In one embodiment, the pharmaceutical composition is a vaccine. The method could also be adapted to produce T cell clones for down-stream applications, such as TCR isolations, or soluble antibodies, and other treatment options.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group or set of peptides that have been pre-screened for immunogenicity and/or over-presentation in a particular tumor type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored. The warehouse (e.g. in the form of a database) is composed of tumor-associated peptides which were highly overexpressed in the tumor tissue of HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL patients with various HLA-A HLA-B and HLA-C alleles. It may contain MHC class I and MHC class II peptides or elongated MHC class I peptides. In addition to the tumor associated peptides collected from several tumor tissues, the warehouse may contain HLA-A*02 and HLA-A*24 marker peptides. These peptides allow comparison of the magnitude of T-cell immunity induced by TUMAPs in a quantitative manner and hence allow important conclusion to be drawn on the capacity of the vaccine to elicit anti-tumor responses. Secondly, they function as important positive control peptides derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient.

TUMAPs for the present invention and the warehouse are identified by using an integrated functional genomics approach combining gene expression analysis, mass spectrometry, and T-cell immunology (XPresident®). The approach assures that only TUMAPs truly present on a high percentage of tumors but not or only minimally expressed on normal tissue, are chosen for further analysis. For initial peptide selection, HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL samples from patients and blood from healthy donors were analyzed in a stepwise approach:

1. Genome-wide messenger ribonucleic acid (mRNA) expression analysis was used to identify genes expressed at very low levels in important normal (non-cancerous) tissues. It was assessed whether those genes are over-expressed in the malignant tissue (HCC, CRC, GB, GC, NSCLC, PC, RCC, BPH/PCA, SCLC, NHL, AML, GBC, CCC, UBC, UEC) compared with a range of normal organs and tissues 2. HLA ligands from the malignant material (HCC, CRC, GB, GC, esophageal cancer, NSCLC, PC, RCC, BPH/PCA, OC, MCC, melanoma, breast cancer, SCLC, NHL, AML, GBC, CCC, UBC, UEC, CLL) were identified by mass spectrometry.

3. Identified HLA ligands were compared to gene expression data. Peptides over-presented or selectively presented on tumor tissue, preferably encoded by selectively expressed or over-expressed genes as detected in step 2 were considered suitable TUMAP candidates for a multi-peptide vaccine.

4. Literature research was performed in order to identify additional evidence supporting the relevance of the identified peptides as TUMAPs 5. The relevance of over-expression at the mRNA level was confirmed by redetection of selected TUMAPs from step 3 on tumor tissue and lack of (or infrequent) detection on healthy tissues.

6. In order to assess, whether an induction of in vivo T-cell responses by the selected peptides may be feasible, in vitro immunogenicity assays were performed using human T cells from healthy donors as well as from HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed, the warehouse allows a significantly higher matching of the actual expression of antigens in the tumor with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, or as below.

The HLA phenotype, transcriptomic and peptidomic data is gathered from the patient's tumor material, and blood samples to identify the most suitable peptides for each patient containing "warehouse" and patient-unique (i.e. mutated) TUMAPs. Those peptides will be chosen, which are selectively or over-expressed in the patients tumor and, where possible, show strong in vitro immunogenicity if tested with the patients' individual PBMCs.

Preferably, the peptides included in the vaccine are identified by a method comprising: (a) identifying tumor-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumor-associated peptide identified in the patient. For example, the TUMAPs presented by the tumor sample are identified by: (a1)) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo, and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumor and of corresponding normal tissue can be sequenced by whole genome sequencing: For discovery of non-synonymous mutations in the protein-coding regions of genes, genomic DNA and RNA are extracted from tumor tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumor mRNA is sequenced for direct quantification of gene expression and validation that mutated genes are expressed in the patients' tumors. The resultant millions of sequence reads are processed through software algorithms. The output list contains mutations and gene expression. Tumor-specific somatic mutations are determined by comparison with the PBMC-derived germ line variations and prioritized. The de novo identified peptides can then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumor-associated peptides (TUMAPs) presented by a tumor sample from the individual patient by the method as described above; (b) comparing the peptides identified in a) with a warehouse of peptides that have been prescreened for immunogenicity and overpresentation in tumors as compared to corresponding normal tissue; (c) selecting at least one peptide from the warehouse that correlates with a tumor-associated peptide identified in the patient; and (d) optionally, selecting at least one peptide identified de novo in (a) confirming its immunogenicity.

In one exemplary embodiment, the peptides included in the vaccine are identified by: (a) identifying tumor-associated peptides (TUMAPs) presented by a tumor sample from the individual patient; and (b) selecting at least one peptide identified de novo in (a) and confirming its immunogenicity.

Once the peptides for a personalized peptide based vaccine are selected, the vaccine is produced. The vaccine preferably is a liquid formulation consisting of the individual peptides dissolved in between 20-40% DMSO, preferably about 30-35% DMSO, such as about 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 µm sterile filter. The final bulk solution is obtained.

Final bulk solution is filled into vials and stored at −20° C. until use. One vial contains 700 µL solution, containing 0.578 mg of each peptide. Of this, 500 µL (approx. 400 µg per peptide) will be applied for intradermal injection.

In addition to being useful for treating cancer, the peptides of the present invention are also useful as diagnostics. Since the peptides were generated from HCC, CRC, GB, GC, esophageal cancer, NSCLC, PC, RCC, BPH/PCA, OC, MCC, melanoma, breast cancer, SCLC, NHL, AML, GBC, CCC, UBC, UEC, and CLL cells and since it was determined that these peptides are not or at lower levels present in normal tissues, these peptides can be used to diagnose the presence of a cancer.

The presence of claimed peptides on tissue biopsies in blood samples can assist a pathologist in diagnosis of cancer. Detection of certain peptides by means of antibodies, mass spectrometry or other methods known in the art can tell the pathologist that the tissue sample is malignant or inflamed or generally diseased, or can be used as a biomarker for HCC, CRC, GB, GC, esophageal cancer, NSCLC, PC, RCC, BPH/PCA, OC, MCC, melanoma, breast cancer, SCLC, NHL, AML, GBC, CCC, UBC, UEC, or CLL. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate response markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The present invention will now be described in the following examples which describe preferred embodiments thereof, and with reference to the accompanying figures, nevertheless, without being limited thereto. For the purposes of the present invention, all references as cited herein are incorporated by reference in their entireties.

BRIEF DESCRIPTION OF THE DRAWINGS

FIGS. 1A-1J show the over-presentation of various peptides in different cancer tissues compared to normal tissues. The analyses included data from more than 170 normal tissue samples, and 376 cancer samples. Shown are only samples where the peptide was found to be presented. FIG. 1A) Gene: CENPE, Peptide: KLQEKIQEL (SEQ ID NO.: 1), Tissues from left to right: 4 leucocytic cancer cell lines, 1 pancreatic cancer cell line, 1 melanoma cell line, 2 normal tissue samples (1 adrenal gland, 1 spleen), 31 primary cancer tissue samples (1 brain cancer, 4 colon cancers, 1 esophageal cancer, 1 kidney cancer, 2 liver cancers, 16 lung cancers, 4 ovarian cancers, 1 rectum cancer, 1 gastric cancer), FIG. 1B) Gene: KIF15, Peptide: QLIEKNWLL (SEQ ID NO.: 10), Tissues from left to right: 5 leucocytic cancer cell lines, 1 pancreatic cancer cell line, 1 myeloid leukemia cell line, 1 normal tissue sample (1 adrenal gland), 29 cancer tissue samples (4 colon cancers, 2 esophageal cancers, 1 leukocytic cancer, 1 liver cancer, 10 lung cancers, 11 ovarian cancers), FIG. 1C) Gene: HAVCR1, Peptide: LLDPKTIFL (SEQ ID NO.: 11), Tissues from left to right: 1 kidney cancer cell line, 13 cancer tissue samples (8 kidney cancers, 1 liver cancer, 2 lung cancers, 2 rectal cancers), FIG. 1D) Gene: RPGRIP1L, Peptide: RLHDENILL (SEQ ID NO.: 13), Tissues from left to right: 1 kidney cancer cell lines, 1 prostate cancer cell line, 1 melanoma cell line, 50 cancer tissue samples (4 brain cancers, 1 colon cancer, 2 esophageal cancers, 3 kidney cancers, 2 liver cancers, 23 lung cancers, 7 ovarian cancers, 2 pancreatic cancers, 2 prostate cancers, 3 rectum cancers, 1 gastric cancer), FIG. 1E-J show the over-presentation of various peptides in different cancer tissues compared to normal tissues. The analyses included data from more than 320 normal tissue samples, and 462 cancer samples. Shown are only samples where the peptide was found to be presented. FIG. 1E) Gene: DNAH14, Peptide: SVLEKEIYSI (SEQ ID NO.: 2), Tissues from left to right: 4 cell lines (3 blood cells, 1 pancreatic), 2 normal tissues (1 lymph node, 1 trachea), 52 cancer tissues (2 bile duct cancers, 1 myeloid cells cancer, 3 leukocytic leukemia cancers, 5 breast cancers, 1 esophageal cancer, 1 esophagus and stomach cancer, 1 gallbladder cancer, 4 colon cancers, 7 lung cancers, 6 lymph node cancers, 7 ovarian cancers, 4 prostate cancers, 4 skin cancers, 2 urinary bladder cancers, 4 uterus cancers), FIG. 1F) Gene: MAGEA3, MAGEA6, Peptide: KIWEELSVLEV (SEQ ID NO.: 40), Tissues from left to right: 8 cancer tissues (1 liver cancer, 3 lung cancers, 2 skin cancers, 1 stomach cancer, 1 urinary bladder cancer), FIG. 1G) Gene: HMX1, Peptide: FLIENLLAA (SEQ ID NO.: 67), Tissues from left to right: 7 cancer tissues (4 brain cancers, 2 lung cancers, 1 uterus cancer), FIG. 1H) Gene: CCDC138, Peptide: FLLEREQLL (SEQ ID NO.: 84), Tissues from left to right: 3 cell lines (2 blood cells, 1 skin), 24 cancer tissues (1 myeloid cells cancer, 3 leukocytic leukemia cancers, 1 bone marrow cancer, 1 breast cancer, 1 kidney cancer, 2 colon cancers, 3 rectum cancers, 1 lung cancer, 7 lymph node cancers, 3 urinary bladder cancers, 1 uterus cancer), FIG. 1I) Gene: CLSPN, Peptide: SLLNQPKAV (SEQ ID NO.: 235), Tissues from left to right: 13 cell lines (3 blood cells, 2 kidney, 8 pancreas), 30 cancer tissues (1 myeloid cells cancer, 1 leukocytic leukemia cancer, 2 brain cancers, 2 breast cancers, 2 esophageal cancers, 1 gallbladder cancer, 1 rectum cancer, 2 liver cancers, 4 lung cancers, 5 lymph node cancers, 2 ovarian cancers, 2 skin cancers, 4 urinary bladder cancers, 1 uterus cancer), FIG. 1J) Gene: SPC25, Peptide: GLAEFQENV (SEQ ID NO.: 243), Tissues from left to right: 3 cell lines (1 blood cells, 1 kidney, 1 pancreas), 67 cancer tissues (1 bile duct cancer, 4 leukocytic leukemia cancers, 1 myeloid cells cancer, 2 brain cancers, 3 breast cancers, 4 esophageal cancers, 2 gallbladder cancers, 2 colon cancers, 1 rectum cancer, 2 liver cancers, 15 lung cancers, 8 lymph node cancers, 9 ovarian cancers, 3 skin cancers, 4 urinary bladder cancers, 6 uterus cancers).

Figure 2G:
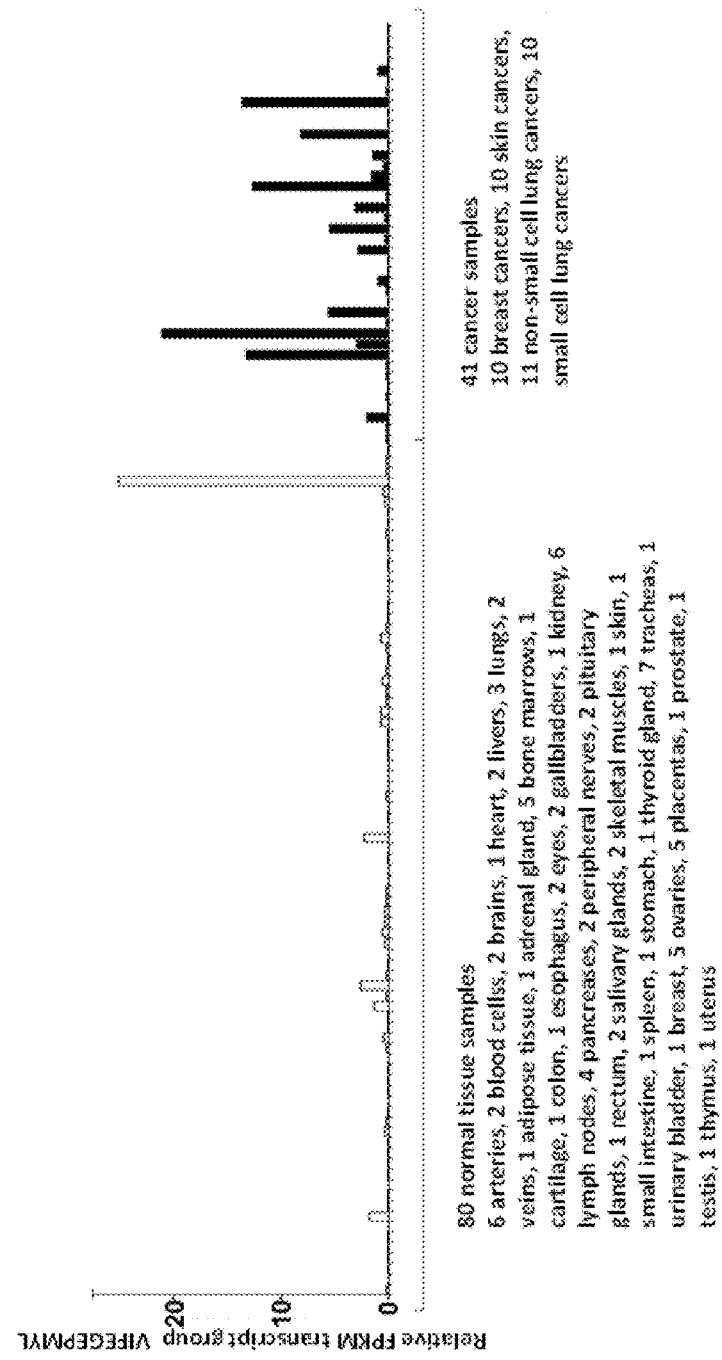

FIGS. 2A-2H shows exemplary expression profiles (relative expression compared to normal kidney) of source genes of the present invention that are highly over-expressed or exclusively expressed in different cancers compared to a panel of normal tissues. FIG. 2A) PRIM2—Tissues from left to right: adrenal gland, artery, bone marrow, brain (whole), breast, colon, esophagus, heart, kidney (triplicate), leukocytes, liver, lung, lymph node, ovary, pancreas, placenta, prostate, salivary gland, skeletal muscle, skin, small intestine, spleen, stomach, testis, thymus, thyroid gland, urinary bladder, uterine cervix, uterus, vein (each normal sample represents a pool of several donors), 22 individual prostate cancer samples, FIG. 2B) CHEK1—Tissues from left to right: adrenal gland, artery, bone marrow, brain (whole), breast, colon, esophagus, heart, kidney (triplicate), leukocytes, liver, lung, lymph node, ovary, pancreas, placenta, prostate, salivary gland, skeletal muscle, skin, small intestine, spleen, stomach, testis, thymus, thyroid gland, urinary bladder, uterine cervix, uterus, vein (each normal sample represents a pool of several donors), 3 individual normal colon samples, 10 individual colorectal cancer samples, FIG. 2C) TTC30A—Tissues from left to right: adrenal gland, artery, bone marrow, brain (whole), breast, colon, esophagus, heart, kidney (triplicate), leukocytes, liver, lung, lymph node, ovary, pancreas, placenta, prostate, salivary gland, skeletal muscle, skin, small intestine, spleen, stomach, testis, thymus, thyroid gland, urinary bladder, uterine cervix, uterus, vein (each normal sample represents a pool of several donors), 30 individual brain cancer samples, FIG. 2D) TRIPI3—Tissues from left to right: adrenal gland, artery, bone marrow, brain (whole), breast, colon, esophagus, heart, kidney (triplicate), leukocytes, liver, lung, lymph node, ovary, pancreas, placenta, prostate, salivary gland, skeletal muscle, skin, small intestine, spleen, stomach, testis, thymus, thyroid gland, urinary bladder, uterine cervix, uterus, vein (each normal sample represents a pool of several donors), 1 individual normal lung sample, 38 individual lung cancer samples, FIG. 2E) MXRA5—Tissues from left to right: adrenal gland, artery, bone marrow, brain (whole), breast, colon, esophagus, heart, kidney (triplicate), leukocytes, liver, lung, lymph node, ovary, pancreas, placenta, prostate, salivary gland, skeletal muscle, skin, small intestine, spleen, stomach, testis, thymus, thyroid gland, urinary bladder, uterine cervix, uterus, vein (each normal sample represents a pool of several donors), 9 individual pancreatic cancer samples. FIG. 2F-H show exemplary expression profiles of source genes of the present invention that are highly over-expressed or exclusively expressed in cancer in a panel of normal tissues (white bars) and different cancer samples (black bars). FIG. 2F) MMP11, MMP13 (Seq ID No 24)—Tissues from left to right: 80 normal tissue samples (6 arteries, 2 blood cells, 2 brains, 1 heart, 2 livers, 3 lungs, 2 veins, 1 adipose tissue, 1 adrenal gland, 5 bone marrows, 1 cartilage, 1 colon, 1 esophagus, 2 eyes, 2 gallbladders, 1 kidney, 6 lymph nodes, 4 pancreases, 2 peripheral nerves, 2 pituitary glands, 1 rectum, 2 salivary glands, 2 skeletal muscles, 1 skin, 1 small intestine, 1 spleen, 1 stomach, 1 thyroid gland, 7 tracheas, 1 urinary bladder, 1 breast, 5 ovaries, 5 placentas, 1 prostate, 1 testis, 1 thymus, 1 uterus), 50 cancer samples (10 breast cancers, 4 bile duct cancers, 6 gallbladder cancers, 11 esophagus cancers, 10 urinary bladder cancers, 10 uterus cancers), FIG. 2G) HORMAD1 (Seq ID No 168)—Tissues from left to right: 80 normal tissue samples (6 arteries, 2 blood cells, 2 brains, 1 heart, 2 livers, 3 lungs, 2 veins, 1 adipose tissue, 1 adrenal gland, 5 bone marrows, 1 cartilage, 1 colon, 1 esophagus, 2 eyes, 2 gallbladders, 1 kidney, 6 lymph nodes, 4 pancreases, 2 peripheral nerves, 2 pituitary glands, 1 rectum, 2 salivary glands, 2 skeletal muscles, 1 skin, 1 small intestine, 1 spleen, 1 stomach, 1 thyroid gland, 7 tracheas, 1 urinary bladder, 1 breast, 5 ovaries, 5 placentas, 1 prostate, 1 testis, 1 thymus, 1 uterus), 41 cancer samples (10 breast cancers, 10 skin cancers, 11 non-small cell lung cancers, 10 small cell lung cancers), FIG. 2H) IGF2BP1, IGF2BP3 (Seq ID No 274)—Tissues from left to right: 80 normal tissue samples (6 arteries, 2 blood cells, 2 brains, 1 heart, 2 livers, 3 lungs, 2 veins, 1 adipose tissue, 1 adrenal gland, 5 bone marrows, 1 cartilage, 1 colon, 1 esophagus, 2 eyes, 2 gallbladders, 1 kidney, 6 lymph nodes, 4 pancreases, 2 peripheral nerves, 2 pituitary glands, 1 rectum, 2 salivary glands, 2 skeletal muscles, 1 skin, 1 small intestine, 1 spleen, 1 stomach, 1 thyroid gland, 7 tracheas, 1 urinary bladder, 1 breast, 5 ovaries, 5 placentas, 1 prostate, 1 testis, 1 thymus, 1 uterus), 53 cancer samples (4 bile duct cancers, 6 gallbladder cancers, 10 lymph node cancers, 12 ovary cancers, 11 esophagus cancers, 10 lung cancers).

Figures 3A, 3B:
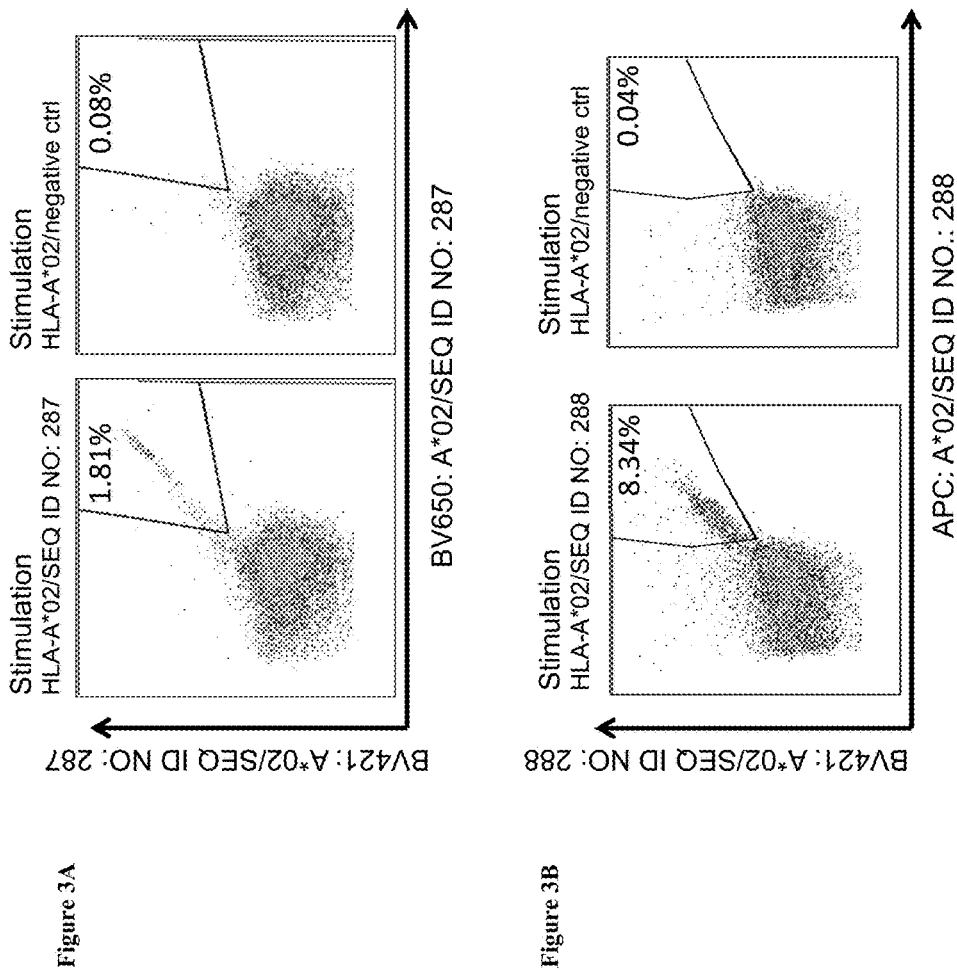

FIGS. 3A and 3B show exemplary immunogenicity data: flow cytometry results after peptide-specific multimer staining.

Figure 4A:
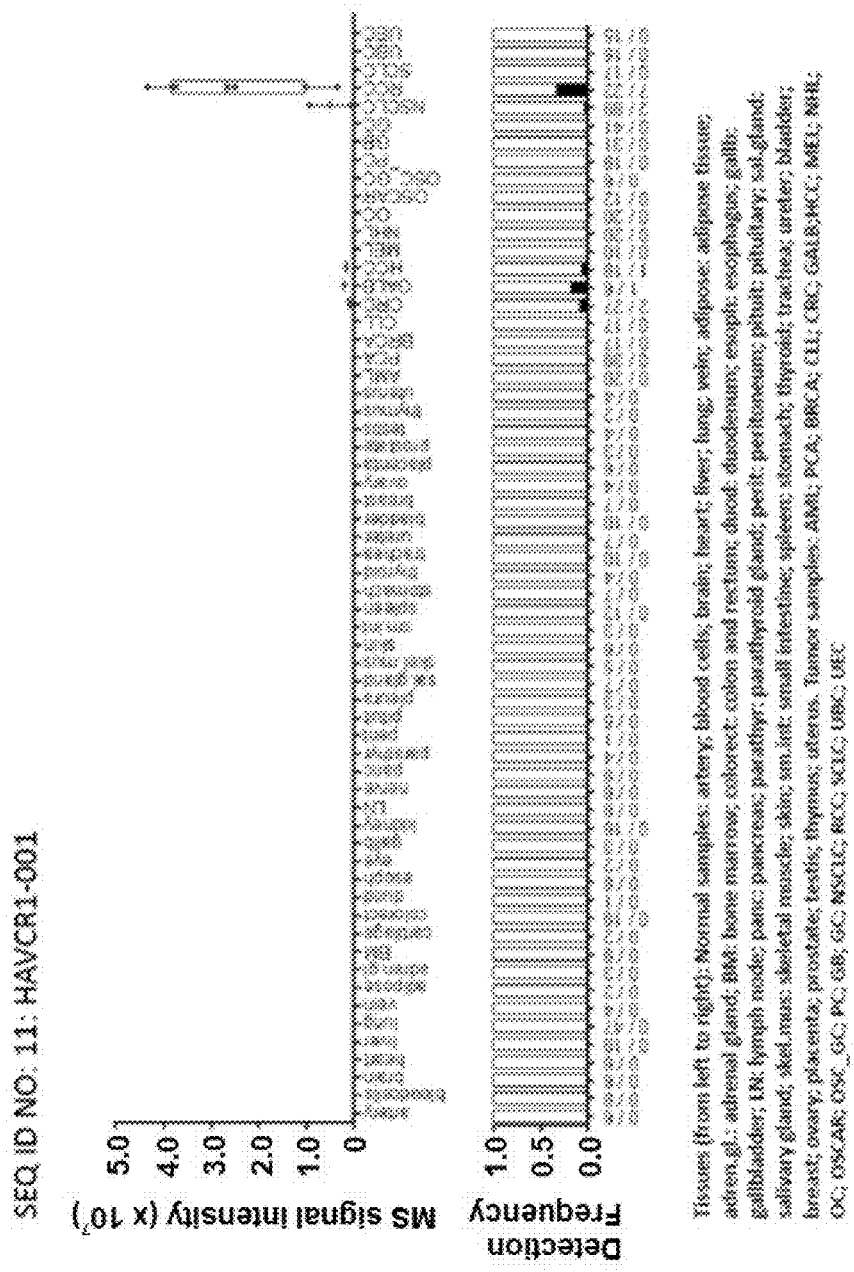
Figure 4B:
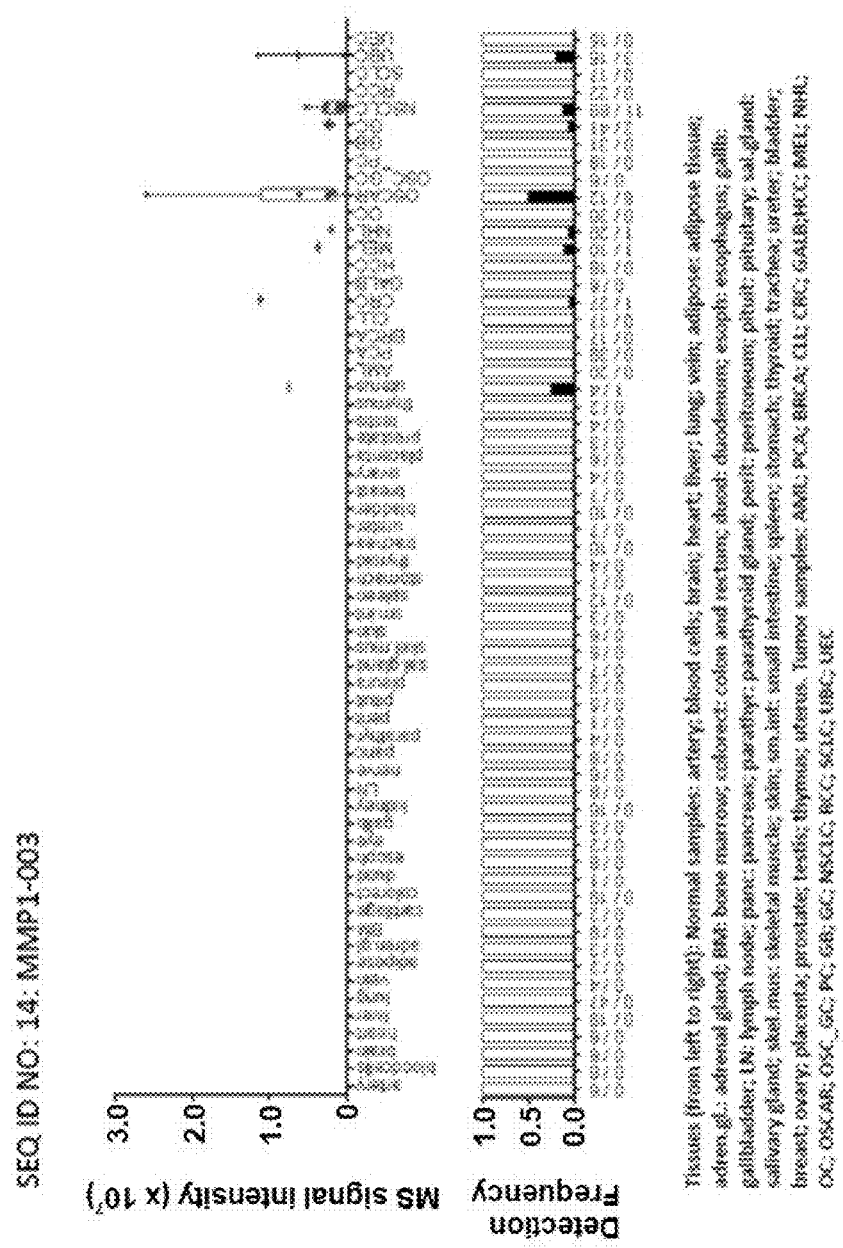
Figure 4C:
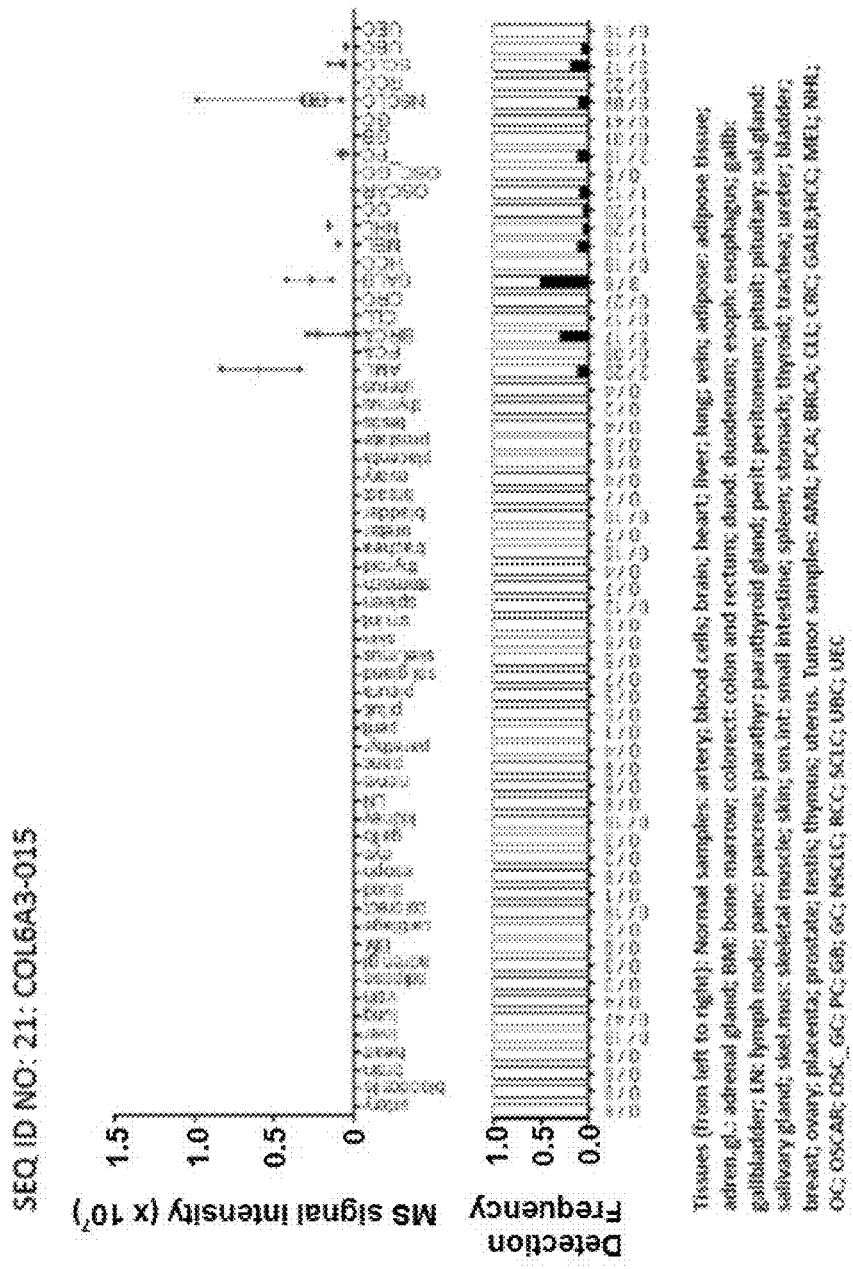
Figure 4D:
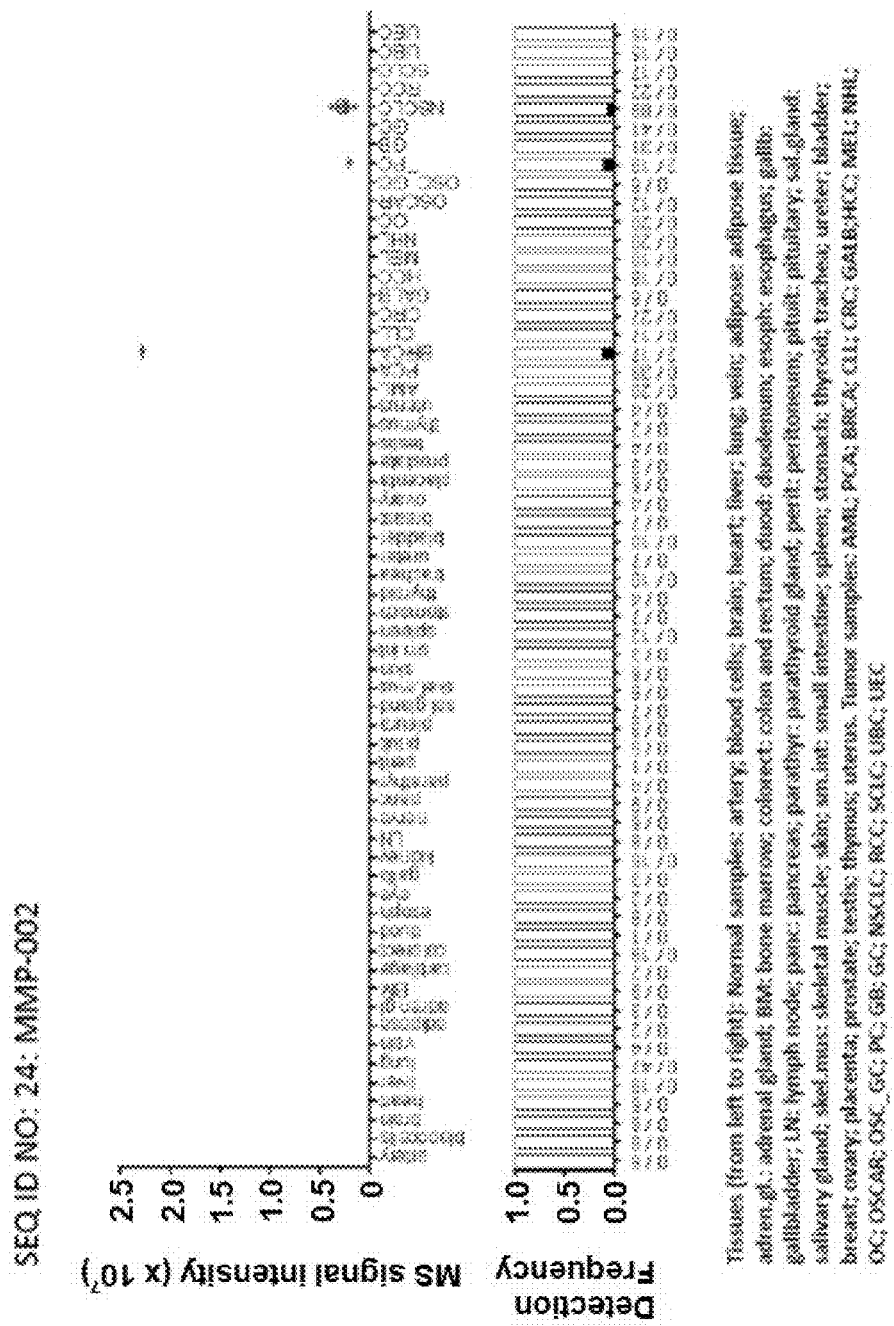
Figure 4E:
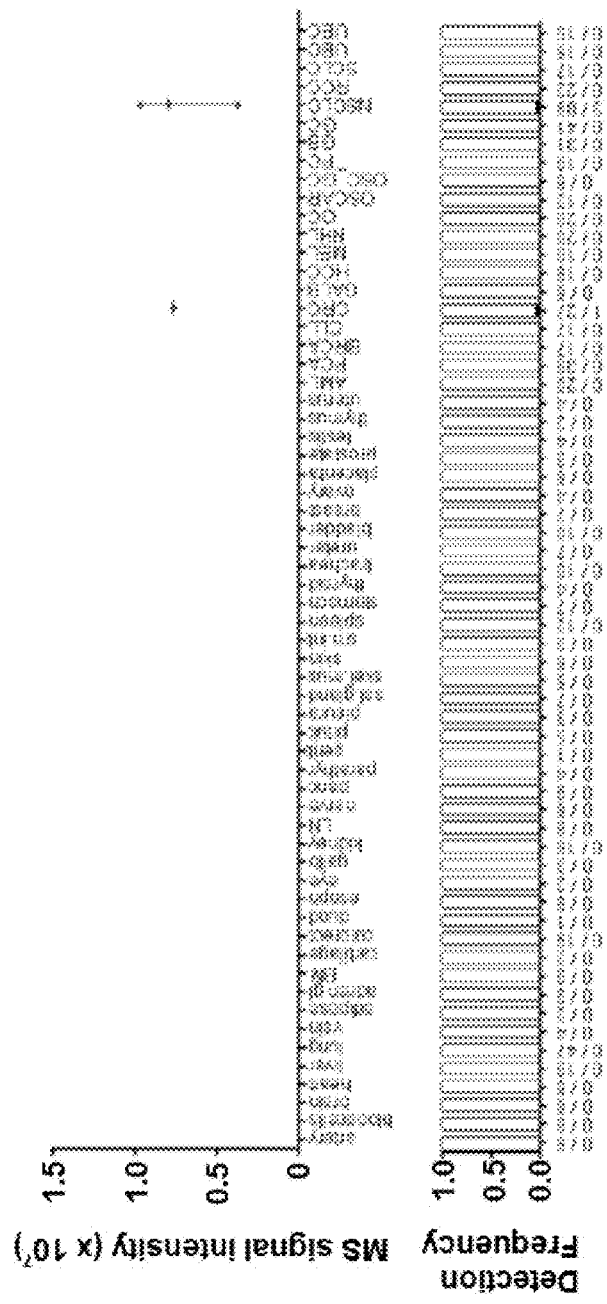
Figure 4F:
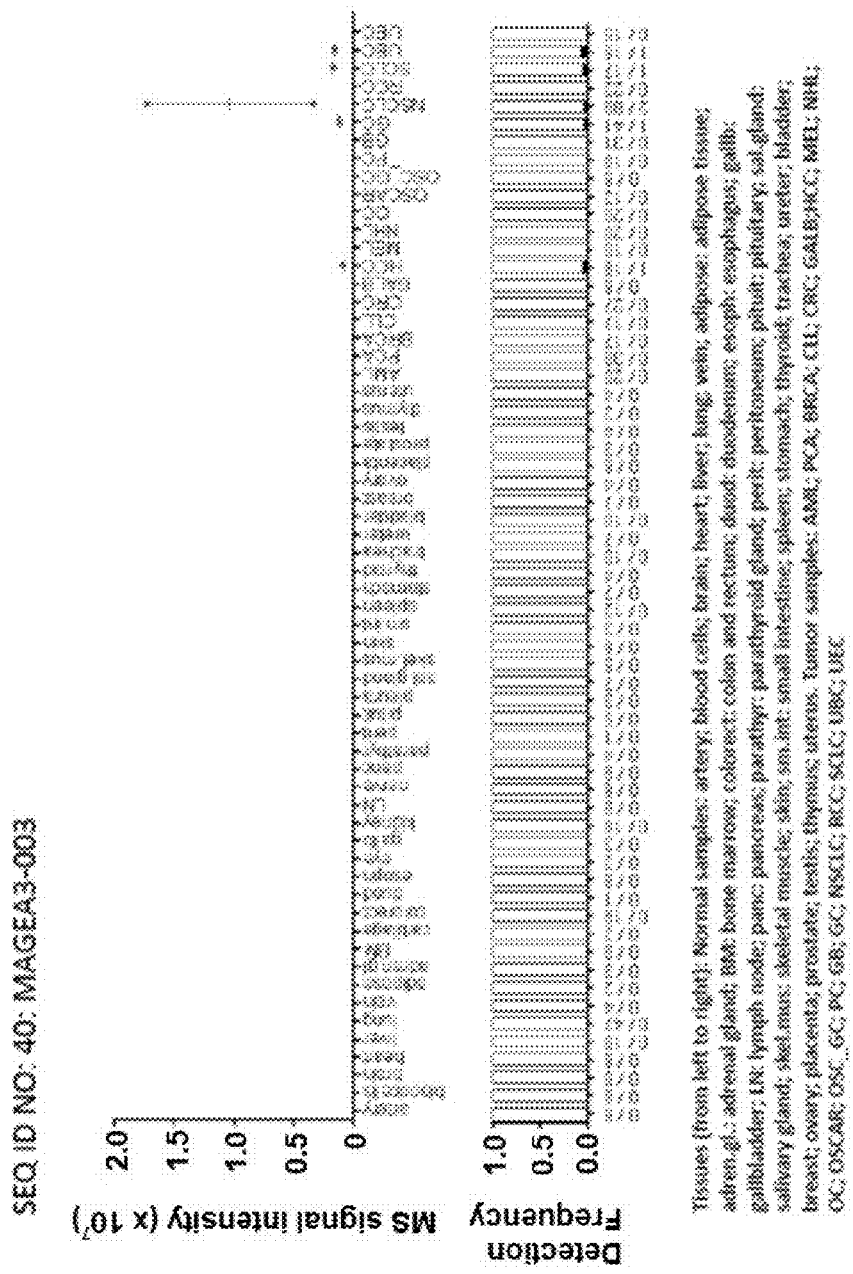
Figure 4G:
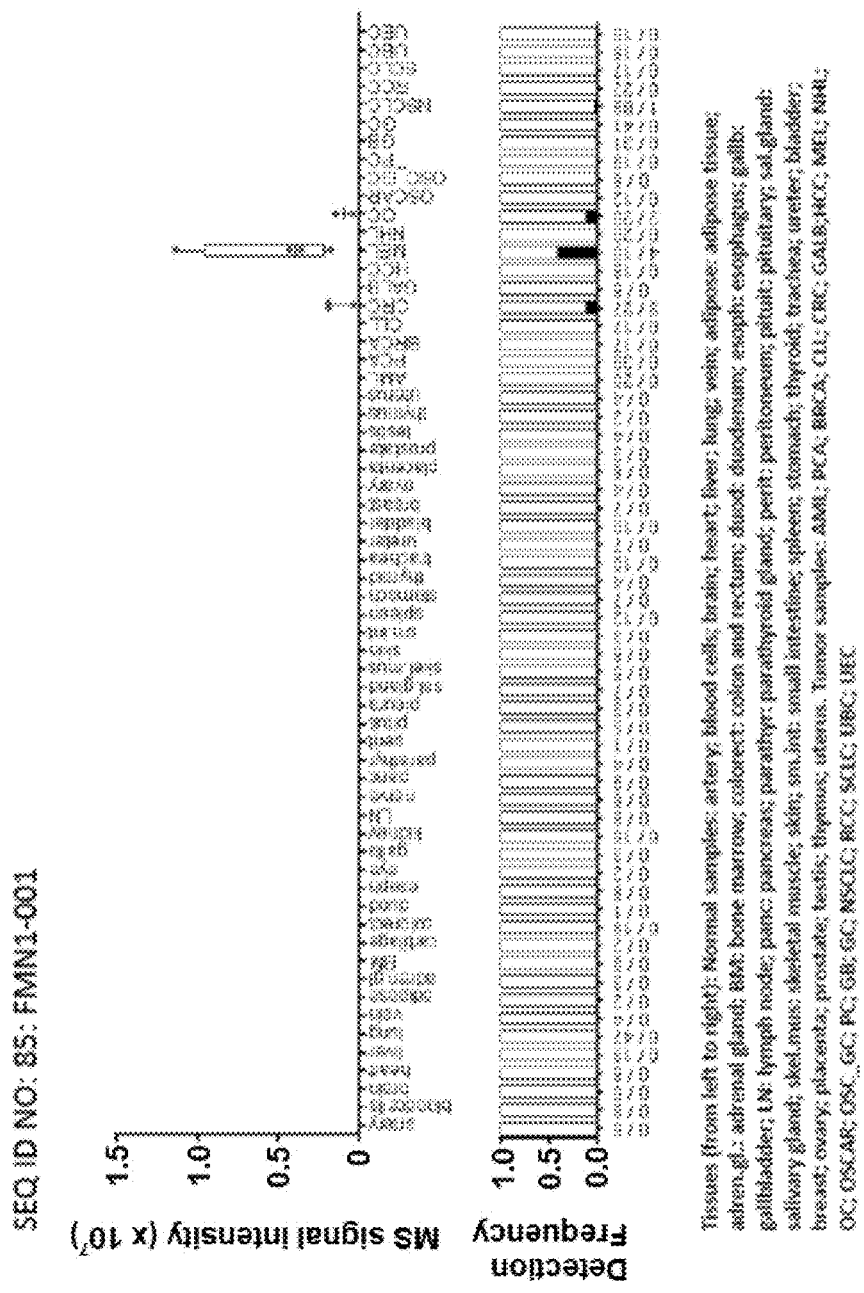
Figure 4H:
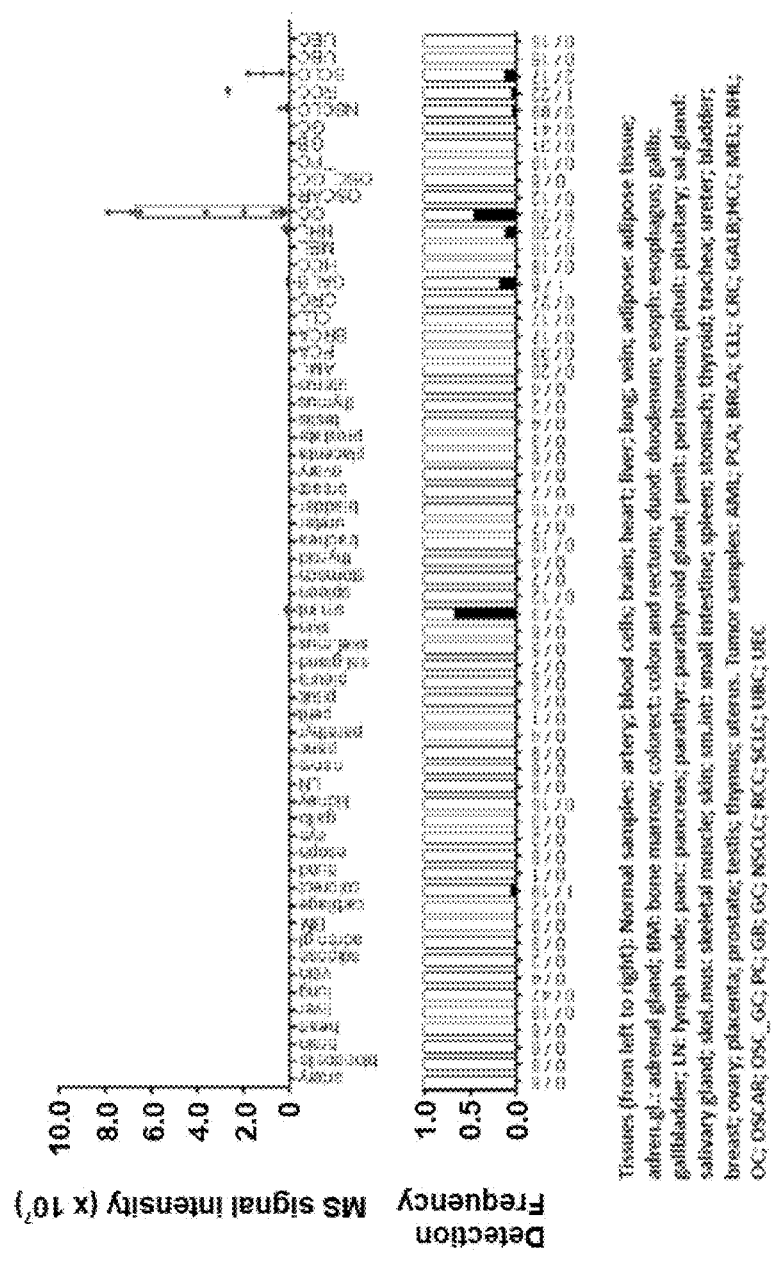
Figure 4J:
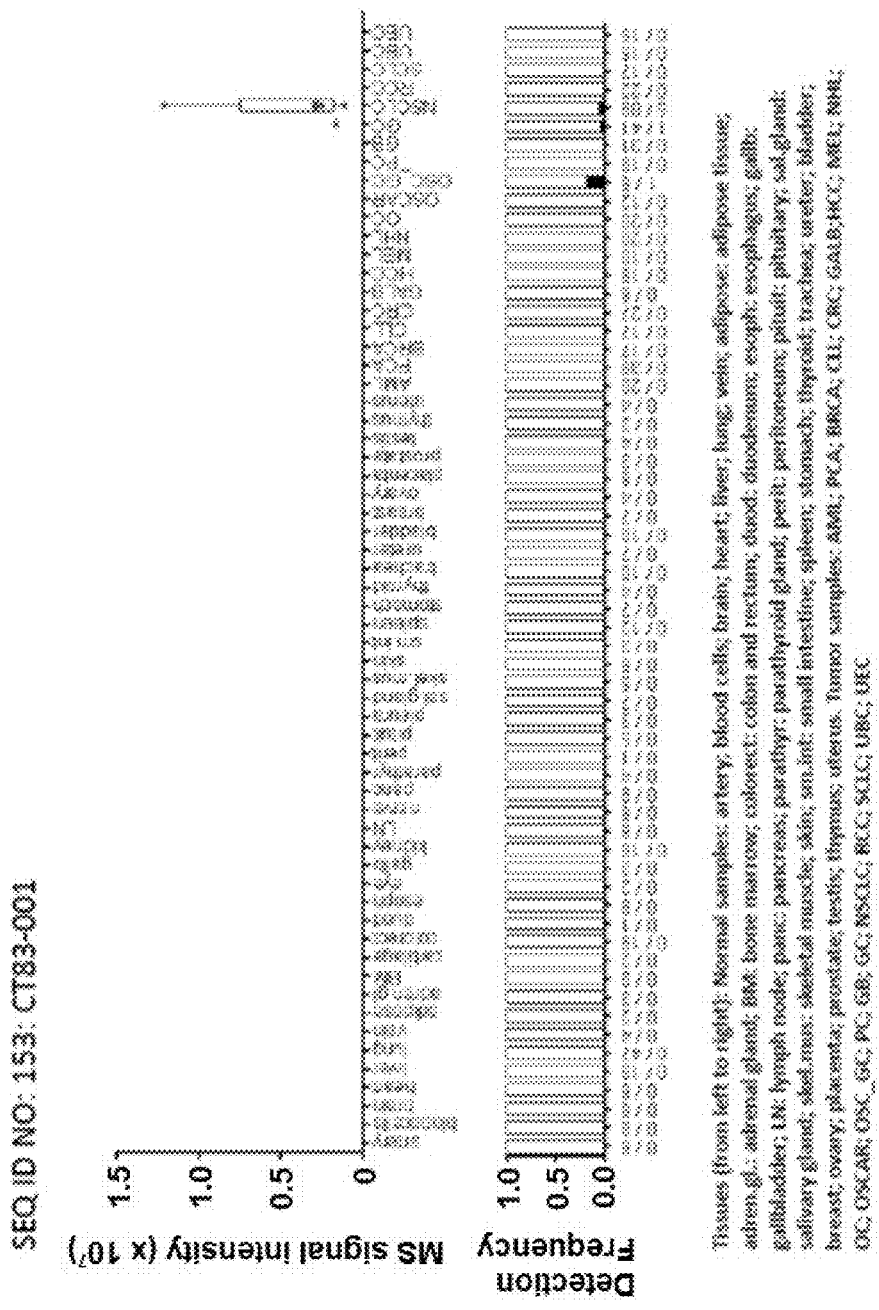
Figure 4K:
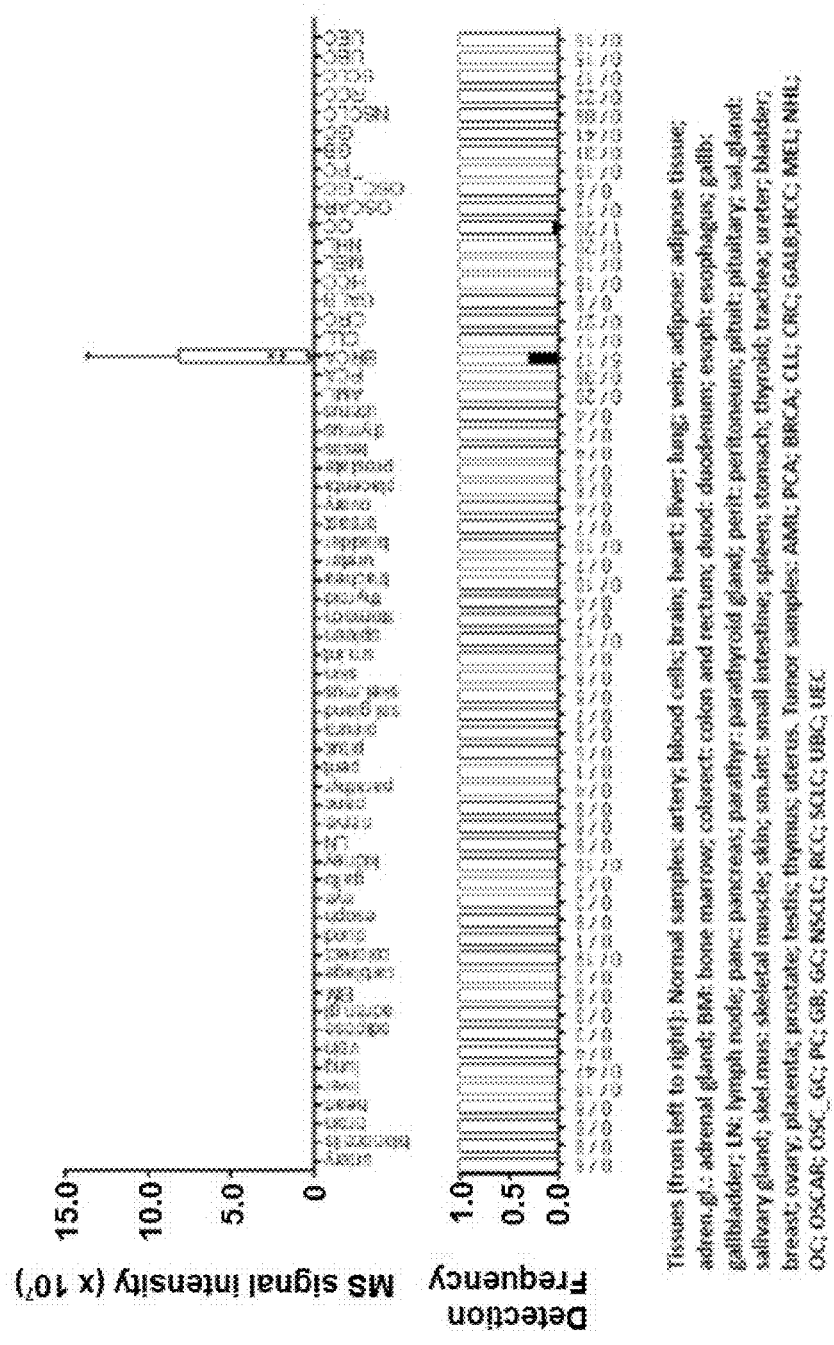
Figure 4M:
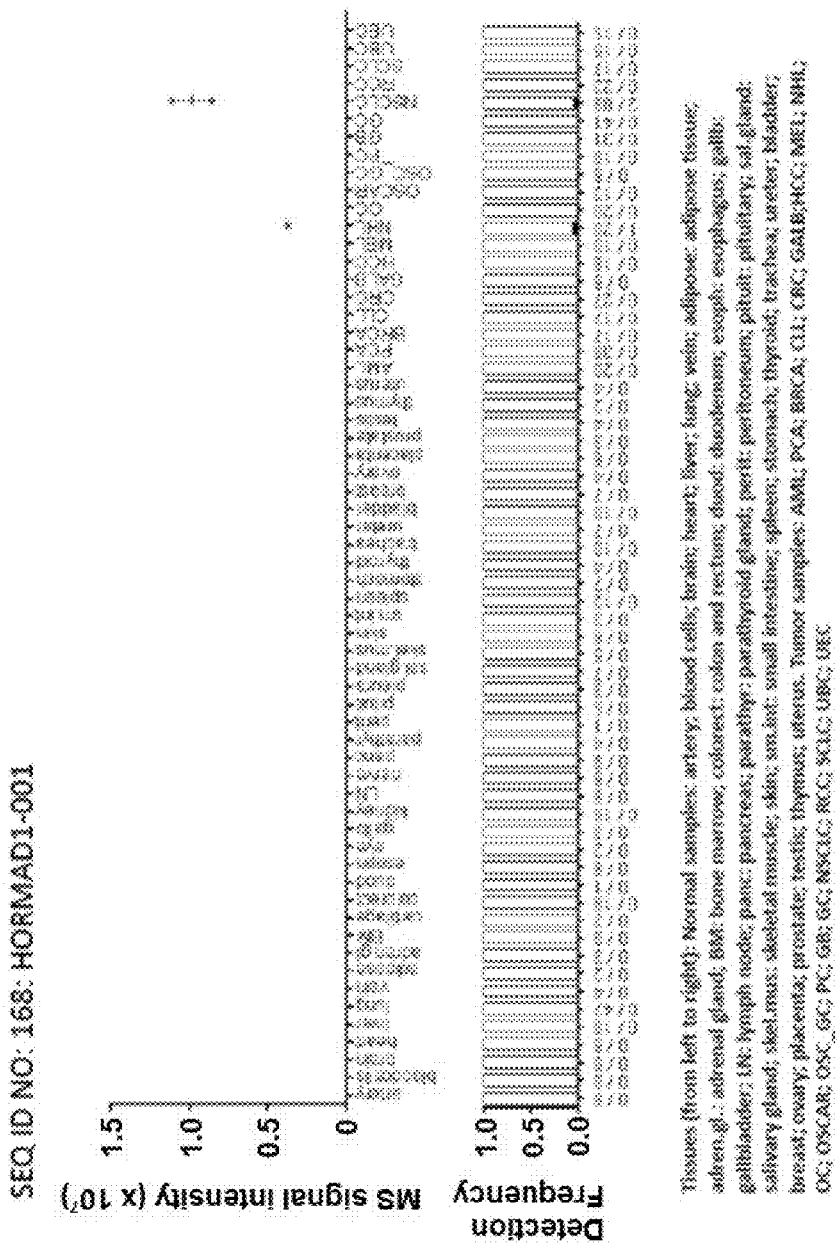
Figure 4N:
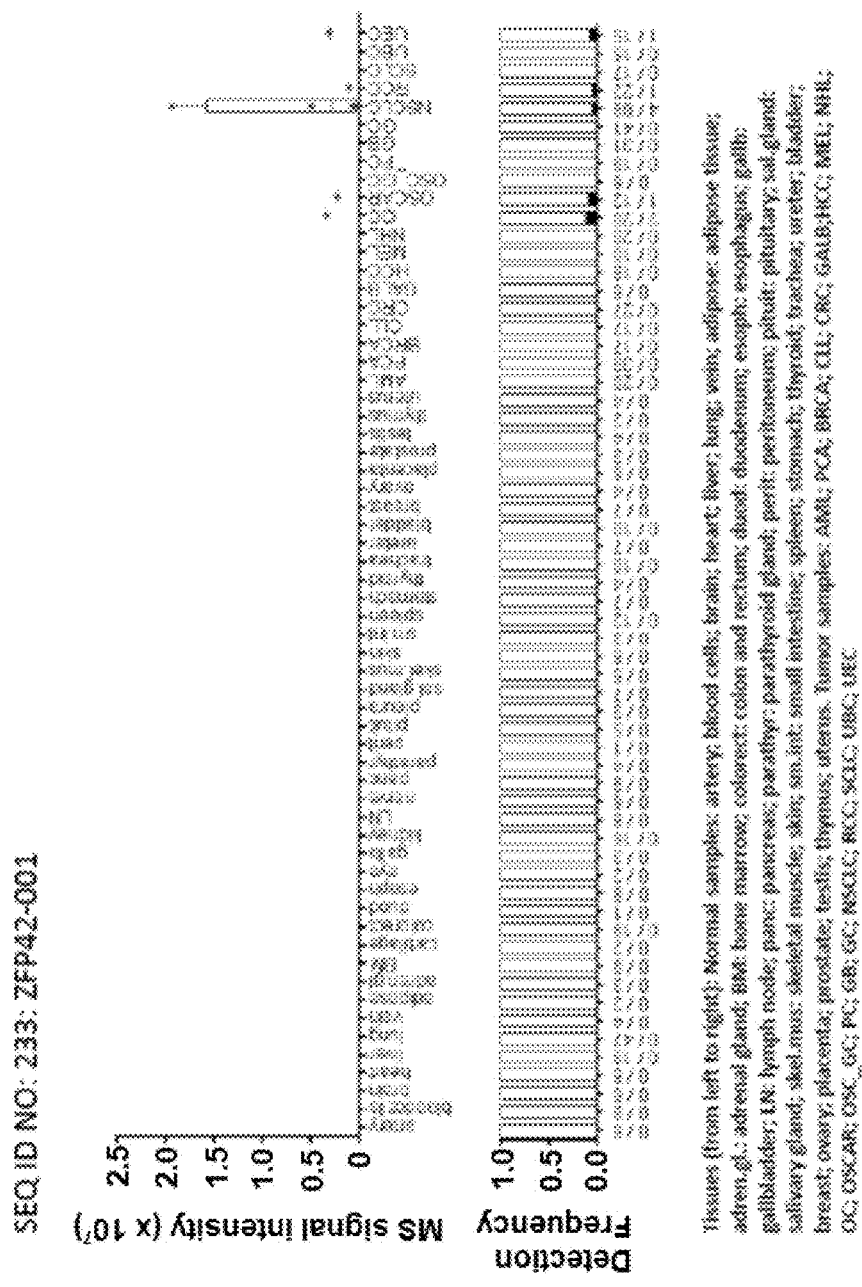
Figure 4O:
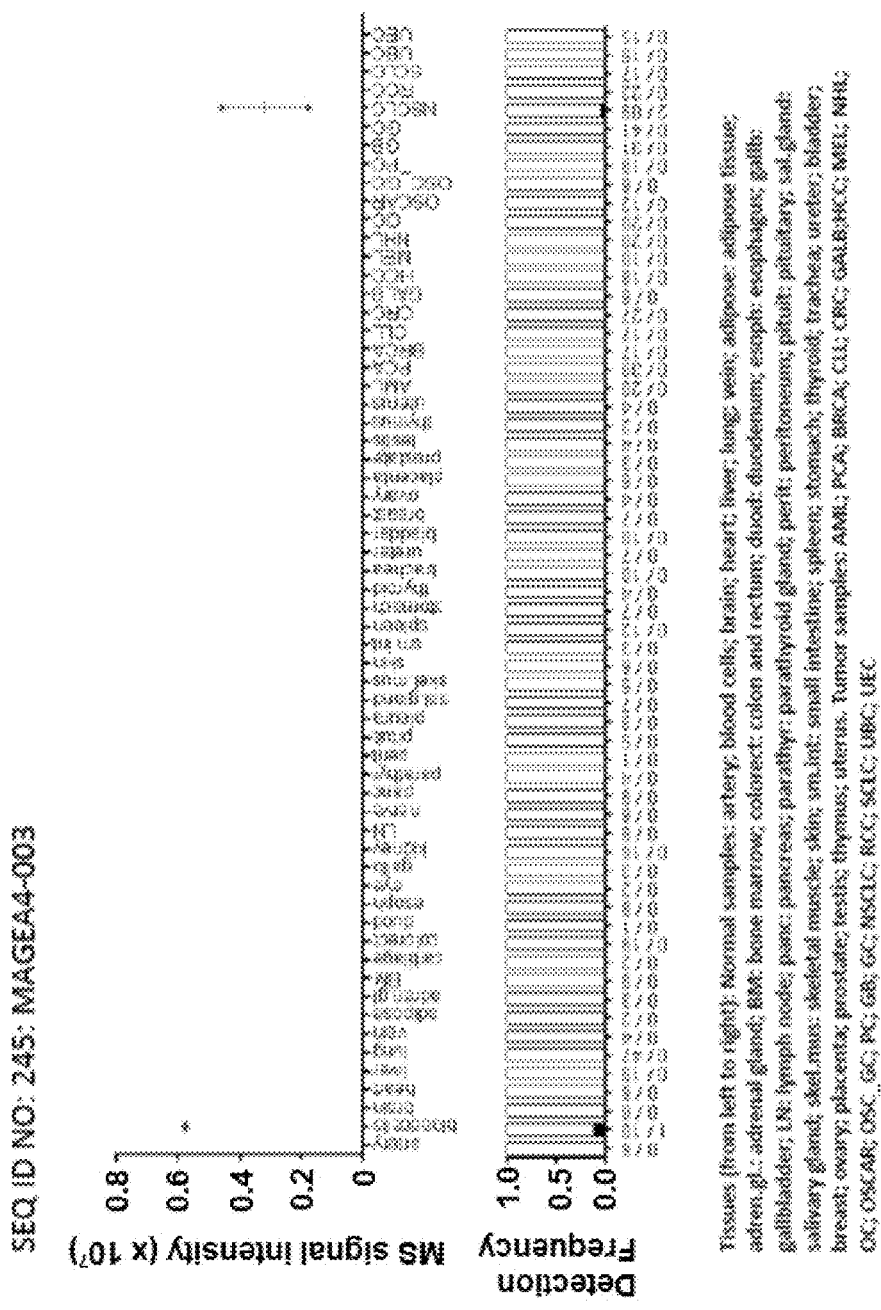
Figure 4P:
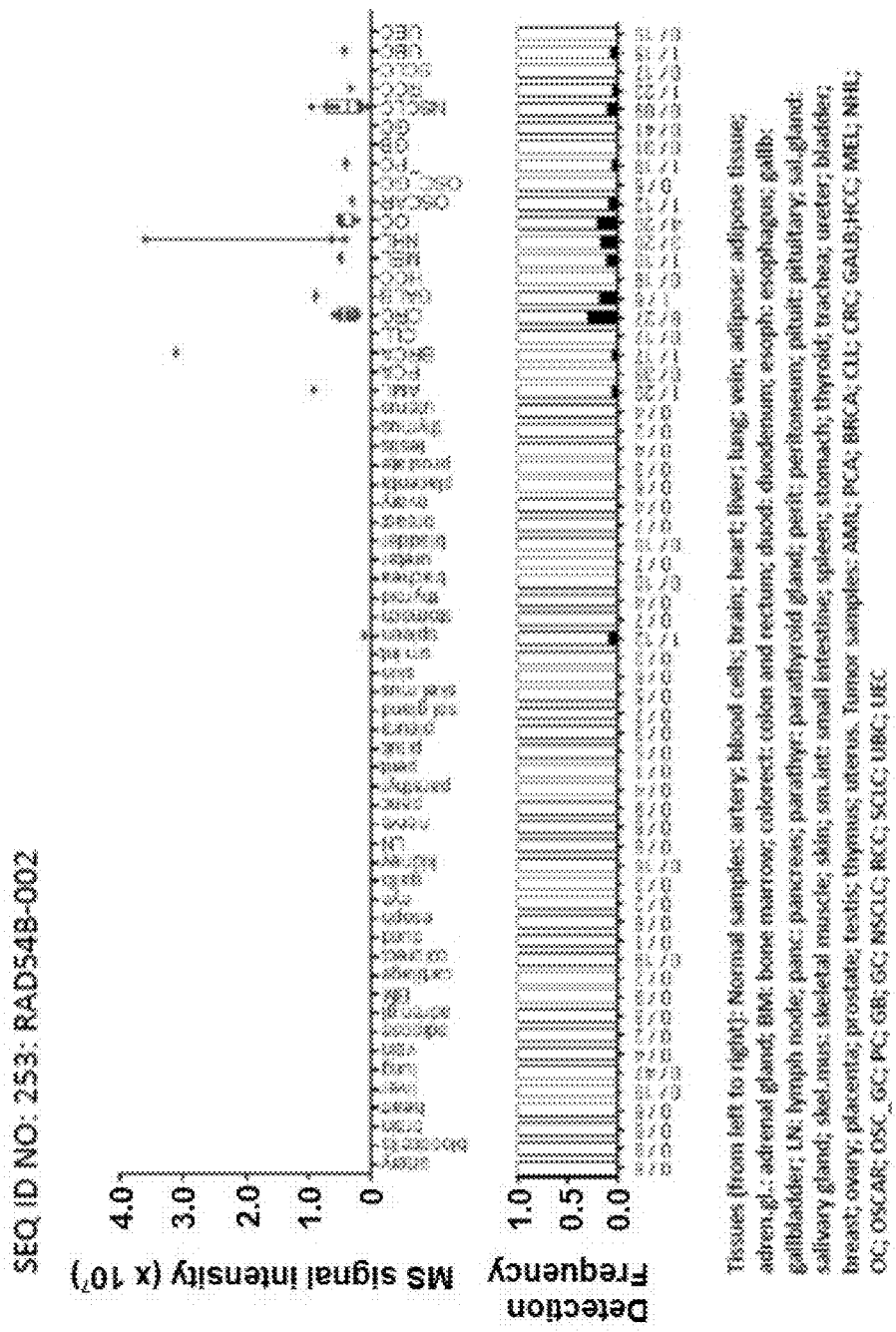
Figure 4Q:
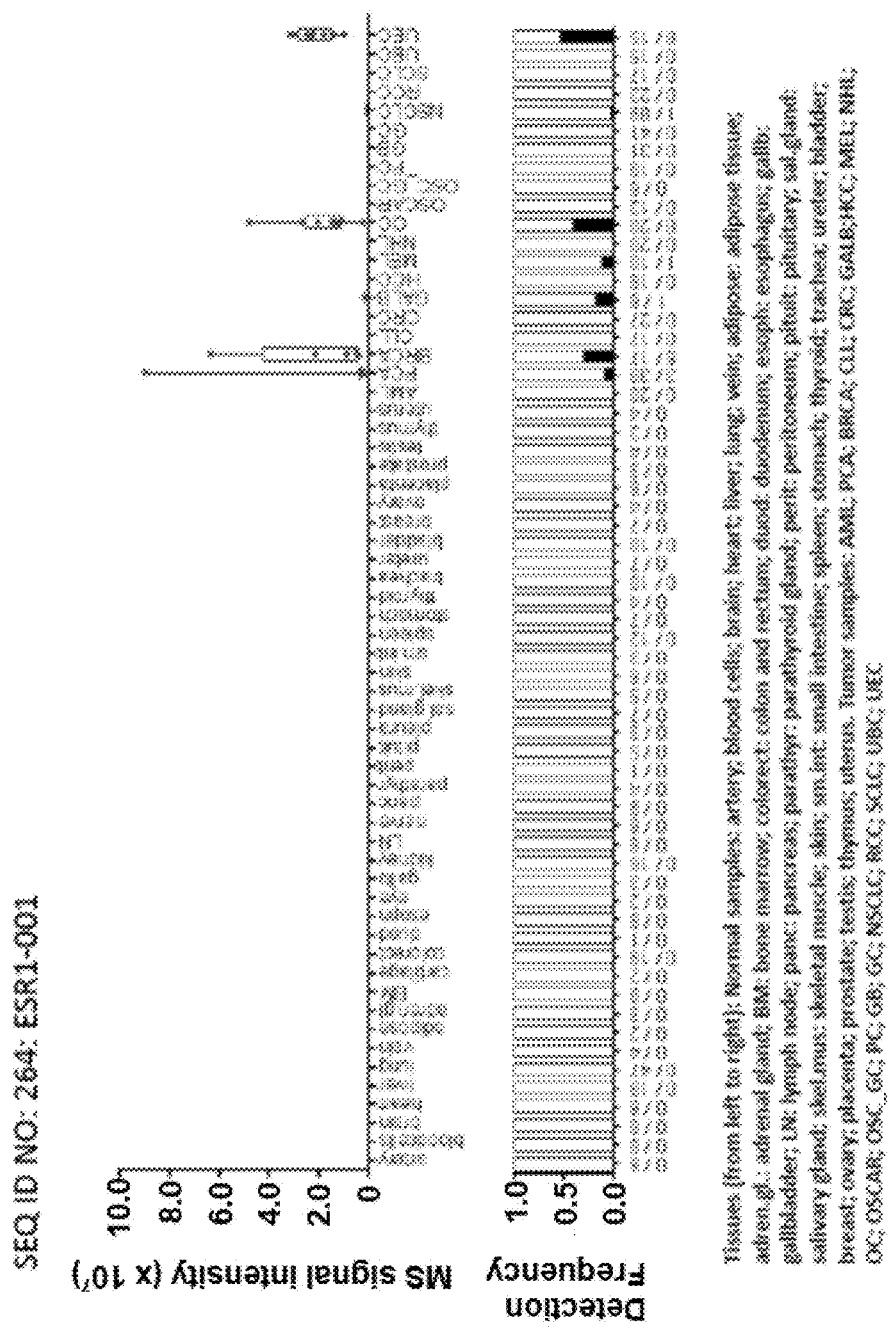
Figure 4R:
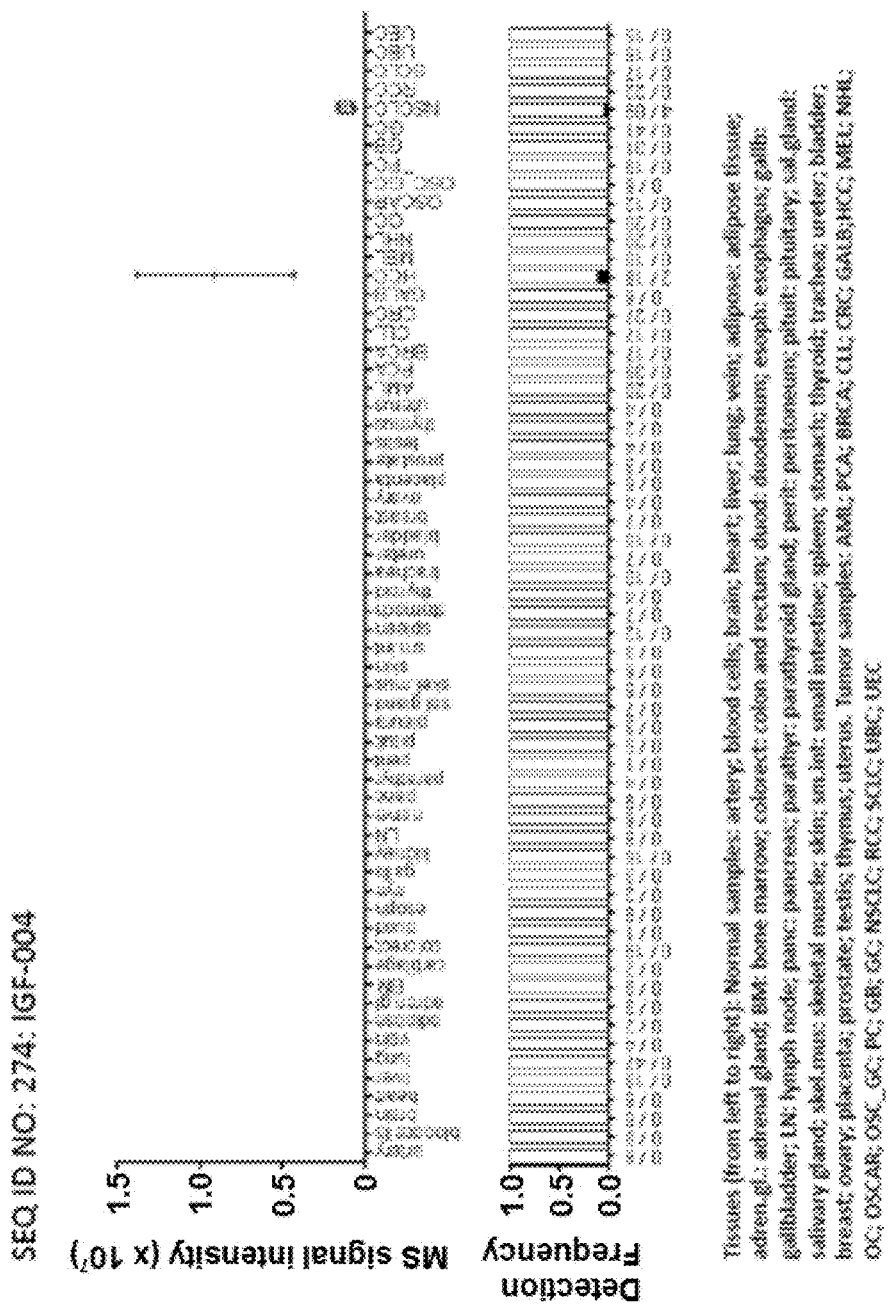

FIGS. 4A-4R show in the upper part: Median MS signal intensities from technical replicate measurements are plotted as colored dots for single HLA-A*02 positive normal (green or grey dots) and tumor samples (red dots) on which the peptide was detected. Tumor and normal samples are grouped according to organ of origin, and box-and-whisker plots represent median, 25th and 75th percentile (box), and minimum and maximum (whiskers) of normalized signal intensities over multiple samples. Normal organs are ordered according to risk categories (blood cells, cardiovascular system, brain, liver, lung: high risk, dark green dots; reproductive organs, breast, prostate: low risk, grey dots; all other organs: medium risk; light green dots). Lower part: The relative peptide detection frequency in every organ is shown as spine plot. Numbers below the panel indicate number of samples on which the peptide was detected out of the total number of samples analyzed for each organ (N=298 for normal samples, N=461 for tumor samples). If the peptide has been detected on a sample but could not be quantified for technical reasons, the sample is included in this representation of detection frequency, but no dot is shown in the upper part of the figure. Tissues (from left to right): Normal samples: artery; blood cells; brain; heart; liver; lung; vein; adipose: adipose tissue; adren.gl.: adrenal gland; BM: bone marrow; colorect: colon and rectum; duod: duodenum; esoph: esophagus; gallb: gallbladder; LN: lymph node; panc: pancreas; parathyr: parathyroid gland; perit: peritoneum; pituit: pituitary; sal.gland: salivary gland; skel.mus: skeletal muscle; skin; sm.int: small intestine; spleen; stomach; thyroid; trachea; ureter; bladder; breast; ovary; placenta; prostate; testis; thymus; uterus. Tumor samples: AML: acute myeloid leukemia; PCA: prostate cancer; BRCA: breast cancer; CLL: chronic lymphocytic leukemia; CRC: colorectal cancer; GALB: gallbladder cancer; HCC: hepatocellular carcinoma; MEL: melanoma; NHL: non-hodgkin lymphoma; OC: ovarian cancer;

OSCAR: esophageal cancer; OSC_GC: esophageal/gastric cancer; PC: pancreatic cancer; GB: glioblastoma; GC: gastric cancer; NSCLC: non-small cell lung cancer; RCC: renal cell carcinoma; SCLC: small cell lung cancer; UBC: urinary bladder carcinoma; UEC: uterine and endometrial cancer.

Figure 5A:
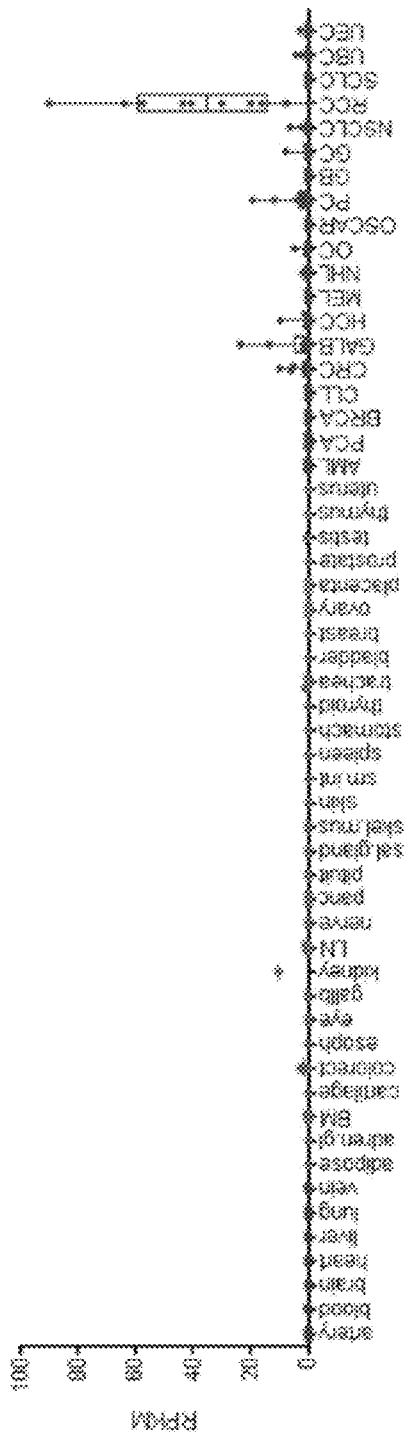
Figure 5G:
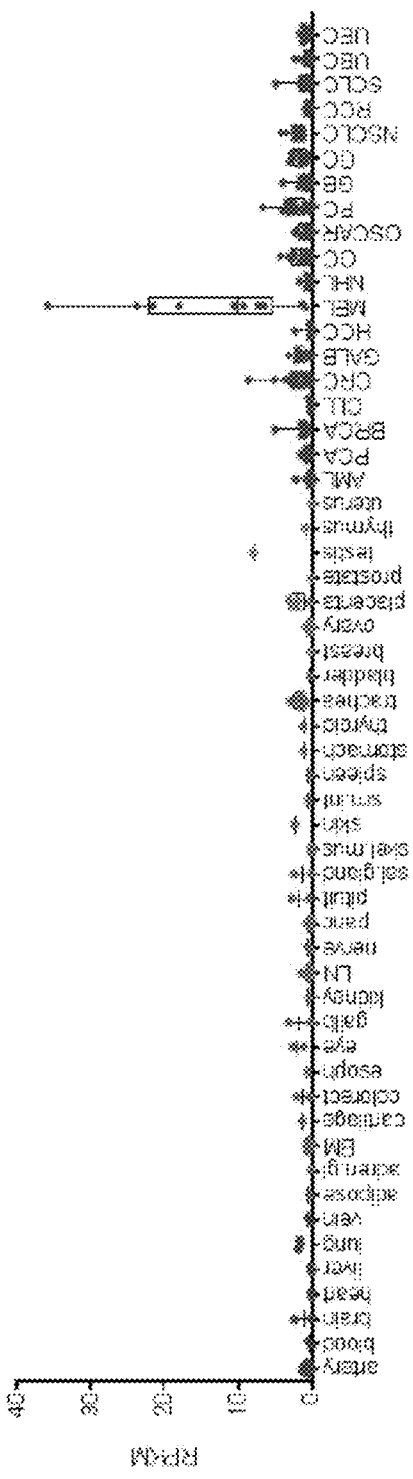
Figure 5K:
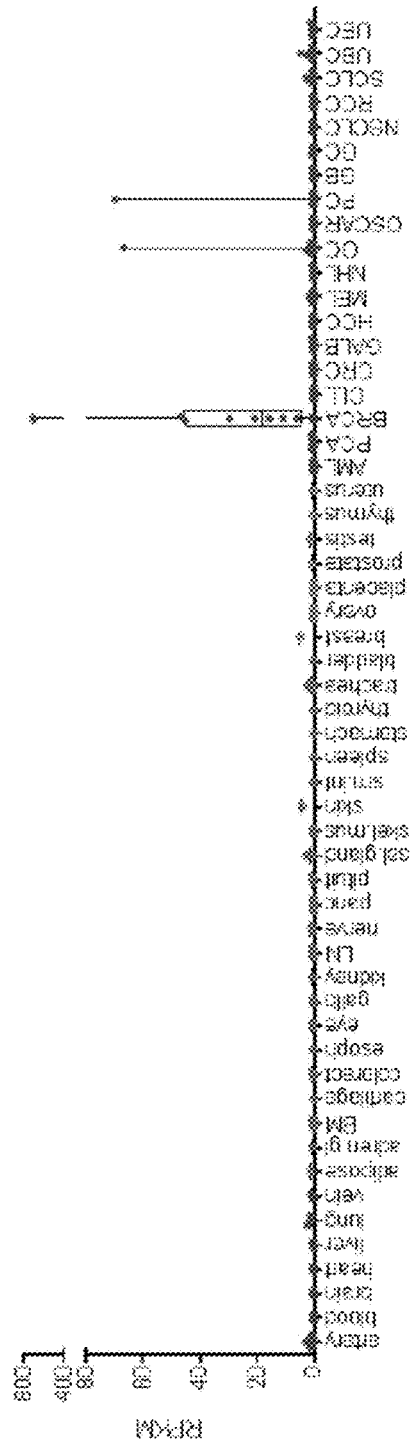
Figure 5L:
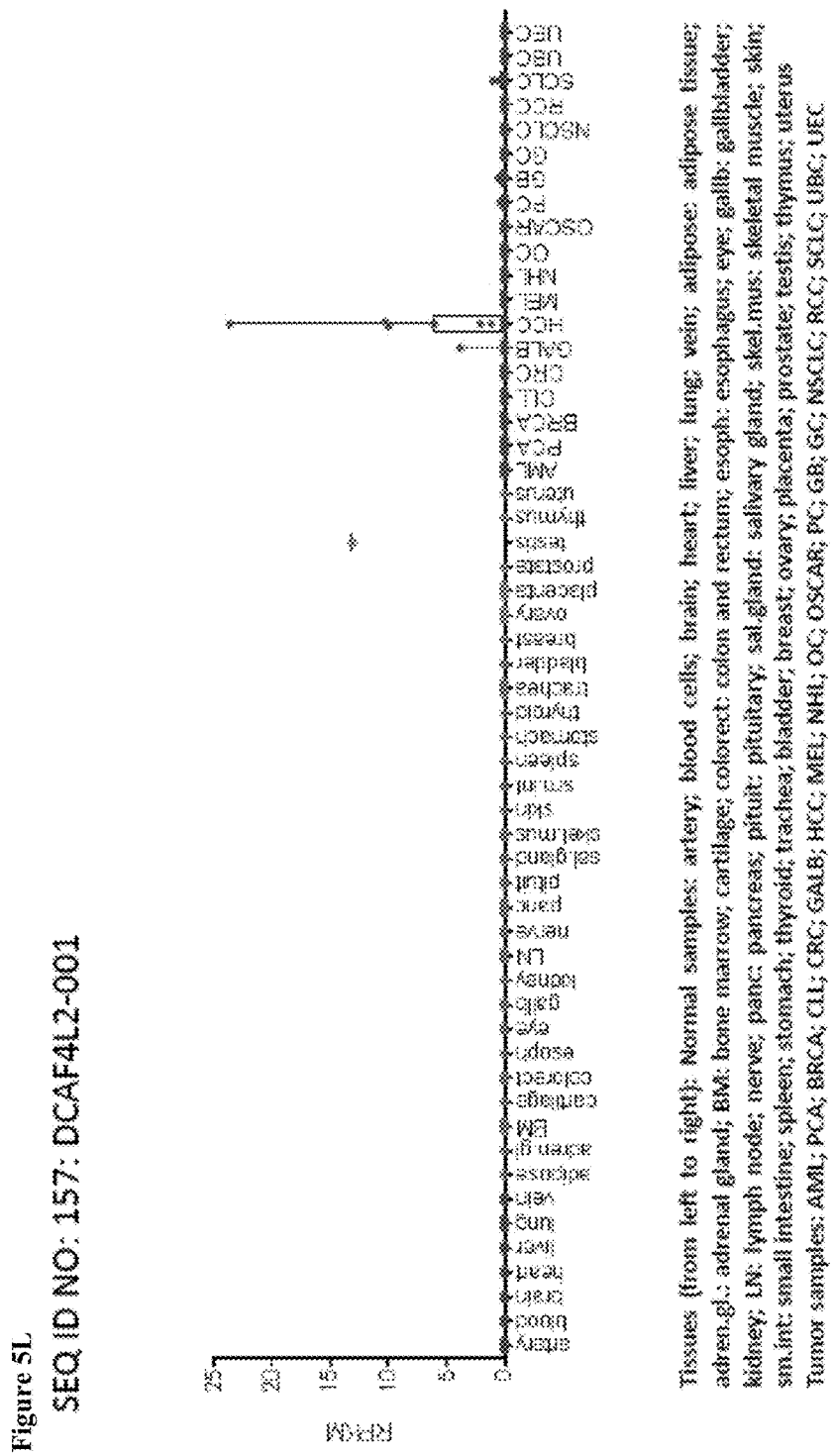

FIGS. 5A-5R show exemplary expression profiles of source genes of the present invention that are over-expressed in different cancer samples. Tumor (red dots) and normal (green or grey dots) samples are grouped according to organ of origin, and box-and-whisker plots represent median, 25th and 75th percentile (box), and minimum and maximum (whiskers) RPKM values. Normal organs are ordered according to risk categories. RPKM=reads per kilobase per million mapped reads. Normal samples: artery; blood cells; brain; heart; liver; lung; vein; adipose: adipose tissue; adren.gl.: adrenal gland; BM: bone marrow; cartilage; colorect: colon and rectum; esoph: esophagus; eye; gallb: gallbladder; kidney; LN: lymph node; nerve; panc: pancreas; pituit: pituitary; sal.gland: salivary gland; skel.mus: skeletal muscle; skin; sm.int: small intestine; spleen; stomach; thyroid; trachea; bladder; breast; ovary; placenta; prostate; testis; thymus; uterus. Tumor samples: AML: acute myeloid leukemia; PCA: prostate cancer; BRCA: breast cancer; CLL: chronic lymphocytic leukemia; CRC: colorectal cancer; GALB: gallbladder cancer; HCC: hepatocellular carcinoma; MEL: melanoma; NHL: non-hodgkin lymphoma; OC: ovarian cancer; OSCAR: esophageal cancer; PC: pancreatic cancer; GB: glioblastoma; GC: gastric cancer; NSCLC: non-small cell lung cancer; RCC: renal cell carcinoma; SCLC: small cell lung cancer; UBC: urinary bladder carcinoma; UEC: uterine and endometrial cancer.

Figure 6A:
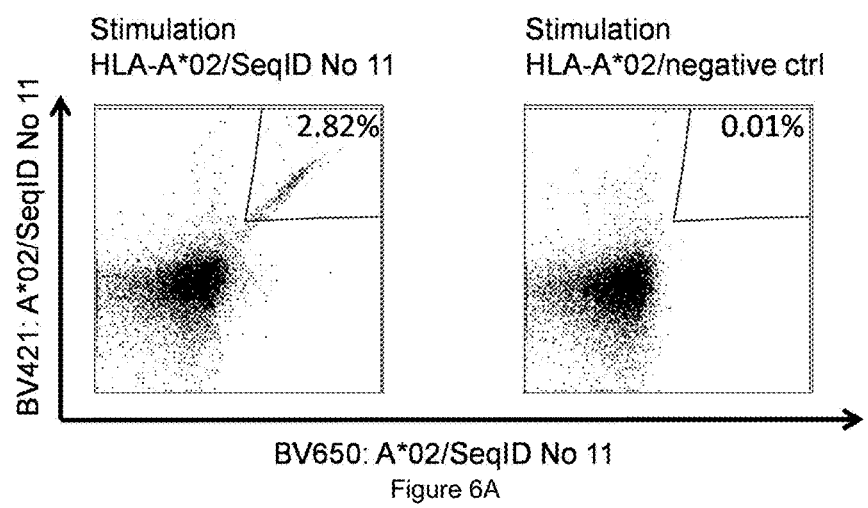
Figure 6B:
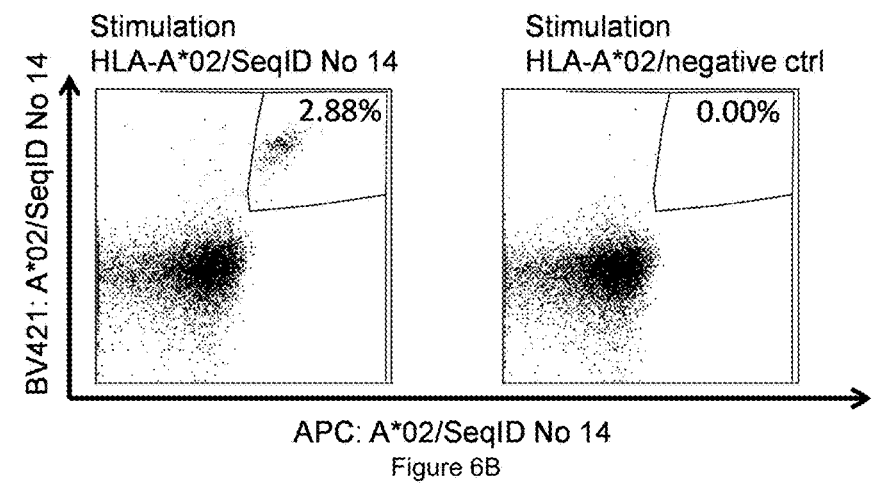
Figure 6C:
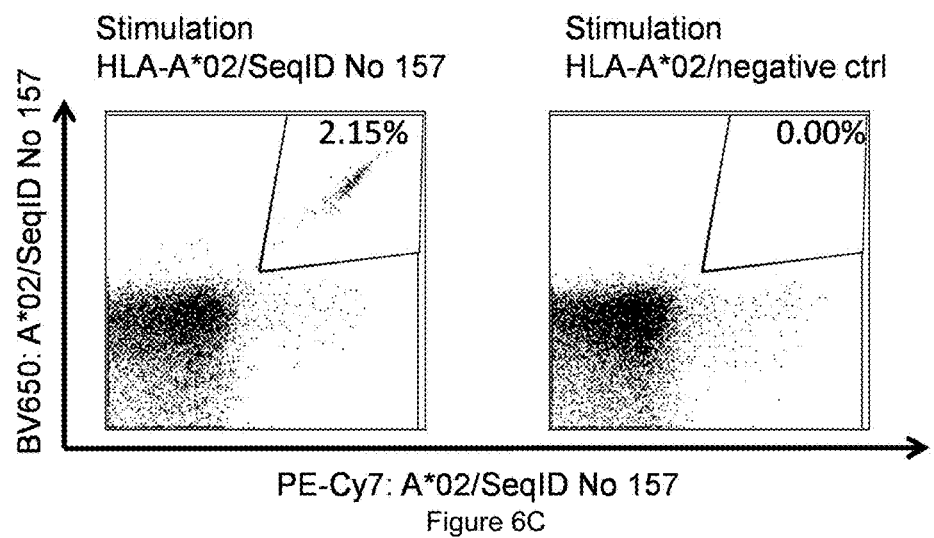
Figure 6D:
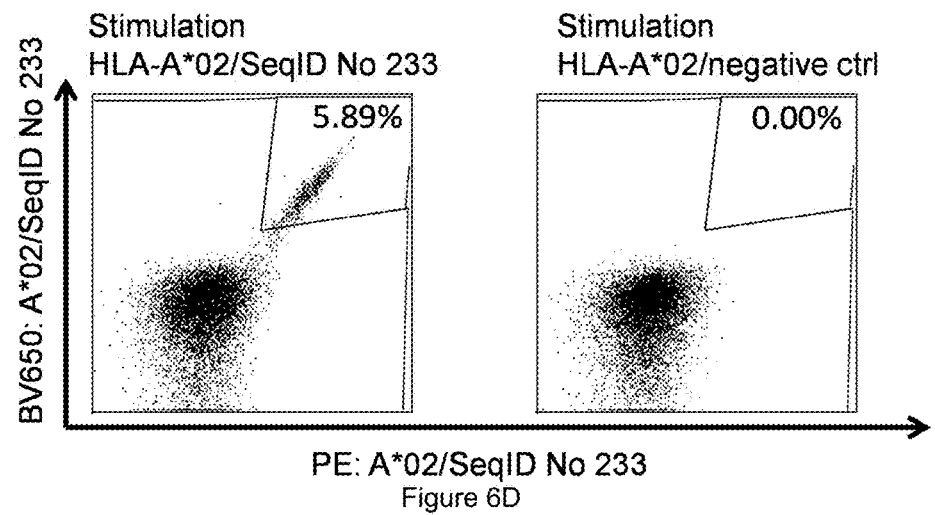
Figure 6E:
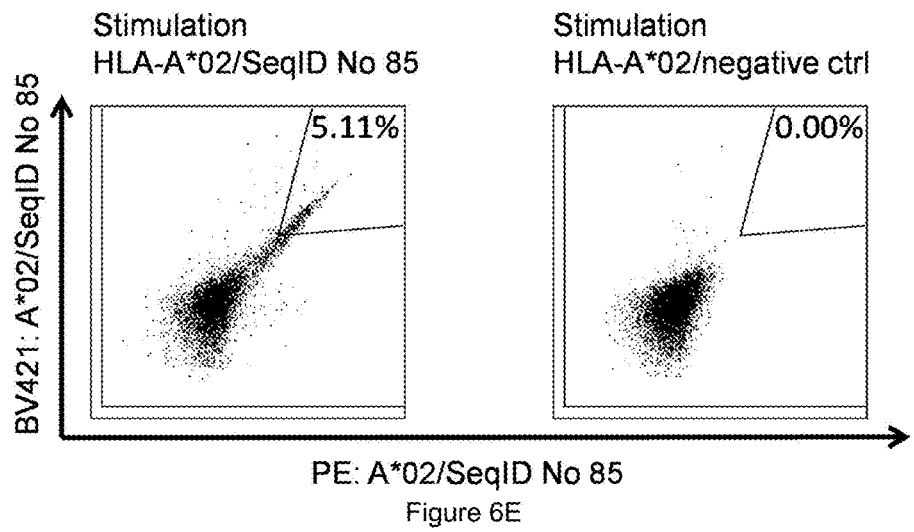
Figure 6F:
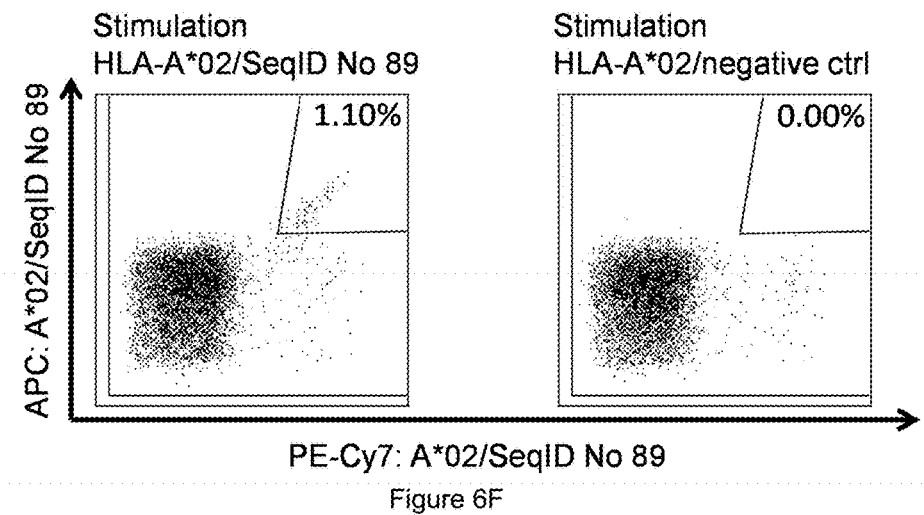
Figure 6G:
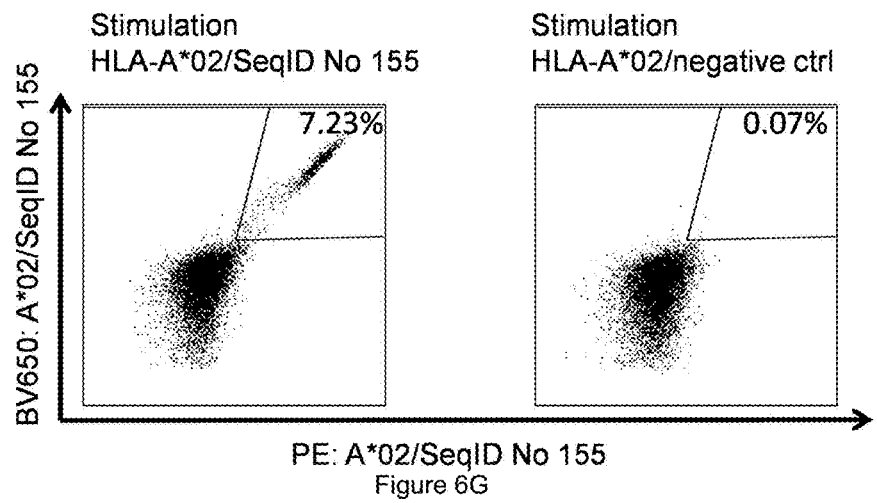
Figure 6H:
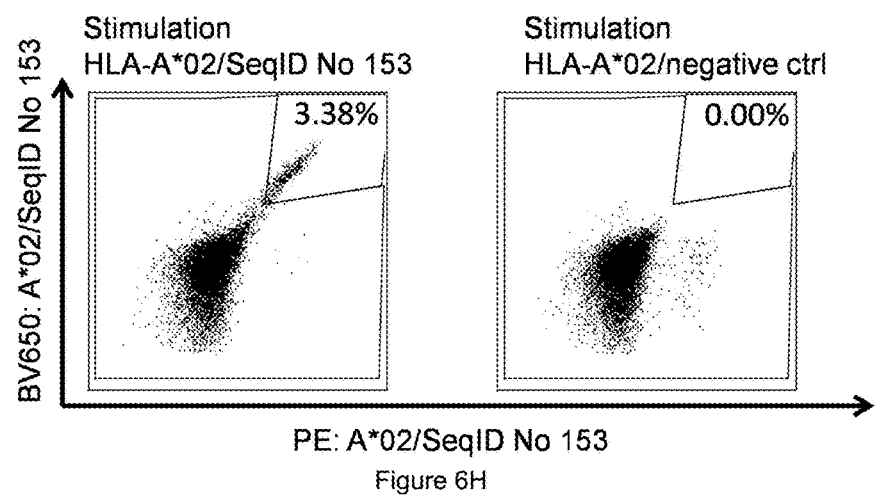
Figure 6I:
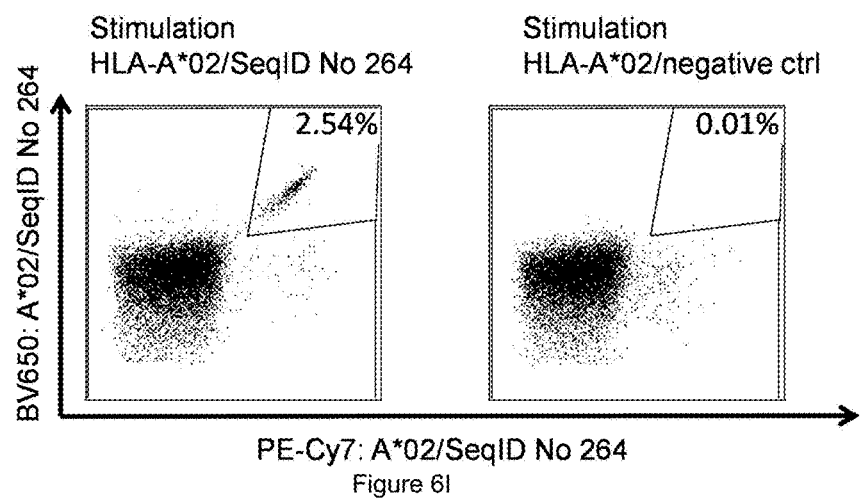
Figure 6J:
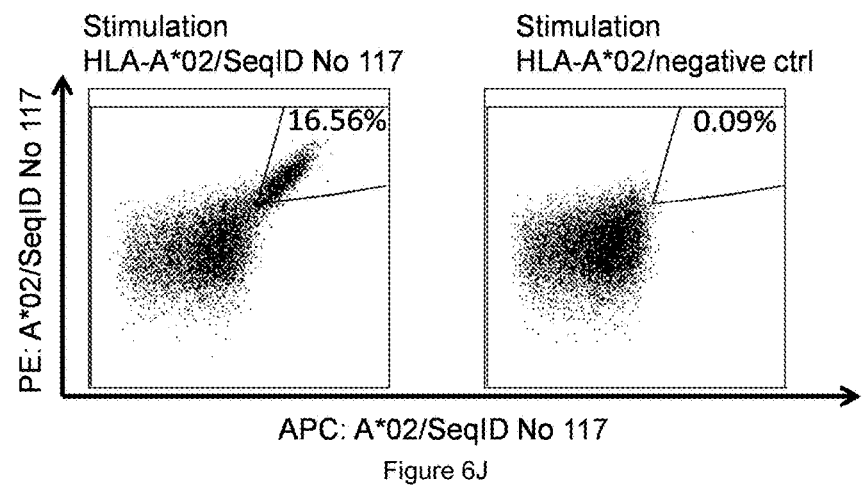
Figure 6K:
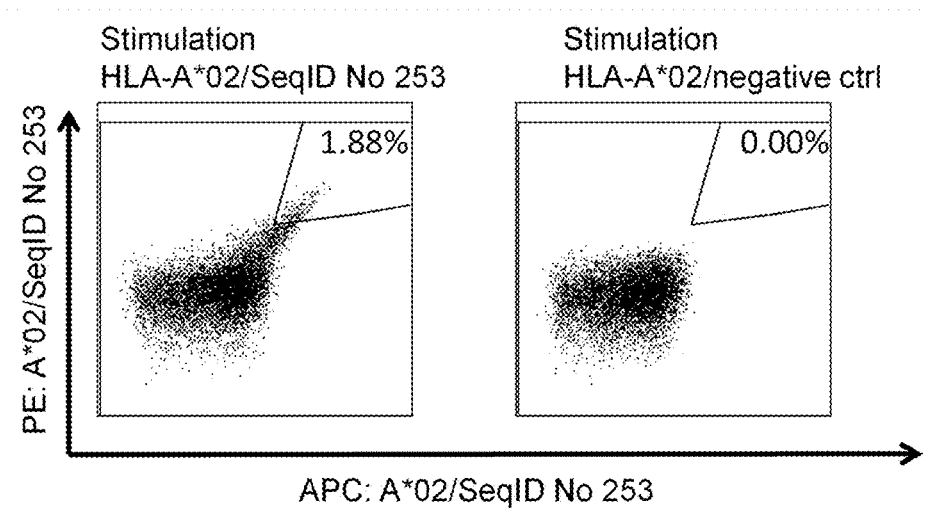
Figure 6L:
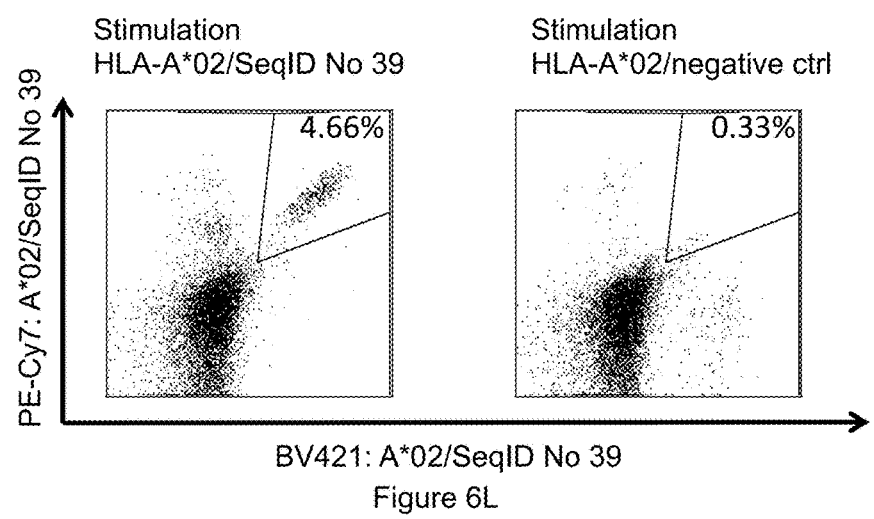
Figure 6M:
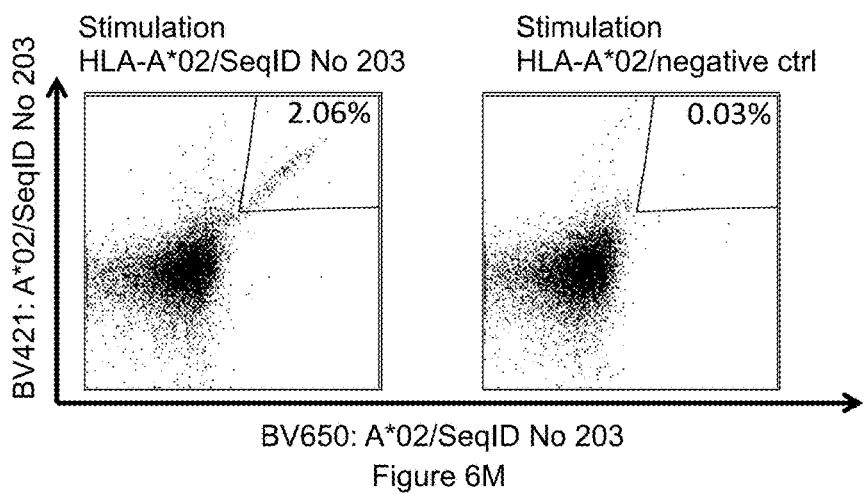

FIGS. 6A to 6M show exemplary results of peptide-specific in vitro CD8+ T cell responses of a healthy HLA-A*02+donor. CD8+ T cells were primed using artificial APCs coated with anti-CD28 mAb and HLA-A*02 in complex with for example SeqID No 11 peptide (FIG. 6A, left panel) or SeqID No 14 peptide (FIG. 6B, left panel), respectively (SeqID No 157 (FIG. 6C), 233 (FIG. 6D), 85 (FIG. 6E), 89 (FIG. 6F), 155 (FIG. 6G), 153 (FIG. 6H), 264 (FIG. 6I), 117 (FIG. 6J), 253 (FIG. 6K), 39 (FIG. 6L), and 203 (FIG. 6M)). After three cycles of stimulation, the detection of peptide-reactive cells was performed by 2D multimer staining with the relevant multimer, for example A*02/SeqID No 11 (FIG. 6A) or A*02/SeqID No 14 (FIG. 6B). Right panels (for example FIGS. 6A and 6B) show control staining of cells stimulated with irrelevant A*02/peptide complexes. Viable singlet cells were gated for CD8+ lymphocytes. Boolean gates helped excluding false-positive events detected with multimers specific for different peptides. Frequencies of specific multimer+ cells among CD8+ lymphocytes are indicated.

Figure 7B:
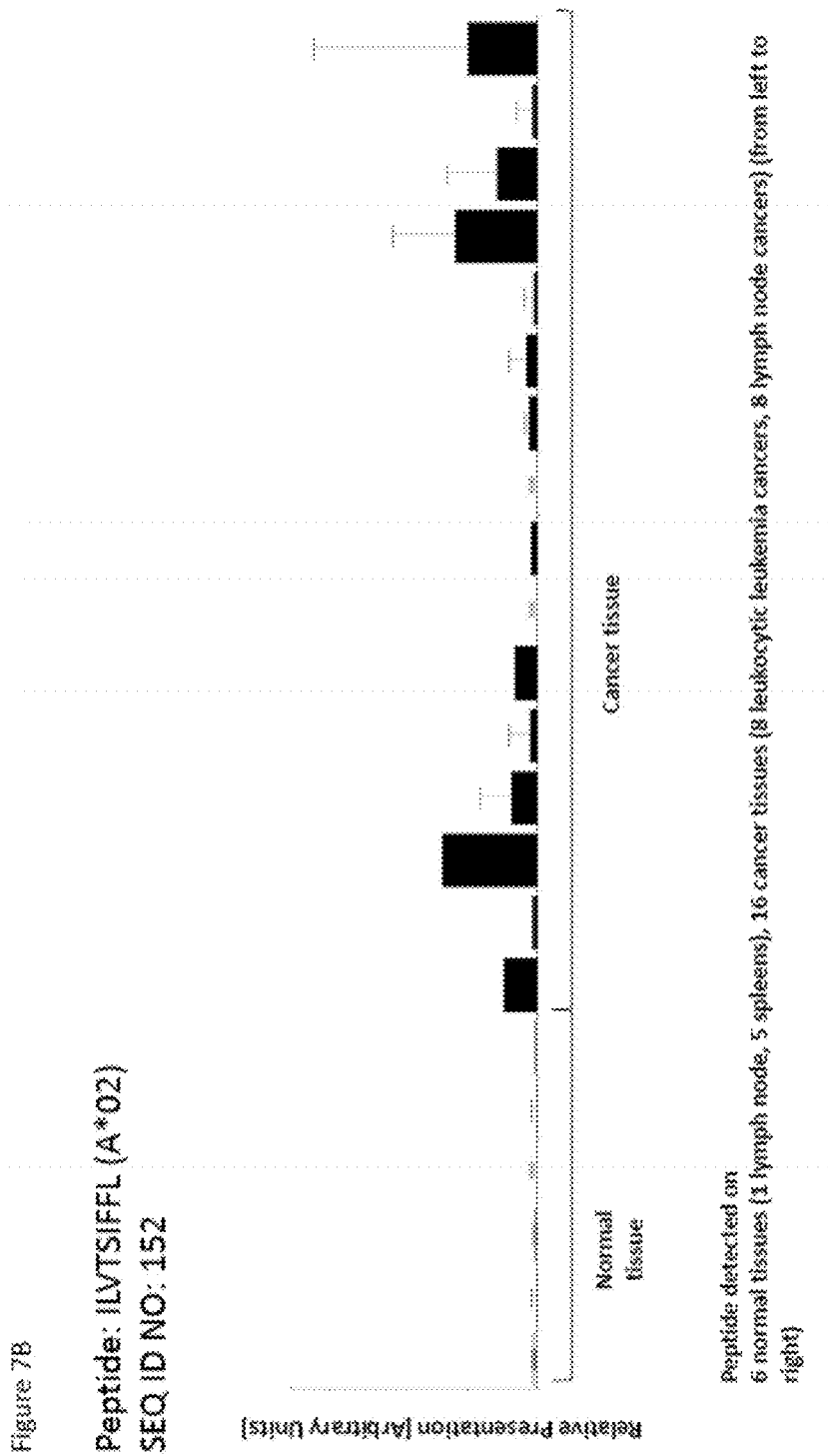

FIGS. 7A-7C show the over-presentation of various peptides in different cancer tissues compared to normal tissues. The analyses included data from more than 320 normal tissue samples, and 462 cancer samples. Shown are only samples where the peptide was found to be presented. FIG. 7A) Gene: CCR8, Peptide: LLIPFTIFM (SEQ ID NO.: 43), Tissues from left to right: 16 cancer tissues (1 bile duct cancer, 1 breast cancer, 1 colon cancer, 7 lung cancers, 2 lymph node cancers, 3 ovarian cancers, 1 skin cancer); FIG. 7B) Gene: CXCR5, Peptide: ILVTSIFFL (SEQ ID NO.: 152), Tissues from left to right: 6 normal tissues (1 lymph node, 5 spleens), 16 cancer tissues (8 leukocytic leukemia cancers, 8 lymph node cancers); FIG. 7C) Gene: CYSLTR1, Peptide: VILTSSPFL (SEQ ID NO.: 156), Tissues from left to right: 3 normal tissues (1 lung, 1 lymph node, 1 spleen), 11 cancer tissues (2 breast cancers, 5 leukocytic leukemia cancers, 3 lymph node cancers, 1 myeloid cells cancer).

EXAMPLES

Example 1

Identification and Quantitation of Tumor Associated Peptides Presented on the Cell Surface Tissue Samples Patients' tumor tissues were obtained from Asterand (Detroit, USA and Royston, Herts, UK); Val d'Hebron University Hospital (Barcelona); BioServe (Beltsville, Md., USA); Center for cancer immune therapy (CCIT), Herlev Hospital (Herlev); Geneticist Inc. (Glendale, Calif., USA); University Hospital of Geneva; University Hospital of Heidelberg; University Hospital of Munich; Kyoto Prefectural University of Medicine (KPUM); Osaka City University (OCU); ProteoGenex Inc., (Culver City, Calif., USA); University Hospital of Tübingen. Normal tissues were obtained from Bio-Options Inc., CA, USA; BioServe, Beltsville, Md., USA; Capital BioScience Inc., Rockville, Md., USA; Geneticist Inc., Glendale, Calif., USA; University Hospital of Geneva; University Hospital of Heidelberg; University Hospital Munich; ProteoGenex Inc., Culver City, Calif., USA; University Hospital of Tübingen. Written informed consents of all patients had been given before surgery or autopsy. Tissues were shock-frozen immediately after excision and stored until isolation of TUMAPs at −70° C. or below.

Isolation of HLA Peptides from Tissue Samples

HLA peptide pools from shock-frozen tissue samples were obtained by immune precipitation from solid tissues according to a slightly modified protocol (Falk et al., 1991; Seeger et al., 1999) using the HLA-A*02-specific antibody BB7.2, the HLA-A, -B, -C-specific antibody W6/32, CNBr-activated sepharose, acid treatment, and ultrafiltration.

Mass Spectrometry Analyses

The HLA peptide pools as obtained were separated according to their hydrophobicity by reversed-phase chromatography (nanoAcquity UPLC system, Waters) and the eluting peptides were analyzed in LTQ-velos and fusion hybrid mass spectrometers (ThermoElectron) equipped with an ESI source. Peptide pools were loaded directly onto the analytical fused-silica micro-capillary column (75 µm i.d.× 250 mm) packed with 1.7 µm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOPS strategy. In brief, a scan cycle was initiated with a full scan of high mass accuracy in the Orbitrap (R=30 000), which was followed by MS/MS scans also in the Orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Label-free relative LC-MS quantitation was performed by ion counting i.e. by extraction and analysis of LC-MS features (Mueller et al., 2007). The method assumes that the peptide's LC-MS signal area correlates with its abundance in the sample. Extracted features were further processed by charge state deconvolution and retention time alignment (Mueller et al., 2008; Sturm et al., 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose cancer samples to a baseline of normal tissue samples. Presentation profiles of exemplary over-presented peptides are shown in FIG. 1. An overview of peptide presentation across entities is shown in Table 4 for selected peptides.

TABLE 4

Overview of presentation of selected peptides across entities. A peptide was considered interesting in an entity if it was over-presented on cancer samples of this entity compared to normal tissues. MEL = melanoma, BRCA = breast cancer, OSCAR = esophageal carcinoma. BPH includes benign prostate hyperplasia as well as pancreatic cancer.

| SEQ ID NO. | Sequence | Entities of particular interest |
|---|---|---|
| 1 | KLQEKIQEL | GB, GC, NSCLC, HCC, OC, RCC, CRC, PC, OSCAR |
| 2 | SVLEKEIYSI | NSCLC, HCC, BPH, OC, CRC, PC |
| 3 | RVIDDSLVVGV | NSCLC, HCC, OC, MEL, CRC, PC, OSCAR |
| 4 | VLFGELPAL | GB, NSCLC, BRCA, RCC, PC, OC, PC |
| 5 | GLVDIMVHL | NSCLC, RCC, OC |
| 7 | ALLQALMEL | GC, NSCLC, RCC, CRC, PC |
| 8 | ALSSSQAEV | GB, NSCLC, OC, CRC, PC |
| 9 | SLITGQDLLSV | NSCLC, BPH, OC, MEL, PC, OSCAR |
| 10 | QLIEKNWLL | NSCLC, OC, CRC, PC, HCC, CLL, OSCAR |
| 11 | LLDPKTIFL | NSCLC, HCC, RCC, CRC |
| 12 | RLLDPKTIFL | NSCLC, RCC |
| 13 | RLHDENILL | GB, GC, NSCLC, HCC, BPH, OC, RCC, CRC, PC, OSCAR |
| 14 | YTFSGDVQL | GC, NSCLC, CRC, PC, OSCAR |
| 15 | GLPSATTTV | GC, NSCLC, OC, PC |
| 16 | SLADLSLLL | NSCLC, HCC, PC |
| 17 | GLLPSAESIKL | NSCLC, BPH, OC, OSCAR |
| 18 | KTASINQNV | NSCLC, CRC, PC, OSCAR, OC |
| 19 | KVFELDLVTL | GC, NSCLC, CRC, OSCAR |
| 21 | YLMDDFSSL | PC, NSCLC |
| 22 | LMYPYIYHV | GB, NSCLC, OC, OSCAR |
| 23 | ALLSPLSLA | PC |
| 24 | KVWSDVTPL | PC, NSCLC |
| 25 | LLWGHPRVALA | CRC, PC, NSCLC |
| 26 | VLDGKVAVV | HCC, MEL, OC, GB, GC, NSCLC |
| 27 | GLLGKVTSV | NSCLC, BRCA |
| 29 | KMISAIPTL | NSCLC, OC |

TABLE 4-continued

Overview of presentation of selected peptides across entities. A peptide was considered interesting in an entity if it was over-presented on cancer samples of this entity compared to normal tissues. MEL = melanoma, BRCA = breast cancer, OSCAR = esophageal carcinoma. BPH includes benign prostate hyperplasia as well as pancreatic cancer.

| SEQ ID NO. | Sequence | Entities of particular interest |
|---|---|---|
| 34 | TLNTLDINL | OC, PC |
| 35 | VIIKGLEEI | GC, NSCLC, OSCAR |
| 36 | TVLQELINV | NSCLC, PC, OSCAR |
| 37 | QIVELIEKI | GC, NSCLC, OSCAR |
| 39 | YLEDGFAYV | GB, NSCLC, HCC, PC |
| 40 | KIWEELSVLEV | GC, NSCLC, HCC, MEL |
| 43 | LLIPFTIFM | NSCLC, MEL, CRC, OC |
| 44 | AVFNLVHVV | GC, NSCLC, PC |
| 46 | ISLDEVAVSL | GB, NSCLC, HCC, OC |
| 47 | GLNGFNVLL | PC, OSCAR |
| 48 | KISDFGLATV | GB, NSCLC, PC, OSCAR |
| 49 | KLIGNIHGNEV | GB, NSCLC, OC |
| 50 | ILLSVLHQL | NSCLC, CRC |
| 51 | LDSEALLTL | GB, NSCLC, HCC |
| 52 | TIGIPFPNV | NSCLC, PC, OC |
| 53 | AQHLSTLLL | GC, NSCLC |
| 54 | YLVPGLVAA | NSCLC, OC |
| 55 | HLFDKIIKI | GC, CRC |
| 56 | VLQENSSDYQSNL | NSCLC, HCC |
| 57 | TLYPGRFDYV | NSCLC, PC |
| 58 | HLLGEGAFAQV | NSCLC, PC |
| 59 | ALADGIKSFLL | NSCLC, PC |
| 60 | YLFSQGLQGL | NSCLC, PC |
| 61 | ALYPKEITL | NSCLC, CRC |
| 63 | KLLPMVIQL | NSCLC, PC |
| 65 | SLSEKSPEV | NSCLC, OC, OSCAR, MEL |
| 66 | AMFPDTIPRV | NSCLC, OC |
| 67 | FLIENLLAA | GB, NSCLC |
| 68 | QLMNLIRSV | HCC, PC |
| 69 | LKVLKADVVL | GC, NSCLC |
| 70 | GLTEKTVLV | NSCLC, PC |
| 71 | HMSGKLTNV | NSCLC, PC |
| 73 | SVPKTLGV | GB, RCC |
| 74 | GLAFLPASV | GC, CRC |

TABLE 4-continued

Overview of presentation of selected peptides across entities. A peptide was considered interesting in an entity if it was over-presented on cancer samples of this entity compared to normal tissues. MEL = melanoma, BRCA = breast cancer, OSCAR = esophageal carcinoma. BPH includes benign prostate hyperplasia as well as pancreatic cancer.

| SEQ ID NO. | Sequence | Entities of particular interest |
|---|---|---|
| 76 | FTAEFLEKV | NSCLC, PC, GB, OSCAR |
| 77 | ALYGNVQQV | NSCLC, OC |
| 82 | ILAEEPIYIRV | NSCLC, PC, OSCAR, OC |
| 83 | GLLENSPHL | NSCLC, OC |
| 84 | FLLEREQLL | NSCLC, MEL, RCC, CRC, PC |
| 85 | KLLDKPEQFL | NSCLC, OC, MEL, CRC |
| 86 | SLFSNIESV | NSCLC, BPH, CRC |
| 88 | LLLPLELSLA | GB, NSCLC, PC |
| 89 | SLAETIFIV | GC, NSCLC, OC |
| 92 | RLFEEVLGV | NSCLC, HCC, OC, OC |
| 93 | RLYGYFHDA | NSCLC, PC |
| 94 | YLDEVAFML | NSCLC, HCC, OC |
| 95 | KLIDEDEPLFL | NSCLC, OC |
| 96 | ALDTTRHEL | NSCLC, PC |
| 97 | KLFEKSTGL | NSCLC, CRC |
| 98 | FVQEKIPEL | GC, CRC |
| 100 | ALQSFEFRV | OC, RCC |
| 101 | SLLEVNEASSV | GC, CLL |
| 102 | GLYPVTLVGV | BPH, OC |
| 114 | *LLFPSDVQTL* | PC, OSCAR |
| 116 | ALLSSVAEA | NSCLC, OSCAR, OC |
| 117 | TLLEGISRA | NSCLC, OC |
| 134 | SLYKSFLQL | NSCLC, OSCAR, OC |
| 137 | KLIYKDLVSV | NSCLC, OC, PC |
| 146 | VVAAHLAGA | NSCLC, OSCAR, OC |
| 158 | YLDPLWHQL | PC, OC |
| 165 | SLLDYEVSI | NSCLC, OSCAR, OC |
| 166 | LLGDSSFFL | NSCLC, HCC, OSCAR, OC, PC |
| 170 | FIAAVVEKV | NSCLC, OC |
| 175 | SLLDLVQSL | PC, OC |
| 176 | VQSGLRILL | NSCLC, OSCAR |
| 184 | ALDSTIAHL | NSCLC, OC |
| 191 | AAIEIFEKV | NSCLC, OSCAR, OC |
| 203 | FLFVDPELV | NSCLC, GC, OC |
| 229 | YLYELEHAL | NSCLC, OC |

TABLE 4-continued

Overview of presentation of selected peptides across entities. A peptide was considered interesting in an entity if it was over-presented on cancer samples of this entity compared to normal tissues. MEL = melanoma, BRCA = breast cancer, OSCAR = esophageal carcinoma. BPH includes benign prostate hyperplasia as well as pancreatic cancer.

| SEQ ID NO. | Sequence | Entities of particular interest |
|---|---|---|
| 233 | SLFESLEYL | NSCLC, OSCAR, OC |
| 234 | VLLNEILEQV | GC, NSCLC, HCC, OC, MEL, RCC, CRC, PC, OSCAR |
| 235 | SLLNQPKAV | GB, NSCLC, HCC, OC, MEL, CRC, PC, OSCAR |
| 236 | KMSELQTYV | GB, NSCLC, HCC, OC, MEL, CRC, PC |
| 237 | ALLEQTGDMSL | NSCLC, OC, MEL, CRC |
| 239 | VIIKGLEEITV | GC, NSCLC, HCC, OC, MEL, CRC, PC |
| 241 | KQFEGTVEI | NSCLC, MCC, OC, CRC, PC, OSCAR |
| 242 | KLQEEIPVL | GB, NSCLC, CRC |
| 243 | GLAEFQENV | GB, NSCLC, HCC, OC, CRC, PC, OSCAR |
| 244 | NVAEIVIHI | GC, NSCLC |
| 246 | ALAGIVTNV | NSCLC, HCC, OC, MEL, RCC |
| 247 | NLLIDDKGTIKL | NSCLC, HCC, MEL, CRC, PC |
| 248 | VLMQDSRLYL | NSCLC, CRC, PC |
| 251 | LLWGNLPEI | NSCLC, MEL, CRC, PC, OC |
| 252 | SLMEKNQSL | NSCLC, OC, CRC, OSCAR, RCC |
| 253 | KLLAVIHEL | NSCLC, RCC, CRC, PC, OSCAR, OC |
| 254 | ALGDKFLLRV | NSCLC, HCC, MEL, OC |
| 255 | FLMKNSDLYGA | NSCLC, HCC, MEL, PC, OSCAR |
| 256 | FLNDIFERI | NSCLC, HCC, CLL, OC |
| 257 | KLIDHQGLYL | NSCLC, OC, CRC, OSCAR |
| 258 | QLVQRVASV | NSCLC, OC |
| 259 | GPGIFPPPPPQP | NSCLC, BPH, OSCAR, OC |
| 260 | ALNESLVEC | NSCLC, MEL, OSCAR, OC |
| 261 | GLAALAVHL | NSCLC, OC, MEL, CRC, PC, OSCAR |
| 262 | LLLEAVWHL | NSCLC, CRC |
| 263 | SIIEYLPTL | NSCLC, MEL, PC |
| 264 | TLHDQVHLL | NSCLC, BPH, OC |
| 265 | FLLDKPQDLSI | NSCLC, OC, RCC |
| 266 | FLLDKPQDL | RCC, OC |
| 267 | YLLDMPLWYL | NSCLC, RCC, CRC, OC, MEL |
| 269 | GLLDCPIFL | NSCLC, CRC, OSCAR, OC |
| 270 | TLLTFFHEL | GB, PC |
| 271 | VLIEYNFSI | NSCLC, OC |
| 272 | FVMEGEPPKL | NSCLC, OC |

TABLE 4-continued

Overview of presentation of selected peptides across entities. A peptide was considered interesting in an entity if it was over-presented on cancer samples of this entity compared to normal tissues. MEL = melanoma, BRCA = breast cancer, OSCAR = esophageal carcinoma. BPH includes benign prostate hyperplasia as well as pancreatic cancer.

| SEQ ID NO. | Sequence | Entities of particular interest |
|---|---|---|
| 273 | SLNKQIETV | NSCLC, OC |
| 274 | TLYNPERTITV | NSCLC, PC, HCC |
| 277 | KLQEELNKV | HCC, OC |
| 281 | LLLESDPKVYSL | PC, OC |
| 284 | KLMDPGSLPPL | NSCLC, OC |
| 287 | KIQEILTQV | GB, GC, NSCLC, HCC, CLL, OC, MEL, RCC, CRC, PC, OSCAR |
| 288 | SLYKGLLSV | GB, NSCLC, HCC, BPH, OC, RCC, CRC, PC, OSCAR |

TABLE 4B

Overview of presentation of selected peptides across entities.

| SEQ ID NO. | Sequence | Additional entities of particular interest |
|---|---|---|
| 1 | KLQEKIQEL | MEL, AML, NHL |
| 2 | SVLEKEIYSI | GC, CLL, OSCAR, SCLC, UBC, UTC, BRCA, GBC_CCC, MEL, AML, NHL |
| 3 | RVIDDSLVVGV | UBC |
| 4 | VLFGELPAL | SCLC, UBC, UTC |
| 5 | GLVDIMVHL | SCLC, UBC, BRCA, MEL, PC |
| 6 | FLNAIETAL | RCC |
| 7 | ALLQALMEL | CLL, OSCAR, OC, SCLC, UTC, BRCA, GBC_CCC, MEL, AML, NHL |
| 8 | ALSSSQAEV | BPH, OSCAR, SCLC, UBC, UTC, BRCA, GBC_CCC, MEL, AML, NHL |
| 9 | SLITGQDLLSV | SCLC, UBC, UTC, BRCA, GBC_CCC |
| 10 | QLIEKNWLL | SCLC, UBC, UTC, BRCA, GBC_CCC, MEL, AML, NHL |
| 11 | LLDPKTIFL | GBC_CCC |
| 13 | RLHDENILL | SCLC, UBC, UTC, BRCA, MEL, AML, NHL |
| 14 | YTFSGDVQL | SCLC, UBC, UTC, GBC_CCC, MEL |
| 15 | GLPSATTTV | UBC, UTC, MEL |
| 16 | SLADLSLLL | GB, GC, BPH, CLL, OSCAR, OC, SCLC, UBC, UTC, BRCA, GBC_CCC, MEL, RCC, CRC, AML, NHL |
| 17 | GLLPSAESIKL | UBC |
| 18 | KTASINQNV | SCLC, UBC, UTC, MEL |
| 19 | KVFELDLVTL | AML, NHL |
| 21 | YLMDDFSSL | OSCAR, OC, SCLC, UBC, BRCA, GBC_CCC, MEL, AML, NHL |

TABLE 4B-continued

Overview of presentation of selected peptides across entities.

| SEQ ID NO. | Sequence | Additional entities of particular interest |
|---|---|---|
| 22 | LMYPYIYHV | HCC, CLL, SCLC, UBC, BRCA, GBC_CCC, MEL, CRC, NHL |
| 24 | KVWSDVTPL | BRCA |
| 26 | VLDGKVAVV | CLL, UTC, NHL |
| 27 | GLLGKVTSV | SCLC, UBC |
| 28 | IKVTDPQLLEL | NSCLC, MEL |
| 29 | KMISAIPTL | UTC |
| 30 | IITEVITRL | OC, UTC |
| 31 | GLLETTGLLAT | OC |
| 33 | TLDRNSLYV | OC, UTC |
| 34 | TLNTLDINL | UTC |
| 35 | VIIKGLEEI | OC |
| 36 | TVLQELINV | UBC, UTC, MEL, CRC, AML, NHL |
| 38 | VLQQESNFL | AML |
| 39 | YLEDGFAYV | CLL, UBC, UTC, MEL, NHL |
| 40 | KIWEELSVLEV | SCLC, UBC |
| 41 | IVTEIISEI | CLL, SCLC, UTC, GBC_CCC, AML, NHL |
| 43 | LLIPFTIFM | SCLC, GBC_CCC, NHL |
| 46 | ISLDEVAVSL | BRCA |
| 47 | GLNGFNVLL | SCLC, UTC, GBC_CCC, MEL, CRC, AML, NHL |
| 48 | KISDFGLATV | OC, MEL |
| 51 | LDSEALLTL | BRCA |
| 52 | TIGIPFPNV | MEL, NHL |
| 53 | AQHLSTLLL | SCLC, GBC_CCC |
| 56 | VLQENSSDYQSNL | UTC |
| 57 | TLYPGRFDYV | OSCAR, UBC |
| 59 | ALADGIKSFLL | BRCA, MEL |
| 64 | SLYAGSNNQV | NSCLC |
| 65 | SLSEKSPEV | HCC, SCLC, UBC, UTC, BRCA, NHL |
| 67 | FLIENLLAA | UTC |
| 68 | QLMNLIRSV | UBC, AML |
| 70 | GLTEKTVLV | CRC, AML, NHL |
| 75 | ALLDGALQL | GC, CRC |
| 76 | FTAEFLEKV | UBC, MEL, AML, NHL |
| 77 | ALYGNVQQV | BRCA, NHL |
| 78 | LFQSRIAGV | BPH |
| 80 | VLTGQVHEL | GB |
| 83 | GLLENSPHL | BRCA, MEL, AML, NHL |

TABLE 4B-continued

Overview of presentation of selected peptides across entities.

| SEQ ID NO. | Sequence | Additional entities of particular interest |
|---|---|---|
| 84 | FLLEREQLL | CLL, UBC, UTC, BRCA, AML, NHL |
| 85 | KLLDKPEQFL | NHL |
| 86 | SLFSNIESV | SCLC, BRCA, GBC_CCC |
| 87 | KLLSLLEEA | NSCLC, BPH |
| 89 | SLAETIFIV | SCLC, GBC_CCC, RCC, NHL |
| 90 | AILNVDEKNQV | OC |
| 91 | LLPSIFLMV | OC |
| 92 | RLFEEVLGV | OSCAR, SCLC, UBC, BRCA, AML |
| 94 | YLDEVAFML | UBC, BRCA, GBC_CCC |
| 95 | KLIDEDEPLFL | SCLC, UTC, GBC_CCC |
| 96 | ALDTTRHEL | OSCAR, UBC, UTC |
| 98 | FVQEKIPEL | GBC_CCC |
| 99 | TLFGIQLTEA | GC, GBC_CCC |
| 101 | SLLEVNEASSV | NHL |
| 102 | GLYPVTLVGV | SCLC, BRCA, AML |
| 103 | YLADTVQKL | NSCLC |
| 104 | DLPTQEPALGTT | BPH |
| 106 | VLLGSVVIFA | BPH |
| 108 | FIANLPPELKA | BPH |
| 109 | ILGSFELQL | BPH |
| 110 | QIQGQVSEV | BPH |
| 112 | ILAQDVAQL | MEL, AML, NHL |
| 113 | FLFLKEVKV | CRC |
| 116 | ALLSSVAEA | SCLC, BRCA, CRC |
| 117 | TLLEGISRA | BRCA |
| 118 | IAYNPNGNAL | NSCLC, CLL, AML |
| 119 | SLIEESEEL | OC, UTC |
| 121 | ALYVQAPTV | NSCLC, UTC, NHL |
| 122 | SIIDTELKV | AML |
| 124 | ALLLRLFTI | NSCLC |
| 128 | SILTNISEV | NSCLC |
| 129 | KMASKVTQV | HCC |
| 130 | QLYGSAITL | HCC |
| 132 | ALLNNVIEV | HCC, BRCA |
| 133 | FLDGRPLTL | UTC, MEL |
| 135 | HLDTVKIEV | GB |
| 136 | LLWDAPAKC | CRC |
| 139 | IILENIQSL | UBC, BRCA, AML |

TABLE 4B-continued

Overview of presentation of selected peptides across entities.

| SEQ ID NO. | Sequence | Additional entities of particular interest |
|---|---|---|
| 140 | FLDSQITTV | MEL |
| 142 | LLDAAHASI | NSCLC |
| 143 | MLWESIMRV | NSCLC, UTC |
| 144 | FLISQTPLL | NSCLC, SCLC, UBC |
| 145 | ALEEKLENV | NSCLC |
| 146 | VVAAHLAGA | GC, MEL |
| 147 | GLLSALENV | CLL, NHL |
| 148 | YLILSSHQL | CLL, NHL |
| 150 | VLLDMVHSL | HCC, UTC |
| 151 | DISKRIQSL | NSCLC |
| 152 | ILVTSIFFL | CLL, NHL |
| 153 | KLVELEHTL | GC, NSCLC, OSCAR |
| 154 | AIIKEIQTV | GB, NSCLC, HCC, UBC, MEL |
| 155 | TLDSYLKAV | OC, BRCA |
| 156 | VILTSSPFL | CLL, BRCA, AML, NHL |
| 157 | ILQDGQFLV | HCC, UBC |
| 158 | YLDPLWHQL | CLL, MEL, NHL |
| 159 | QLGPVPVTI | UBC, RCC, NHL |
| 160 | TLQEWLTEV | NSCLC, GBC_CCC |
| 161 | NLLDENVCL | CRC |
| 162 | GLLGNLLTSL | NSCLC |
| 163 | GLEERLYTA | NSCLC, CLL, AML, NHL |
| 164 | MLIIRVPSV | NSCLC |
| 165 | SLLDYEVSI | GBC_CCC |
| 166 | LLGDSSFFL | CLL, UBC, UTC, BRCA, GBC_CCC, MEL, AML |
| 167 | LVVDEGSLVSV | OC, SCLC |
| 168 | VIFEGEPMYL | NSCLC, BRCA, NHL |
| 169 | ALADLSVAV | NSCLC, HCC, OSCAR, OC, UBC, UTC, GBC_CCC, MEL, AML |
| 170 | FIAAVVEKV | SCLC, NHL |
| 171 | LLLLDVPTA | NSCLC, UTC, BRCA, CRC, NHL |
| 172 | SLYLQMNSLRTE | NSCLC |
| 173 | RLIDIYKNV | OC |
| 174 | ALYSGDLHAA | HCC |
| 175 | SLLDLVQSL | BRCA, AML, NHL |
| 177 | ALINVLNAL | AML |
| 179 | TLGEIIKGV | NSCLC |
| 180 | RLYEEEIRI | NSCLC |

TABLE 4B-continued

Overview of presentation of selected peptides across entities.

| SEQ ID NO. | Sequence | Additional entities of particular interest |
|---|---|---|
| 181 | LLWAPTAQA | GB, NSCLC, RCC, CRC |
| 182 | GLQDGFQITV | GC |
| 183 | ALSYILPYL | NSCLC, SCLC, UTC, BRCA, CRC, AML, NHL |
| 184 | ALDSTIAHL | UTC, MEL |
| 185 | TLYQGLPAEV | GC, NSCLC, HCC, OSCAR, OC, UBC, UTC, BRCA, RCC, CRC |
| 186 | SLLSLESRL | GC |
| 187 | SILKEDPFL | NSCLC |
| 188 | VLGEEQEGV | NSCLC |
| 189 | MAVSDLLIL | GB |
| 190 | SLSTELFKV | HCC |
| 192 | TLLPSSGLVTL | BRCA |
| 193 | ALFHMNILL | NSCLC |
| 194 | KLLEEVQLL | NSCLC |
| 195 | VIIQNLPAL | CRC |
| 196 | TLHQWIYYL | CRC |
| 198 | ILTNKVVSV | OC |
| 199 | SVADLAHVL | GC |
| 200 | IMPTFDLTKV | HCC |
| 201 | LLFSLLCEA | BPH |
| 203 | FLFVDPELV | CRC, AML, NHL |
| 204 | SEWGSPHAAVP | PC |
| 205 | LAFGYDDEL | HCC |
| 206 | GLDAFRIFL | CRC |
| 207 | KLFETVEEL | GB |
| 208 | HLNNDRNPL | BPH |
| 210 | GLAGDNIYL | RCC |
| 211 | LLTTVLINA | RCC |
| 212 | MTLSEIHAV | CRC |
| 213 | ILAVDGVLSV | NSCLC, BRCA, MEL |
| 214 | ALFETLIQL | HCC |
| 215 | QIADIVTSV | HCC |
| 216 | ALSTVTPRI | HCC |
| 217 | LLWPSSVPA | GB, MEL, AML |
| 220 | ALSELERVL | BPH, UTC |
| 221 | IMLNSVEEI | BPH, NHL |
| 222 | LLTGVFAQL | CLL, UTC, BRCA, CRC, NHL |
| 223 | ALHPVQFYL | OC, CRC |

TABLE 4B-continued

Overview of presentation of selected peptides across entities.

| SEQ ID NO. | Sequence | Additional entities of particular interest |
|---|---|---|
| 224 | LLFDWSGTGRADA | GBC_CCC |
| 225 | FLPQPVPLSV | CLL, MEL, NHL |
| 226 | SLAGNLQEL | GB |
| 227 | SEMEELPSV | HCC |
| 228 | SLLELDGINLRL | NSCLC |
| 230 | KLLNMIFSI | BPH |
| 231 | LLDDIFIRL | MEL |
| 233 | SLFESLEYL | UTC, RCC |
| 234 | VLLNEILEQV | CLL, SCLC, UBC, UTC, BRCA, AML, NHL |
| 235 | SLLNQPKAV | SCLC, UBC, UTC, BRCA, GBC_CCC, AML, NHL |
| 236 | KMSELQTYV | GC, BPH, CLL, OSCAR, SCLC, UBC, UTC, BRCA, GBC_CCC, RCC, AML, NHL |
| 237 | ALLEQTGDMSL | SCLC, UBC, BRCA, AML, NHL |
| 238 | HLQEKLQSL | HCC |
| 239 | VIIKGLEEITV | CLL, SCLC, UBC, UTC, AML, NHL |
| 240 | SVQENIQQK | RCC, NHL |
| 241 | KQFEGTVEI | CLL, NHL |
| 242 | KLQEEIPVL | BRCA, MEL, NHL |
| 243 | GLAEFQENV | CLL, SCLC, UBC, UTC, BRCA, GBC_CCC, MEL, AML, NHL |
| 244 | NVAEIVIHI | GB |
| 245 | ALLEEEEGV | NSCLC, UBC, GBC_CCC |
| 246 | ALAGIVTNV | GB, CLL, SCLC, BRCA, GBC_CCC, AML |
| 248 | VLMQDSRLYL | CLL, UBC, UTC, AML, NHL |
| 251 | LLWGNLPEI | CLL, SCLC, UTC, GBC_CCC, AML, NHL |
| 252 | SLMEKNQSL | AML |
| 253 | KLLAVIHEL | UBC, BRCA, GBC_CCC, MEL, AML, NHL |
| 254 | ALGDKFLLRV | NHL |
| 255 | FLMKNSDLYGA | UBC, UTC, GBC_CCC, AML, NHL |
| 256 | FLNDIFERI | UTC, MEL, AML, NHL |
| 258 | QLVQRVASV | UBC, NHL |
| 260 | ALNESLVEC | SCLC, UBC, UTC, CRC, AML, NHL |
| 261 | GLAALAVHL | GC, CLL, SCLC, UBC, UTC, BRCA, GBC_CCC, AML, NHL |
| 262 | LLLEAVWHL | BRCA, NHL |
| 263 | SIIEYLPTL | CLL, OSCAR, OC, SCLC, UBC, GBC_CCC, AML, NHL |
| 264 | TLHDQVHLL | UTC, BRCA, GBC_CCC, MEL |
| 265 | FLLDKPQDLSI | GBC_CCC |
| 267 | YLLDMPLWYL | AML, NHL |
| 269 | GLLDCPIFL | CLL, UTC, AML, NHL |

TABLE 4B-continued

Overview of presentation of selected peptides across entities.

| SEQ ID NO. | Sequence | Additional entities of particular interest |
|---|---|---|
| 270 | TLLTFFHEL | UTC, GBC_CCC, AML, NHL |
| 271 | VLIEYNFSI | CLL, SCLC, MEL, AML, NHL |
| 272 | FVMEGEPPKL | CLL, UTC |
| 273 | SLNKQIETV | AML |
| 275 | AVPPPPSSV | NSCLC, HCC |
| 276 | RMPTVLQCV | BPH |
| 277 | KLQEELNKV | NSCLC, OSCAR, UBC, BRCA, NHL |
| 279 | VLMDEGAVLTL | CLL, CRC, NHL |
| 280 | HLWGHALFL | HCC |
| 281 | LLLESDPKVYSL | OSCAR, SCLC |
| 282 | SLYALHVKA | OC, SCLC |
| 283 | ALSELLQQV | NSCLC, HCC, OC, SCLC, UTC, MEL, CRC, AML, NHL |
| 285 | MLLDTVQKV | NSCLC |
| 286 | FLTEMVHFI | NSCLC, CLL, SCLC, UBC, NHL |

GB = glioblastoma,
BRCA = breast cancer,
CRC = colorectal cancer,
RCC = renal cell carcinoma,
CLL = chronic lymphocytic leukemia,
HCC = hepatocellular carcinoma,
NSCLC = non-small cell lung cancer,
SCLC = small cell lung cancer,
NHL = non-Hodgkin lymphoma,
AML = acute myeloid leukemia,
OC = ovarian cancer,
PC = pancreatic cancer,
BPH = prostate cancer and benign prostate hyperplasia,
OSCAR = esophageal cancer, including cancer of the gastric-oesophageal junction,
GBC_CCC = gallbladder adenocarcinoma and cholangiocarcinoma,
MEL = melanoma,
GC = gastric cancer,
UBC = urinary bladder cancer,
UTC = uterine cancer.

Example 2

Expression Profiling of Genes Encoding the Peptides of the Invention

Over-presentation or specific presentation of a peptide on tumor cells compared to normal cells is sufficient for its usefulness in immunotherapy, and some peptides are tumor-specific despite their source protein occurring also in normal tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on normal tissues. For this invention, normal tissue expression of all source genes was shown to be minimal based on the above-described database of RNA expression data covering about 3000 normal tissue samples. Further RNA analyses of normal and tumor tissues were added in case of some cancer entities (HCC, CRC, GB, GC, NSCLC, PC, RCC, BPH/PCA) to estimate the target coverage in the population of patients having the respective cancer.

RNA Sources and Preparation

Surgically removed tissue specimens were provided as indicated above (see Example 1) after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; Bio-Chain, Hayward, Calif., USA). The RNA from several individuals (between 2 and 123 individuals) was mixed such that RNA from each individual was equally weighted. Quality and quantity of all RNA samples were assessed on an Agilent 2100 Bioanalyzer (Agilent, Waldbronn, Germany) using the RNA 6000 Pico LabChip Kit (Agilent).

Total RNA from healthy human tissues for RNASeq experiments was obtained from: Asterand (Detroit, Mich., USA & Royston, Herts, UK), BioCat GmbH (Heidelberg, Germany), BioServe (Beltsville, Md., USA), Capital BioScience Inc. (Rockville, Md., USA), Geneticist Inc. (Glendale, Calif., USA), Istituto Nazionale Tumori "Pascale" (Naples, Italy), ProteoGenex Inc. (Culver City, Calif., USA), University Hospital Heidelberg (Heidelberg, Germany)

Total RNA from tumor tissues for RNASeq experiments was obtained from: Asterand (Detroit, Mich., USA & Royston, Herts, UK), Bio-Options Inc. (Brea, Calif., USA), BioServe (Beltsville, Md., USA), Geneticist Inc. (Glendale, Calif., USA), ProteoGenex Inc. (Culver City, Calif., USA), Tissue Solutions Ltd (Glasgow, UK), University Hospital Bonn (Bonn, Germany), University Hospital Heidelberg (Heidelberg, Germany), University Hospital Tübingen (Tübingen, Germany)

Microarray Experiments

Coverage was estimated by analysis of RNA expression profiles (Affymetrix microarrays) of 30 GB, 16 CRC, 56 RCC, 12 HCC, 38 NSCLC, 11 PC, 34 GC, and 20 prostate cancer samples.

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 μg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalization, 100 housekeeping genes provided by Affymetrix were used. Relative expression values were calculated from the signal log ratios given by the software and the normal kidney sample was arbitrarily set to 1.0. Exemplary expression profiles of source genes of the present invention that are highly over-expressed or exclusively expressed in HCC, CRC, GB, GC, NSCLC, PC, RCC, or BPH/PCA are shown in FIG. 2. An overview of coverage for selected genes is shown in Table.

TABLE 5A

Target coverage for source genes of selected peptides.

| SEQ ID NO. | Sequence | GB (%) | CRC (%) | RCC (%) | HCC (%) | NSCLC (%) | PC (%) | BPH/ PCA (%) | GC (%) | Gene ID | Official gene symbol |
|---|---|---|---|---|---|---|---|---|---|---|---|
| 116 | ALLSSVAEA | I | II | I | I | II | I | I | I | 9048 | ARTN |
| 263 | SIIEYLPTL | I | II | I | I | II | I | I | I | 79915 | ATAD5 |
| 93 | RLYGYFHDA | II | III | I | II | II | II | I | III | 6790 | AURKA |
| 27 | GLLGKVTSV | I | I | I | I | II | I | I | I | 51297 | BPIFA1 |
| 28 | IKVTDPQLLEL | I | I | I | I | II | I | I | I | 51297 | BPIFA1 |
| 62 | SLVENIHVL | II | III | II | I | III | III | I | III | 675 | BRCA2 |
| 241 | KQFEGTVEI | II | III | II | I | III | III | I | III | 675 | BRCA2 |
| 52 | TIGIPFPNV | III | I | I | II | II | I | I | II | 83990 | BRIP1 |
| 58 | HLLGEGAFAQV | III | III | I | I | III | II | I | III | 699 | BUB1 |
| 117 | TLLEGISRA | I | I | I | I | II | II | I | I | 26256 | CABYR |
| 94 | YLDEVAFML | I | I | I | I | I | II | I | I | 1238 | CCBP2 |
| 103 | YLADTVQKL | II | I | I | I | I | I | I | I | 100526761, 54937 | CCDC169-SOHLH2, SOHLH2 |
| 79 | TVLEEIGNRV | II | IV | I | I | II | I | I | II | 9133 | CCNB2 |
| 247 | NLLIDDKGTIKL | IV | IV | II | II | IV | III | I | IV | 983 | CDK1 |
| 248 | VLMQDSRLYL | IV | IV | II | II | IV | III | I | IV | 983 | CDK1 |
| 249 | YLYQILQGI | IV | IV | II | II | IV | III | I | IV | 983 | CDK1 |
| 250 | LMQDSRLYL | IV | IV | II | II | IV | III | I | IV | 983 | CDK1 |
| 1 | KLQEKIQEL | III | II | I | I | II | I | I | II | 1062 | CENPE |
| 242 | KLQEEIPVL | III | II | I | I | II | I | I | II | 1062 | CENPE |
| 19 | KVFELDLVTL | IV | III | I | I | I | I | I | I | 1063 | CENPF |

TABLE 5A-continued

Target coverage for source genes of selected peptides.

| SEQ ID NO. | Sequence | GB (%) | CRC (%) | RCC (%) | HCC (%) | NSCLC (%) | PC (%) | BPH/PCA (%) | GC (%) | Gene ID | Official gene symbol |
|---|---|---|---|---|---|---|---|---|---|---|---|
| 20 | ALVEKGEFAL | IV | III | I | I | I | I | I | I | 1063 | CENPF |
| 236 | KMSELQTYV | IV | III | I | I | I | I | I | I | 1063 | CENPF |
| 237 | ALLEQTGDMSL | IV | III | I | I | I | I | I | I | 1063 | CENPF |
| 238 | HLQEKLQSL | IV | III | I | I | I | I | I | I | 1063 | CENPF |
| 60 | YLFSQGLQGL | III | IV | I | III | III | II | I | III | 2491 | CENPI |
| 260 | ALNESLVEC | I | III | I | I | II | I | I | II | 55165 | CEP55 |
| 48 | KISDFGLATV | IV | IV | II | II | IV | II | I | IV | 1111 | CHEK1 |
| 49 | KLIGNIHGNEV | I | I | I | I | I | II | I | I | 8532 | CPZ |
| 50 | ILLSVLHQL | I | I | I | I | I | II | I | I | 8532 | CPZ |
| 284 | KLMDPGSLPPL | I | IV | I | I | II | I | I | II | 2118 | ETV4 |
| 261 | GLAALAVHL | I | III | I | II | II | I | I | I | 2175 | FANCA |
| 262 | LLLEAVWHL | I | III | I | II | II | I | I | I | 2175 | FANCA |
| 270 | TLLTFFHEL | II | III | I | I | II | I | I | II | 55215 | FANCI |
| 271 | VLIEYNFSI | II | III | I | I | II | I | I | II | 55215 | FANCI |
| 11 | LLDPKTIFL | I | I | II | I | I | I | I | I | 26762 | HAVCR1 |
| 12 | RLLDPKTIFL | I | I | II | I | I | I | I | I | 26762 | HAVCR1 |
| 111 | AQLEGKLVSI | I | III | I | I | II | I | I | III | 3161 | HMMR |
| 277 | KLQEELNKV | I | III | I | I | II | I | I | III | 3161 | HMMR |
| 67 | FLIENLLAA | I | I | I | II | I | I | I | I | 3166 | HMX1 |
| 56 | VLQENSSDYQSNL | II | III | I | I | I | I | I | I | 3188 | HNRNPH2 |
| 89 | SLAETIFIV | I | I | I | I | II | I | I | I | 3359 | HTR3A |
| 90 | AILNVDEKNQV | I | I | I | I | II | I | I | I | 3359 | HTR3A |
| 91 | LLPSIFLMV | I | I | I | I | II | I | I | I | 3359 | HTR3A |
| 287 | KIQEILTQV | IV | II | II | III | IV | IV | I | II | 10643 | IGF2BP3 |
| 97 | KLFEKSTGL | IV | IV | II | II | I | II | III | II | 23421 | ITGB3BP |
| 35 | VIIKGLEEI | I | II | I | I | I | I | I | I | 3832 | KIF11 |
| 36 | TVLQELINV | I | II | I | I | I | I | I | I | 3832 | KIF11 |
| 37 | QIVELIEKI | I | II | I | I | I | I | I | I | 3832 | KIF11 |
| 239 | VIIKGLEEITV | I | II | I | I | I | I | I | I | 3832 | KIF11 |
| 240 | SVQENIQQK | I | II | I | I | I | I | I | I | 3832 | KIF11 |
| 10 | QLIEKNWLL | IV | IV | I | II | III | II | I | IV | 56992 | KIF15 |
| 112 | ILAQDVAQL | III | IV | I | I | II | II | I | III | 24137 | KIF4A |
| 70 | GLTEKTVLV | III | IV | I | I | II | II | I | III | 24,137, 285,643 | KIF4A, KIF4B |
| 252 | SLMEKNQSL | III | IV | I | II | II | I | I | III | 24,137, 285,643 | KIF4A, KIF4B |
| 104 | DLPTQEPALGTT | I | I | I | I | I | IV | I | I | 354 | KLK3 |
| 118 | IAYNPNGNAL | I | I | I | I | I | II | I | I | 3824 | KLRD1 |
| 113 | FLFLKEVKV | I | II | I | I | I | I | I | I | 54596 | L1TD1 |

TABLE 5A-continued

Target coverage for source genes of selected peptides.

| SEQ ID NO. | Sequence | GB (%) | CRC (%) | RCC (%) | HCC (%) | NSCLC (%) | PC (%) | BPH/PCA (%) | GC (%) | Gene ID | Official gene symbol |
|---|---|---|---|---|---|---|---|---|---|---|---|
| 279 | VLMDEGAVLTL | I | II | I | I | I | I | I | I | 54596 | L1TD1 |
| 119 | SLIEESEEL | I | II | I | I | I | I | I | I | 284217 | LAMA1 |
| 105 | AMLASQTEA | II | I | I | II | I | IV | I | I | 4295 | MLN |
| 106 | VLLGSVVIFA | I | I | I | I | I | I | IV | II | 4477 | MSMB |
| 29 | KMISAIPTL | I | I | I | I | III | II | II | I | 94025 | MUC16 |
| 30 | IITEVITRL | I | I | I | I | III | II | II | I | 94025 | MUC16 |
| 31 | GLLETTGLLAT | I | I | I | I | III | II | II | I | 94025 | MUC16 |
| 32 | VVMVLVLML | I | I | I | I | III | II | II | I | 94025 | MUC16 |
| 33 | TLDRNSLYV | I | I | I | I | III | II | II | I | 94025 | MUC16 |
| 34 | TLNTLDINL | I | I | I | I | III | II | II | I | 94025 | MUC16 |
| 41 | IVTEIISEI | III | IV | I | I | III | I | I | III | 64151 | NCAPG |
| 42 | KQMSISTGL | III | IV | I | I | III | I | I | III | 64151 | NCAPG |
| 234 | VLLNEILEQV | III | IV | I | I | III | I | I | III | 64151 | NCAPG |
| 285 | MLLDTVQKV | I | II | I | I | I | I | I | I | 54892 | NCAPG2 |
| 114 | LLFPSDVQTL | II | III | I | I | III | I | I | III | 23397 | NCAPH |
| 107 | RVLPGQAVTGV | I | III | I | I | I | I | I | I | 55247 | NEIL3 |
| 81 | ILAEEPIYI | I | I | I | I | II | II | II | II | 55655 | NLRP2 |
| 82 | ILAEEPIYIRV | I | I | I | I | II | II | II | II | 55655 | NLRP2 |
| 115 | ILHGEVNKV | I | II | I | I | I | I | I | I | 54830 | NUP62CL |
| 39 | YLEDGFAYV | II | IV | I | I | III | II | IV | IV | 5558 | PRIM2 |
| 83 | GLLENSPHL | III | II | II | II | I | III | I | II | 25788 | RAD54B |
| 253 | KLLAVIHEL | III | II | II | II | I | III | I | II | 25788 | RAD54B |
| 288 | SLYKGLLSV | III | II | II | II | I | III | I | II | 25788 | RAD54B |
| 108 | FIANLPPELKA | I | II | I | I | I | I | IV | I | 6013 | RLN1 |
| 13 | RLHDENILL | III | II | II | I | I | I | I | I | 23322 | RPGRIP1L |
| 120 | LQLJPLKGLSL | II | IV | I | II | III | II | I | III | 6241 | RRM2 |
| 76 | FTAEFLEKV | III | I | I | I | I | II | I | I | 79801 | SHCBP1 |
| 255 | FLMKNSDLYGA | III | I | I | I | I | II | I | I | 79801 | SHCBP1 |
| 74 | GLAFLPASV | I | II | I | I | I | I | I | I | 6570 | SLC18A1 |
| 75 | ALLDGALQL | I | II | I | I | I | I | I | I | 6570 | SLC18A1 |
| 243 | GLAEFQENV | II | I | I | I | II | II | I | II | 57405 | SPC25 |
| 281 | LLLESDPKVYSL | I | III | I | I | I | I | I | I | 6491 | STIL |
| 109 | ILGSFELQL | I | I | I | I | I | I | IV | I | 7047 | TGM4 |
| 110 | QIQGQVSEV | I | I | I | I | I | I | IV | I | 7047 | TGM4 |
| 267 | YLLDMPLWYL | IV | IV | II | II | IV | III | I | IV | 7153 | TOP2A |
| 268 | SLDKDIVAL | IV | IV | II | II | IV | III | I | IV | 7153 | TOP2A |
| 121 | ALYVQAPTV | IV | IV | II | II | IV | IV | I | IV | 9319 | TRIP13 |
| 122 | SIIDTELKV | IV | IV | II | II | IV | IV | I | IV | 9319 | TRIP13 |

TABLE 5A-continued

Target coverage for source genes of selected peptides.

| SEQ ID NO. | Sequence | GB (%) | CRC (%) | RCC (%) | HCC (%) | NSCLC (%) | PC (%) | BPH/ PCA (%) | GC (%) | Gene ID | Official gene symbol |
|---|---|---|---|---|---|---|---|---|---|---|---|
| 123 | QTAPEEAFIKL | IV | II | III | III | III | II | IV | III | 15,073, 792,104 | TTC30B, TTC30A |
| 124 | ALLLRLFTI | III | IV | II | II | IV | IV | I | IV | 11169 | WDHD1 |
| 125 | AALEVLAEV | I | III | I | I | I | I | I | I | 11130 | ZWINT |
| 126 | QLREAFEQL | I | III | I | I | I | I | I | I | 11130 | ZWINT |

Over-expression was defined as more than 1.5-fold higher expression on a tumor compared to the relevant normal tissue that showed highest expression of the gene. <19% over-expression = I, 20-49% = II, 50-69% = III, >70% = IV. If a peptide could be derived from several source genes, the gene with minimal coverage was decisive.

RNAseq Experiments

Gene expression analysis of—tumor and normal tissue RNA samples was performed by next generation sequencing (RNAseq) by CeGaT (Tübingen, Germany). Briefly, sequencing libraries are prepared using the Illumina HiSeq v4 reagent kit according to the provider's protocol (Illumina Inc., San Diego, Calif., USA), which includes RNA fragmentation, cDNA conversion and addition of sequencing adaptors. Libraries derived from multiple samples are mixed equimolarly and sequenced on the Illumina HiSeq 2500 sequencer according to the manufacturer's instructions, generating 50 bp single end reads. Processed reads are mapped to the human genome (GRCh38) using the STAR software.

Expression data are provided on transcript level as RPKM (Reads Per Kilobase per Million mapped reads, generated by the software Cufflinks) and on exon level (total reads, generated by the software Bedtools), based on annotations of the ensembl sequence database (Ensembl77). Exon reads are normalized for exon length and alignment size to obtain RPKM values.

Exemplary expression profiles of source genes of the present invention that are highly over-expressed or exclusively expressed in NHL, BRCA, GBC, CCC, MEL, OC, OSCAR, SCLC, UBC, UEC are shown in FIG. 2F-H. Expression scores for further exemplary genes are shown in Table 5B.

TABLE 5B

Target coverage for source genes of selected peptides.

| SEQ ID NO. | Sequence | AML (%) | NHL (%) | BRCA (%) | CLL (%) | GBC_CCC (%) | MEL (%) | OC (%) | OSCAR (%) | SCLC (%) | UBC (%) | UTC (%) |
|---|---|---|---|---|---|---|---|---|---|---|---|---|
| 1 | KLQEKIQEL | I | I | I | I | I | I | I | I | I | I | I |
| 2 | SVLEKEIYSI | I | I | I | I | I | I | I | I | I | I | I |
| 3 | RVIDDSLVVGV | I | II | I | I | I | I | I | I | II | I | I |
| 4 | VLFGELPAL | I | I | I | I | I | I | I | I | I | I | I |
| 5 | GLVDIMVHL | I | I | I | I | I | I | I | I | I | I | I |
| 7 | ALLQALMEL | I | II | II | I | II | III | II | II | I | II | I |
| 8 | ALSSSQAEV | I | I | I | I | I | I | I | I | I | I | I |
| 9 | SLITGQDLLSV | I | I | I | I | I | I | I | I | II | I | I |
| 10 | QLIEKNWLL | I | II | I | I | I | I | I | I | II | I | I |
| 11 | LLDPKTIFL | I | I | I | I | II | I | I | I | I | I | I |
| 13 | RLHDENILL | I | I | II | I | I | I | I | I | II | I | I |
| 14 | YTFSGDVQL | I | I | I | I | I | II | I | IV | I | III | I |
| 17 | GLLPSAESIKL | I | I | I | I | I | I | I | I | I | I | I |
| 18 | KTASINQNV | I | I | I | I | I | I | I | I | II | I | I |
| 21 | YLMDDFSSL | I | I | II | I | I | I | I | I | II | I | I |
| 22 | LMYPYIYHV | I | I | II | I | I | I | I | I | I | I | I |
| 24 | KVWSDVTPL | I | I | IV | I | IV | II | II | IV | II | IV | IV |
| 39 | YLEDGFAYV | I | II | II | I | II | II | III | I | III | I | I |
| 40 | KIWEELSVLEV | I | I | II | I | III | IV | I | III | IV | III | II |

TABLE 5B-continued

Target coverage for source genes of selected peptides.

| SEQ ID NO. | Sequence | AML (%) | NHL (%) | BRCA (%) | CLL (%) | GBC_CCC (%) | MEL (%) | OC (%) | OSCAR (%) | SCLC (%) | UBC (%) | UTC (%) |
|---|---|---|---|---|---|---|---|---|---|---|---|---|
| 41 | IVTEIISEI | I | I | I | I | I | I | I | I | II | I | I |
| 43 | LLIPFTIFM | I | II | II | I | II | II | I | IV | I | II | I |
| 46 | ISLDEVAVSL | I | I | I | I | I | I | I | I | III | I | I |
| 47 | GLNGFNVLL | I | II | I | I | I | I | I | I | III | I | II |
| 49 | KLIGNIHGNEV | I | I | I | I | I | I | I | I | I | I | I |
| 50 | ILLSVLHQL | I | I | I | I | I | I | I | I | I | I | I |
| 67 | FLIENLLAA | I | I | I | I | I | I | I | I | I | I | I |
| 76 | FTAEFLEKV | I | I | I | I | I | I | I | I | I | I | I |
| 83 | GLLENSPHL | I | II | II | I | I | II | II | I | III | I | III |
| 84 | FLLEREQLL | I | II | I | I | I | I | I | I | II | I | II |
| 85 | KLLDKPEQFL | I | I | I | I | I | IV | I | I | I | I | I |
| 86 | SLFSNIESV | I | I | I | I | I | I | I | I | I | I | I |
| 88 | LLLPLELSLA | I | I | I | I | I | I | I | I | III | I | I |
| 89 | SLAETIFIV | I | III | I | I | I | I | II | I | II | I | I |
| 92 | RLFEEVLGV | I | I | I | I | I | I | I | I | II | I | I |
| 95 | KLIDEDEPLFL | I | I | I | I | I | I | I | I | I | I | I |
| 96 | ALDTTRHEL | I | II | I | I | I | I | I | I | I | I | I |
| 102 | GLYPVTLVGV | I | I | I | I | I | I | I | I | II | I | I |
| 116 | ALLSSVAEA | I | I | II | I | I | I | I | IV | I | II | I |
| 117 | TLLEGISRA | I | I | I | I | I | I | I | II | I | I | I |
| 147 | GLLSALENV | I | III | I | IV | I | I | I | I | I | I | I |
| 148 | YLILSSHQL | I | III | I | IV | I | I | I | I | I | I | I |
| 152 | ILVTSIFFL | I | II | I | II | I | I | I | I | I | I | I |
| 153 | KLVELEHTL | I | I | II | I | II | II | I | II | I | II | I |
| 155 | TLDSYLKAV | I | I | III | I | I | I | I | I | I | I | I |
| 156 | VILTSSPFL | I | I | I | II | I | I | I | I | I | I | I |
| 157 | ILQDGQFLV | I | I | I | II | I | III | I | I | II | I | I |
| 158 | YLDPLWHQL | I | I | I | I | I | I | I | I | II | I | I |
| 166 | LLGDSSFFL | I | I | I | I | I | I | I | I | I | I | I |
| 169 | ALADLSVAV | I | I | I | I | I | I | I | II | I | III | I |
| 170 | FIAAVVEKV | I | I | I | I | I | II | II | I | I | I | I |
| 181 | LLWAPTAQA | I | I | I | I | II | I | I | I | II | I | I |
| 185 | TLYQGLPAEV | I | I | II | I | I | I | III | IV | I | II | IV |
| 203 | FLFVDPELV | II | I | I | I | I | I | I | I | I | I | I |
| 220 | ALSELERVL | I | I | I | I | I | I | I | I | I | I | I |
| 222 | LLTGVFAQL | I | I | I | I | II | I | I | I | I | II | I |
| 233 | SLFESLEYL | I | I | II | I | II | II | II | II | I | I | I |

TABLE 5B-continued

Target coverage for source genes of selected peptides.

| SEQ ID NO. | Sequence | AML (%) | NHL (%) | BRCA (%) | CLL (%) | GBC_CCC (%) | MEL (%) | OC (%) | OSCAR (%) | SCLC (%) | UBC (%) | UTC (%) |
|---|---|---|---|---|---|---|---|---|---|---|---|---|
| 234 | VLLNEILEQV | I | I | I | I | I | I | I | I | III | I | I |
| 235 | SLLNQPKAV | I | I | I | I | I | I | II | I | II | I | I |
| 236 | KMSELQTYV | I | II | I | I | I | I | I | I | II | I | I |
| 237 | ALLEQTGDMSL | I | II | I | I | I | I | I | I | II | I | I |
| 241 | KQFEGTVEI | I | II | II | I | I | I | I | I | II | I | I |
| 242 | KLQEEIPVL | I | I | I | I | I | I | I | I | I | I | I |
| 243 | GLAEFQENV | I | II | I | I | I | I | I | I | II | I | I |
| 245 | ALLEEEGV | I | I | I | I | I | II | I | II | II | II | I |
| 246 | ALAGIVTNV | I | I | II | I | II | I | III | I | I | II | I |
| 248 | VLMQDSRLYL | I | II | I | I | I | I | I | I | I | I | I |
| 251 | LLWGNLPEI | I | II | I | I | I | I | I | I | I | I | I |
| 252 | SLMEKNQSL | I | I | I | I | I | I | I | I | II | I | I |
| 253 | KLLAVIHEL | I | II | II | I | I | II | II | I | III | I | III |
| 255 | FLMKNSDLYGA | I | I | I | I | I | I | I | I | I | I | I |
| 257 | KLIDHQGLYL | I | I | I | I | I | I | II | I | II | I | I |
| 260 | ALNESLVEC | I | III | I | I | II | I | II | IV | II | II | II |
| 261 | GLAALAVHL | I | II | I | I | I | I | I | I | III | I | I |
| 263 | SIIEYLPTL | I | I | I | I | I | I | I | I | II | I | I |
| 264 | TLHDQVHLL | I | I | IV | I | I | I | IV | I | I | I | IV |
| 265 | FLLDKPQDLSI | I | I | I | I | II | I | II | I | I | I | I |
| 267 | YLLDMPLWYL | I | II | I | I | I | I | I | I | III | I | I |
| 269 | GLLDCPIFL | I | I | I | I | I | I | I | I | I | I | I |
| 270 | TLLTFFHEL | I | I | I | I | I | II | I | II | II | I | I |
| 271 | VLIEYNFSI | I | I | I | I | I | II | I | III | II | I | I |
| 274 | TLYNPERTITV | II | IV | II | III | IV | IV | IV | IV | IV | II | II |
| 277 | KLQEELNKV | I | I | I | I | I | I | I | I | I | I | I |
| 279 | VLMDEGAVLTL | I | I | I | II | I | I | I | I | I | I | I |
| 283 | ALSELLQQV | I | I | I | I | I | I | I | I | II | I | I |
| 286 | FLTEMVHFI | I | I | I | I | I | I | I | I | II | II | I |

Over-expression was defined as more than 1.5-fold higher expression on a tumor compared to the relevant normal tissue that showed highest expression of the gene. <19% over-expression = I, 20-49% = II, 50-69% = III, >70% = IV. If a peptide could be derived from several source genes, the gene with minimal coverage was decisive. The baseline included the following relevant normal tissues: adipose tissue, adrenal gland, artery, bone marrow, brain, cartilage, colon, esophagus, gallbladder, heart, kidney, liver, lung, lymph node, pancreas, pituitary, rectum, skeletal muscle, skin, small intestine, spleen, stomach, thymus, thyroid gland, trachea, urinary bladder and vein. In case expression data for several samples of the same tissue type were available, the arithmetic mean of all respective samples was used for the calculation.
AML = acute myeloid leukemia,
NHL = non-Hodgkin lymphoma,
BRCA = breast cancer,
CLL = chronic lymphocytic leukemia,
GBC_CCC = gallbladder adenocarcinoma and cholangiocarcinoma,
MEL = melanoma,
OC = ovarian cancer,
OSCAR = esophageal cancer, including cancer of the gastric-oesophageal junction,
SCLC = small cell lung cancer,
UBC = urinary bladder cancer,
UTC = uterine cancer.

Example 3

In Vitro Immunogenicity of MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for 47 HLA-A*0201 restricted TUMAPs of the invention so far, demonstrating that these peptides are T-cell epitopes against which CD8+ precursor T cells exist in humans (Table 6A and B).

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent. PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) were also added to the TCM at this step. Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO. 289) from modified Melan-A/MART-1) and A*0201/DDX5-001 (YLLPAIVHI from DDX5, SEQ ID NO. 290), respectively.

800,000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating 1×10$^6$ CD8+ T cells with 2×10$^5$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oreg., USA). In vitro priming of specific multimer+CD8+ lymphocytes was detected by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity of Peptides

For tested HLA class I peptides, in vitro immunogenicity could be demonstrated by generation of peptide specific T-cell lines. Exemplary flow cytometry results after TUMAP-specific multimer staining for 15 peptides of the invention are shown in FIGS. 3 and 6 together with corresponding negative controls. Results for two peptides from the invention are summarized in Table 6A and B.

TABLE 6A in vitro immunogenicity of HLA class I peptides of the invention

| Seq ID | Sequence | wells | donors |
|---|---|---|---|
| 288 | SLYKGLLSV | ++ | ++++ |
| 287 | KIQEILTQV | + | +++ |

Exemplary results of in vitro immunogenicity experiments conducted by the applicant for the peptides of the invention.
<20% = +;
21%-49% = ++;
50%-69% =+++;
>= 70% = ++++

TABLE 6B

In vitro immunogenicity of HLA class I peptides of the invention

| SEQ ID | Sequence | Wells positive [%] |
|---|---|---|
| 4 | VLFGELPAL | + |
| 7 | ALLQALMEL | ++ |
| 9 | SLITGQDLLSV | + |
| 11 | LLDPKTIFL | ++ |
| 14 | YTFSGDVQL | + |
| 17 | GLLPSAESIKL | + |
| 18 | KTASINQNV | +++ |
| 27 | GLLGKVTSV | + |
| 29 | KMISAIPTL | + |
| 34 | TLNTLDINL | ++++ |
| 35 | VIIKGLEEI | + |
| 39 | YLEDGFAYV | ++++ |
| 48 | KISDFGLATV | ++ |

TABLE 6B-continued

In vitro immunogenicity of HLA class I peptides of the invention

| SEQ ID | Sequence | Wells positive [%] |
|---|---|---|
| 50 | ILLSVLHQL | + |
| 66 | AMFPDTIPRV | + |
| 77 | ALYGNVQQV | + |
| 82 | ILAEEPIYIRV | +++ |
| 89 | SLAETIFIV | + |
| 92 | RLFEEVLGV | ++ |
| 97 | KLFEKSTGL | + |
| 101 | SLLEVNEASSV | + |
| 102 | GLYPVTLVGV | + |
| 117 | TLLEGISRA | ++ |
| 121 | ALYVQAPTV | + |
| 157 | ILQDGQFLV | + |
| 166 | LLGDSSFFL | ++ |
| 183 | ALSYILPYL | +++ |
| 203 | FLFVDPELV | +++ |
| 233 | SLFESLEYL | + |
| 234 | VLLNEILEQV | ++ |
| 236 | KMSELQTYV | + |
| 242 | KLQEEIPVL | + |
| 246 | ALAGIVTNV | + |
| 248 | VLMQDSRLYL | ++ |
| 251 | LLWGNLPEI | ++ |
| 253 | KLLAVIHEL | ++ |
| 254 | ALGDKFLLRV | + |
| 255 | FLMKNSDLYGA | + |
| 257 | KLIDHQGLYL | + |
| 260 | ALNESLVEC | + |
| 261 | GLAALAVHL | ++ |
| 263 | SIIEYLPTL | + |
| 264 | TLHDQVHLL | + |
| 267 | YLLDMPLWYL | + |
| 275 | AVPPPPSSV | ++ |

Exemplary results of in vitro immunogenicity experiments conducted by the applicant for HLA-A*02 restricted peptides of the invention. Results of in vitro immunogenicity experiments are indicated. Percentage of positive wells and donors (among evaluable) are summarized as indicated <20% = +; 20%-49% = ++; 50%-69% = +++; >=70% = ++++

Example 4

Synthesis of Peptides

All peptides were synthesized using standard and well-established solid phase peptide synthesis using the Fmoc-strategy.

Identity and purity of each individual peptide have been determined by mass spectrometry and analytical RP-HPLC. The peptides were obtained as white to off-white lyophilizates (trifluoro acetate salt) in purities of >50%.

All TUMAPs are preferably administered as trifluoro-acetate salts or acetate salts, other salt-forms are also possible.

Example 5

MHC Binding Assays

Candidate peptides for T cell based therapies according to the present invention were further tested for their MHC binding capacity (affinity). The individual peptide-MHC complexes were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko et al., 2006).

96 well MAXISorp plates (NUNC) were coated over night with 2 ug/ml streptavidin in PBS at room temperature, washed 4× and blocked for 1 h at 37° C. in 2% BSA containing blocking buffer. Refolded HLA-A*02:01/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2 ug/ml HRP conjugated anti-β2m for 1 h at 37° C., washed again and detected with TMB solution that is stopped with $NH_2SO_4$. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

TABLE 7

MHC class I binding scores

| SEQ ID | Sequence | Peptide exchange |
|---|---|---|
| 1 | KLQEKIQEL | ++++ |
| 3 | RVIDDSLVVGV | +++ |
| 4 | VLFGELPAL | +++ |
| 5 | GLVDIMVHL | +++ |
| 6 | FLNAIETAL | ++++ |
| 7 | ALLQALMEL | +++ |

TABLE 7-continued

MHC class I binding scores

| SEQ ID | Sequence | Peptide exchange |
|---|---|---|
| 9 | SLITGQDLLSV | +++ |
| 10 | QLIEKNWLL | +++ |
| 11 | LLDPKTIFL | +++ |
| 12 | RLLDPKTIFL | +++ |
| 13 | RLHDENILL | +++ |
| 14 | YTFSGDVQL | +++ |
| 16 | SLADLSLLL | +++ |
| 17 | GLLPSAESIKL | ++++ |
| 18 | KTASINQNV | ++ |
| 19 | KVFELDLVTL | ++ |
| 20 | ALVEKGEFAL | ++ |
| 21 | YLMDDFSSL | +++ |
| 22 | LMYPYIYHV | +++ |
| 23 | ALLSPLSLA | +++ |
| 24 | KVWSDVTPL | +++ |
| 25 | LLWGHPRVALA | +++ |
| 26 | VLDGKVAVV | +++ |
| 27 | GLLGKVTSV | +++ |
| 28 | IKVTDPQLLEL | ++ |
| 29 | KMISAIPTL | ++ |
| 30 | IITEVITRL | +++ |
| 31 | GLLETTGLLAT | +++ |
| 33 | TLDRNSLYV | ++ |
| 34 | TLNTLDINL | +++ |
| 35 | VIIKGLEEI | ++ |
| 36 | TVLQELINV | +++ |
| 37 | QIVELIEKI | ++ |
| 38 | VLQQESNFL | ++ |
| 39 | YLEDGFAYV | +++ |
| 40 | KIWEELSVLEV | +++ |
| 41 | IVTEIISEI | +++ |
| 42 | KQMSISTGL | ++ |
| 44 | AVFNLVHVV | +++ |
| 45 | FLPVSVVYV | +++ |
| 47 | GLNGFNVLL | +++ |
| 48 | KISDFGLATV | +++ |
| 49 | KLIGNIHGNEV | ++ |
| 50 | ILLSVLHQL | +++ |
| 51 | LDSEALLTL | ++ |
| 52 | TIGIPFPNV | ++ |
| 53 | AQHLSTLLL | + |
| 54 | YLVPGLVAA | +++ |
| 55 | HLFDKIIKI | +++ |
| 57 | TLYPGRFDYV | ++ |
| 58 | HLLGEGAFAQV | +++ |
| 59 | ALADGIKSFLL | +++ |
| 60 | YLFSQGLQGL | +++ |
| 61 | ALYPKEITL | +++ |
| 62 | SLVENIHVL | +++ |
| 63 | KLLPMVIQL | +++ |
| 64 | SLYAGSNNQV | ++ |
| 65 | SLSEKSPEV | ++ |
| 66 | AMFPDTIPRV | ++ |
| 67 | FLIENLLAA | +++ |
| 68 | QLMNLIRSV | +++ |
| 69 | LKVLKADVVL | ++ |
| 70 | GLTEKTVLV | ++ |
| 71 | HMSGKLTNV | ++ |
| 72 | VLSTRVTNV | ++ |
| 74 | GLAFLPASV | ++ |
| 75 | ALLDGALQL | +++ |
| 76 | FTAEFLEKV | +++ |
| 77 | ALYGNVQQV | +++ |
| 79 | TVLEEIGNRV | ++ |
| 80 | VLTGQVHEL | +++ |
| 81 | ILAEEPIYI | ++ |
| 82 | ILAEEPIYIRV | +++ |
| 83 | GLLENSPHL | ++ |
| 84 | FLLEREQLL | ++++ |
| 85 | KLLDKPEQFL | ++ |
| 86 | SLFSNIESV | +++ |
| 87 | KLLSLLEEA | +++ |
| 88 | LLLPLELSLA | +++ |
| 89 | SLAETIFIV | +++ |
| 90 | AILNVDEKNQV | ++ |
| 91 | LLPSIFLMV | ++ |

TABLE 7-continued

MHC class I binding scores

| SEQ ID | Sequence | Peptide exchange |
|---|---|---|
| 92 | RLFEEVLGV | ++++ |
| 93 | RLYGYFHDA | ++ |
| 94 | YLDEVAFML | +++ |
| 95 | KLIDEDEPLFL | +++ |
| 96 | ALDTTRHEL | ++ |
| 97 | KLFEKSTGL | +++ |
| 98 | FVQEKIPEL | +++ |
| 99 | TLFGIQLTEA | +++ |
| 100 | ALQSFEFRV | +++ |
| 101 | SLLEVNEASSV | +++ |
| 102 | GLYPVTLVGV | +++ |
| 103 | YLADTVQKL | ++ |
| 105 | AMLASQTEA | ++ |
| 106 | VLLGSVVIFA | ++ |
| 107 | RVLPGQAVTGV | ++ |
| 108 | FIANLPPELKA | +++ |
| 109 | ILGSFELQL | +++ |
| 110 | QIQGQVSEV | ++ |
| 111 | AQLEGKLVSI | +++ |
| 112 | ILAQDVAQL | +++ |
| 113 | FLFLKEVKV | ++ |
| 114 | LLFPSDVQTL | ++ |
| 115 | ILHGEVNKV | ++ |
| 116 | ALLSSVAEA | ++ |
| 117 | TLLEGISRA | ++ |
| 119 | SLIEESEEL | ++ |
| 121 | ALYVQAPTV | ++ |
| 122 | SIIDTELKV | +++ |
| 123 | QTAPEEAFIKL | + |
| 124 | ALLLRLFTI | ++ |
| 125 | AALEVLAEV | +++ |
| 126 | QLREAFEQL | +++ |
| 128 | SILTNISEV | ++ |
| 129 | KMASKVTQV | ++ |
| 130 | QLYGSAITL | +++ |
| 131 | SLYPHFTLL | +++ |
| 132 | ALLNNVIEV | +++ |
| 133 | FLDGRPLTL | ++ |
| 134 | SLYKSFLQL | ++ |
| 136 | LLWDAPAKC | +++ |
| 137 | KLIYKDLVSV | ++ |
| 138 | GIINKLVTV | ++ |
| 139 | IILENIQSL | +++ |
| 140 | FLDSQITTV | +++ |
| 141 | NIDINNNEL | ++ |
| 142 | LLDAAHASI | ++ |
| 143 | MLWESIMRV | +++ |
| 144 | FLISQTPLL | +++ |
| 145 | ALEEKLENV | +++ |
| 146 | VVAAHLAGA | ++ |
| 147 | GLLSALENV | +++ |
| 148 | YLILSSHQL | +++ |
| 149 | NMADGQLHQV | ++ |
| 150 | VLLDMVHSL | +++ |
| 151 | DISKRIQSL | ++ |
| 153 | KLVELEHTL | +++ |
| 154 | AIIKEIQTV | ++ |
| 155 | TLDSYLKAV | ++ |
| 157 | ILQDGQFLV | ++ |
| 158 | YLDPLWHQL | +++ |
| 159 | QLGPVPVTI | +++ |
| 160 | TLQEWLTEV | +++ |
| 161 | NLLDENVCL | ++++ |
| 162 | GLLGNLLTSL | +++ |
| 163 | GLEERLYTA | ++ |
| 164 | MLIIRVPSV | +++ |
| 165 | SLLDYEVSI | +++ |
| 166 | LLGDSSFFL | +++ |
| 167 | LVVDEGSLVSV | +++ |
| 168 | VIFEGEPMYL | +++ |
| 169 | ALADLSVAV | +++ |
| 170 | FIAAVVEKV | ++ |
| 171 | LLLLDVPTA | ++ |
| 173 | RLIDIYKNV | +++ |
| 174 | ALYSGDLHAA | ++ |
| 175 | SLLDLVQSL | +++ |

TABLE 7-continued

MHC class I binding scores

| SEQ ID | Sequence | Peptide exchange |
|---|---|---|
| 176 | VQSGLRILL | ++ |
| 177 | ALINVLNAL | +++ |
| 178 | SLVSWQLLL | ++++ |
| 179 | TLGEIIKGV | +++ |
| 180 | RLYEEEIRI | +++ |
| 181 | LLWAPTAQA | +++ |
| 182 | GLQDGFQITV | +++ |
| 183 | ALSYILPYL | +++ |
| 184 | ALDSTIAHL | ++ |
| 185 | TLYQGLPAEV | ++ |
| 187 | SILKEDPFL | ++ |
| 188 | VLGEEQEGV | ++ |
| 190 | SLSTELFKV | +++ |
| 191 | AAIEIFEKV | +++ |
| 192 | TLLPSSGLVTL | ++ |
| 193 | ALFHMNILL | +++ |
| 194 | KLLEEVQLL | ++ |
| 195 | VIIQNLPAL | +++ |
| 198 | ILTNKVVSV | ++ |
| 199 | SVADLAHVL | ++ |
| 200 | IMPTFDLTKV | +++ |
| 203 | FLFVDPELV | ++ |
| 204 | SEWGSPHAAVP | +++ |
| 206 | GLDAFRIFL | ++++ |
| 207 | KLFETVEEL | +++ |
| 208 | HLNNDRNPL | ++ |
| 210 | GLAGDNIYL | +++ |
| 211 | LLTTVLINA | +++ |
| 212 | MTLSEIHAV | ++ |
| 213 | ILAVDGVLSV | +++ |
| 214 | ALFETLIQL | +++ |
| 215 | QIADIVTSV | ++ |
| 216 | ALSTVTPRI | ++ |
| 217 | LLWPSSVPA | +++ |
| 218 | SLTGANITV | +++ |
| 219 | GVVPTIQKV | ++ |
| 220 | ALSELERVL | +++ |
| 221 | IMLNSVEEI | ++ |
| 222 | LLTGVFAQL | ++ |
| 223 | ALHPVQFYL | +++ |
| 224 | LLFDWSGTGRADA | +++ |
| 225 | FLPQPVPLSV | +++ |
| 226 | SLAGNLQEL | +++ |
| 227 | SEMEELPSV | + |
| 228 | SLLELDGINLRL | +++ |
| 229 | YLYELEHAL | ++ |
| 230 | KLLNMIFSI | +++ |
| 231 | LLDDIFIRL | +++ |
| 233 | SLFESLEYL | +++ |
| 234 | VLLNEILEQV | ++++ |
| 235 | SLLNQPKAV | ++ |
| 236 | KMSELQTYV | +++ |
| 237 | ALLEQTGDMSL | +++ |
| 238 | HLQEKLQSL | ++ |
| 239 | VIIKGLEEITV | +++ |
| 241 | KQFEGTVEI | +++ |
| 242 | KLQEEIPVL | +++ |
| 243 | GLAEFQENV | ++ |
| 244 | NVAEIVIHI | +++ |
| 245 | ALLEEEEGV | ++ |
| 246 | ALAGIVTNV | +++ |
| 247 | NLLIDDKGTIKL | ++ |
| 248 | VLMQDSRLYL | +++ |
| 249 | YLYQILQGI | +++ |
| 250 | LMQDSRLYL | +++ |
| 251 | LLWGNLPEI | +++ |
| 252 | SLMEKNQSL | ++ |
| 253 | KLLAVIHEL | +++ |
| 254 | ALGDKFLLRV | ++ |
| 255 | FLMKNSDLYGA | +++ |
| 256 | FLNDIFERI | +++ |
| 257 | KLIDHQGLYL | +++ |
| 258 | QLVQRVASV | ++ |
| 259 | GPGIFPPPPPQP | + |
| 260 | ALNESLVEC | +++ |
| 261 | GLAALAVHL | +++ |

TABLE 7-continued

MHC class I binding scores

| SEQ ID | Sequence | Peptide exchange |
|---|---|---|
| 262 | LLLEAVWHL | +++ |
| 263 | SIIEYLPTL | +++ |
| 264 | TLHDQVHLL | ++ |
| 265 | FLLDKPQDLSI | +++ |
| 266 | FLLDKPQDL | ++ |
| 267 | YLLDMPLWYL | +++ |
| 268 | SLDKDIVAL | ++ |
| 269 | GLLDCPIFL | ++++ |
| 270 | TLLTFFHEL | +++ |
| 271 | VLIEYNFSI | +++ |
| 272 | FVMEGEPPKL | ++ |
| 273 | SLNKQIETV | ++ |
| 274 | TLYNPERTITV | +++ |
| 275 | AVPPPPSSV | ++ |
| 276 | RMPTVLQCV | +++ |
| 277 | KLQEELNKV | +++ |
| 278 | VLEDKVLSV | +++ |
| 279 | VLMDEGAVLTL | ++ |
| 280 | HLWGHALFL | +++ |
| 281 | LLLESDPKVYSL | ++ |
| 282 | SLYALHVKA | ++ |
| 283 | ALSELLQQV | +++ |
| 284 | KLMDPGSLPPL | ++ |
| 285 | MLLDTVQKV | +++ |
| 286 | FLTEMVHFI | +++ |

Binding of HLA-class I restricted peptides to HLA-A*02:01 was evaluated by peptide exchange yield:
≥10% = +;
≥20% = ++;
≥50 = +++;
≥75% = ++++

Example 6

TABLE 8

Preferred peptides according to the present invention

| SEQ ID No | Sequence | Peptide Code |
|---|---|---|
| 11 | LLDPKTIFL | HAVCR1-001 |
| 14 | YTFSGDVQL | MMP1-003 |
| 21 | YLMDDFSSL | COL6A3-015 |
| 24 | KVWSDVTPL | MMP-002 |
| 25 | LLWGHPRVALA | MXRA5-003 |
| 40 | KIWEELSVLEV | MAGEA3-003 |
| 85 | KLLDKPEQFL | FMN1-001 |
| 89 | SLAETIFIV | HTR3A-001 |
| 117 | TLLEGISRA | CABY-001 |
| 153 | KLVELEHTL | CT83-001 |
| 155 | TLDSYLKAV | CYP4Z-001 |
| 157 | ILQDGQFLV | DCAF4L2-001 |
| 168 | VIFEGEPMYL | HORMAD1-001 |
| 233 | SLFESLEYL | ZFP42-001 |
| 245 | ALLEEEEGV | MAGEA4-003 |
| 253 | KLLAVIHEL | RAD54B-002 |
| 264 | TLHDQVHLL | ESR1-001 |
| 274 | TLYNPERTITV | IGF-004 |

Absolute Quantitation of Tumor Associated Peptides Presented on the Cell Surface The generation of binders, such as antibodies and/or TCRs, is a laborious process, which may be conducted only for a number of selected targets. In the case of tumor-associated and—specific peptides, selection criteria include but are not restricted to exclusiveness of presentation and the density of peptide presented on the cell surface. In addition to the isolation and relative quantitation of peptides as described herein, the inventors did analyze absolute peptide copies per cell as described. The quantitation of TUMAP copies per cell in solid tumor samples requires the absolute quantitation of the isolated TUMAP, the efficiency of TUMAP isolation, and the cell count of the tissue sample analyzed.

Peptide Quantitation by nanoLC-MS/MS

For an accurate quantitation of peptides by mass spectrometry, a calibration curve was generated for each peptide using the internal standard method. The internal standard is a double-isotope-labelled variant of each peptide, i.e. two isotope-labelled amino acids were included in TUMAP synthesis. It differs from the tumor-associated peptide only in its mass but shows no difference in other physicochemical properties (Anderson et al., 2012). The internal standard was spiked to each MS sample and all MS signals were normalized to the MS signal of the internal standard to level out potential technical variances between MS experiments.

The calibration curves were prepared in at least three different matrices, i.e. HLA peptide eluates from natural samples similar to the routine MS samples, and each preparation was measured in duplicate MS runs. For evaluation, MS signals were normalized to the signal of the internal standard and a calibration curve was calculated by logistic regression.

For the quantitation of tumor-associated peptides from tissue samples, the respective samples were also spiked with the internal standard; the MS signals were normalized to the internal standard and quantified using the peptide calibration curve.

Efficiency of Peptide/MHC Isolation

As for any protein purification process, the isolation of proteins from tissue samples is associated with a certain loss of the protein of interest. To determine the efficiency of TUMAP isolation, peptide/MHC complexes were generated for all TUMAPs selected for absolute quantitation. To be able to discriminate the spiked from the natural peptide/MHC complexes, single-isotope-labelled versions of the TUMAPs were used, i.e. one isotope-labelled amino acid was included in TUMAP synthesis. These complexes were spiked into the freshly prepared tissue lysates, i.e. at the earliest possible point of the TUMAP isolation procedure, and then captured like the natural peptide/MHC complexes in the following affinity purification. Measuring the recovery of the single-labelled TUMAPs therefore allows conclusions regarding the efficiency of isolation of individual natural TUMAPs.

The efficiency of isolation was analyzed in a low number of samples and was comparable among these tissue samples. In contrast, the isolation efficiency differs between individual peptides. This suggests that the isolation efficiency, although determined in only a limited number of tissue samples, may be extrapolated to any other tissue preparation. However, it is necessary to analyze each TUMAP individually as the isolation efficiency may not be extrapolated from one peptide to others.

Determination of the Cell Count in Solid, Frozen Tissue

In order to determine the cell count of the tissue samples subjected to absolute peptide quantitation, the inventors applied DNA content analysis. This method is applicable to a wide range of samples of different origin and, most importantly, frozen samples (Alcoser et al., 2011; Forsey and Chaudhuri, 2009; Silva et al., 2013). During the peptide isolation protocol, a tissue sample is processed to a homogenous lysate, from which a small lysate aliquot is taken. The aliquot is divided in three parts, from which DNA is isolated (QiaAmp DNA Mini Kit, Qiagen, Hilden, Germany). The total DNA content from each DNA isolation is quantified using a fluorescence-based DNA quantitation assay (Qubit dsDNA HS Assay Kit, Life Technologies, Darmstadt, Germany) in at least two replicates.

In order to calculate the cell number, a DNA standard curve from aliquots of single healthy blood cells, with a range of defined cell numbers, has been generated. The standard curve is used to calculate the total cell content from the total DNA content from each DNA isolation. The mean total cell count of the tissue sample used for peptide isolation is extrapolated considering the known volume of the lysate aliquots and the total lysate volume.

Peptide Copies Per Cell

With data of the aforementioned experiments, the inventors calculated the number of TUMAP copies per cell by dividing the total peptide amount by the total cell count of the sample, followed by division through isolation efficiency. Copy cell number for selected peptides are shown in Table 9.

TABLE 9

Absolute copy numbers. The table lists the results of absolute peptide quantitation in tumor samples. The median number of copies per cell are indicated for each peptide: <100 = +; >= 100 = ++; >= 1,000 +++; >= 10,000 = ++++. The number of samples, in which evaluable, high quality MS data are available is indicated.

| SEQ ID No. | Peptide Code | Copies per cell (median) | Number of samples |
| --- | --- | --- | --- |
| 11 | HAVCR1-001 | + | 22 |
| 14 | MMP1-003 | ++ | 10 |
| 21 | COL6A3-015 | + | 35 |
| 24 | MMP-002 | + | 33 |
| 85 | FMN1-001 | + | 18 |
| 89 | HTR3A-001 | +++ | 17 |
| 117 | CABY-001 | + | 17 |
| 155 | CYP4Z-001 | ++ | 18 |
| 157 | DCAF4L2-001 | ++ | 16 |
| 245 | MAGEA4-003 | + | 33 |
| 253 | RAD54B-002 | +++ | 6 |
| 264 | ESR1-001 | + | 16 |
| 274 | IGF-004 | + | 6 |

REFERENCE LIST

Adelaide, J. et al., Cancer Res 67 (2007): 11565-11575
Alcoser, S. Y. et al., BMC. Biotechnol. 11 (2011): 124
Allison, J. P. et al., Science 270 (1995): 932-933
American Cancer Society
Ampie, L. et al., Front Oncol. 5 (2015): 12
Andersen, R. S. et al., Nat. Protoc. 7 (2012): 891-902
Anderson, N. L. et al., J Proteome. Res 11 (2012): 1868-1878
Appay, V. et al., Eur. J Immunol. 36 (2006): 1805-1814
Arafat, H. et al., Surgery 150 (2011): 306-315
Aung, P. P. et al., Oncogene 25 (2006): 2546-2557
Avigan, D. et al., Clin Cancer Res. 10 (2004): 4699-4708
Baba, T. et al., Eur. J Cardiothorac. Surg. 43 (2013): 759-764
Bahnassy, A. A. et al., World J Gastroenterol. 20 (2014): 18240-18248
Banchereau, J. et al., Cell 106 (2001): 271-274
Band, A. M. et al., J Mammary. Gland. Biol Neoplasia. 16 (2011): 109-115
Bankovic, J. et al., Lung Cancer 67 (2010): 151-159
Beatty, G. et al., J Immunol 166 (2001): 2276-2282
Beaty, T. H. et al., Hum. Genet. 132 (2013): 771-781
Beggs, J. D., Nature 275 (1978): 104-109
Bell, J. L. et al., J Clin Oncol 33 (2015): 1285-1293
Bell, J. L. et al., Cell Mol Life Sci. 70 (2013): 2657-2675

Benjamini, Y. et al., Journal of the Royal Statistical Society. Series B (Methodological), 57 (1995): 289-300
Berger, C. et al., Curr. Mol. Med. 13 (2013): 1229-1240
Berman, R. S. et al., National Cancer Institute: PDQ(R) Colon Cancer Treatment (2015a)
Berman, R. S. et al., National Cancer Institute: PDQ(R) Rectal Cancer Treatment (2015b)
Bhan, S. et al., Oncol Rep. 28 (2012): 1498-1502
Bode, P. K. et al., Mod. Pathol. 27 (2014): 899-905
Bogush, T. A. et al., Antibiot. Khimioter. 54 (2009): 41-49
Bonventre, J. V., Trans. Am. Clin Climatol. Assoc. 125 (2014): 293-299
Boulter, J. M. et al., Protein Eng 16 (2003): 707-711
Braumuller, H. et al., Nature (2013)
Bray, F. et al., Int J Cancer 132 (2013): 1133-1145
Brossart, P. et al., Blood 90 (1997): 1594-1599
Bruckdorfer, T. et al., Curr. Pharm. Biotechnol. 5 (2004): 29-43
Butterfield, L. H. et al., Clin Cancer Res 12 (2006): 2817-2825
Butterfield, L. H. et al., Clin Cancer Res 9 (2003): 5902-5908
Caballero, O. L. et al., PLoS. One. 5 (2010)
Carballido, E. et al., Cancer Control 19 (2012): 54-67
Card, K. F. et al., Cancer Immunol Immunother. 53 (2004): 345-357
Chang, Y. S. et al., Cancer Chemother. Pharmacol. 59 (2007): 561-574
Chanock, S. J. et al., Hum. Immunol. 65 (2004): 1211-1223
Chapiro, J. et al., Radiol. Med. 119 (2014): 476-482
Chen, H. S. et al., Zhonghua Gan Zang. Bing. Za Zhi. 11 (2003): 145-148
Chen, S. T. et al., Cancer Sci. 102 (2011b): 2191-2198
Chen, Y. L. et al., Int J Surg. 11 (2013c): 85-91
Chen, Y. T. et al., Cancer Immun. 5 (2005): 9
Cierna, Z. et al., BMC. Cancer 14 (2014): 472
Ciruelos Gil, E. M., Cancer Treat. Rev 40 (2014): 862-871
Cohen, C. J. et al., J Mol Recognit. 16 (2003a): 324-332
Cohen, C. J. et al., J Immunol 170 (2003b): 4349-4361
Cohen, S. N. et al., Proc. Natl. Acad. Sci. U.S.A 69 (1972): 2110-2114
Coligan, J. E. et al., Current Protocols in Protein Science (1995)
Colombetti, S. et al., J Immunol. 176 (2006): 2730-2738
Coosemans, A. et al., Anticancer Res 33 (2013): 5495-5500
Coulie, P. G. et al., Immunol. Rev 188 (2002): 33-42
Counter, C. M. et al., Blood 85 (1995): 2315-2320
Cuadros, T. et al., Cancer Res 74 (2014): 1416-1428
Cuadros, T. et al., Eur. J Cancer 49 (2013): 2034-2047
Dalerba, P. et al., Int. J Cancer 93 (2001): 85-90
De, Plaen E. et al., Immunogenetics 40 (1994): 360-369
Dengjel, J. et al., Clin Cancer Res 12 (2006): 4163-4170
Denkberg, G. et al., J Immunol 171 (2003): 2197-2207
Downie, D. et al., Clin Cancer Res. 11 (2005): 7369-7375
Du, X. et al., Clin Cancer Res 20 (2014): 6324-6335
Duan, Z. et al., Clin Cancer Res 9 (2003): 2778-2785
Ek, S. et al., Cancer Res 62 (2002): 4398-4405
Emens, L. A., Expert. Rev. Anticancer Ther. 12 (2012): 1597-1611
Enguita-German, M. et al., World J Hepatol. 6 (2014): 716-737
Estey, E. H., Am. J Hematol. 89 (2014): 1063-1081
Falk, K. et al., Nature 351 (1991): 290-296
Ferlay et al., GLOBOCAN 2012 v1.0, Cancer Incidence and Mortality Worldwide: IARC CancerBase No. 11 [Internet], (2013), globocan.iarc.fr
Findeis-Hosey, J. J. et al., Biotech. Histochem. 87 (2012): 24-29
Fong, L. et al., Proc. Natl. Acad. Sci. U.S.A 98 (2001): 8809-8814
Forsey, R. W. et al., Biotechnol. Lett. 31 (2009): 819-823
Frasor, J. et al., Mol. Cell Endocrinol. 418 Pt 3 (2015): 235-239
Fuge, O. et al., Res Rep. Urol. 7 (2015): 65-79
Fujiyama, T. et al., J Dermatol. Sci. 75 (2014): 43-48
Fukuyama, T. et al., Cancer Res. 66 (2006): 4922-4928
Fuqua, S. A. et al., Breast Cancer Res Treat. 144 (2014): 11-19
Gabrilovich, D. I. et al., Nat Med. 2 (1996): 1096-1103
Gandhi, A. V. et al., Ann Surg. Oncol 20 Suppl 3 (2013): S636-S643
Gardina, P. J. et al., BMC. Genomics 7 (2006): 325
Gattinoni, L. et al., Nat Rev. Immunol 6 (2006): 383-393
Giannopoulos, K. et al., Leukemia 24 (2010): 798-805
Giannopoulos, K. et al., Int. J Oncol 29 (2006): 95-103
Gibbs, P. et al., Melanoma Res 10 (2000): 259-264
Gnjatic, S. et al., Proc Natl. Acad. Sci. U.S.A 100 (2003): 8862-8867
Godkin, A. et al., Int. Immunol 9 (1997): 905-911
Gong, Y. et al., Adv. Anat. Pathol. 21 (2014): 191-200
Grah, J. J. et al., Tumori 100 (2014): 60-68
Granziero, L. et al., Blood 97 (2001): 2777-2783
Green, M. R. et al., Molecular Cloning, A Laboratory Manual 4th (2012)
Greenfield, E. A., Antibodies: A Laboratory Manual 2nd (2014)
Gu, X. et al., Sci. Rep. 4 (2014): 6625
Gunawardana, C. et al., Br. J Haematol. 142 (2008): 606-609
Hall, R. D. et al., Cancer Control 20 (2013): 22-31
Hamilton, K. E. et al., Mol. Cancer Res 13 (2015): 1478-1486
Han, L. et al., Int J Clin Exp. Pathol. 7 (2014): 6734-6742
Hanagiri, T. et al., Anticancer Res. 33 (2013): 2123-2128
Harig, S. et al., Blood 98 (2001): 2999-3005
Hasegawa, H. et al., Arch. Pathol. Lab Med. 122 (1998): 551-554
Hayashi, S. I. et al., Endocr. Relat Cancer 10 (2003): 193-202
Hennard, C. et al., J Pathol. 209 (2006): 430-435
Herbert, N. et al., J Immunol. 185 (2010): 902-916
Hinrichs, C. S. et al., Nat. Biotechnol. 31 (2013): 999-1008
Hiramoto, T. et al., Oncogene 18 (1999): 3422-3426
Hoffmann, N. E. et al., Cancer 112 (2008): 1471-1479
Holtl, L. et al., Clin. Cancer Res. 8 (2002): 3369-3376
Hsu, H. C. et al., Biochem. Biophys. Res Commun. 329 (2005): 1108-1117
Hu, S. et al., J Cancer Res Clin Oncol 140 (2014): 883-893
Huang, X. et al., Cell Prolif. 48 (2015b): 593-599
Hui, L. et al., Oncol Rep. 34 (2015): 2627-2635
Hussein, Y. M. et al., Med. Oncol 29 (2012): 3055-3062
Hwang, M. L. et al., J Immunol. 179 (2007): 5829-5838
Ioannidis, P. et al., Anticancer Res 23 (2003): 2179-2183
Jeng, Y. M. et al., Br. J Surg. 96 (2009): 66-73
Jung, G. et al., Proc Natl Acad Sci USA 84 (1987): 4611-4615
Kalos, M. et al., Sci. Transl. Med. 3 (2011): 95ra73
Kang, C. Y. et al., J Gastrointest. Surg. 18 (2014): 7-15
Kibbe, A. H., Handbook of Pharmaceutical Excipients rd (2000)
Kim, Y. D. et al., Int. J Mol. Med. 29 (2012): 656-662
Kobayashi, H. et al., Oncol Lett. 10 (2015): 612-618
Koido, S. et al., World J Gastroenterol. 19 (2013): 8531-8542

Krackhardt, A. M. et al., Blood 100 (2002): 2123-2131
Krieg, A. M., Nat Rev. Drug Discov. 5 (2006): 471-484
Lederer, M. et al., Semin. Cancer Biol 29 (2014): 3-12
Lee, M. Y. et al., J Cell Physiol 224 (2010): 17-27
Lee, W. C. et al., J Immunother. 28 (2005): 496-504
Leitlinien für Diagnostik and Therapie in der Neurologie, 030/099, (2014)
Leivo, I. et al., Cancer Genet. Cytogenet. 156 (2005): 104-113
Leonetti, M. D. et al., Proc. Natl. Acad. Sci. U.S.A 109 (2012): 19274-19279
Li, H. et al., Bull. Cancer 99 (2012): E26-E33
Li, M. et al., Clin Cancer Res 11 (2005): 1809-1814
Li, W. M. et al., J Surg. Oncol (2016)
Li, Y. et al., Cancer Epidemiol. 39 (2015): 8-13
Liddy, N. et al., Nat Med. 18 (2012): 980-987
Lin, J. et al., Clin Cancer Res 10 (2004): 5708-5716
Lin, L. et al., Oncol Lett. 6 (2013): 740-744
Lisitskaia, K. V. et al., Mol. Gen. Mikrobiol. Virusol. (2010): 34-37
Liu, X. et al., Int. Immunopharmacol. 25 (2015): 416-424
Ljunggren, H. G. et al., J Exp. Med. 162 (1985): 1745-1759
Llovet, J. M. et al., N. Engl. J Med. 359 (2008): 378-390
Longenecker, B. M. et al., Ann N. Y. Acad. Sci. 690 (1993): 276-291
Lonsdale, J., Nat. Genet. 45 (2013): 580-585
Lukas, T. J. et al., Proc. Natl. Acad. Sci. U.S.A 78 (1981): 2791-2795
Lundblad, R. L., Chemical Reagents for Protein Modification 3rd (2004)
Luo, C. et al., Clin Cancer Res 13 (2007): 1288-1297
Mantia-Smaldone, G. M. et al., Hum. Vaccin. Immunother. 8 (2012): 1179-1191
Marten, A. et al., Cancer Immunol. Immunother. 51 (2002): 637-644
Mason, J. M. et al., Nucleic Acids Res. 43 (2015): 3180-3196
Massari, F. et al., Cancer Treat. Rev. 41 (2015): 114-121
Matsueda, S. et al., World J Gastroenterol. 20 (2014): 1657-1666
Maus, M. V. et al., Blood 123 (2014): 2625-2635
Mayr, C. et al., Exp. Hematol. 34 (2006): 44-53
Mayr, C. et al., Blood 105 (2005): 1566-1573
Mehta, A. et al., Breast 23 (2014): 2-9
Meziere, C. et al., J Immunol 159 (1997): 3230-3237
Miyagi, Y. et al., Clin Cancer Res 7 (2001): 3950-3962
Miyoshi, Y. et al., Med. Mol. Morphol. 43 (2010): 193-196
Molina, J. R. et al., Mayo Clin Proc. 83 (2008): 584-594
Mongan, N. P. et al., Mol. Carcinog 45 (2006): 887-900
Morgan, R. A. et al., Science 314 (2006): 126-129
Mori, M. et al., Transplantation 64 (1997): 1017-1027
Mortara, L. et al., Clin Cancer Res. 12 (2006): 3435-3443
Moulton, H. M. et al., Clin Cancer Res 8 (2002): 2044-2051
Mueller, L. N. et al., J Proteome. Res 7 (2008): 51-61
Mueller, L. N. et al., Proteomics. 7 (2007): 3470-3480
Mumberg, D. et al., Proc. Natl. Acad. Sci. U.S.A 96 (1999): 8633-8638
Murray, G. I. et al., Histopathology 57 (2010): 202-211
National Cancer Institute, (May 6, 2015)
Noubissi, F. K. et al., J Invest Dermatol. 134 (2014): 1718-1724
Oehlrich, N. et al., Int. J Cancer 117 (2005): 256-264
Okuno, K. et al., Exp. Ther Med. 2 (2011): 73-79
Ottaviani, S. et al., Cancer Immunol. Immunother. 55 (2006): 867-872
Otte, M. et al., Cancer Res 61 (2001): 6682-6687
Ozeki, N. et al., Int. J Mol. Sci. 17 (2016)
Pai, V. P. et al., Breast Cancer Res 11 (2009): R81
Palmer, D. H. et al., Hepatology 49 (2009): 124-132
Palomba, M. L., Curr. Oncol Rep. 14 (2012): 433-440
Perez, C. A. et al., Expert. Rev Anticancer Ther. 11 (2011): 1599-1605
Phan, G. Q. et al., Cancer Control 20 (2013): 289-297
Pineda, C. T. et al., Cell 160 (2015): 715-728
Pinheiro, J. et al., nlme: Linear and Nonlinear Mixed Effects Models (CRAN.R-project.org/packe=nlme) (2015)
Plebanski, M. et al., Eur. J Immunol 25 (1995): 1783-1787
Porta, C. et al., Virology 202 (1994): 949-955
Porter, D. L. et al., N. Engl. J Med. 365 (2011): 725-733
Prasad, M. L. et al., Head Neck 26 (2004): 1053-1057
Qian, Z. et al., Mol. Cancer Res 12 (2014): 335-347
Quinn, D. I. et al., Urol. Oncol. (2015)
Raman, J. D. et al., Carcinogenesis 27 (2006): 499-507
Rammensee, H. G. et al., Immunogenetics 50 (1999): 213-219
Reck, M., Ann. Oncol 23 Suppl 8 (2012): viii28-viii34
Ref Seq, The NCBI handbook [Internet], Chapter 18, (2002)
C. M. et al., Int. J Exp. Pathol. 92 (2011): 326-332
Reinisch, W. et al., J Immunother. 25 (2002): 489-499
Reinmuth, N. et al., Dtsch. Med. Wochenschr. 140 (2015): 329-333
Ries, J. et al., Int. J Oncol 26 (2005): 817-824
Rinaldi, A. et al., Pathobiology 77 (2010): 129-135
Rini, B. I. et al., Curr. Opin. Oncol. 20 (2008): 300-306
Rini, B. I. et al., Cancer 107 (2006): 67-74
Risinger, J. I. et al., Clin Cancer Res 13 (2007): 1713-1719
Rock, K. L. et al., Science 249 (1990): 918-921
Rodenko, B. et al., Nat Protoc. 1 (2006): 1120-1132
S3-Leitlinie Exokrines Pankreaskarzinom, 032-010OL, (2013)
S3-Leitlinie Lungenkarzinom, 020/007, (2011)
S3-Leitlinie maligne Ovarialtumore, 032-035OL, (2013)
S3-Leitlinie Mammakarzinom, 032-045OL, (2012)
S3-Leitlinie Melanom, 032-024OL, (2013)
S3-Leitlinie Prostatakarzinom, 043/022OL, (2014)
Saiki, R. K. et al., Science 239 (1988): 487-491
Salman, B. et al., Oncoimmunology. 2 (2013): e26662
Sangro, B. et al., J Clin Oncol 22 (2004): 1389-1397
Schmidt, S. M. et al., Cancer Res 64 (2004): 1164-1170
Seeger, F. H. et al., Immunogenetics 49 (1999): 571-576
Shahzad, M. M. et al., Cancer Lett. 330 (2013): 123-129
Sherman, F. et al., Laboratory Course Manual for Methods in Yeast Genetics (1986)
Sherman-Baust, C. A. et al., Cancer Cell 3 (2003): 377-386
Shi, M. et al., World J Gastroenterol. 10 (2004): 1146-1151
Showel, M. M. et al., F1000Prime. Rep. 6 (2014): 96
Siegel, S. et al., Blood 102 (2003): 4416-4423
Silva, L. P. et al., Anal. Chem. 85 (2013): 9536-9542
Singh-Jasuja, H. et al., Cancer Immunol. Immunother. 53 (2004): 187-195
Skandalis, S. S. et al., Matrix Biol 35 (2014): 182-193
Small, E. J. et al., J Clin Oncol. 24 (2006): 3089-3094
Smith, M. J. et al., Br. J Cancer 100 (2009): 1452-1464
Son, M. Y. et al., Stem Cells 31 (2013): 2374-2387
Springelkamp, H. et al., Genet. Epidemiol. 39 (2015): 207-216
Stahl, M. et al., Ann. Oncol. 24 Suppl 6 (2013): vi51-vi56
Sturm, M. et al., BMC. Bioinformatics. 9 (2008): 163
Su, Z. et al., Cancer Res. 63 (2003): 2127-2133
Sun, H. et al., J BUON. 20 (2015): 296-308
Szajnik, M. et al., Gynecol. Obstet. (Sunnyvale.) Suppl 4 (2013): 3
Szarvas, T. et al., Int J Cancer 135 (2014): 1596-1604
Takayama, T. et al., Cancer 68 (1991): 2391-2396

Takayama, T. et al., Lancet 356 (2000): 802-807
Tanaka, F. et al., Int. J Oncol 10 (1997): 1113-1117
Teufel, R. et al., Cell Mol Life Sci. 62 (2005): 1755-1762
Thakkar, J. P. et al., Cancer Epidemiol. Biomarkers Prev. 23 (2014): 1985-1996
Thorsen, K. et al., Mol Cell Proteomics. 7 (2008): 1214-1224
Tian, X. et al., J Transl. Med. 13 (2015): 337
Toomey, P. G. et al., Cancer Control 20 (2013): 32-42
Tradonsky, A. et al., Am. J Clin Pathol. 137 (2012): 918-930
Tran, E. et al., Science 344 (2014): 641-645
Urgard, E. et al., Cancer Inform. 10 (2011): 175-183
van der Bruggen, P. et al., Immunol. Rev 188 (2002): 51-64
van, Duin M. et al., Haematologica 96 (2011): 1662-1669
Velinov, N. et al., Khirurgiia (Sofiia) (2010): 44-49
Walter, S. et al., J Immunol 171 (2003): 4974-4978
Walter, S. et al., Nat Med. 18 (2012): 1254-1261
Wang, G. H. et al., Oncol Lett. 5 (2013): 544-548
Wang, Y. et al., Anticancer Res 33 (2013): 207-214
Wilhelm, S. M. et al., Cancer Res 64 (2004): 7099-7109
Willcox, B. E. et al., Protein Sci. 8 (1999): 2418-2423
Wittig, B. et al., Hum. Gene Ther. 12 (2001): 267-278
Wlodarski, M. W. et al., J Leukoc. Biol 83 (2008): 589-601
World Cancer Report, (2014)
Wu, Z. Y. et al., Scand. J Immunol. 74 (2011): 561-567
Xie, X. et al., Oncol Lett. 7 (2014): 1537-1543
Xiong, D. et al., Carcinogenesis 33 (2012): 1797-1805
Xu, J. et al., J Mol. Biol 377 (2008): 28-46
Xu, L. et al., Zhongguo Fei. Ai. Za Zhi. 14 (2011): 727-732
Xu, X. et al., Exp. Mol. Pathol. 97 (2014): 579-584
Xu, Y. et al., Sci. Rep. 5 (2015): 12104
Yakimchuk, K. et al., Mol. Cell Endocrinol. 375 (2013): 121-129
Yamada, R. et al., Tissue Antigens 81 (2013): 428-434
Yang, S. et al., Biochim. Biophys. Acta 1772 (2007): 1033-1040
Yao, J. et al., Cancer Immunol. Res. 2 (2014): 371-379
Yin, B. et al., Int. J Clin Exp. Pathol. 7 (2014a): 2934-2941
Yu, J. et al., Gut 64 (2015): 636-645
Yu, W. et al., Toxicol. Appl. Pharmacol. 264 (2012): 73-83
Yuan, R. H. et al., Ann Surg. Oncol 16 (2009): 1711-1719
Zamuner, F. T. et al., Mol. Cancer Ther. 14 (2015): 828-834
Zaremba, S. et al., Cancer Res. 57 (1997): 4570-4577
Zhan, W. et al., Clin Res Hepatol. Gastroenterol. (2015)
Zhang, H. et al., Carcinogenesis 35 (2014): 1863-1871
Zhang, J. et al., Oncotarget. 6 (2015): 42040-42052
Zhang, S. et al., Int. J Clin Exp. Pathol. 8 (2015): 541-550
Zhang, X. et al., Int. J Oncol (2016)
Zhao, H. et al., Zhonghua Gan Zang. Bing. Za Zhi. 10 (2002): 100-102
Zou, T. T. et al., Oncogene 21 (2002): 4855-4862
Follenzi A, et al. Nat Genet. 2000 June; 25(2):217-22.
Zufferey R, et al. J Virol. 1999 April; 73(4):2886-92.
Scholten K B, et al. Clin Immunol. 2006 May; 119(2):135-45.
Gustafsson C, et al. Trends Biotechnol. 2004 Jul; 22(7):346-53. Review.
Kuball, J., et al. (2007). *Blood* 109, 2331-2338.
Schmitt, T. M., et al. (2009). *Hum. Gene Ther.* 20, 1240-1248

The invention claimed is:

1. A fusion protein comprising a peptide consisting of the amino acid sequence of ALAGIVTNV (SEQ ID NO: 246) and N-terminal amino acids of the HLA-DR antigen-associated invariant chain (Ii).

2. A pharmaceutical composition comprising
    a peptide consisting of the amino acid sequence of ALAGIVTNV (SEQ ID NO: 246) and an adjuvant; or
    a fusion protein comprising a peptide consisting of the amino acid sequence of ALAGIVTNV (SEQ ID NO: 246) and the N-terminal amino acids 1 to 80 of the HLA-DR antigen-associated invariant chain (Ii);
    wherein said composition comprises a pharmaceutically acceptable carrier, and optionally, pharmaceutically acceptable excipients and/or stabilizers.

3. The pharmaceutical composition of claim 2, wherein the pharmaceutically acceptable carrier is selected from the group consisting of saline, Ringer's solution, and dextrose solution.

4. The pharmaceutical composition of claim 2, wherein said composition comprises a peptide consisting of the amino acid sequence of ALAGIVTNV (SEQ ID NO: 246, an adjuvant, a pharmaceutically acceptable carrier, and a pharmaceutically acceptable excipient and/or stabilizer.

5. The pharmaceutical composition of claim 4, wherein the pharmaceutically acceptable excipients are selected from the group consisting of buffers, binding agents, diluents, flavors, and lubricants.

6. The pharmaceutical composition of claim 2, wherein said composition consists essentially of a peptide consisting of the amino acid sequence of ALAGIVTNV (SEQ ID NO: 246, an adjuvant, and a pharmaceutically acceptable carrier.

7. An artificial antigen presenting cell (aAPC) comprising an WIC complex of a peptide consisting of the amino acid sequence of ALAGIVTNV (SEQ ID NO: 246) on the surface of the aAPC.

8. The aAPC of claim 7, further comprising an anti-CD28 antibody on the surface of the aAPC.

9. The pharmaceutical composition of claim 2, wherein the adjuvant is selected from the group consisting of anti-CD40 antibody, imiquimod, resiquimod, GM-CSF, cyclophosphamide, sunitinib, bevacizumab, interferon-alpha, interferon-beta, CpG oligonucleotides and derivates, poly-(I:C) and derivates, RNA, sildenafil, particulate formulations with poly(lactid co-glycolid) (PLG), virosomes, interleukin (IL)-1, IL-2, IL-4, IL-7, IL-12, IL-13, IL-15, IL-21, and IL-23.

* * * * *